(12) United States Patent
Fan

(10) Patent No.: US 10,011,829 B2
(45) Date of Patent: Jul. 3, 2018

(54) PEPTIDES AND USES THEREOF

(71) Applicant: Avantgen, Inc., San Diego, CA (US)

(72) Inventor: Xiaomin Fan, San Diego, CA (US)

(73) Assignee: AVANTGEN, INC., San Diego, CA (US)

( * ) Notice: Subject to any disclaimer, the term of this patent is extended or adjusted under 35 U.S.C. 154(b) by 0 days.

(21) Appl. No.: 14/945,343

(22) Filed: Nov. 18, 2015

(65) Prior Publication Data

US 2016/0304856 A1 Oct. 20, 2016

Related U.S. Application Data

(63) Continuation of application No. 13/810,417, filed as application No. PCT/US2011/044289 on Jul. 15, 2011, now abandoned.

(60) Provisional application No. 61/365,146, filed on Jul. 16, 2010.

(51) Int. Cl.
*C40B 40/02* (2006.01)
*C12N 15/10* (2006.01)
*C07K 16/30* (2006.01)

(52) U.S. Cl.
CPC ...... *C12N 15/1037* (2013.01); *C07K 16/3069* (2013.01); *C07K 2317/21* (2013.01); *C07K 2317/24* (2013.01); *C07K 2317/52* (2013.01); *C07K 2317/55* (2013.01); *C07K 2317/565* (2013.01); *C07K 2317/92* (2013.01); *C40B 40/02* (2013.01)

(58) Field of Classification Search
None
See application file for complete search history.

(56) References Cited

U.S. PATENT DOCUMENTS

| 6,844,171 | B1 | 1/2005 | Hogle et al. |
| 2002/0091085 | A1 | 7/2002 | Kay et al. |
| 2006/0105387 | A1 | 5/2006 | Prior et al. |
| 2007/0212703 | A1 | 9/2007 | Stemmer et al. |
| 2009/0062142 | A1 | 3/2009 | Daugherty et al. |

OTHER PUBLICATIONS

Feldhaus et al., "Flow-cytometric isolation of human antibodies from a nonimmune *Saccharomyces cerevisiae* surface display library", Nat Biotechnol., 21(2):163-170 (2003).

(Continued)

*Primary Examiner* — Christian C Boesen
(74) *Attorney, Agent, or Firm* — Jones Day

(57) ABSTRACT

The present disclosure relates to novel peptides and their uses including, proline-rich peptides that are useful for displaying a protein of interest at the surfaces of a host cell such as a yeast. Polynucleotides, proteins, vectors and host cells that comprise or encode the novel proline-rich peptides, including libraries comprising such polynucleotides, proteins, vectors and/or host cells that comprise or encode novel proline-rich peptides are provided. Methods and materials for display and expression of proteins of interest are provided. Methods and materials are also provided by the present disclosure for isolating peptides capable of displaying a protein of interest (e.g., a marker protein), for generating libraries to display and/or express proteins of interest (e.g., antibodies such as humanized antibodies), for generating secretion vectors for such proteins of interest, and for generating proteins of interest (e.g., antibodies).

14 Claims, 9 Drawing Sheets

(56) References Cited

OTHER PUBLICATIONS

Fidler et al., "Comparative analysis of avian BMAL1 and CLOCK protein sequences: a search for features associated with owl nocturnal behaviour", Comp Biochem Physiol B Biochem Mol Biol., 136(4):861-874 (2003).
Rickles et al., "Identification of Src, Fyn, Lyn, PI3K and Abl SH3 domain ligands using phage display libraries", EMBO J., 13(23):5598-5604 (1994).
Silverman et al., "Multivalent avimer proteins evolved by exon shuffling of a family of human receptor domains", Nat Biotechnol., 23(12):1556-1561 (2005).
Sparks et al., "Distinct ligand preferences of Src homology 3 domains from Src, Yes, Abl, Cortactin, p53bp2, PLCgamma, Crk, and Grb2", Proc Natl Acad Sci U.S.A., 93(4):1540-1544 (1996).

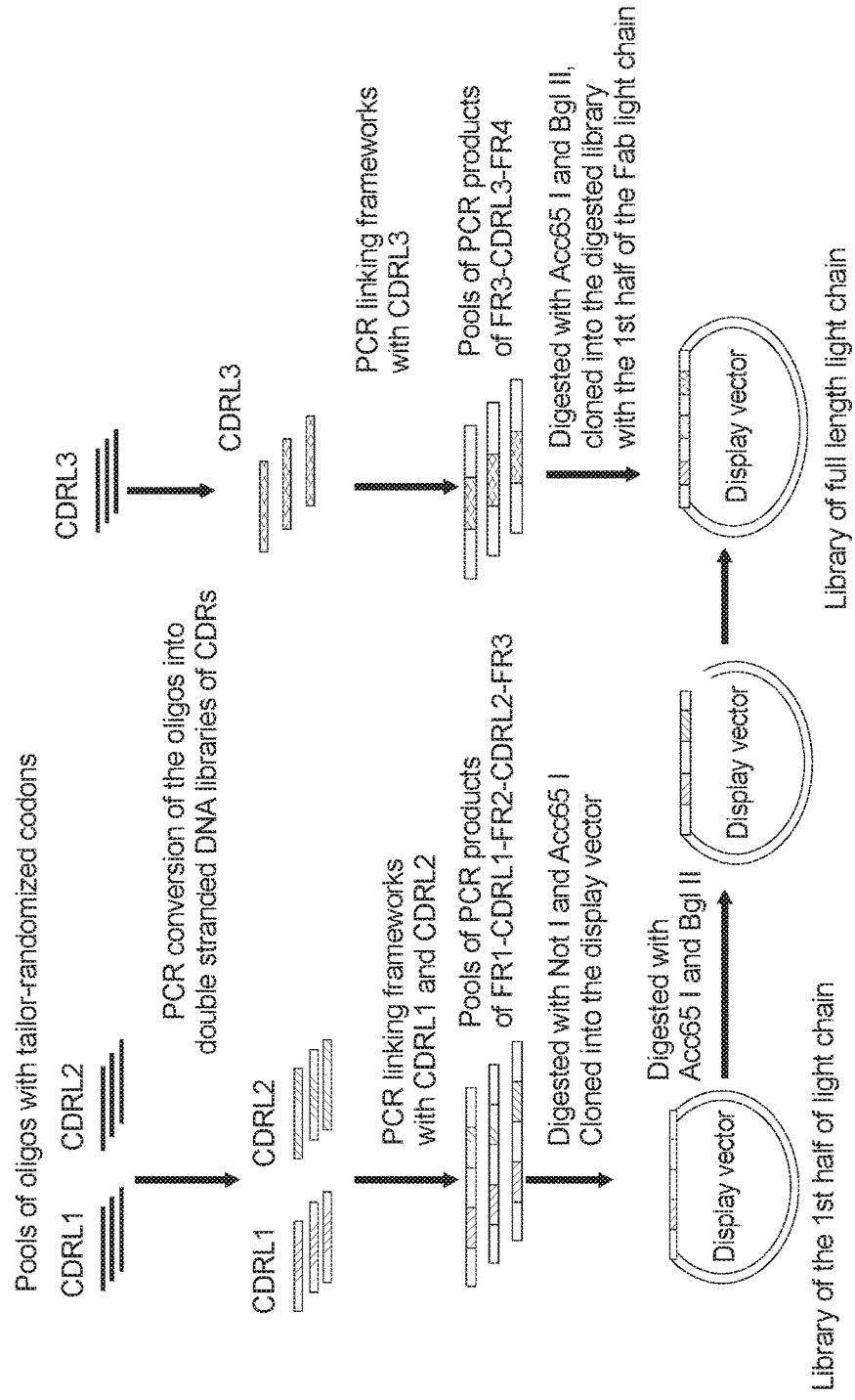

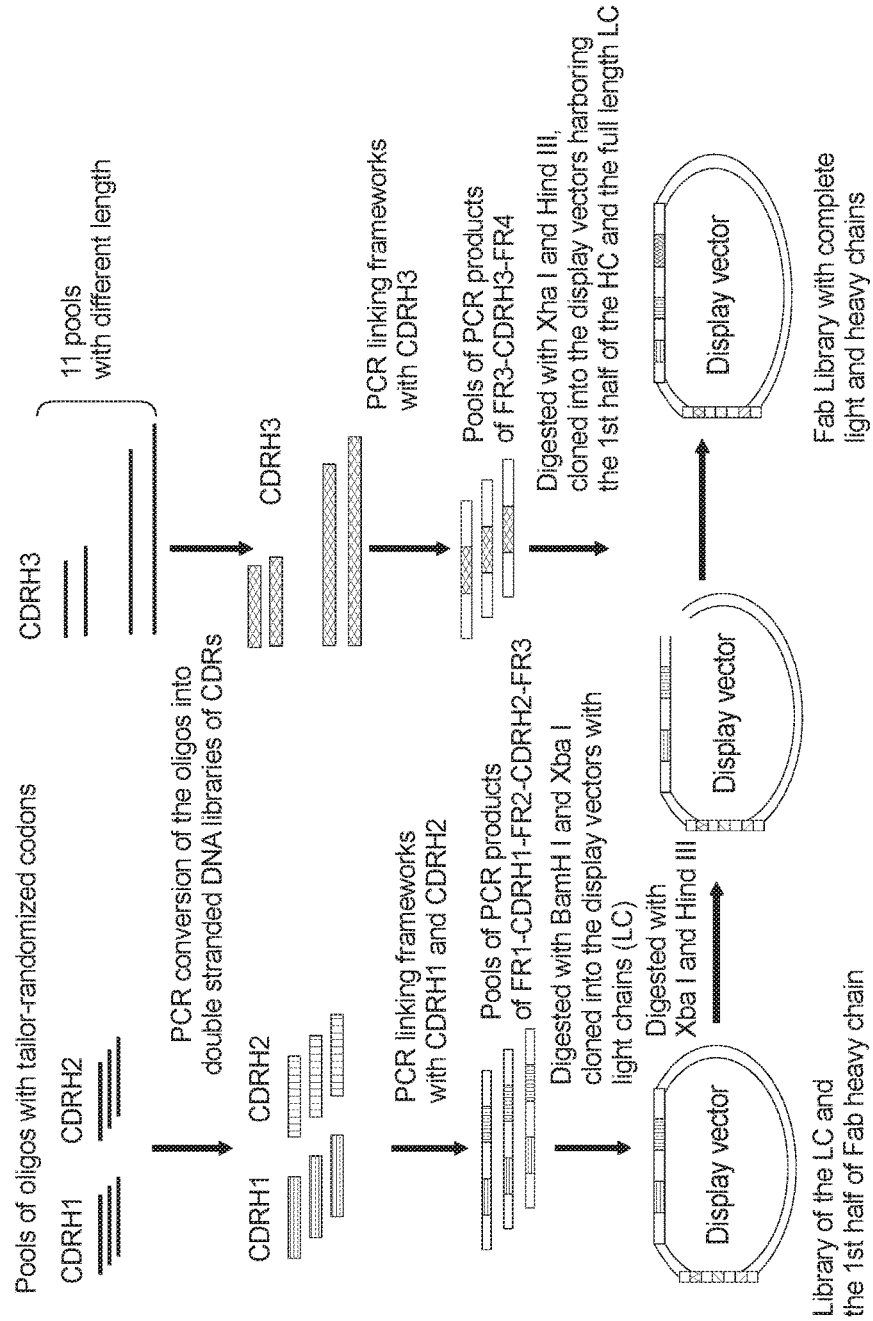

PEPTIDES AND USES THEREOF

CROSS-REFERENCE TO RELATED APPLICATIONS

This application is a continuation of U.S. application Ser. No. 13/810,417, filed Jan. 15, 2013, which is a U.S. national stage application of International Application No. PCT/US2011/044289, filed Jul. 15, 2011, which claims benefit of priority to U.S. Provisional Application No. 61/365,146, filed Jul. 16, 2010, the disclosure of each of which is incorporated herein by reference.

SEQUENCE LISTING

The content of the following submission on ASCII text file is incorporated herein by reference in its entirety: a computer readable form (CRF) of the Sequence Listing, entitled 13366-004-999_SUB_SEQ_LISTING.txt, of size 104,098 bytes, and created on Feb. 12, 2018.

FIELD

The present disclosure relates to novel peptides and their uses. Polynucleotides, proteins, vectors and host cells that comprise a proline-rich peptide are provided by the present disclosure, including libraries of such polynucleotides, proteins, vectors and host cells. The novel proline-rich peptides of the present disclosure may be used for display of proteins of interest on host cells, including yeast cells. Methods and materials for the display and expression of proteins of interest are provided by the present disclosure. Methods and materials are also provided by the present disclosure for isolating peptides capable of displaying a protein of interest (e.g., a marker protein), for generating libraries to display and/or express proteins of interest (e.g., antibodies such as humanized antibodies), for generating secretion vectors for such proteins of interest, and for generating proteins of interest (e.g., antibodies).

BACKGROUND

Display technologies have substantially impacted basic and applied research applications ranging from drug discovery to materials synthesis (see, e.g., Clackson and Wells (1994) *Trends In Biotech.* 12(5):173-184; Lee et al. (2002) *Science* 296 (5569):892-859; and Nixon (2002) *Curr. Pharm. Biotechnol.* 3(1):1-12). The strength of these methods derives from the ability to generate libraries containing billions of diverse molecules using the biosynthetic machinery of the cell, and subsequently, to identify rare desired peptides and proteins using selection or high-throughput screening methods. For example, display systems have been routinely employed to isolate and engineer proteins including, for example, antibodies.

Surface display libraries, for example, of antibodies, allow for the enrichment of specific binding clones by subjecting the organism displaying the binding molecule (e.g., phage and yeast) to successive rounds of selection (e.g., Kretzschmar et al. 2002, *Curr Opin* Biotechol 13: 598-602). Display systems include mRNA and ribosome display, eukaryotic virus display, and bacterial and yeast cell surface display (see, e.g., Wilson et al. 2001 *PNAS* 98(7): 3750-3511; Muller et al. (2003) *Nat. Biotechnol.* 3:312; Bupp and Roth (2002) *Md. Ther.* 5(3):329-3513; Georgiou et al. (1997) *Nat. Biotechnol.* 15(1):29-3414; and Boder and Wittrup (1997) *Nature Biotech.* 15(6):553-557). Surface display methods are attractive since they enable application of fluorescence-activated cell sorting (FACS) for library analysis and screening (see, e.g., Georgiou (2000) *Adv. Protein Chem.* 55:293-315; and Boder et al. (2000) *PNAS* 97(20):10701-10705). However, available surface display systems generally rely on the fusion of a protein of interest to a coat protein or cell wall protein which anchors the protein of interest on the cell surface. Such fusion may affect proliferation of the host and/or the expression level of the display protein. Use of naturally occurring coat proteins of higher eukaryotic species, such as yeast, may be better tolerated than phage coat proteins but the requirement of normal assembly into the cell wall of such native proteins can impose limitations on the host species that may be used for or support display.

SUMMARY

The present disclosure relates to novel peptides and their uses. Novel proline-rich peptides may be used to display proteins of interest on the surface of host cells, including yeast cells. The present disclosure provides polynucleotides, proteins, vectors and host cells that comprise or encode the novel proline-rich peptides, including libraries comprising such polynucleotides, proteins, vectors and/or host cells. Methods and materials for the display and expression of proteins of interest are provided by the present disclosure. Methods and materials are also provided by the present disclosure for isolating peptides capable of displaying a protein of interest (e.g., a marker protein), for generating libraries to display and/or express proteins of interest (e.g., antibodies such as humanized antibodies), for generating secretion vectors for such proteins of interest, and for generating proteins of interest (e.g., antibodies).

The present disclosure provides libraries of host cells displaying on their surface proteins of interest associated with (e.g., linked to) a proline-rich peptide.

In some embodiments, the host cells are yeast.

In some embodiments, the protein of interest is an antibody or fragment thereof (e.g., an antigen binding fragment). In some embodiments, the antibody or fragment thereof is selected from the group consisting of a full length antibody, Fab, scFv, Fv, an antibody heavy chain or fragment thereof, an antibody light chain or fragment thereof and a single chain antibody (SCA).

In some embodiments, the proline-rich peptide is an amino acid sequence comprising PPP or any of the amino acid sequences depicted in SEQ ID NOS: 1-116.

In some embodiments, the proline-rich peptide is an amino acid sequence comprising one or more of the following features:

(i) at least 3, 4, 5, 6 or more contiguous proline residues;

(ii) a number of contiguous proline (P) or (XP) residues (where X is any amino acid) sufficient to produce a polyproline Type II helix with at least 2 turns;

(iii) at least about 60%, 65%, 70%, 75%, 80%, 85%, 90%, 95%, 99% or 100% sequence identity to any of the amino acid sequences depicted in SEQ ID NOS: 1 and 55-116;

(iv) any of the amino acid sequences depicted in SEQ ID NOS: 2-54;

(v) about 3 to about 26 proline residues in a length of about 3 to s 50 amino acid residues (e.g., about 3 to about 26 amino acid residues);

(vi) about 20% to about 100% proline;

(vii) a C-terminal amino acid residue of the peptide that is not proline or histidine;

(viii) at the C-terminus of the peptide at least 1, 2, 3, 4, 5, 6, 7, 8, 9, 10, 11, 12, 13, 14 or more non-proline amino acid residues; or (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu).

In some embodiments, the proline-rich peptide is an amino acid sequence:
- (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues;
- (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues;
- (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues;
- (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or
- (v) that is 3 to 11 amino acid residues and wherein no less than 3 and no more than 9 of the amino acid residues of the peptide are proline residues.

In some embodiments, the C-terminal non-proline amino acids residues comprise a S (Ser), L (Leu), C (Cys), V (Val), CV (Cys-Val), HHHHHH (SEQ ID NO: 118), HHHHHHV (SEQ ID NO: 119), LHHHHHH (SEQ ID NO: 122), LLLLLLLL (residues 1-8 of SEQ ID NO: 121), LHHHH-HHCV (SEQ ID NO: 120), or LLLLLLLLS (SEQ ID NO: 121).

In some embodiments, the proline-rich peptide comprises SEQ ID NO: 1.

In some embodiments, the protein of interest and the proline-rich peptide are directly associated. In some embodiments, the protein of interest and the proline-rich peptide are indirectly associated. In some embodiments, the protein of interest and the proline-rich peptide are associated through a peptide linker such as $(GGGGS)_3$ (SEQ ID NO: 123). In some embodiments, when the protein of interest and the proline-rich peptide are associated, the proline-rich peptide is associated at (e.g., linked to) either the N-terminal or C-terminal of a protein of interest.

In some embodiments, the proline-rich peptide does not comprise hydroxyproline.

In some embodiments, the proline-rich peptide and/or the protein of interest further comprise a tag. In some embodiments, the tag is a histidine tag (e.g., hexa-histidine tag) and/or a myc tag.

The present disclosure provides libraries of host cells comprising polynucleotides coding for a protein of interest associated with (e.g., linked to) a proline-rich peptide.

In some embodiments, the host cells are yeast.

In some embodiments, the protein of interest is an antibody or fragment thereof (e.g., an antigen binding fragment). In some embodiments, the antibody or fragment thereof is selected from the group consisting of a scFv, Fv, an antibody heavy chain or fragment thereof, an antibody light chain or fragment thereof and a single chain antibody (SCA).

In some embodiments, the proline-rich peptide is an amino acid sequence comprising PPP or any of the amino acid sequences depicted in SEQ ID NOS: 1-116.

In some embodiments, the proline-rich peptide is an amino acid sequence comprising one or more of the following features:
- (i) at least 3, 4, 5, 6 or more contiguous proline residues;
- (ii) a number of contiguous proline (P) or (XP) residues (where X is any amino acid) sufficient to produce a polyproline Type II helix with at least 2 turns;
- (iii) at least about 60%, 65%, 70%, 75%, 80%, 85%, 90%, 95%, 99% or 100% sequence identity to any of the amino acid sequences depicted in SEQ ID NOS: 1 and 55-116;
- (iv) any of the amino acid sequences depicted in SEQ ID NOS: 2-54;
- (v) about 3 to about 26 proline residues in a length of about 3 to s 50 amino acid residues (e.g., about 3 to about 26 amino acid residues);
- (vi) about 20% to about 100% proline;
- (vii) a C-terminal amino acid residue of the peptide that is not proline or histidine;
- (viii) at the C-terminus of the peptide at least 1, 2, 3, 4, 5, 6, 7, 8, 9, 10, 11, 12, 13, 14 or more non-proline amino acid residues; or
- (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu).

In some embodiments, the proline-rich peptide is an amino acid sequence:
- (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues;
- (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues;
- (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues;
- (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or (v) that is 3 to 11 amino acid residues and wherein no less than 3 and no more than 9 of the amino acid residues of the peptide are proline residues.

In some embodiments, the C-terminal non-proline amino acids residues comprise a S (Ser), L (Leu), C (Cys), V (Val), CV (Cys-Val), HHHHHH (SEQ ID NO: 118), HHHHHHV (SEQ ID NO: 119), LHHHHHH (SEQ ID NO: 122), LLLLLLLL (residues 1-8 of SEQ ID NO: 121), LHHHH-HHCV (SEQ ID NO: 120), or LLLLLLLLS (SEQ ID NO: 121).

In some embodiments, the proline-rich peptide comprises SEQ ID NO: 1.

In some embodiments, the protein of interest and the proline-rich peptide are directly associated. In some embodiments, the protein of interest and the proline-rich peptide are indirectly associated. In some embodiments, the protein of interest and the proline-rich peptide are associated through a peptide linker such as (GGGGS)$_3$ (SEQ ID NO: 123). In some embodiments, when the protein of interest and the proline-rich peptide are associated, the proline-rich peptide is associated at (e.g., linked to) either the N-terminal or C-terminal of a protein of interest.

In some embodiments, the proline-rich peptide does not comprise hydroxyproline.

In some embodiments, the proline-rich peptide and/or the protein of interest further comprise a tag. In some embodiments, the tag is a histidine tag (e.g., hexa-histidine tag) and/or a myc tag.

In some embodiments, the polynucleotide coding for the protein of interest is linked to one or more expression control elements. In some embodiments, the expression control element is a promoter. In some embodiments, the promoter is a yeast promoter.

The present disclosure provides nucleic acid libraries comprising a plurality of polynucleotides coding for proteins of interest and a proline-rich peptide.

In some embodiments, the protein of interest is an antibody or fragment thereof (e.g., an antigen binding fragment). In some embodiments, the antibody or fragment thereof is selected from the group consisting of a scFv, Fv, an antibody heavy chain or fragment thereof, an antibody light chain or fragment thereof and a single chain antibody (SCA).

In some embodiments, the proline-rich peptide is an amino acid sequence comprising PPP or any of the amino acid sequences depicted in SEQ ID NOS: 1-116.

In some embodiments, the proline-rich peptide is an amino acid sequence comprising one or more of the following features:
(i) at least 3, 4, 5, 6 or more contiguous proline residues;
(ii) a number of contiguous proline (P) or (XP) residues (where X is any amino acid) sufficient to produce a polyproline Type II helix with at least 2 turns;
(iii) at least about 60%, 65%, 70%, 75%, 80%, 85%, 90%, 95%, 99% or 100% sequence identity to any of the amino acid sequences depicted in SEQ ID NOS: 1 and 55-116;
(iv) any of the amino acid sequences depicted in SEQ ID NOS: 2-54;
(v) about 3 to about 26 proline residues in a length of about 3 to s 50 amino acid residues (e.g., about 3 to about 26 amino acid residues);
(vi) about 20% to about 100% proline;
(vii) a C-terminal amino acid residue of the peptide that is not proline or histidine;
(viii) at the C-terminus of the peptide at least 1, 2, 3, 4, 5, 6, 7, 8, 9, 10, 11, 12, 13, 14 or more non-proline amino acid residues; or (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu).

In some embodiments, the proline-rich peptide is an amino acid sequence:
(i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues;
(ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues;
(iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues;
(iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or
(v) that is 3 to 11 amino acid residues and wherein no less than 3 and no more than 9 of the amino acid residues of the peptide are proline residues.

In some embodiments, the C-terminal non-proline amino acids residues comprise a S (Ser), L (Leu), C (Cys), V (Val), CV (Cys-Val), HHHHHH (SEQ ID NO: 118), HHHHHHV (SEQ ID NO: 119), LHHHHHH (SEQ ID NO: 122), LLLLLLLL (residues 1-8 of SEQ ID NO: 121), LHHHH-HHCV (SEQ ID NO: 120), or LLLLLLLLS (SEQ ID NO: 121).

In some embodiments, the proline-rich peptide comprises SEQ ID NO: 1.

In some embodiments, the protein of interest and the proline-rich peptide are directly associated. In some embodiments, the protein of interest and the proline-rich peptide are indirectly associated. In some embodiments, the protein of interest and the proline-rich peptide are associated through a peptide linker such as (GGGGS)$_3$ (SEQ ID NO: 123). In some embodiments, when the protein of interest and the proline-rich peptide are associated, the proline-rich peptide is associated at (e.g., linked to) either the N-terminal or C-terminal of a protein of interest.

In some embodiments, the proline-rich peptide does not comprise hydroxyproline.

In some embodiments, the proline-rich peptide and/or the protein of interest further comprise a tag. In some embodiments, the tag is a histidine tag (e.g., hexa-histidine tag) and/or a myc tag.

In some embodiments, the polynucleotide coding for the protein of interest is operably linked to one or more expression control elements. In some embodiments, the expression control element is a promoter. In some embodiments, the promoter is a yeast promoter.

The present disclosure provides a recombinant protein that comprises a protein of interest associated with a proline-rich peptide.

In some embodiments, the protein of interest is an antibody or fragment thereof (e.g., an antigen binding fragment). In some embodiments, the antibody or fragment thereof is selected from the group consisting of a scFv, Fv, an antibody heavy chain or fragment thereof, an antibody light chain or fragment thereof and a single chain antibody (SCA).

In some embodiments, the proline-rich peptide is an amino acid sequence comprising PPP or any of the amino acid sequences depicted in SEQ ID NOS: 1-116.

In some embodiments, the proline-rich peptide is an amino acid sequence comprising one or more of the following features:
  (i) at least 3, 4, 5, 6 or more contiguous proline residues;
  (ii) a number of contiguous proline (P) or (XP) residues (where X is any amino acid) sufficient to produce a polyproline Type II helix with at least 2 turns;
  (iii) at least about 60%, 65%, 70%, 75%, 80%, 85%, 90%, 95%, 99% or 100% sequence identity to any of the amino acid sequences depicted in SEQ ID NOS: 1 and 55-116;
  (iv) any of the amino acid sequences depicted in SEQ ID NOS: 2-54;
  (v) about 3 to about 26 proline residues in a length of about 3 to s 50 amino acid residues (e.g., about 3 to about 26 amino acid residues);
  (vi) about 20% to about 100% proline;
  (vii) a C-terminal amino acid residue of the peptide that is not proline or histidine;
  (viii) at the C-terminus of the peptide at least 1, 2, 3, 4, 5, 6, 7, 8, 9, 10, 11, 12, 13, 14 or more non-proline amino acid residues; or
  (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu).

In some embodiments, the proline-rich peptide is an amino acid sequence:
  (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues;
  (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues;
  (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues;
  (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or
  (v) that is 3 to 11 amino acid residues and wherein no less than 3 and no more than 9 of the amino acid residues of the peptide are proline residues.

In some embodiments, the C-terminal non-proline amino acids residues comprise a S (Ser), L (Leu), C (Cys), V (Val), CV (Cys-Val), HHHHHH (SEQ ID NO: 118), HHHHHHV (SEQ ID NO: 119), LHHHHHH (SEQ ID NO: 122), LLLLLLLL (residues 1-8 of SEQ ID NO: 121), LHHHHHCV (SEQ ID NO: 120), or LLLLLLLLS (SEQ ID NO: 121).

In some embodiments, the proline-rich peptide comprises SEQ ID NO: 1.

In some embodiments, the protein of interest and the proline-rich peptide are directly associated. In some embodiments, the protein of interest and the proline-rich peptide are indirectly associated. In some embodiments, the protein of interest and the proline-rich peptide are associated through a peptide linker such as (GGGGS)$_3$ (SEQ ID NO: 123). In some embodiments, when the protein of interest and the proline-rich peptide are associated, the proline-rich peptide is associated at (e.g., linked to) either the N-terminal or C-terminal of a protein of interest.

In some embodiments, the proline-rich peptide does not comprise hydroxyproline.

In some embodiments, the proline-rich peptide and/or the protein of interest further comprise a tag. In some embodiments, the tag is a histidine tag (e.g., hexa-histidine tag) and/or a myc tag.

The present disclosure provides recombinant polynucleotides comprising polynucleotides coding for a protein of interest and a proline-rich peptide.

In some embodiments, the protein of interest and the proline-rich peptide are coded by the same polynucleotide. In some embodiments, the protein of interest and the proline-rich peptide are coded by different polynucleotides.

In some embodiments, the protein of interest is an antibody or fragment thereof (e.g., an antigen binding fragment). In some embodiments, the antibody or fragment thereof is selected from the group consisting of a scFv, Fv, an antibody heavy chain or fragment thereof, an antibody light chain or fragment thereof and a single chain antibody (SCA).

In some embodiments, the proline-rich peptide is an amino acid sequence comprising PPP or any of the amino acid sequences depicted in SEQ ID NOS: 1-116.

In some embodiments, the proline-rich peptide is an amino acid sequence comprising one or more of the following features:
  (i) at least 3, 4, 5, 6 or more contiguous proline residues;
  (ii) a number of contiguous proline (P) or (XP) residues (where X is any amino acid) sufficient to produce a polyproline Type II helix with at least 2 turns;
  (iii) at least about 60%, 65%, 70%, 75%, 80%, 85%, 90%, 95%, 99% or 100% sequence identity to any of the amino acid sequences depicted in SEQ ID NOS: 1 and 55-116;
  (iv) any of the amino acid sequences depicted in SEQ ID NOS: 2-54;
  (v) about 3 to about 26 proline residues in a length of about 3 to S 50 amino acid residues (e.g., about 3 to about 26 amino acid residues);
  (vi) about 20% to about 100% proline;
  (vii) a C-terminal amino acid residue of the peptide that is not proline or histidine;
  (viii) at the C-terminus of the peptide at least 1, 2, 3, 4, 5, 6, 7, 8, 9, 10, 11, 12, 13, 14 or more non-proline amino acid residues; or (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu).

In some embodiments, the proline-rich peptide is an amino acid sequence:
(i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues;
(ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues;
(iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues;
(iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or
(v) that is 3 to 11 amino acid residues and wherein no less than 3 and no more than 9 of the amino acid residues of the peptide are proline residues.

In some embodiments, the C-terminal non-proline amino acids residues comprise a S (Ser), L (Leu), C (Cys), V (Val), CV (Cys-Val), HHHHHH (SEQ ID NO: 118), HHHHHHV (SEQ ID NO: 119), LHHHHHH (SEQ ID NO: 122), LLLLLLLL (residues 1-8 of SEQ ID NO: 121), LHHHH-HHCV (SEQ ID NO: 120), or LLLLLLLLS (SEQ ID NO: 121).

In some embodiments, the proline-rich peptide comprises SEQ ID NO: 1.

In some embodiments, the protein of interest and the proline-rich peptide are directly associated. In some embodiments, the protein of interest and the proline-rich peptide are indirectly associated. In some embodiments, the protein of interest and the proline-rich peptide are associated through a peptide linker such as (GGGGS)$_3$ (SEQ ID NO: 123). In some embodiments, when the protein of interest and the proline-rich peptide are associated, the proline-rich peptide is associated at (e.g., linked to) either the N-terminal or C-terminal of a protein of interest.

In some embodiments, the proline-rich peptide does not comprise hydroxyproline.

In some embodiments, the proline-rich peptide and/or the protein of interest further comprise a tag. In some embodiments, the tag is a histidine tag (e.g., hexa-histidine tag) and/or a myc tag.

The present disclosure provides vectors comprising a polynucleotide that codes for a protein of interest and a polynucleotide that codes for a proline-rich peptide.

In some embodiments, the protein of interest is an antibody or fragment thereof (e.g., an antigen binding fragment). In some embodiments, the antibody or fragment thereof is selected from the group consisting of a scFv, Fv, an antibody heavy chain or fragment thereof, an antibody light chain or fragment thereof and a single chain antibody (SCA).

In some embodiments, the proline-rich peptide is an amino acid sequence comprising PPP or any of the amino acid sequences depicted in SEQ ID NOS: 1-116.

In some embodiments, the proline-rich peptide is an amino acid sequence comprising one or more of the following features:
(i) at least 3, 4, 5, 6 or more contiguous proline residues;
(ii) a number of contiguous proline (P) or (XP) residues (where X is any amino acid) sufficient to produce a polyproline Type II helix with at least 2 turns;
(iii) at least about 60%, 65%, 70%, 75%, 80%, 85%, 90%, 95%, 99% or 100% sequence identity to any of the amino acid sequences depicted in SEQ ID NOS: 1 and 55-116;
(iv) any of the amino acid sequences depicted in SEQ ID NOS: 2-54;
(v) about 3 to about 26 proline residues in a length of about 3 to s 50 amino acid residues (e.g., about 3 to about 26 amino acid residues);
(vi) about 20% to about 100% proline;
(vii) a C-terminal amino acid residue of the peptide that is not proline or histidine;
(viii) at the C-terminus of the peptide at least 1, 2, 3, 4, 5, 6, 7, 8, 9, 10, 11, 12, 13, 14 or more non-proline amino acid residues; or
(ix) at the C-terminus of the peptide an amino acid sequence with at least about 60%, 65%, 70%, 75%, 80%, 85%, 90%, 95%, or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu).

In some embodiments, the proline-rich peptide is an amino acid sequence:
(i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues;
(ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues;
(iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues;
(iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or
(v) that is 3 to 11 amino acid residues and wherein no less than 3 and no more than 9 of the amino acid residues of the peptide are proline residues.

In some embodiments, the C-terminal non-proline amino acids residues comprise a S (Ser), L (Leu), C (Cys), V (Val), CV (Cys-Val), HHHHHH (SEQ ID NO: 118), HHHHHHV (SEQ ID NO: 119), LHHHHHH (SEQ ID NO: 122), LLLLLLLL (residues 1-8 of SEQ ID NO: 121), LHHHH-HHCV (SEQ ID NO: 120), or LLLLLLLLS (SEQ ID NO: 121).

In some embodiments, the proline-rich peptide comprises SEQ ID NO: 1.

In some embodiments, the protein of interest and the proline-rich peptide are directly associated. In some embodiments, the protein of interest and the proline-rich peptide are indirectly associated. In some embodiments, the protein of interest and the proline-rich peptide are associated through a peptide linker such as (GGGGS)$_3$ (SEQ ID NO: 123). In some embodiments, when the protein of interest and the proline-rich peptide are associated, the proline-rich peptide is associated at (e.g., linked to) either the N-terminal or C-terminal of a protein of interest.

In some embodiments, the proline-rich peptide does not comprise hydroxyproline.

In some embodiments, the proline-rich peptide and/or the protein of interest further comprise a tag. In some embodiments, the tag is a histidine tag (e.g., hexa-histidine tag) and/or a myc tag.

The present disclosure provides host cells comprising a polynucleotide that codes for a protein of interest and a polynucleotide that codes for one or more proline-rich peptides.

In some embodiments, the protein of interest and the proline-rich peptide are coded by the same polynucleotide. In some embodiments, the protein of interest and the proline-rich peptide are coded by different polynucleotides.

In some embodiments, the protein of interest is an antibody or fragment thereof (e.g., an antigen binding fragment). In some embodiments, the antibody or fragment thereof is selected from the group consisting of a scFv, Fv, an antibody heavy chain or fragment thereof, an antibody light chain or fragment thereof and a single chain antibody (SCA).

In some embodiments, the proline-rich peptide is an amino acid sequence comprising PPP or any of the amino acid sequences depicted in SEQ ID NOS: 1-116.

In some embodiments, the proline-rich peptide is an amino acid sequence comprising one or more of the following features:
  (i) at least 3, 4, 5, 6 or more contiguous proline residues;
  (ii) a number of contiguous proline (P) or (XP) residues (where X is any amino acid) sufficient to produce a polyproline Type II helix with at least 2 turns;
  (iii) at least about 60%, 65%, 70%, 75%, 80%, 85%, 90%, 95%, 99% or 100% sequence identity to any of the amino acid sequences depicted in SEQ ID NOS: 1 and 55-116;
  (iv) any of the amino acid sequences depicted in SEQ ID NOS: 2-54;
  (v) about 3 to about 26 proline residues in a length of about 3 to s 50 amino acid residues (e.g., about 3 to about 26 amino acid residues);
  (vi) about 20% to about 100% proline;
  (vii) a C-terminal amino acid residue of the peptide that is not proline or histidine;
  (viii) at the C-terminus of the peptide at least 1, 2, 3, 4, 5, 6, 7, 8, 9, 10, 11, 12, 13, 14 or more non-proline amino acid residues; or
  (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu).

In some embodiments, the proline-rich peptide is an amino acid sequence:
  (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues;
  (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues;
  (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues;
  (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or
  (v) that is 3 to 11 amino acid residues and wherein no less than 3 and no more than 9 of the amino acid residues of the peptide are proline residues.

In some embodiments, the C-terminal non-proline amino acids residues comprise a S (Ser), L (Leu), C (Cys), V (Val), CV (Cys-Val), HHHHHH (SEQ ID NO: 118), HHHHHHV (SEQ ID NO: 119), LHHHHHH (SEQ ID NO: 122), LLLLLLLL (residues 1-8 of SEQ ID NO: 121), LHHHH-HHCV (SEQ ID NO: 120), or LLLLLLLLS (SEQ ID NO: 121).

In some embodiments, the proline-rich peptide comprises SEQ ID NO: 1.

In some embodiments, the protein of interest and the proline-rich peptide are directly associated. In some embodiments, the protein of interest and the proline-rich peptide are indirectly associated. In some embodiments, the protein of interest and the proline-rich peptide are associated through a peptide linker such as (GGGGS)$_3$ (SEQ ID NO: 123). In some embodiments, when the protein of interest and the proline-rich peptide are associated, the proline-rich peptide is associated at (e.g., linked to) either the N-terminal or C-terminal of a protein of interest.

In some embodiments, the proline-rich peptide does not comprise hydroxyproline.

In some embodiments, the proline-rich peptide and/or the protein of interest further comprise a tag. In some embodiments, the tag is a histidine tag (e.g., hexa-histidine tag) and/or a myc tag.

In some embodiments, the host cell is a yeast cell.

The present disclosure provides methods of producing a protein of interest associated with (e.g., linked to) a proline-rich peptide comprising culturing a host cell comprising a polynucleotide coding for a protein of interest and a polynucleotide coding for a proline-rich peptide under conditions wherein the polynucleotide sequences are expressed and the protein of interest and the proline-rich peptide is produced.

The present disclosure also provides methods of displaying a protein of interest associated with (e.g., linked to) a proline-rich peptide on a surface of a host cell, comprising culturing a host cell comprising a polynucleotide coding for a protein of interest and a polynucleotide coding for a proline-rich peptide under conditions wherein the polynucleotide sequences are expressed and the protein of interest and the proline-rich peptide is displayed.

In some embodiments, the protein of interest and the proline-rich peptide are coded by the same polynucleotide. In some embodiments, the protein of interest and the proline-rich peptide are coded by different polynucleotides.

In some embodiments, the protein of interest is an antibody or fragment thereof (e.g., an antigen binding fragment). In some embodiments, the antibody or fragment thereof is selected from the group consisting of a scFv, Fv, an antibody heavy chain or fragment thereof, an antibody light chain or fragment thereof and a single chain antibody (SCA).

In some embodiments, the proline-rich peptide is an amino acid sequence comprising PPP or any of the amino acid sequences depicted in SEQ ID NOS: 1-116.

In some embodiments, the proline-rich peptide is an amino acid sequence comprising one or more of the following features:
  (i) at least 3, 4, 5, 6 or more contiguous proline residues;
  (ii) a number of contiguous proline (P) or (XP) residues (where X is any amino acid) sufficient to produce a polyproline Type II helix with at least 2 turns;
  (iii) at least about 60%, 65%, 70%, 75%, 80%, 85%, 90%, 95%, 99% or 100% sequence identity to any of the amino acid sequences depicted in SEQ ID NOS: 1 and 55-116;
  (iv) any of the amino acid sequences depicted in SEQ ID NOS: 2-54;
  (v) about 3 to about 26 proline residues in a length of about 3 to s 50 amino acid residues (e.g., about 3 to about 26 amino acid residues);
  (vi) about 20% to about 100% proline;
  (vii) a C-terminal amino acid residue of the peptide that is not proline or histidine;
  (viii) at the C-terminus of the peptide at least 1, 2, 3, 4, 5, 6, 7, 8, 9, 10, 11, 12, 13, 14 or more non-proline amino acid residues; or
  (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu).

In some embodiments, the proline-rich peptide is an amino acid sequence:
  (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues;
  (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues;
  (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues;
  (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or
  (v) that is 3 to 11 amino acid residues and wherein no less than 3 and no more than 9 of the amino acid residues of the peptide are proline residues.

In some embodiments, the C-terminal non-proline amino acids residues comprise a S (Ser), L (Leu), C (Cys), V (Val), CV (Cys-Val), HHHHHH (SEQ ID NO: 118), HHHHHHV (SEQ ID NO: 119), LHHHHHH (SEQ ID NO: 122), LLLLLLLL (residues 1-8 of SEQ ID NO: 121), LHHHHHHCV (SEQ ID NO: 120), or LLLLLLLLS (SEQ ID NO: 121).

In some embodiments, the proline-rich peptide comprises SEQ ID NO: 1.

In some embodiments, the protein of interest and the proline-rich peptide are directly associated. In some embodiments, the protein of interest and the proline-rich peptide are indirectly associated. In some embodiments, the protein of interest and the proline-rich peptide are associated through a peptide linker such as (GGGGS)$_3$ (SEQ ID NO: 123). In some embodiments, when the protein of interest and the proline-rich peptide are associated, the proline-rich peptide is associated at (e.g., linked to) either the N-terminal or C-terminal of a protein of interest.

In some embodiments, the proline-rich peptide does not comprise hydroxyproline.

In some embodiments, the proline-rich peptide and/or the protein of interest further comprise a tag. In some embodiments, the tag is a histidine tag (e.g., hexa-histidine tag) and/or a myc tag.

In some embodiments, the host cell is a yeast cell.

In some embodiments, the methods may further comprise recovering the protein from the host cell culture.

The present disclosure provides methods for selecting a host cell that expresses a protein of interest from a library of host cells, the method comprising: contacting the host cell library with an agent that binds to the protein of interest or the proline-rich peptide; and selecting host cells that bind to the agent, wherein the host cells comprise a polynucleotide coding for a protein of interest and a polynucleotide coding for a proline-rich peptide.

In some embodiments, the protein of interest and the proline-rich peptide are coded by the same polynucleotide. In some embodiments, the protein of interest and the proline-rich peptide are coded by different polynucleotides.

In some embodiments, the host cells comprise a polynucleotide coding for a protein of interest associated with (e.g., linked to) one or more proline-rich peptides.

In some embodiments, the protein of interest is an antibody or fragment thereof (e.g., an antigen binding fragment). In some embodiments, the antibody or fragment thereof is selected from the group consisting of a scFv, Fv, an antibody heavy chain or fragment thereof, an antibody light chain or fragment thereof and a single chain antibody (SCA).

In some embodiments, the proline-rich peptide is an amino acid sequence comprising PPP or any of the amino acid sequences depicted in SEQ ID NOS: 1-116.

In some embodiments, the proline-rich peptide is an amino acid sequence comprising one or more of the following features:
  (i) at least 3, 4, 5, 6 or more contiguous proline residues;
  (ii) a number of contiguous proline (P) or (XP) residues (where X is any amino acid) sufficient to produce a polyproline Type II helix with at least 2 turns;

(iii) at least about 60%, 65%, 70%, 75%, 80%, 85%, 90%, 95%, 99% or 100% sequence identity to any of the amino acid sequences depicted in SEQ ID NOS: 1 and 55-116;

(iv) any of the amino acid sequences depicted in SEQ ID NOS: 2-54;

(v) about 3 to about 26 proline residues in a length of about 3 to ≤50 amino acid residues (e.g., about 3 to about 26 amino acid residues);

(vi) about 20% to about 100% proline;

(vii) a C-terminal amino acid residue of the peptide that is not proline or histidine;

(viii) at the C-terminus of the peptide at least 1, 2, 3, 4, 5, 6, 7, 8, 9, 10, 11, 12, 13, 14 or more non-proline amino acid residues; or (ix) at the C-terminus of the peptide an amino acid sequence with at least about 60%, 65%, 70%, 75%, 80%, 85%, 90%, 95%, or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu).

In some embodiments, the proline-rich peptide is an amino acid sequence:
(i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues;
(ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues;
(iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues;
(iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or
(v) that is 3 to 11 amino acid residues and wherein no less than 3 and no more than 9 of the amino acid residues of the peptide are proline residues.

In some embodiments, the C-terminal non-proline amino acids residues comprise a S (Ser), L (Leu), C (Cys), V (Val), CV (Cys-Val), HHHHHH (SEQ ID NO: 118), HHHHHHV (SEQ ID NO: 119), LHHHHHH (SEQ ID NO: 122), LLLLLLLL (residues 1-8 of SEQ ID NO: 121), LHHHH-HHCV (SEQ ID NO: 120), or LLLLLLLLS (SEQ ID NO: 121).

In some embodiments, the proline-rich peptide comprises SEQ ID NO: 1.

In some embodiments, the protein of interest and the proline-rich peptide are directly associated. In some embodiments, the protein of interest and the proline-rich peptide are indirectly associated. In some embodiments, the protein of interest and the proline-rich peptide are associated through a peptide linker such as (GGGGS)$_3$ (SEQ ID NO: 123). In some embodiments, when the protein of interest and the proline-rich peptide are associated, the proline-rich peptide is associated at (e.g., linked to) either the N-terminal or C-terminal of a protein of interest.

In some embodiments, the proline-rich peptide does not comprise hydroxyproline.

In some embodiments, the proline-rich peptide and/or the protein of interest further comprise a tag. In some embodiments, the tag is a histidine tag (e.g., hexa-histidine tag) and/or a myc tag.

In some embodiments, the polynucleotide coding for the protein of interest is operably linked to one or more expression control elements. In some embodiments, the expression control element is a promoter. In some embodiments, the promoter is a yeast promoter.

The present disclosure provides methods for isolating a polynucleotide coding for a protein of interest from a host cell library that displays the protein of interest associated with a proline-rich peptide at its surface by contacting the host cell library with an agent that binds to the protein of interest or the proline-rich peptide; selecting host cells that bind to the agent; and recovering a polynucleotide coding for the protein of interest from the host cells that bind to the agent.

In some embodiments, the protein of interest is a binding molecule and the agent is a binding partner.

In some embodiments the binding molecule is an antibody or binding fragment thereof and the binding partner is an antigen.

In some embodiments, the methods further comprise identifying the sequence of the nucleic acid coding for a protein of interest linked to one or more proline-rich peptides.

In some embodiments, the host cell is a yeast cell.

In some embodiments, the protein of interest is an antibody or binding fragment thereof (e.g., an antigen binding fragment). In some embodiments, the antibody binding fragment is selected from the group consisting of scFv, Fv, an antibody heavy chain or fragment thereof, an antibody light chain or fragment thereof and a single chain antibody (SCA).

In some embodiments, the proline-rich peptide is an amino acid sequence comprising PPP or any of the amino acid sequences depicted in SEQ ID NOS: 1-116.

In some embodiments, the proline-rich peptide is an amino acid sequence comprising one or more of the following features:
(i) at least 3, 4, 5, 6 or more contiguous proline residues;
(ii) a number of contiguous proline (P) or (XP) residues (where X is any amino acid) sufficient to produce a polyproline Type II helix with at least 2 turns;
(iii) at least about 60%, 65%, 70%, 75%, 80%, 85%, 90%, 95%, 99% or 100% sequence identity to any of the amino acid sequences depicted in SEQ ID NOS: 1 and 55-116;
(iv) any of the amino acid sequences depicted in SEQ ID NOS: 2-54;
(v) about 3 to about 26 proline residues in a length of about 3 to ≤ 50 amino acid residues (e.g., about 3 to about 26 amino acid residues);
(vi) about 20% to about 100% proline;
(vii) a C-terminal amino acid residue of the peptide that is not proline or histidine;
(viii) at the C-terminus of the peptide at least 1, 2, 3, 4, 5, 6, 7, 8, 9, 10, 11, 12, 13, 14 or more non-proline amino acid residues; or
(ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu).

In some embodiments, the proline-rich peptide is an amino acid sequence:
(i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues;
(ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues;
(iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues;
(iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or
(v) that is 3 to 11 amino acid residues and wherein no less than 3 and no more than 9 of the amino acid residues of the peptide are proline residues.

In some embodiments, the C-terminal non-proline amino acids residues comprise a S (Ser), L (Leu), C (Cys), V (Val), CV (Cys-Val), HHHHHH (SEQ ID NO: 118), HHHHHHV (SEQ ID NO: 119), LHHHHHH (SEQ ID NO: 122), LLLLLLLL (residues 1-8 of SEQ ID NO: 121), LHHHH-HHCV (SEQ ID NO: 120), or LLLLLLLLS (SEQ ID NO: 121).

In some embodiments, the proline-rich peptide comprises SEQ ID NO: 1.

In some embodiments, the protein of interest and the proline-rich peptide are directly associated. In some embodiments, the protein of interest and the proline-rich peptide are indirectly associated. In some embodiments, the protein of interest and the proline-rich peptide are associated through a peptide linker such as (GGGGS)$_3$ (SEQ ID NO: 123). In some embodiments, when the protein of interest and the proline-rich peptide are associated, the proline-rich peptide is associated at (e.g., linked to) either the N-terminal or C-terminal of a protein of interest.

In some embodiments, the proline-rich peptide does not comprise hydroxyproline.

In some embodiments, the proline-rich peptide and/or protein of interest further comprise a tag. In some embodiments, the tag is a histidine tag (e.g., hexa-histidine tag) and/or a myc tag.

The present disclosure provides methods for isolating a peptide capable of displaying a protein of interest, for example, a marker protein at a surface of a host cell by contacting the host cell library with an agent that bind's to a marker protein; selecting host cells that bind to the agent; and recovering a peptide capable of displayed a marker protein at a surface of a host cell, wherein the peptide displayed on the surface of the host cell is associated with the marker protein.

In some embodiments, the agent is a binding partner for the marker protein. In some embodiments, the binding partner is an antigen and the marker protein is an antibody.

In some embodiments, the host cell is a yeast cell.

In some embodiments, the marker protein is an antibody or binding fragment thereof. In some embodiments, the antibody binding fragment is selected from the group consisting of scFv, Fv, an antibody heavy chain or fragment thereof, an antibody light chain or fragment thereof and a single chain antibody (SCA).

In some embodiments, the marker protein and the peptide capable of displaying the marker protein at a surface of a host cell are directly associated. In some embodiments, the marker protein and the peptide capable of displaying the marker protein at a surface of a host cell are indirectly associated. In some embodiments, the marker protein and the peptide capable of displaying the marker protein at a surface of a host cell are associated through a peptide linker such as (GGGGS)$_3$ (SEQ ID NO: 123).

In some embodiments, the peptide capable of displaying the marker protein at a surface of a host cell does not comprise hydroxyproline.

In some embodiments, the marker protein further comprises a tag. In some embodiments, the tag is a histidine tag (e.g., hexa-histidine tag) and/or a myc tag.

The present disclosure provides methods for isolating a polynucleotide coding for a peptide capable of displaying a marker protein at a surface of a host cell by generating a library of oligonucleotides that comprise degenerate codons; linking polynucleotides coding for a marker protein to an oligonucleotide from the generated library; constructing vectors that comprise the polynucleotide coding for the marker protein linked to the oligonucleotide; introducing the vectors into host cells; expressing the polynucleotide coding for the marker protein linked to the oligonucleotide; selecting host cells that display the marker protein at their surface; and recovering the polynucleotide coding for the peptide capable of displaying the marker protein at the surface of the host cells.

The present disclosure provides methods for isolating a peptide capable of displaying a marker protein at a surface of a host cell by generating a library of oligonucleotides that comprise degenerate codons; linking polynucleotides coding for a marker protein to an oligonucleotide from the generated library; constructing vectors that comprise the polynucleotide coding for the marker protein linked to the oligonucleotide; introducing the vectors into host cells; expressing the polynucleotide coding for the marker protein linked to the oligonucleotide; selecting host cells that display the marker protein at their surface; recovering the polynucleotide coding for the peptide capable of displaying the marker protein at the surface of the host cells; and obtaining the peptide capable of displaying the marker protein at a surface of the host cell.

In some embodiments, the oligonucleotides comprise a repeat of degenerate VBT codons that code for threonine, alanine, proline, isoleucine, valine, leucine, serine, glycine or arginine.

In some embodiments, the oligonucleotides further comprise one or more degenerate NNS codons. In some embodiments, the oligonucleotides comprise twenty-three VBT codons and three NNS codons. In some embodiments, codons 1-23 are VBT codons and codons 24-26 are NNS codons.

In some embodiments, the oligonucleotides and/or polynucleotide comprises a tag. In some embodiments, the tag is a histidine tag (e.g., hexa-histidine tag) and/or a myc tag.

The present disclosure provides proline-rich peptides coded by a randomized polynucleotide comprising a repeat of degenerate VBT codons, wherein the VBT codons code for threonine, alanine, proline, isoleucine, valine, leucine, serine, glycine or arginine. In some embodiments, the polynucleotide comprises twenty-three VBT codons.

In some embodiments, the polynucleotide further comprises one or more NNS codons, wherein the NNS codons code for any amino acid. In some embodiments, the polynucleotide comprises twenty-three VBT codons and three NNS codons In some embodiments, the polynucleotide codes for a tag such as a histidine tag (e.g., hexa-histidine tag) and/or a myc tag.

In some embodiments, the library of oligonucleotides comprise degenerated codons of NNN, NNS, or NNK.

In some embodiments, the host cell is a yeast cell.

In some embodiments, the marker protein is an antibody.

The present disclosure provides a vector for display of a proline-rich peptide associated with a protein of interest, the vector comprising a polynucleotide coding for a protein of interest, a polynucleotide coding for a proline-rich peptide, a yeast replication origin, a first polynucleotide for selection in yeast and an inducible yeast promoter.

In some embodiments, the vector may further comprise a bacteria origin of replication and a polynucleotide for selection in bacteria.

In some embodiments, the vector may further comprise a portion (e.g., fragment) of a second polynucleotide for selection in yeast.

In some embodiments, the protein of interest is an antibody or binding fragment thereof (e.g., an antigen binding fragment). In some embodiments, the antibody binding fragment is selected from the group consisting of scFv, Fv, an antibody heavy chain or fragment thereof, an antibody light chain or fragment thereof and a single chain antibody (SCA).

In some embodiments, the yeast replication origin is a low copy replication origin. In some embodiments, the yeast low copy replication origin is CEN6/ARS4.

In some embodiments, the polynucleotide for selection in yeast is Zeocin.

In some embodiments, the bacteria is *E. coli*.

In some embodiments, the bacteria replication origin is a high copy replication origin. In some embodiments, the bacteria high copy replication origin is pUC Ori.

In some embodiments, the polynucleotide for selection in bacteria is ampicillin.

In some embodiments, the inducible yeast promoter is Gal 1/10.

In some embodiments, the portion of the second polynucleotide for selection in yeast is the N-terminus of Leu-2.

In some embodiments, the protein of interest or the proline-rich peptide further comprise a tag. In some embodiments, the tag is a histidine tag (e.g., hexa-histidine tag) and/or a myc tag.

In some embodiments, the proline-rich peptide is an amino acid sequence comprising PPP or any of the amino acid sequences depicted in SEQ ID NOS: 1-116.

In some embodiments, the proline-rich peptide is an amino acid sequence comprising one or more of the following features:
  (i) at least 3, 4, 5, 6 or more contiguous proline residues;
  (ii) a number of contiguous proline (P) or (XP) residues (where X is any amino acid) sufficient to produce a polyproline Type II helix with at least 2 turns;
  (iii) at least about 60%, 65%, 70%, 75%, 80%, 85%, 90%, 95%, 99% or 100% sequence identity to any of the amino acid sequences depicted in SEQ ID NOS: 1 and 55-116;
  (iv) any of the amino acid sequences depicted in SEQ ID NOS: 2-54;
  (v) about 3 to about 26 proline residues in a length of about 3 to s 50 amino acid residues (e.g., about 3 to about 26 amino acid residues);
  (vi) about 20% to about 100% proline;
  (vii) a C-terminal amino acid residue of the peptide that is not proline or histidine;
  (viii) at the C-terminus of the peptide at least 1, 2, 3, 4, 5, 6, 7, 8, 9, 10, 11, 12, 13, 14 or more non-proline amino acid residues; or
  (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu).

In some embodiments, the proline-rich peptide is an amino acid sequence:
  (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues;
  (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues;
  (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues;
  (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or
  (v) that is 3 to 11 amino acid residues and wherein no less than 3 and no more than 9 of the amino acid residues of the peptide are proline residues.

In some embodiments, the C-terminal non-proline amino acids residues comprise a S (Ser), L (Leu), C (Cys), V (Val), CV (Cys-Val), HHHHHH (SEQ ID NO: 118), HHHHHHV (SEQ ID NO: 119), LHHHHHH (SEQ ID NO: 122), LLLLLLLL (residues 1-8 of SEQ ID NO: 121), LHHHH-HHCV (SEQ ID NO: 120), or LLLLLLLLS (SEQ ID NO: 121).

The present disclosure provides a proline-rich peptide produced by: generating a library of oligonucleotides that comprise degenerate codons; linking polynucleotides coding for a protein of interest to a generated oligonucleotide; constructing vectors that comprise the polynucleotide coding for the protein of interest linked to the oligonucleotide; introducing the vectors into host cells; expressing the polynucleotide coding for the protein of interest linked to the oligonucleotide; selecting host cells that display the protein of interest at their surface; and recovering the proline-rich peptide from host cells that bind to a detecting agent.

In some embodiments, the oligonucleotides comprise a repeat of degenerate VBT codons that code for threonine, alanine, proline, isoleucine, valine, leucine, serine, glycine or arginine.

In some embodiments, the oligonucleotides further comprise one or more degenerate NNS codons.

In some embodiments, the oligonucleotides comprise twenty-three VBT codons and three NNS codons. In some embodiments, codons 1-23 are VBT codons and codons 24-26 are NNS codons.

In some embodiments, the oligonucleotides and/or polynucleotide comprises a tag. In some embodiments, the tag is a histidine tag (e.g., hexa-histidine tag) and/or a myc tag.

The present disclosure provides methods for randomizing one or more amino acid residues in an antibody complementarity determining region (CDR) by (a) selecting one or more amino acid residues in a CDR for randomization; (b) synthesizing oligonucleotides comprising one or more nucleotides that are positioned 3' of a codon for a first CDR residue selected for randomization; (c) splitting the synthesized oligonucleotides into a first number of pools, wherein the number of pools permit a frequency of randomized amino acid residues at the first amino acid position selected for randomization to approximate a predetermined frequency of amino acid residues at the selected position; (d) joining 3 nucleotides, one at a time to the 5' end of the oligonucleotides in each pool, wherein the 3 nucleotides form a codon that is selected to approximate a predetermined frequency of an amino acid residue occurring at the position selected for randomization; and (e) combining the pools comprising oligonucleotides joined to the codon.

In some embodiments, the methods may further comprise steps for randomizing a second amino acid residue in a CDR selected for randomization by (f) splitting the oligonucleotides of step (e) into a second number of pools, wherein the number of pools permit a frequency of randomized amino acid residues at the second amino acid position selected for randomization to approximate a predetermined frequency of amino acid residues at the selected position; (g) joining 3 nucleotides, one at a time, to the 5' end of the oligonucleotides in each pool, wherein the 3 nucleotides form a codon that is selected to approximate a predetermined frequency of an amino acid residue occurring at the position selected for randomization; and (h) combining the pools comprising oligonucleotides joined to the codon.

In some embodiments, the methods may further comprise steps for randomizing additional amino acid residues in a CDR selected for randomization, for example, 3, 4, 5, 6, 7, 8, 9, 10, 11, 12, 13, 14, 15, 16, 17, 18, 19, 20 . . . n, where n is the total number of amino acids selected for randomization, by repeating the splitting, joining and combining steps.

In some embodiments, the first number of pools and the second number of pools are the same. In some embodiments, the first number of pools and the second number of pools are different.

In some embodiments, the method may further comprise generating an oligonucleotide coding for a CDR with one or more randomized amino acids.

In some embodiments, the amino acid residues in HCDR1 are randomized.

In some embodiments, the synthesized oligonucleotides are split into 13 pools.

In some embodiments, for Kabat position 33 in HCDR1 codons GCT and TAT are each joined to three of the oligonucleotide pools, codon TGG is joined to two of the oligonucleotide pools, and codons GGT, TCT, GAT, ACT and GTT are each joined to one of the oligonucleotide pools.

In some embodiments, for Kabat position 32 in HCDR1 codon TAT is joined to eight of the oligonucleotide pools and codons TCT, AAT, GGT, TTT and GCT are each joined to one of the oligonucleotide pools.

In some embodiments, for Kabat position 31 in HCDR1 codon TCT is joined to six of the oligonucleotides, codon AAT is joined to two of the oligonucleotide pools, and codons GGT, ACT, GAT, AGA and GCT are each joined to one of the oligonucleotide pools.

In some embodiments, for position 30 in HCDR1 codon TCT is joined to seven of the oligonucleotide pools, codon ACT is joined to two of the oligonucleotide pools, and codons AAT, AGA, GAT, GGT are each joined to one of the oligonucleotide pools.

In some embodiments, amino acid residues in HCDR2 are randomized.

In some embodiments, the synthesized oligonucleotides are split into 12 pools.

In some embodiments, for Kabat position 58 in HCDR2 codon TAT is joined to four of the oligonucleotide pools, codon AAT is joined to two of the oligonucleotide pools, and codons GAT, AGA, TCT, ATT, ACT and CAT are each joined to one of the oligonucleotide pools.

In some embodiments, for Kabat position 57 in HCDR2 codon ACT is joined to all twelve of the oligonucleotide pools.

In some embodiments, for Kabat position 56 in HCDR2 codon TCT is joined to four of the oligonucleotide pools, codon ACT is joined to two of the oligonucleotide pools, and codons AAT, GAT, TAT, GAA, GGT, and GCT are each joined to one of the oligonucleotide pools.

In some embodiments, for Kabat position 55 in HCDR2 codon GGT is joined to all twelve of the oligonucleotide pools.

In some embodiments, for Kabat position 54 in HCDR2 codon GGT is joined to four of the oligonucleotide pools, codon TCT is joined to three of the oligonucleotide pools, and codons GAT, AAT, AAA, TTT, ACT are each joined to one of the oligonucleotide pools.

In some embodiments, for Kabat position 53 in HCDR2 codon TCT is joined to three of the oligonucleotide pools, codon GAT is joined to two of the oligonucleotide pools, and codons TAT, GGT, CAT, AAT, ATT, ACT and TGG are each joined to one of the oligonucleotide pools.

In some embodiments, for Kabat position 52a in HCDR2 codon CCA is joined to five of the oligonucleotide pools, codon GGT is joined to four of the oligonucleotide pools and codon TCT is joined to three of the oligonucleotide pools.

In some embodiments, for Kabat position 52 in HCDR2 codon TCT is joined to three of the oligonucleotide pools, codon TAT is joined to three of the oligonucleotide pools, and codons AAT, AAA, ATT, AGA, GAT, ACT are each joined to one of the oligonucleotide pools.

In some embodiments, for Kabat position 51 in HCDR2 codon ATC is joined to all twelve of the oligonucleotide pools.

In some embodiments, for Kabat position 50 in HCDR2 codon AGA is joined to two of the oligonucleotide pools, and codons TAT, TGG, GTT, GGT, ATT, GAA, GCT, TCT, AAT, TTA are each joined to one of the oligonucleotide pools.

In some embodiments, for Kabat position 49 in HCDR2 codon GGT is joined to six of the oligonucleotide pools, codon TCT is joined to three of the oligonucleotide pools, and codon GCT is joined to three of the oligonucleotide pools.

In some embodiments, amino acid residues in LCDR1 are randomized.

In some embodiments, the synthesized oligonucleotides are split into 11 pools.

In some embodiments, for Kabat position 32 in LCDR1 codon TAT is joined to six of the oligonucleotide pools, and codons AAT, TGG, TTT, TCT and GAT are each joined to one of the oligonucleotide pools.

In some embodiments, for Kabat position 31a in LCDR1 codon TCT is joined to seven of the oligonucleotide pools, codon AAT is joined to two of the oligonucleotide pools and codon ACT is joined to two of the oligonucleotide pools.

In some embodiments, for Kabat position 31 in LCDR1 codon TCT is joined to four of the oligonucleotide pools, codon AAT is joined to two of the oligonucleotide pools, and codons ACT, AGA, ATT, GAT and AAA are each joined to one of the oligonucleotide pools.

In some embodiments, for Kabat position 30 in LCDR1 codon TCT is joined to five of the oligonucleotide pools, codon AAT is joined to two of the oligonucleotide pools, and codons MA, GGT, AGA and TAT are each joined to one of the oligonucleotide pools.

In some embodiments, for Kabat position 29 in LCDR1 codon ATT is joined to five of the oligonucleotide pools, codon TCT is joined to two of the oligonucleotide pools, codon GTT is joined to two of the oligonucleotide pools, and codons GGT and AAT are each joined to one of the oligonucleotide pools.

In some embodiments, for Kabat position 28 in LCDR1 codon TCT is joined to three of the oligonucleotide pools, codon MT is joined to two of the oligonucleotide pools, codon GTT is joined to two of the oligonucleotide pools, codon GGT is joined to two of the oligonucleotide pools, and codon GAT is joined to two of the oligonucleotide pools.

In some embodiments, amino acid residues in LCDR2 are randomized.

In some embodiments, the synthesized oligonucleotides are split into 10 pools.

In some embodiments, for Kabat position 55 in LCDR2 codon GCT is joined to four of the oligonucleotide pools, codon CM is joined to three of the oligonucleotide pools, and codon GAA is joined to three of the oligonucleotide pools.

In some embodiments, for Kabat position 53 in LCDR2 codon TCT is joined to four of the oligonucleotide pools, codon MT is joined to three of the oligonucleotide pools and codon ACT is joined to three of the oligonucleotide pools.

In some embodiments, for Kabat position 51 in LCDR2 codon GCT is joined to all ten of the oligonucleotide pools.

In some embodiments, for Kabat position 50 in LCDR2 codon GGT is joined to two of the oligonucleotide pools, codon GCT is joined to two of the oligonucleotide pools, codon GAT is joined to two of the oligonucleotide pools, and codons TGG, AAA, TTA and GAA are each joined to one of the oligonucleotide pools.

In some embodiments, amino acid residues in LCDR3 are randomized.

In some embodiments, the synthesized oligonucleotides are split into 12 pools.

In some embodiments, for Kabat position 96 in LCDR3 codon TTA is joined to three of the oligonucleotide pools, codon TAT is joined to two of the oligonucleotide pools, codon TGG is joined to two of the oligonucleotide pools, and codons TTT, ATT, AGA, CCA and TAT are each joined to one of the oligonucleotide pools.

In some embodiments, for Kabat position 94 in LCDR3 codon TCT is joined to two of the oligonucleotide pools, codon ACT is joined to two of the oligonucleotide pools, codon TGG is joined to two of the oligonucleotide pools, codon TAT is joined to two of the oligonucleotide pools, and codons TTA, TTT, GCT and CCA are each joined to one of the oligonucleotide pools.

In some embodiments, for Kabat position 93 in LCDR3 codon TCT is joined to five of the oligonucleotide pools, codon AAT is joined to two of the oligonucleotide pools, and codons CAA, ACT, CAT, GGT and GAT are each joined to one of the oligonucleotide pools.

In some embodiments, for Kabat position 92 in LCDR3 codon TAT is joined to three of the oligonucleotide pools, codon GGT is joined to two of the oligonucleotide pools, and codons AAT, TCT, GAT, TTA, ACT, CAT and ATT are each joined to one of the oligonucleotide pools.

In some embodiments, for Kabat position 91 in LCDR3 codon TAT is joined to seven of the oligonucleotide pools, codon TCT is joined to two of the oligonucleotide pools, and codons AGA, GCT and GGT are each joined to one of the oligonucleotide pools.

In some embodiments, amino acid residues in HCDR3 are randomized.

In some embodiments, the synthesized oligonucleotides are split into 29 pools.

In some embodiments, for Kabat position 100b in HCDR3 codon GGT is joined to four of the oligonucleotide pools, codon TAT is joined to four of the oligonucleotide pools, codon TCT is joined to four of the oligonucleotide pools, codon GAT is joined to two of the oligonucleotide pools, and codons AGA, TTA, GTT, GCT, CCA, ACT, AAT, TTT, ATT, GAA, CAT, CAA, AAA, ATG and TGG are each joined to one of the oligonucleotide pools.

In some embodiments, for Kabat position 100a in HCDR3 codon GGT is joined to four of the oligonucleotide pools, codon TAT is joined to four of the oligonucleotide pools, codon TCT is joined to four of the oligonucleotide pools, codon GAT is joined to two of the oligonucleotide pools, and codons AGA, TTA, GTT, GCT, CCA, ACT, AAT, TTT, ATT, GAA, CAT, CAA, AAA, ATG and TGG are each joined to one of the oligonucleotide pools.

In some embodiments, for Kabat position 100 in HCDR3 codon GGT is joined to four of the oligonucleotide pools, codon TAT is joined to four of the oligonucleotide pools, codon TCT is joined to four of the oligonucleotide pools, codon GAT is joined to two of the oligonucleotide pools, and codons AGA, TTA, GTT, GCT, CCA, ACT, AAT, TTT, ATT, GAA, CAT, CAA, AAA, ATG and TGG are each joined to one of the oligonucleotide pools.

In some embodiments, for Kabat position 99 in HCDR3 codon GGT is joined to four of the oligonucleotide pools, codon TAT is joined to four of the oligonucleotide pools, codon TCT is joined to four of the oligonucleotide pools, codon GAT is joined to two of the oligonucleotide pools, and codons AGA, TTA, GTT, GCT, CCA, ACT, AAT, TTT, ATT, GAA, CAT, CAA, AAA, ATG and TGG are each joined to one of the oligonucleotide pools.

In some embodiments, for Kabat position 98 in HCDR3 codon GGT is joined to four of the oligonucleotide pools, codon TAT is joined to four of the oligonucleotide pools, codon TCT is joined to four of the oligonucleotide pools, codon GAT is joined to two of the oligonucleotide pools, and codons AGA, TTA, GU, GCT, CCA, ACT, AAT, TTT, ATT, GAA, CAT, CAA, AAA, ATG and TGG are each joined to one of the oligonucleotide pools.

In some embodiments, for Kabat position 97 in HCDR3 codon GGT is joined to four of the oligonucleotide pools, codon TAT is joined to four of the oligonucleotide pools, codon TCT is joined to four of the oligonucleotide pools, codon GAT is joined to two of the oligonucleotide pools, and codons AGA, TTA, GTT, GCT, CCA, ACT, AAT, TTT, ATT, GAA, CAT, CAA, AAA, ATG and TGG are each joined to one of the oligonucleotide pools.

In some embodiments, for Kabat position 96 in HCDR3 codon GGT is joined to four of the oligonucleotide pools, codon TAT is joined to four of the oligonucleotide pools, codon TCT is joined to four of the oligonucleotide pools, codon GAT is joined to two of the oligonucleotide pools, and codons AGA, TTA, GU, GCT, CCA, ACT, AAT, TTT, ATT, GAA, CAT, CAA, AAA, ATG and TGG are each joined to one of the oligonucleotide pools.

In some embodiments, for Kabat position 95 in HCDR3 codon GGT is joined to four of the oligonucleotide pools, codon TAT is joined to four of the oligonucleotide pools, codon TCT is joined to four of the oligonucleotide pools, codon GAT is joined to two of the oligonucleotide pools, and codons AGA, TTA, GTT, GCT, CCA, ACT, AAT, TTT, ATT, GAA, CAT, CAA, AAA, ATG and TGG are each joined to one of the oligonucleotide pools.

In some embodiments, the synthesized oligonucleotides comprise framework nucleotides.

In some embodiments, all of the amino acid resides in a CDR are randomized.

In some embodiments, the CDRs are from an antibody heavy chain.

In some embodiments, the CDRs are from an antibody light chain.

In some embodiments, the prevalence of an amino acid residue naturally occurring at the position selected for randomization is shown in Table 5.

The present disclosure also provides methods for generating a library of antibody variable region sequences that comprise randomized amino acid residues at one or more positions in a CDR that approximate a predetermined frequency of the amino acid residue occurring in antibodies (e.g., human antibodies) at the one or more positions by converting the oligonucleotides generated by the methods for randomizing one or amino acid residues in an antibody complementarity determining region (CDR) as described herein to a double stranded DNA fragment; linking the double-stranded DNA fragment to antibody framework regions; and introducing the linked fragments into a vector thereby generating a library of antibody variable regions.

In some embodiments, the oligonucleotides are converted to double-stranded DNA fragments by PCR amplification where the forward and reverse primers anneal to the 5' and 3' end of the generated oligonucleotide.

The present disclosure provides methods for the in-vivo conversion of an antibody display vector to an antibody secretion vector, the method comprising: mixing: (i) a display vector that comprises a first polynucleotide region and a second polynucleotide region, wherein the display vector further comprises a polynucleotide coding for an antibody fragment associated with one or more proline-rich peptides and a polynucleotide that codes for a selectable marker fragment positioned between the first and the second polynucleotide regions, and wherein the display vector is digested to remove a polynucleotide fragment from the vector that comprises a coding region for the proline-rich peptide; and (ii) a replacement fragment that comprises a first polynucleotide region and a second polynucleotide region that are homologous to the first polynucleotide region and the second polynucleotide region in the digested display vector, wherein the replacement fragment further comprises a polynucleotide coding for an antibody fragment and a selectable marker fragment positioned between the first and the second polynucleotide regions; permitting the digested display vector and the replacement fragment to undergo homologous recombination to create a secretion vector, wherein the antibody fragment from the display vector and the antibody fragment from the replacement fragment are recombined to generate a full-length antibody and wherein the selectable marker fragment from the display vector and the selectable marker fragment from the replacement fragment are recombined to generate a complete selectable marker; expressing the secretion vector; and selecting yeast cells that are capable of growth on a selectable medium, wherein cells that are capable of growth on the selectable medium have undergone homologous recombination between the display vector and the replacement fragment resulting in the production of an secretion vector that comprises a full-length antibody and that expresses a selectable marker.

In some embodiments, the replacement vector comprises the full length constant region of an IgG heavy chain.

In some embodiments, the replacement vector comprises a 2p Ori.

In some embodiments, the selectable marker is isopropylmalate dehydrogenase (Leu2).

The present disclosure also provides methods for the in-vivo conversion of a display vector to a secretion vector by mixing: (i) a display vector that comprises a first polynucleotide region and a second polynucleotide region, wherein the display vector further comprises a polynucleotide coding for an antibody fragment associated with one or more cell wall proteins and a polynucleotide that codes for a selectable marker fragment positioned between the first and the second polynucleotide regions, and wherein the display vector is digested to remove a polynucleotide fragment from the vector that comprises a coding region for the yeast cell wall protein; and (ii) a replacement fragment that comprises a first polynucleotide region and a second polynucleotide region that are homologous to the first polynucleotide region and the second polynucleotide region in the digested display vector, wherein the replacement fragment further comprises a polynucleotide coding for an antibody fragment and a selectable marker fragment positioned between the first and the second polynucleotide regions; permitting the digested display vector and the replacement fragment to undergo homologous recombination to create a secretion vector, wherein the antibody fragment from the display vector and the antibody fragment from the replacement fragment are recombined to generate a full-length antibody and wherein the selectable marker fragment from the display vector and the selectable marker fragment from the replacement fragment are recombined to generate a complete selectable marker; expressing the secretion vector; and selecting yeast cells that are capable of growth on a selectable medium, wherein cells that are capable of growth on the selectable medium have undergone homologous recombination between the display vector and the replacement fragment resulting in the production of an secretion vector that comprises a full-length antibody and that expresses a selectable marker.

In some embodiments, the replacement vector comprises the full length constant region of an IgG heavy chain.

In some embodiments, the selectable marker is isopropylmalate isomerase.

In some embodiments, the display vector comprises low copy replication origin positioned between the first and the second polynucleotide regions. In some embodiments, the replication origin is ARSH4.

In some embodiments, the replacement fragment comprises a high copy replication origin positioned between the first and the second polynucleotide regions. In some embodiments, the replication origin is 2μ.

In some embodiments, the cell wall protein is an endogenous yeast cell wall protein such as Aga1, Aga2p or FLO1.

The present disclosure also provides a novel antibody or fragment thereof specific for prostate specific antigen (PSA) comprising a heavy chain variable region comprising SEQ ID NO: 130.

The present disclosure provides a novel antibody or fragment thereof specific for prostate specific antigen (PSA) comprising a light chain variable region comprising SEQ ID NO: 131.

The present disclosure provides a novel antibody or fragment thereof specific for prostate specific antigen (PSA) comprising a heavy chain variable region comprising SEQ ID NO: 130 and a light chain variable region comprising SEQ ID NO: 131.

The present disclosure provides a novel antibody or fragment thereof specific for prostate specific antigen (PSA) comprising a heavy chain variable region that is 70%, 75%, 80%, 85%, 90%, 95% or 99% identical to SEQ ID NO: 130.

The present disclosure provides a novel antibody or fragment thereof specific for prostate specific antigen (PSA) comprising a light chain variable region that is 70%, 75%, 80%, 85%, 90%, 95% or 99% identical to SEQ ID NO: 131.

In some embodiments, the antibody fragment is a Fab.

In some embodiments, the heavy chain variable region is coupled to a CH1 region of IgG1.

In some embodiments, the light chain variable region sequence is coupled to a constant region of kappa 1.

The present disclosure also provides methods for obtaining a humanized antibody by generating a library of humanized antibody molecules comprising: (i.) CDRH3 from a non-human antibody of interest; and (ii.) CDRH1, CDRH2, CDRL1, CDRL2 and CDRL3 from a synthetic human antibody library, wherein one or more amino acid residues in CDRH1, CDRH2, CDRL1, CDRL2 and/or CDRL3 are randomized; exposing the antibody library to a labeled antigen comprising an epitope recognized by the non-human antibody of interest; washing unbound labeled antigen from the antibody library; exposing the antibody library to the non-human antibody labeled with a different label than the antigen; and selecting members from the antibody library that bind to the labeled antigen and that inhibit binding of the non-human antibody to the labeled antigen, wherein the library of antibody molecules are displayed at a surface of a host cell associated with a proline-rich peptide.

In some embodiments, the host cell is a yeast cell.

In some embodiments, the one or more amino acid residues in CDRH1, CDRH2, CDRL1, CDRL2 and/or CDRL3 are randomized by (a) selecting one or more amino acid residues in a CDR for randomization; (b) synthesizing oligonucleotides comprising one or more nucleotides that are positioned 3' of a codon for a first CDR residue selected for randomization; (c) splitting the synthesized oligonucleotides into a first number of pools, wherein the number of pools permit a frequency of randomized amino acid residues at the first amino acid position selected for randomization to approximate a predetermined frequency of amino acid residues at the selected position; (d) joining 3 nucleotides, one at a time, to the 5' end of the oligonucleotides in each pool, wherein the 3 nucleotides form a codon that is selected to approximate a predetermined frequency of an amino acid residue occurring at the position selected for randomization; and (e) combining the pools comprising oligonucleotides joined to the codon.

In some embodiments, the methods may further comprise randomizing a second amino acid residue in a CDR selected for randomization by (f) splitting the oligonucleotides of step (e) into a second number of pools, wherein the number of pools permit a frequency of randomized amino acid residues at the second amino acid position selected for randomization to approximate a predetermined frequency of amino acid residues at the selected position; (g) joining 3 nucleotides, one at a time, to the 5' end of the oligonucleotides in each pool, wherein the 3 nucleotides form a codon that is selected to approximate a predetermined frequency of an amino acid residue occurring at the position selected for randomization; and (h) combining the pools comprising oligonucleotides joined to the codon.

In some embodiments, the methods may further comprise steps for randomizing additional amino acid residues in a CDR selected for randomization, for example, 3, 4, 5, 6, 7, 8, 9, 10, 11, 12, 13, 14, 15, 16, 17, 18, 19, 20 . . . n, where n is the total number of amino acids selected for randomization, by repeating the splitting, joining and combining steps.

In some embodiments, the first number of pools and the second number of pools are the same.

In some embodiments, the first number of pools and the second number of pools are different.

In some embodiments, each of the residues in CDRH1, CDRH2, CDRL1, CDRL2 and/or CDRL3 are randomized.

Additional features and advantages are described herein, and will be apparent from, the following Detailed Description and the Figures.

BRIEF DESCRIPTION OF THE DRAWINGS

The foregoing summary, as well as the following detailed description of the disclosure, may be read in conjunction with the appended figures. For the purpose of illustrating the disclosure, shown in the figures are exemplary embodiments. It should be understood, however, that the disclosure is not limited to the embodiments or the precise arrangements, examples and instrumentalities shown in the figures.

FIGS. 3A-3B show a schematic representation of an exemplary human Fab library construction. The upper panel shows the construction of an exemplary light chain (LC) library. The lower panel shows the construction of an exemplary heavy chain (HC) library.

DETAILED DESCRIPTION

Figure 1:
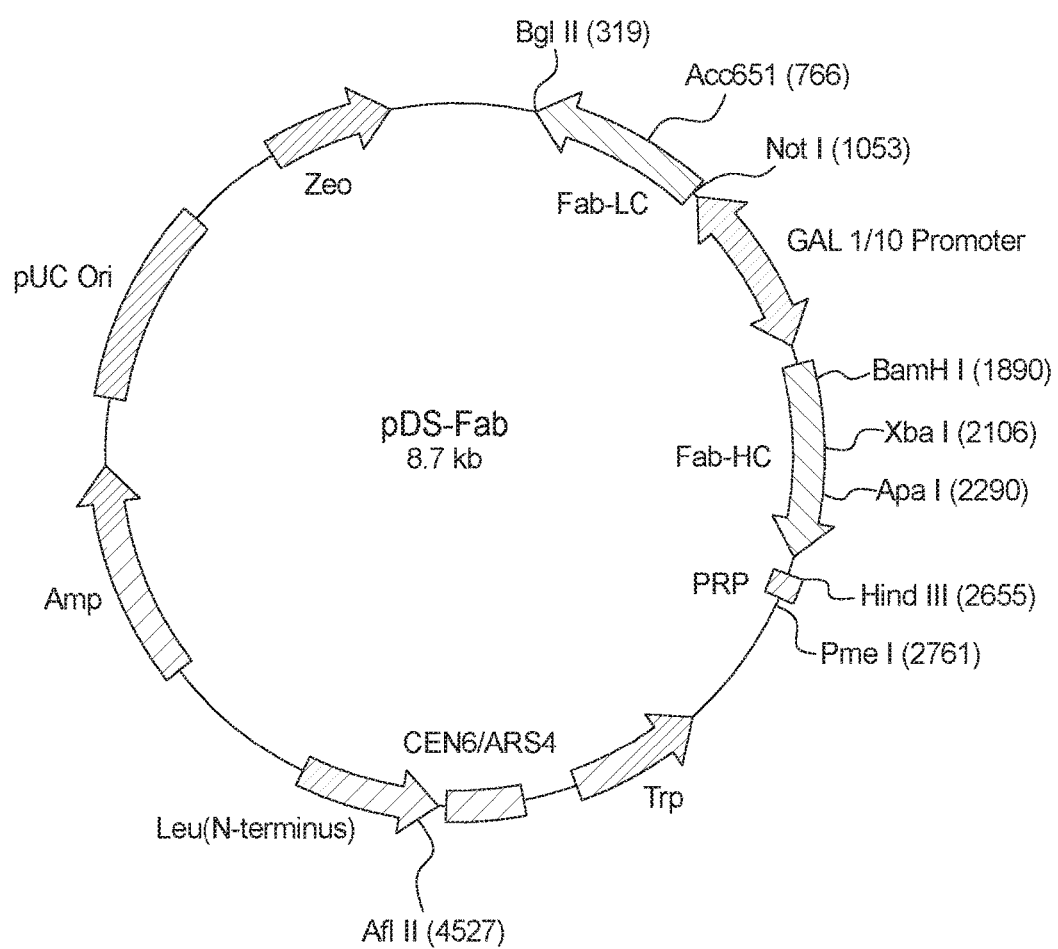
FIG. 1 depicts an exemplary display vector for expression of a proline-rich peptide linked to a protein of interest.

Current techniques for the display of a protein of interest on the surface of a host generally rely upon linking the protein of interest to a protein that is naturally expressed by the host and anchored in its surface. However, linkage of the protein of interest to a naturally occurring protein which is anchored in the host surface may affect proliferation of the host and/or the expression level of the library. Unexpectedly, the inventor has discovered novel proline-rich peptides, as disclosed herein, that are able to display a protein of interest (e.g., a library of proteins of interest) at a cell surface including, for example, a yeast cell surface. Such novel proline-rich peptides do not rely upon a protein naturally expressed by a host and anchored in the cell surface for display. The proline-rich peptides of the present disclosure may be used to display a library of proteins of interest at a host cell surface including, for example, a library of binding molecules such as antibodies or binding fragments thereof (e.g., full length antibody (such as IgG), Fab, scFv, Fv, heavy chain or fragment thereof, light chain or fragment thereof, or single chain antibody). Novel methods and materials for the display and expression of proteins of interest are provided by the present disclosure. Methods and materials are also provided by the present disclosure for isolating peptides capable of displaying a protein of interest (e.g., a marker protein), for generating libraries to display and/or express proteins of interest (e.g., antibodies such as humanized antibodies), for generating secretion vectors for such proteins of interest, and for generating proteins of interest (e.g., antibodies).

The present disclosure provides libraries of host cells (e.g., yeast) displaying on their surface proteins of interest (e.g., full length antibody, Fab, scFv, Fv, an antibody heavy chain or fragment thereof, an antibody light chain or fragment thereof and a single chain antibody (SCA)) associated with a proline-rich peptide. The proline-rich peptide may be an amino acid sequence comprising PPP or any of the amino acid sequences depicted in SEQ ID NOS: 1-116. Alternatively, the proline-rich peptide may be an amino acid sequence comprising one or more of the following features: (i) at least 3, 4, 5, 6 or more contiguous proline residues; (ii) a number of contiguous proline (P) or (XP) residues (where X is any amino acid) sufficient to produce a polyproline Type II helix with at least 2 turns; (iii) at least about 60%, 65%, 70%, 75%, 80%, 85%, 90%, 95%, 99% or 100% sequence identity to any of the amino acid sequences depicted in SEQ ID NOS: 1 and 55-116; (iv) any of the amino acid sequences depicted in SEQ ID NOS: 2-54; (v) about 3 to about 26 proline residues in a length of about 3 to ≤50 amino acid residues (e.g., about 3 to about 26 amino acid residues); (vi) about 20% to about 100% proline; (vii) a C-terminal amino acid residue of the peptide that is not proline or histidine; (viii) at the C-terminus of the peptide at least 1, 2, 3, 4, 5, 6, 7, 8, 9, 10, 11, 12, 13, 14 or more non-proline amino acid residues; or (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu). Alternatively, the proline-rich peptide may be an amino acid sequence: (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues; (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues; (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues; (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or (v) that is 3 to 11 amino acid residues and wherein no less than 3 and no more than 9 of the amino acid residues of the peptide are proline residues.

The present disclosure also provides libraries of host cells (e.g., yeast) comprising polynucleotides coding for a protein of interest (e.g., scFv, Fv, an antibody heavy chain or fragment thereof, an antibody light chain or fragment thereof and a single chain antibody (SCA)) and a proline-rich peptide. The proline-rich peptide may be an amino acid sequence comprising PPP or any of the amino acid sequences depicted in SEQ ID NOS: 1-116. Alternatively, the proline-rich peptide may be an amino acid sequence comprising one or more of the following features: (i) at least 3, 4, 5, 6 or more contiguous proline residues; (ii) a number of contiguous proline (P) or (XP) residues (where X is any amino acid) sufficient to produce a polyproline Type II helix with at least 2 turns; (iii) at least about 60%, 65%, 70%, 75%, 80%, 85%, 90%, 95%, 99% or 100% sequence identity to any of the amino acid sequences depicted in SEQ ID NOS: 1 and 55-116; (iv) any of the amino acid sequences depicted in SEQ ID NOS: 2-54; (v) about 3 to about 26 proline residues in a length of about 3 to ≤50 amino acid residues (e.g., about 3 to about 26 amino acid residues); (vi) about 20% to about 100% proline; (vii) a C-terminal amino acid residue of the peptide that is not proline or histidine; (viii) at the C-terminus of the peptide at least 1, 2, 3, 4, 5, 6, 7, 8, 9, 10, 11, 12, 13, 14 or more non-proline amino acid residues; or (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu). Alternatively, the proline-rich peptide may be an amino acid sequence: (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues; (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues; (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues; (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or (v) that is 3 to 11 amino acid residues and wherein no less than 3 and no more than 9 of the amino acid residues of the peptide are proline residues.

The present disclosure also provides nucleic acid libraries comprising a plurality of polynucleotides coding for proteins of interest (e.g., scFv, Fv, an antibody heavy chain or fragment thereof, an antibody light chain or fragment thereof and a single chain antibody (SCA)) and a proline-rich peptide. The proline-rich peptide may be an amino acid sequence comprising PPP or any of the amino acid sequences depicted in SEQ ID NOS: 1-116. Alternatively, the proline-rich peptide may be an amino acid sequence comprising one or more of the following features: (i) at least 3, 4, 5, 6 or more contiguous proline residues; (ii) a number of contiguous proline (P) or (XP) residues (where X is any amino acid) sufficient to produce a polyproline Type II helix with at least 2 turns; (iii) at least about 60%, 65%, 70%, 75%, 80%, 85%, 90%, 95%, 99% or 100% sequence identity to any of the amino acid sequences depicted in SEQ ID NOS: 1 and 55-116; (iv) any of the amino acid sequences depicted in SEQ ID NOS: 2-54; (v) about 3 to about 26 proline residues in a length of about 3 to ≤50 amino acid residues (e.g., about 3 to about 26 amino acid residues); (vi) about 20% to about 100% proline; (vii) a C-terminal amino acid residue of the peptide that is not proline or histidine; (viii) at the C-terminus of the peptide at least 1, 2, 3, 4, 5, 6, 7, 8, 9, 10, 11, 12, 13, 14 or more non-proline amino acid residues; or (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu). Alternatively, the proline-rich peptide may be an amino acid sequence: (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues; (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues; (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues; (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or (v) that is 3 to 11 amino acid residues and wherein no less than 3 and no more than 9 of the amino acid residues of the peptide are proline residues.

The present disclosure also provides recombinant proteins that comprises a protein of interest (e.g., scFv, Fv, an antibody heavy chain or fragment thereof, an antibody light chain or fragment thereof and a single chain antibody (SCA)) associated with a proline-rich peptide. The proline-rich peptide may be an amino acid sequence comprising PPP or any of the amino acid sequences depicted in SEQ ID NOS: 1-116. Alternatively, the proline-rich peptide may be an amino acid sequence comprising one or more of the following features: (i) at least 3, 4, 5, 6 or more contiguous proline residues; (ii) a number of contiguous proline (P) or (XP) residues (where X is any amino acid) sufficient to produce a polyproline Type II helix with at least 2 turns; (iii) at least about 60%, 65%, 70%, 75%, 80%, 85%, 90%, 95%, 99% or 100% sequence identity to any of the amino acid sequences depicted in SEQ ID NOS: 1 and 55-116; (iv) any of the amino acid sequences depicted in SEQ ID NOS: 2-54; (v) about 3 to about 26 proline residues in a length of about 3 to ≤50 amino acid residues (e.g., about 3 to about 26 amino acid residues); (vi) about 20% to about 100% proline; (vii) a C-terminal amino acid residue of the peptide that is not proline or histidine; (viii) at the C-terminus of the peptide at least 1, 2, 3, 4, 5, 6, 7, 8, 9, 10, 11, 12, 13, 14 or more non-proline amino acid residues; or (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu). Alternatively, the proline-rich peptide may be an amino acid sequence: (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues; (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues; (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues; (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or (v) that is 3 to 11 amino acid residues and wherein no less than 3 and no more than 9 of the amino acid residues of the peptide are proline residues.

The present disclosure also provides for recombinant polynucleotides comprising a polynucleotide coding for a protein of interest (e.g., scFv, Fv, an antibody heavy chain or fragment thereof, an antibody light chain or fragment thereof and a single chain antibody (SCA)) and a proline-rich peptide. The proline-rich peptide may be an amino acid sequence comprising PPP or any of the amino acid sequences depicted in SEQ ID NOS: 1-116. Alternatively, the proline-rich peptide may be an amino acid sequence comprising one or more of the following features: (i) at least 3, 4, 5, 6 or more contiguous proline residues; (ii) a number of contiguous proline (P) or (XP) residues (where X is any amino acid) sufficient to produce a polyproline Type II helix with at least 2 turns; (iii) at least about 60%, 65%, 70%, 75%, 80%, 85%, 90%, 95%, 99% or 100% sequence identity to any of the amino acid sequences depicted in SEQ ID NOS: 1 and 55-116; (iv) any of the amino acid sequences depicted in SEQ ID NOS: 2-54; (v) about 3 to about 26 proline residues in a length of about 3 to ≤50 amino acid residues (e.g., about 3 to about 26 amino acid residues); (vi) about 20% to about 100% proline; (vii) a C-terminal amino acid residue of the peptide that is not proline or histidine;

(viii) at the C-terminus of the peptide at least 1, 2, 3, 4, 5, 6, 7, 8, 9, 10, 11, 12, 13, 14 or more non-proline amino acid residues; or (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu). Alternatively, the proline-rich peptide may be an amino acid sequence: (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues; (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues; (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues; (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or (v) that is 3 to 11 amino acid residues and wherein no less than 3 and no more than 9 of the amino acid residues of the peptide are proline residues.

The present disclosure also provides vectors comprising a polynucleotide that codes for a protein of interest (e.g., scFv, Fv, an antibody heavy chain or fragment thereof, an antibody light chain or fragment thereof and a single chain antibody (SCA)) and a polynucleotide that codes for a proline-rich peptide. The proline-rich peptide may be an amino acid sequence comprising PPP or any of the amino acid sequences depicted in SEQ ID NOS: 1-116. Alternatively, the proline-rich peptide may be an amino acid sequence comprising one or more of the following features: (i) at least 3, 4, 5, 6 or more contiguous proline residues; (ii) a number of contiguous proline (P) or (XP) residues (where X is any amino acid) sufficient to produce a polyproline Type II helix with at least 2 turns; (iii) at least about 60%, 65%, 70%, 75%, 80%, 85%, 90%, 95%, 99% or 100% sequence identity to any of the amino acid sequences depicted in SEQ ID NOS: 1 and 55-116; (iv) any of the amino acid sequences depicted in SEQ ID NOS: 2-54; (v) about 3 to about 26 proline residues in a length of about 3 to 50 amino acid residues (e.g., about 3 to about 26 amino acid residues); (vi) about 20% to about 100% proline; (vii) a C-terminal amino acid residue of the peptide that is not proline or histidine; (viii) at the C-terminus of the peptide at least 1, 2, 3, 4, 5, 6, 7, 8, 9, 10, 11, 12, 13, 14 or more non-proline amino acid residues; or (ix) at the C-terminus of the peptide an amino acid sequence with at least about 60%, 65%, 70%, 75%, 80%, 85%, 90%, 95%, 99% A or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu). Alternatively, the proline-rich peptide may be an amino acid sequence: (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues; (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues; (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues; (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or (v) that is 3 to 11 amino acid residues and wherein no less than 3 and no more than 9 of the amino acid residues of the peptide are proline residues.

The present disclosure also provides host cells comprising a polynucleotide coding for a protein of interest (e.g., scFv, Fv, an antibody heavy chain or fragment thereof, an antibody light chain or fragment thereof and a single chain antibody (SCA)) and a polynucleotide coding for a proline-rich peptide. The proline-rich peptide may be an amino acid sequence comprising PPP or any of the amino acid sequences depicted in SEQ ID NOS: 1-116. Alternatively, the proline-rich peptide may be an amino acid sequence comprising one or more of the following features: (i) at least 3, 4, 5, 6 or more contiguous proline residues; (ii) a number of contiguous proline (P) or (XP) residues (where X is any amino acid) sufficient to produce a polyproline Type II helix with at least 2 turns; (iii) at least about 60%, 65%, 70%, 75%, 80%, 85%, 90%, 95%, 99% or 100% sequence identity to any of the amino acid sequences depicted in SEQ ID NOS: 1 and 55-116; (iv) any of the amino acid sequences depicted in SEQ ID NOS: 2-54; (v) about 3 to about 26 proline residues in a length of about 3 to ≤50 amino acid residues (e.g., about 3 to about 26 amino acid residues); (vi) about 20% to about 100% proline; (vii) a C-terminal amino acid residue of the peptide that is not proline or histidine; (viii) at the C-terminus of the peptide at least 1, 2, 3, 4, 5, 6, 7, 8, 9, 10, 11, 12, 13, 14 or more non-proline amino acid residues; or (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu). Alternatively, the proline-rich peptide may be an amino acid sequence: (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues; (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues; (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues; (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or (v) that is 3 to 11 amino acid residues and wherein no less than 3 and no more than 9 of the amino acid residues of the peptide are proline residues.

The present disclosure also provides methods of producing a protein of interest (e.g., a full length antibody, Fab, scFv, Fv, an antibody heavy chain or fragment thereof, an antibody light chain or fragment thereof and a single chain antibody (SCA)) associated with a proline-rich peptide comprising culturing a host cell comprising a polynucleotide coding for a protein of interest and a polynucleotide coding for a proline-rich peptide under conditions wherein the polynucleotides are expressed and the protein of interest and the proline-rich peptide is produced. The proline-rich peptide may be an amino acid sequence comprising PPP or any of the amino acid sequences depicted in SEQ ID NOS: 1-116. Alternatively, the proline-rich peptide may be an amino acid sequence comprising one or more of the following features: (i) at least 3, 4, 5, 6 or more contiguous proline residues; (ii) a number of contiguous proline (P) or (XP) residues (where X is any amino acid) sufficient to produce a polyproline Type II helix with at least 2 turns; (iii) at least about 60%, 65%, 70%, 75%, 80%, 85%, 90%, 95%, 99% or 100% sequence identity to any of the amino acid sequences depicted in SEQ ID NOS: 1 and 55-116; (iv) any of the amino acid sequences depicted in SEQ ID NOS: 2-54; (v) about 3 to about 26 proline residues in a length of about 3 to ≤50 amino acid residues (e.g., about 3 to about 26 amino acid residues); (vi) about 20% to about 100% proline; (vii) a C-terminal amino acid residue of the peptide that is not proline or histidine; (viii) at the C-terminus of the peptide at least 1, 2, 3, 4, 5, 6, 7, 8, 9, 10, 11, 12, 13, 14 or more non-proline amino acid residues; or (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu). Alternatively, the proline-rich peptide may be an amino acid sequence: (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues; (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues; (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues; (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or (v) that is 3 to 11 amino acid residues and wherein no less than 3 and no more than 9 of the amino acid residues of the peptide are proline residues.

The present disclosure also provides methods for selecting a host cell including, for example a host cell that displays a protein of interest (e.g., a binding molecule such as an antibody or binding fragment thereof) associated with a proline-rich peptide at its surface, from a library of host cells by contacting the host cell library with an agent that binds to the protein of interest associated with the proline-rich peptide; and selecting host cells that bind to the agent, wherein the host cells comprise a polynucleotide coding for a protein of interest and a polynucleotide coding for a proline-rich peptide. The proline-rich peptide may be an amino acid sequence comprising PPP or any of the amino acid sequences depicted in SEQ ID NOS: 1-116. Alternatively, the proline-rich peptide may be an amino acid sequence comprising one or more of the following features: (i) at least 3, 4, 5, 6 or more contiguous proline residues; (ii) a number of contiguous proline (P) or (XP) residues (where X is any amino acid) sufficient to produce a polyproline Type II helix with at least 2 turns; (iii) at least about 60%, 65%, 70%, 75%, 80%, 85%, 90%, 95%, 99% or 100% sequence identity to any of the amino acid sequences depicted in SEQ ID NOS: 1 and 55-116; (iv) any of the amino acid sequences depicted in SEQ ID NOS: 2-54; (v) about 3 to about 26 proline residues in a length of about 3 to ≤50 amino acid residues (e.g., about 3 to about 26 amino acid residues); (vi) about 20% to about 100% proline; (vii) a C-terminal amino acid residue of the peptide that is not proline or histidine; (viii) at the C-terminus of the peptide at least 1, 2, 3, 4, 5, 6, 7, 8, 9, 10, 11, 12, 13, 14 or more non-proline amino acid residues; or (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu). Alternatively, the proline-rich peptide may be an amino acid sequence: (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues; (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues; (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues; (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or (v) that is 3 to 11 amino acid residues and wherein no less than 3 and no more than 9 of the amino acid residues of the peptide are proline residues.

The present disclosure provides methods for isolating a polynucleotide coding for a protein of interest (e.g., an antibody protein of interest, including a scFv, Fv, an antibody heavy chain or fragment thereof, an antibody light chain or fragment thereof and a single chain antibody (SCA)) from a host cell library that displays the protein of interest associated with a proline-rich peptide at its surface by contacting the host cell library with an agent that binds to the protein of interest associated with the proline-rich peptide (e.g., a detecting agent, including a binding partner such as an antigen); selecting host cells that bind to the agent; and recovering a polynucleotide coding for the protein of interest from the host cells that bind to the agent.

The present disclosure provides methods for isolating a polynucleotide coding for a peptide capable of displaying a marker protein at a surface of a host cell by generating a library of oligonucleotides that comprise degenerate codons; linking polynucleotides coding for a marker protein to the generated oligonucleotides; constructing vectors that comprise the polynucleotide coding for the marker protein linked to the oligonucleotides; introducing the vectors into host cells; expressing the polynucleotide coding for the marker protein linked to the oligonucleotides; selecting host cells that display the marker protein at their surface; and recovering the polynucleotide coding for the peptide capable of displaying the marker protein at the surface of the host cells. The polynucleotides coding for the randomized peptides may comprise a repeat of degenerate codons including, for example, VBT codons that code for threonine, alanine, proline, isoleucine, valine, leucine, serine, glycine or arginine.

The present disclosure provides methods for isolating a peptide capable of displaying a marker protein at the surface of a host cell by generating a library of oligonucleotides that comprise degenerate codons; linking polynucleotides coding for a marker protein to the generated oligonucleotides; constructing vectors that comprise the polynucleotide coding for the marker protein linked to the oligonucleotides; introducing the vectors into host cells; expressing the polynucleotide coding for the marker protein linked to the oligonucleotides; selecting host cells that display the marker protein at their surface; and recovering the polynucleotide coding for the peptide capable of displaying the marker protein at the surface of the host cells; and obtaining the peptide capable of displaying the marker protein at the surface of the host cells. The polynucleotides coding for the randomized peptides may comprise a repeat of degenerate codons including, for example, VBT codons that code for threonine, alanine, proline, isoleucine, valine, leucine, serine, glycine or arginine.

The present disclosure provides a library of peptides coded by a randomized polynucleotide comprising a repeat of degenerate VBT codons, wherein the VBT codons code for threonine, alanine, proline, isoleucine, valine, leucine, serine, glycine or arginine.

The present disclosure provides a vector for display of a proline-rich peptide comprising a yeast low copy replication origin (e.g., CEN6/ARS4); a first gene for selection in yeast (e.g., Zeocin); a portion of a second gene for selection in yeast (e.g., N-terminal portion of Leu-2); an E. coli high copy replication origin (e.g., pUC Ori); a gene for selection in bacteria (e.g., ampicillin); a proline-rich peptide linked to a protein of interest; and an inducible yeast promoter (e.g., Gal 1/10). In some embodiments, the proline-rich peptide is an amino acid sequence comprising PPP or any of the amino acid sequences depicted in SEQ ID NOS: 1-116. In some embodiments, the proline-rich peptide may be an amino acid sequence comprising one or more of the following features: (i) at least 3, 4, 5, 6 or more contiguous proline residues; (ii) a number of contiguous proline (P) or (XP) residues (where X is any amino acid) sufficient to produce a polyproline Type II helix with at least 2 turns; (iii) at least about 60%, 65%, 70%, 75%, 80%, 85%, 90%, 95%, 99% or 100% sequence identity to any of the amino acid sequences depicted in SEQ ID NOS: 1 and 55-116; (iv) any of the amino acid sequences depicted in SEQ ID NOS: 2-54; (v) about 3 to about 26 proline residues in a length of about 3 to 50 amino acid residues (e.g., about 3 to about 26 amino acid residues); (vi) about 20% to about 100% proline; (vii) a C-terminal amino acid residue of the peptide that is not proline or histidine; (viii) at the C-terminus of the peptide at least 1, 2, 3, 4, 5, 6, 7, 8, 9, 10, 11, 12, 13, 14 or more non-proline amino acid residues; or (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu). Alternatively, the proline-rich peptide may be an amino acid sequence: (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues; (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues; (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues; (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or (v) that is 3 to 11 amino acid residues and wherein no less than 3 and no more than 9 of the amino acid residues of the peptide are proline residues.

The present disclosure provides a proline-rich peptide produced by: generating a library of oligonucleotides that comprise degenerate codons; linking polynucleotides coding for a protein of interest to a generated oligonucleotide; constructing vectors that comprise the polynucleotide coding for the protein of interest linked to the oligonucleotide; introducing the vectors into host cells; expressing the polynucleotide coding for the protein of interest linked to the oligonucleotide; selecting host cells that display the protein of interest at their surface; and recovering the proline-rich peptide from host cells that bind to a detecting agent.

The present disclosure provides methods for randomizing one or more amino acid residues in one or more antibody complementarity determining regions (CDRs) (e.g., HCDR1, HCDR2, HCDR3, LCDR1, LCDR2 or LCDR3) by (a) selecting one or more amino acid residues in a CDR for randomization; (b) synthesizing oligonucleotides comprising one or more nucleotides that are positioned 3' of a codon for a first CDR residue selected for randomization; (c) splitting the synthesized oligonucleotides into a first number of pools (e.g., columns), wherein the number of pools (e.g., columns) permit a frequency of randomized amino acid residues at the first amino acid position selected for randomization to approximate a predetermined (e.g., preselected) frequency of amino acid residues at the first selected position; (d) joining 3 nucleotides, one at a time, to the 5' end of the oligonucleotides in each pool (e.g., column), wherein the 3 nucleotides form a codon that is selected to approximate a predetermined (e.g., preselected) frequency of an amino acid residue occurring at the position selected for randomization; and (e) combining the pools (e.g., columns) comprising oligonucleotides joined to the codon. The methods may further comprise steps for randomizing a second amino acid residue in a CDR selected for randomization by (f) splitting the oligonucleotides of step (e) into a second number of pools (e.g., columns), wherein the number of pools (e.g., columns) permit a frequency of randomized amino acid residues at the second amino acid position selected for randomization to approximate a predetermined (e.g., preselected) frequency of amino acid residues at the selected position; (g) joining 3 nucleotides, one at a time, to the 5' end of the oligonucleotides in each pool (e.g., column), wherein the 3 nucleotides form a codon that is selected to approximate a predetermined (e.g., preselected) frequency of an amino acid residue occurring at the second amino acid position selected for randomization; and (h) combining the pools (e.g., columns) comprising oligonucleotides joined to the codon. The methods may further comprise steps for randomizing additional amino acids residues in a CDR selected for randomization, for example, 3, 4, 5, 6, 7, 8, 9, 10, 11, 12, 13, 14, 15, 16, 17, 18, 19, 20 . . . n, where n is the total number of amino acids selected for randomization (see, e.g., step (a)) by repeating the splitting, joining and combining steps (e.g., steps (c-e) for the first CDR residue selected for randomization and steps (f-h) for the second CDR residue selected for randomization). Optionally, one or more nucleotides may be synthesized that are positioned 3' of a codon for a second CDR residue selected for randomization. The methods may further comprise joining one or more nucleotides positioned 5' of the codons coding for the CDR residues selected for randomization to generate an oligonucleotide coding for a CDR with one or more randomized amino acids. For example, the predetermined frequency (e.g., the prevalence or percentage) of each codon at the one or more amino acid positions selected for randomization may be based on the frequency (e.g., the prevalence or percentage) of each amino acid in the 3,600 natural human antibodies included in the Kabat database (see, e.g., Johnson, G. and T. T. Wu (2000) *Nucleic Acids Res* 28(1): 214-8). Alternatively, the frequency (e.g., the prevalence or percentage) of each codon at the one or more amino acid positions selected for randomization may be based on naturally occurring frequencies of the amino acid residues within CDRs of human antibodies including, for example, as described in U.S. Patent Application Publication No. 2008/0003617 (see, e.g., Table 2), Knappik et al., *Mol Biol* 296:57-86 (see, e.g., Table 1), Lee et al., *J. Mol. Biol.* 340:1073-1093 (2004) (see, e.g., Tables 1 and 2) or U.S. Patent Application Publication No. 2005/119455 (see, e.g., FIGS. 1-3). Preferably, the predetermined frequency (e.g., the prevalence or percentage) of each codon at the one or more amino acid positions selected for randomization may be based on naturally occurring frequencies of the amino acid residues within CDRs of human antibodies as set forth in Table 4 herein. Additionally, the number of pools (e.g., columns) may be selected to permit the oligonucleotide pools to comprise the minimal number of columns needed to obtain an approximate representation of amino acids residues at a predetermined frequency at the selected position.

The present disclosure also provides methods for generating a library of antibody variable region sequences that comprises randomized amino acid residues at one or more positions in a CDR that approximate a predetermined frequency (e.g., the prevalence or percentage) of an amino acid residue naturally occurring in antibodies (e.g., human antibodies) at the one or more positions by converting the oligonucleotides generated by the methods for randomizing one or amino acid residues in an antibody complementarity determining region (CDR) as described herein to a double stranded DNA fragment (e.g., the oligonucleotides may be converted to double-stranded DNA fragments by PCR amplification where the forward and reverse primers anneal to the 5' and 3' end of the generated oligonucleotide); linking the double-stranded DNA fragment to antibody framework regions; and introducing the linked fragments into a vector thereby generating a library of antibody variable regions. Accordingly, libraries prepared in accordance with such methods are provided by the present disclosure.

Figure 6:
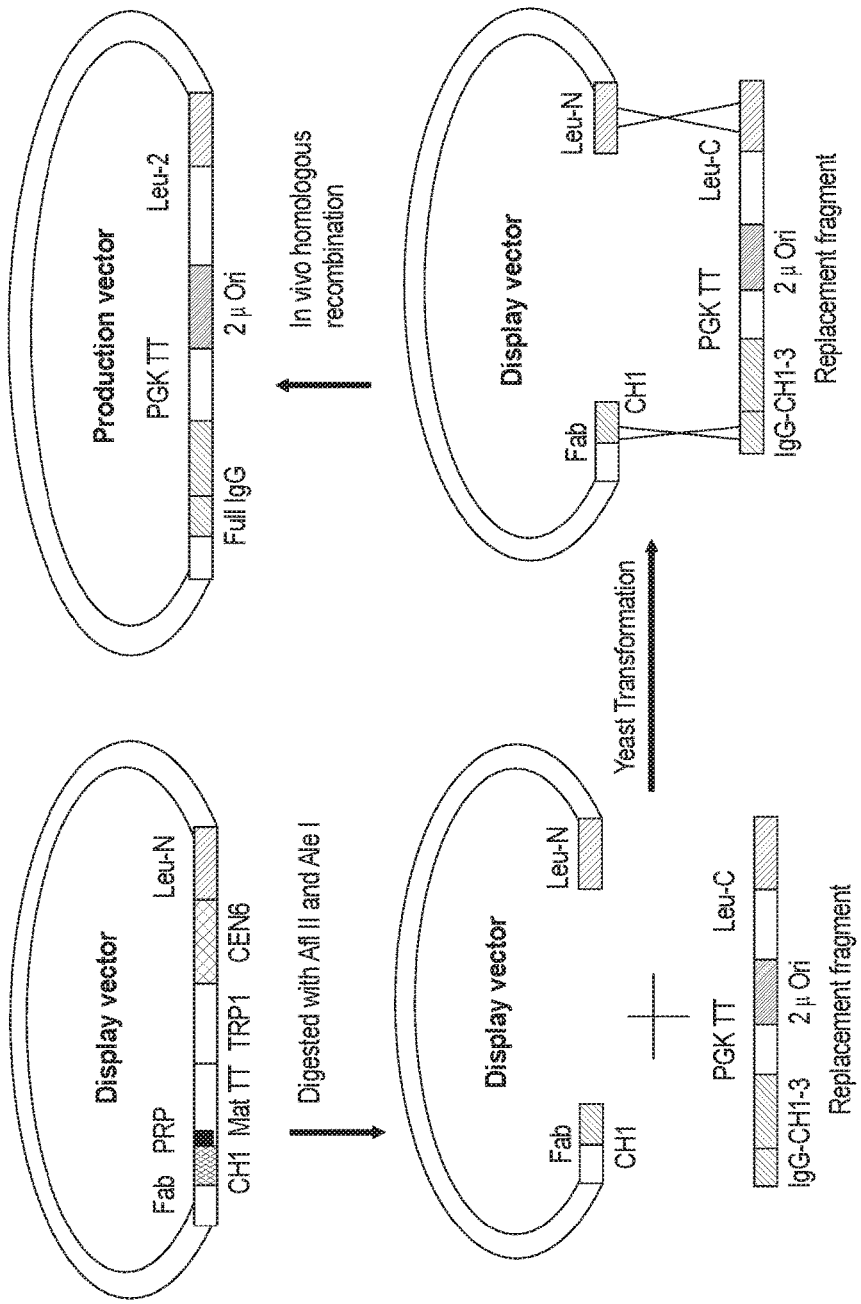
FIG. 6 depicts an exemplary method for in vivo conversion of an exemplary display vector into an exemplary expression/production vector.

The present disclosure provides methods for the in-vivo conversion of a display vector to a secretion vector, the method comprising: mixing: (i) a display vector that comprises a first polynucleotide region and a second polynucleotide region, wherein the display vector further comprises a polynucleotide coding for an antibody fragment (e.g., scFv, Fv, an antibody heavy chain or fragment thereof, an antibody light chain or fragment thereof and a single chain antibody (SCA)) associated with one or more proline-rich peptides (e.g., surface anchoring protein) and a polynucleotide that codes for a selectable marker fragment positioned between the first and the second polynucleotide regions, and wherein the display vector is digested to remove a polynucleotide fragment from the vector that comprises a coding region for the proline-rich peptide; and (ii) a replacement fragment that comprises a first polynucleotide region and a second polynucleotide region that are homologous to the first polynucleotide region and the second polynucleotide region in the digested display vector, wherein the replacement fragment further comprises a polynucleotide coding for an antibody fragment and a selectable marker fragment positioned between the first and the second polynucleotide regions; permitting the digested display vector and the replacement fragment to undergo homologous recombination to create a secretion vector, wherein the antibody fragment from the display vector and the antibody fragment from the replacement fragment are recombined to generate a full-length antibody and wherein the selectable marker fragment from the display vector and the selectable marker fragment from the replacement fragment are recombined to generate a complete selectable marker; expressing the secretion vector; and selecting yeast cells that are capable of growth on a selectable medium, wherein cells that are capable of growth on the selectable medium have undergone homologous recombination between the display vector and the replacement fragment resulting in the production of a secretion vector that comprises a full-length antibody and that expresses a selectable marker. FIG. 6 depicts an exemplary method for in vivo conversion of an exemplary display vector into an exemplary expression/production vector. As shown, the exemplary display vector may comprise a Fab heavy chain constant region 1 (CH1, forward striped box), proline-rich peptide (PRP, black box), mating factor α terminator (Mat TT, open box), gene for tryptophan synthesis (TRP1), single copy replication origin (CEN6, cross striped box), and an N-terminal portion of a Leu 2 gene for leucine synthesis (Leu-N, backward striped box) is shown in the left top panel. An exemplary replacement fragment may comprise a full length human IgG constant region including CH1-3 (IgG-CH1-3, forward stripped box), a PGK terminator (PGK TT, open box), a multiple replication origin (2p Ori, gray-filled box), the C-terminal portion and a portion of the N-terminus of the gene for leucine synthesis (Leu-2, open box and backward striped box) is shown at the left of the lower panel. The proline-rich peptide may be an amino acid sequence comprising PPP or any of the amino acid sequences depicted in SEQ ID NOS: 1-116. Alternatively, the proline-rich peptide may be an amino acid sequence comprising one or more of the following features: (i) at least 3, 4, 5, 6 or more contiguous proline residues; (ii) a number of contiguous proline (P) or (XP) residues (where X is any amino acid) sufficient to produce a polyproline Type II helix with at least 2 turns; (iii) at least about 60%, 65%, 70%, 75%, 80%, 85%, 90%, 95%, 99% or 100% sequence identity to any of the amino acid sequences depicted in SEQ ID NOS: 1 and 55-116; (iv) any of the amino acid sequences depicted in SEQ ID NOS: 2-54; (v) about 3 to about 26 proline residues in a length of about 3 to ≤50 amino acid residues (e.g., about 3 to about 26 amino acid residues); (vi) about 20% to about 100% proline; (vii) a C-terminal amino acid residue of the peptide that is not proline or histidine; (viii) at the C-terminus of the peptide at least 1, 2, 3, 4, 5, 6, 7, 8, 9, 10, 11, 12, 13, 14 or more non-proline amino acid residues; or (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu). Alternatively, the proline-rich peptide may be an amino acid sequence: (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues; (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues; (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues; (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or (v) that is 3 to 11 amino acid residues and wherein no less than 3 and no more than 9 of the amino acid residues of the peptide are proline residues.

The present disclosure also provides methods for the in-vivo conversion of a display vector to a secretion vector by mixing: (i) a display vector that comprises a first polynucleotide region and a second polynucleotide region, wherein the display vector further comprises a polynucleotide coding for an antibody fragment associated with one or more cell wall proteins (e.g., a yeast cell wall protein) and a polynucleotide that codes for a selectable marker fragment positioned between the first and the second polynucleotide regions, and wherein the display vector is digested to remove a polynucleotide fragment from the vector that comprises a coding region for the yeast cell wall protein; and (ii) a replacement fragment that comprises a first polynucleotide region and a second polynucleotide region that are homologous to the first polynucleotide region and the second polynucleotide region in the digested display vector, wherein the replacement fragment further comprises a polynucleotide coding for an antibody fragment and a selectable marker fragment positioned between the first and the second polynucleotide regions; permitting the digested display vector and the replacement fragment to undergo homologous recombination to create a secretion vector, wherein the antibody fragment from the display vector and the antibody fragment from the replacement fragment are recombined to generate a full-length antibody and wherein the selectable marker fragment from the display vector and the selectable marker fragment from the replacement fragment are recombined to generate a complete selectable marker; expressing the secretion vector; and selecting yeast cells that are capable of growth on a selectable medium, wherein cells that are capable of growth on the selectable medium have undergone homologous recombination between the display vector and the replacement fragment resulting in the production of an secretion vector that comprises a full-length antibody and that expresses a selectable marker. Cell wall proteins may include endogenous yeast cell wall proteins, for example, the C-terminal portion of aga1 or FLO1 (see, e.g., U.S. Pat. No. 6,027,910 and U.S. Pat. No. 6,114,147); Aga2p (see, e.g., U.S. Pat. No. 6,300,065); GPI-anchored yeast cell wall proteins such as PIR family members including, WSC1, GAS1 from *S. cerevisiae* or *Hansuela* (see, e.g., U.S. Pat. No. 7,132,273); and Pir1 and 2 (see, e.g., U.S. Patent Application No. 2009/305347 and U.S. 2009/305347). Cell wall proteins may also include yeast cell wall proteins (see, e.g., Wang et al., *Curr Microbiol.* 56(4):352-7). Cell wall proteins may be associated with (e.g., linked to) non-cell wall proteins such as biotin or avidin (see, e.g., U.S. 2009/005264). Such non-cell wall proteins may serve as capture agents for proteins of interest. The term cell wall proteins as used herein does not include the proline-rich peptides as described herein.

The present disclosure also provides novel antibodies or fragments thereof (e.g., Fab) specific for prostate specific antigen (PSA). These novel antibodies described herein may be useful as marker proteins including, for example, a marker protein as described in Example 1.

The present disclosure provides novel antibodies or fragments thereof (e.g., Fab) specific for prostate specific antigen (PSA) comprising a heavy chain variable region that is 70%, 75%, 80%, 85%, 90%, 95%, 99% or 100% identical to SEQ ID NO: 130. The heavy chain variable region may be coupled to a CH1 region of IgG1.

The present disclosure provides novel antibodies or fragments thereof (e.g., Fab) specific for prostate specific antigen (PSA) comprising a light chain variable region that is 70%, 75%, 80%, 85%, 90%, 95%, 99% or 100% identical to SEQ ID NO: 131. The light chain variable region sequence may be coupled to a constant region of kappa 1.

The present disclosure provides novel antibodies or fragments thereof (e.g., Fab) specific for prostate specific antigen (PSA) comprising a heavy chain variable region that is 70%, 75%, 80%, 85%, 90%, 95%, 99% or 100% identical to SEQ ID NO: 130 a light chain variable region that is 70%, 75%, 80%, 85%, 90%, 95%, 99% or 100% identical to SEQ ID NO: 131. The heavy chain variable region may be coupled to a CH1 region of IgG1 and the light chain variable region sequence may be coupled to a constant region of kappa 1.

The present disclosure also provides methods for obtaining a humanized antibody by generating a library of humanized antibody molecules comprising: (i.) CDRH3 from a non-human antibody of interest; and (ii.) CDRH1, CDRH2, CDRL1, CDRL2 and CDRL3 from a synthetic human antibody library, wherein one or more amino acid residues in CDRH1, CDRH2, CDRL1, CDRL2 and/or CDRL3 are randomized; exposing the antibody library to a labeled antigen comprising an epitope recognized by the non-human antibody of interest; washing unbound labeled antigen from the antibody library; exposing the antibody library to the non-human antibody labeled with a different label than the antigen; and selecting members from the antibody library that bind to the labeled antigen and that inhibit binding of the non-human antibody to the labeled antigen, wherein the library of antibody molecules are displayed at a surface of a host cell (e.g., a yeast cell) associated with a proline-rich peptide. Examples of labels that can be used to distinguish antigen from the non-human antibody include different fluorescent tags such as phycoerythrin (PE), rhodamine or the Alexa family of probes such as Alexa 488. The one or more amino acid residues in CDRH1, CDRH2, CDRL1, CDRL2 and/or CDRL3 (e.g., each of the residues in CDRH1, CDRH2, CDRL1, CDRL2 and/or CDRL3) may be randomized by (a) selecting one or more amino acid residues in a CDR for randomization; (b) synthesizing oligonucleotides comprising one or more nucleotides that are positioned 3' of a codon for a first CDR residue selected for randomization; (c) splitting the synthesized oligonucleotides into a first number of pools (e.g., columns), wherein the number of pools (e.g., columns) permit a frequency of randomized amino acid residues at the first amino acid position selected for randomization to approximate a predetermined frequency of amino acid residues at the selected position; (d) joining 3 nucleotides, one at a time, to the 5' end of the oligonucleotides in each pool (e.g., column), wherein the 3 nucleotides form a codon that is selected to approximate a predetermined frequency of an amino acid residue occurring at the position selected for randomization; and (e) combining the pools (e.g., columns) comprising oligonucleotides joined to the codon. The methods may further comprise randomizing a second amino acid residue in a CDR selected for randomization by (f) splitting the oligonucleotides of step (e) into a second number of pools (e.g., columns), wherein the number of pools (e.g., columns) permit a frequency of randomized amino acid residues at the second amino acid position selected for randomization to approximate a predetermined frequency of amino acid residues at the selected position; (g) joining 3 nucleotides, one at a time, to the 5' end of the oligonucleotides in each pool (e.g., column), wherein the 3 nucleotides form a codon that is selected to approximate a predetermined frequency of an amino acid residue occurring at the position selected for randomization; and (h) combining the pools (e.g., columns) comprising oligonucleotides joined to the codon. The methods of the present disclosure may further comprise steps for randomizing additional amino acid residues in a CDR selected for randomization, for example, 3, 4, 5, 6, 7, 8, 9, 10, 11, 12, 13, 14, 15, 16, 17, 18, 19, 20 . . . n, where n is the total number of amino acids selected for randomization, by repeating the splitting, joining and combining steps.

A polynucleotide or nucleic acid sequence may refer to a polymeric form of nucleotides of any length and any three-dimensional structure and single- or multi-stranded (e.g., single-stranded, double-stranded, triple-helical, etc.), which contain deoxyribonucleotides, ribonucleotides, and/or analogs or modified forms of deoxyribonucleotides or ribonucleotides, including modified nucleotides or bases or their analogs. Such polynucleotides or nucleic acid sequences may encode amino acids (e.g., polypeptides or proteins such as fusion proteins). Because the genetic code is degenerate, more than one codon may be used to encode a particular amino acid, and the present disclosure encompasses polynucleotides which encode a particular amino acid sequence. Any type of modified nucleotide or nucleotide analog may be used, so long as the polynucleotide retains the desired functionality under conditions of use, including modifications that increase nuclease resistance (e.g., deoxy, 2'-O-Me, phosphorothioates, etc.). Labels may also be incorporated for purposes of detection or capture, for example, radioactive or nonradioactive labels or anchors, e.g., biotin. The term polynucleotide also includes peptide nucleic acids (PNA). Polynucleotides may be naturally occurring or non-naturally occurring. The terms polynucleotide, nucleic acid, and oligonucleotide are used herein interchangeably. Polynucleotides may contain RNA, DNA, or both, and/or modified forms and/or analogs thereof. A sequence of nucleotides may be interrupted by non-nucleotide components. One or more phosphodiester linkages may be replaced by alternative linking groups. These alternative linking groups include, but are not limited to, embodiments wherein phosphate is replaced by P(O)S (thioate), P(S)S (dithioate), (O)NR$_2$ (amidate), P(O)R, P(O)OR', COCH$_2$ (formacetal), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. Polynucleotides may be linear or circular or comprise a combination of linear and circular portions.

A protein or polypeptide may refer to a composition comprised of amino acids and recognized as a protein by those of skill in the art. The conventional one-letter or three-letter code for amino acid residues is used herein. The terms protein and polypeptide are used interchangeably herein to refer to polymers of amino acids of any length, including those comprising linked (e.g., fused) peptides/polypeptides (e.g., fusion proteins). The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

A vector may refer to a polynucleotide sequence designed to introduce nucleic acids into one or more cell types. Vectors include cloning vectors, expression vectors, shuttle vectors, plasmids, phage particles, cassettes and the like.

Expression may refer to the process by which a polypeptide is produced based on a nucleic acid sequence encoding the polypeptides (e.g., a gene). The process includes both transcription and translation.

An expression vector may refer to a DNA construct containing a polynucleotide or nucleic acid sequence encoding a polypeptide or protein, such as a DNA coding sequence (e.g., gene sequence) that is operably linked to one or more suitable control sequence(s) capable of affecting expression of the coding sequence in a host. Such control sequences include a promoter to affect transcription, an optional operator sequence to control such transcription, a sequence encoding suitable mRNA ribosome binding sites, and sequences which control termination of transcription and translation.

The vector may be a plasmid, a phage particle, or simply a potential genomic insert. Once transformed into a suitable host, the vector may replicate and function independently of the host genome (e.g., independent vector or plasmid), or may, in some instances, integrate into the genome itself (e.g., integrated vector). The plasmid is the most commonly used form of expression vector. However, the disclosure is intended to include such other forms of expression vectors that serve equivalent functions and which are, or become, known in the art.

A promoter may refer to a regulatory sequence that is involved in binding RNA polymerase to initiate transcription of a gene. A promoter may be an inducible promoter or a constitutive promoter. An inducible promoter is a promoter that is active under environmental or developmental regulatory conditions.

Operably linked may refer to a juxtaposition or arrangement of specified elements that allows them to perform in concert to bring about an effect. For example, a promoter may be operably linked to a coding sequence if it controls the transcription of the coding sequence.

A gene may refer to a DNA segment that is involved in producing a polypeptide or protein (e.g., fusion protein) and includes regions preceding and following the coding regions as well as intervening sequences (introns) between individual coding segments (exons).

A host cell may refer to a cell or cell line, including a cell or cell line into which a recombinant expression vector may be transfected for expression and/or display of a polypeptide or protein (e.g., fusion protein). Host cells include progeny of a single host cell, and the progeny may not necessarily be completely identical (in morphology or in total genomic DNA complement) to the original parent cell due to natural, accidental, or deliberate mutation. A host cell may include cells transfected or transformed in vivo with an expression vector.

Recombinant may refer to nucleic acid sequences or polynucleotides, polypeptides or proteins, and cells based thereon, that have been manipulated by man such that they are not the same as nucleic acids, polypeptides, and cells as found in nature. Recombinant may also refer to genetic material (e.g., nucleic acid sequences or polynucleotides, the polypeptides or proteins they encode, and vectors and cells comprising such nucleic acid sequences or polynucleotides) that has been modified to alter its sequence or expression characteristics, such as by mutating the coding sequence to produce an altered polypeptide, fusing the coding sequence to that of another coding sequence or gene, placing a gene under the control of a different promoter, expressing a gene in a heterologous organism, expressing a gene at decreased or elevated levels, expressing a gene conditionally or constitutively in manners different from its natural expression profile, and the like.

A signal sequence may refer to a sequence of amino acids which facilitates the secretion of the mature form of the protein from the cell. The mature form of the extracellular protein lacks the signal sequence which is cleaved off during the secretion process. A signal sequence may be bound to the N-terminal portion of a protein Selective marker or selectable marker may refer to a gene capable of expression in a host cell that allows for ease of selection of those hosts containing an introduced nucleic acid sequence, polynucleotide or vector. Examples of selectable markers include but are not limited to antimicrobial substances (e.g., hygromycin, bleomycin, or chloramphenicol) and/or genes that confer a metabolic advantage, such as a nutritional advantage, on the host cell.

Derived from may encompass the terms originated from, obtained from, obtainable from, isolated from, and created from, and generally indicates that one specified material finds its origin in another specified material or has features that can be described with reference to the another specified material.

Culturing may refer to growing a population of cells, e.g., microbial cells, under suitable conditions for growth, in a liquid or on solid medium.

Heterologous, with reference to a nucleic acid, polynucleotide, protein or peptide, may refer to a nucleic acid, polynucleotide, protein or peptide that does not naturally occur in a specified cell, e.g., a host cell. It is intended that the term encompass proteins that are encoded by naturally occurring genes, mutated genes, and/or synthetic genes. In contrast, the term homologous, with reference to a nucleic acid, polynucleotide, protein or peptide, refers to a nucleic acid, polynucleotide, protein or peptide that occurs naturally in the cell.

Introduced, in the context of inserting a nucleic acid sequence or a polynucleotide sequence into a cell, may include transfection, transformation, or transduction and refers to the incorporation of a nucleic acid sequence or polynucleotide sequence into a eukaryotic or prokaryotic cell wherein the nucleic acid sequence or polynucleotide sequence may be incorporated into the genome of the cell (e.g., chromosome, plasmid, plastid, or mitochondrial DNA), converted into an autonomous replicon, or transiently expressed.

Transfection or transformation may refer to the insertion of an exogenous nucleic acid or polynucleotide into a host cell. The exogenous nucleic acid or polynucleotide may be maintained as a non-integrated vector, for example, a plasmid, or alternatively, may be integrated into the host cell genome. The term transfecting or transfection is intended to encompass all conventional techniques for introducing nucleic acid or polynucleotide into host cells. Examples of transfection techniques include, but are not limited to, calcium phosphate precipitation, DEAE-dextran-mediated transfection, lipofection, electroporation, and microinjection.

Transformed, stably transformed, and transgenic may refer to a cell that has a non-native (e.g., heterologous) nucleic acid sequence or polynucleotide sequence integrated into its genome or as an episomal plasmid that is maintained through multiple generations.

Recovered, isolated, purified, and separated as used herein may refer to a material (e.g., a protein, peptide, nucleic acid, polynucleotide or cell) that is removed from at least one component with which it is naturally associated. For example, these terms may refer to a material which is substantially or essentially free from components which normally accompany it as found in its native state, such as, for example, an intact biological system.

A signal sequence (also termed presequence, signal peptide, leader sequence, or leader peptide) may refer to a sequence of amino acids at the amino terminus of a nascent polypeptide that targets a protein or polypeptide to the secretory pathway and is cleaved from the nascent polypeptide once it is translocated in the endoplasmic reticulum membrane.

Related (and derivative) proteins, polypeptides or peptides may encompass variant proteins, polypeptides or peptides. Variant proteins, polypeptides or peptides differ from a parent protein, polypeptide or peptide and/or from one another by a small number of amino acid residues. In some embodiments, the number of different amino acid residues is any of about 1, 2, 3, 4, 5, 10, 20, 25, 30, 35, 40, 45, or 50. In some embodiments, variants differ by about 1 to about 10 amino acids. Alternatively or additionally, variants may have a specified degree of sequence identity with a reference protein or nucleic acid, e.g., as determined using a sequence alignment tool, such as BLAST, ALIGN, and CLUSTAL (see, infra). For example, variant proteins or nucleic acid may have at least about 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% amino acid sequence identity with a reference sequence.

A wild-type, native, or naturally-occurring proteins may refer to those proteins found in nature. The terms wild-type sequence refers to an amino acid or nucleic acid sequence that is found in nature or naturally occurring. In some embodiments, a wild-type sequence is the starting point of a protein engineering project, for example, production of variant proteins.

Substantially similar and substantially identical in the context of at least two nucleic acids, polynucleotides, proteins or polypeptides may mean that a nucleic acid, polynucleotide, protein or polypeptide comprises a sequence that has at least about 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% sequence identity, in comparison with a reference (e.g., wild-type) nucleic acid, polynucleotide, protein or polypeptide. Sequence identity may be determined using known programs such as BLAST, ALIGN, and CLUSTAL using standard parameters. (See, e.g., Altshul et al. (1990) J. Mol. Biol. 215:403-410; Henikoff et al. (1989) Proc. Natl. Acad. Sci. 89:10915; Karin et al. (1993) Proc. Natl. Acad. Sci. 90:5873; and Higgins et al. (1988) Gene 73:237). Software for performing BLAST analyses is publicly available through the National Center for Biotechnology Information. Also, databases may be searched using FASTA (Person et al. (1988) Proc. Natl. Acad. Sci. 85:2444-2448.) In some embodiments, substantially identical polypeptides differ only by one or more conservative amino acid substitutions. In some embodiments, substantially identical polypeptides are immunologically cross-reactive. In some embodiments, substantially identical nucleic acid molecules hybridize to each other under stringent conditions (e.g., within a range of medium to high stringency).

A fusion protein may refer to a hybrid polypeptide comprised of amino acid sequences from more than one source, linked together to form a non-naturally occurring, unitary polypeptide. Fusion proteins are prepared, for example, by operably linking coding sequences for the component amino acid sequences in frame, such that, upon expression, they are produced in a single polypeptide. Alternatively, fusion proteins can be assembled synthetically, e.g., by creating a peptide bond between two or more separate polypeptides.

A target may refer to a substance that interacts, e.g., by direct binding, with a protein, polypeptide or peptide, such as a protein of interest displayed on a host cell as described herein. For example, targets include antigens with which a displayed antibody or fragment thereof interact.

A receptor may refer to a molecular structure within a cell or on the surface characterized by (1) selective binding of a specific substance and (2) a specific physiologic effect that accompanies the binding, e.g., membrane receptors for peptide hormones, neurotransmitters, antigens, complement fragments, and immunoglobulins and antigen-binding fragments thereof, and include natural and synthetic biomolecules, such as proteins, polypeptides, peptides, nucleic acid molecules, carbohydrates, sugars, lipids, lipoproteins, small molecules, natural and synthetic organic and inorganic materials, and synthetic polymers.

Specifically binds may refer to recognition and interaction of a receptor with a ligand under conditions wherein the receptor does not substantially recognize and interact with other molecules in a sample.

An antibody may refer to an immunoglobulin molecule capable of specific binding to binding partner, including a target, such as a carbohydrate, polynucleotide, lipid, polypeptide, etc., through at least one binding recognition site (e.g., antigen binding site), including a site located in the variable region of the immunoglobulin molecule. As used herein, the term encompasses not only full length antibodies (e.g., IgG), but also fragments thereof (such as Fab, Fab', F(ab')$_2$, Fv), single chain (ScFv), heavy chain or fragment thereof, light chain or fragment thereof, $V_H$ or dimers thereof, $V_L$ or dimers thereof, $V_H V_L$), mutants thereof, fusion proteins comprising an antibody, or any other modified configuration of the immunoglobulin molecule that comprises an antigen recognition site of a desired specificity. An antibody fragment may refer to an antigen binding fragment. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy chain constant domains that correspond to the different classes of immunoglobulins are called alpha, delta, epsilon, gamma, and mu, respectively. The subunit structures and three-dimensional configurations of different classes of immunoglobulins are well known.

A protein of interest may refer to any protein, polypeptide or peptide sequence, the display of which may be desirable for any reason (e.g., selection and/or isolation of antibodies or binding fragments thereof and/or selection and/or isolation of a display peptide such as a proline-rich peptide as described herein). The terms protein of interest and polypeptide of interest may be used interchangeably. A protein of interest may be associated with (e.g., linked to) a peptide including, for example, a proline-rich peptide capable of displaying the protein of interest. Proline-rich peptides may be directly linked to a protein of interest. For example, the disclosure provides fusion proteins that contain a proline-rich peptide as described herein, genetically linked (e.g., fused) to a protein of interest. A protein of interest may be linked at its N-terminus or C-terminus to a proline-rich peptide for display on the surface of a host cell. Exemplary proteins of interest may include single chain proteins or polypeptides and single chain proteins or polypeptides that are a member of a multi-chain protein or fragments thereof (e.g., an antibody or binding fragment thereof such as an antibody heavy or light chain). Proteins of interest may also include multi-chain proteins of interest (e.g., antibodies) where one or more of the chains are associated with (e.g., linked to) a proline-rich peptide. Proteins of interest include, for example, binding molecules such as an antibody or fragment thereof, a ligand or fragment thereof, or a receptor or fragment thereof. Such proteins of interest may be detected by a binding partner such as an antigen, receptor or ligand. A binding partner of a single chain or multi-chain protein of interest may be linked at either its N-terminus or C-terminus to a proline-rich peptide for display on the surface of a host cell and the single chain or multi-chain protein of interest may be associated with the proline-rich peptide by forming a complex with the binding partner. Non-limiting examples of binding partners include, for example, an antibody binding agent such as an Fc receptor, Protein A or Protein G. Such binding partners when associated with (e.g., linked to) a proline-rich peptide may associate with co-expressed proteins of interest including, for example, antibodies. Proteins of interest associated with proline-rich peptides may be detected by agents that bind to the proteins of interest (e.g., a detecting agent, including a binding partner such as an antigen, a ligand, a receptor or fragments thereof). Any protein of interest, including a novel protein, may be used as a marker protein for the identification, selection and/or isolation of novel peptides useful for the display (e.g., capable of displaying) of a protein of interest at a host cell surface, including, as described in Example 1.

A variable region of an antibody may refer to the variable region of the light chain or the variable region of the heavy chain, either alone or in combination. The term variable with reference to antibody chains is used to refer to portions of the antibody chains which differ extensively in sequence among antibodies and participate in the binding and specificity of each particular antibody for its particular antigen. Such variability is concentrated in three segments called hypervariable regions both in the light chain and the heavy chain variable domains. The more highly conserved portions of variable domains are called the framework region (FR). The variable domains of native heavy and light chains each comprise four FRs (FR1, FR2, FR3 and FR4, respectively), connected by three hypervariable regions. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991), pages 647-669.)

Complementarity determining region (CDR) may refer a relatively short amino acid sequence found in the variable regions of antibody molecules. The CDRs contain amino acid residues that determine the specificity of antibody molecules and make contact with a specific antigen.

A monoclonal antibody may refer to a homogeneous antibody population wherein the monoclonal antibody contains amino acids (naturally occurring and/or non-naturally occurring) that are involved in the selective binding of an antigen. A population of monoclonal antibodies (as opposed to polyclonal antibodies) is highly specific, in the sense that they are directed against a single antigenic site. The term monoclonal antibody encompasses not only intact monoclonal antibodies and full-length monoclonal antibodies, but also fragments thereof (such as Fab, Fab', F(ab')$_2$, Fv), single chain (ScFv), mutants thereof, fusion proteins comprising an antibody portion, and any other modified configuration of the immunoglobulin molecule that comprises an antigen recognition site of the required specificity and the ability to bind to an antigen (see definition of antibody). It is not intended to be limited as regards to the source of the antibody or the manner in which it is made (e.g., by hybridoma, phage selection, recombinant expression, transgenic animals, etc.).

A Fv may refer to an antibody fragment that contains a complete antigen-recognition and binding site. In a two-chain Fv species, this region consists of a dimer of one heavy and one light chain variable domain in tight, non-covalent association. In a single-chain Fv species (ScFv), one heavy and one light chain variable domain can be covalently linked by a flexible polypeptide linker such that the light and heavy chains can associate in a dimeric structure analogous to that in a two-chain Fv species. It is in this configuration that the three CDRs of each variable domain interact to define an antigen-binding specificity on the surface of the VH-VL dimer. However, even a single variable domain (or half of a Fv comprising only 3 CDRs specific for an antigen) has the ability to recognize and bind antigen, although generally at a lower affinity than the entire binding site. A Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge regions.

An epitope that specifically binds or preferentially binds (used interchangeably herein) to an antibody is a term understood in the art, and methods to determine such specific or preferential binding are also known in the art. A molecule is said to exhibit specific binding or preferential binding if it reacts or associates more frequently, more rapidly, with greater duration and/or with greater affinity with a particular cell or substance than it does with alternative cells or substances. An antibody specifically binds or preferentially binds to a target if it binds with greater affinity, avidity, more readily, and/or with greater duration than it binds to other substances. For example, an antibody that specifically or preferentially binds to an epitope is an antibody that binds this epitope with greater affinity, avidity, more readily, and/or with greater duration than it binds to other epitopes. It is also understood by reading this definition that, for example, an antibody (or moiety or epitope) that specifically or preferentially binds to a first target may or may not specifically or preferentially bind to a second target. As such, specific binding or preferential binding does not necessarily require (although it can include) exclusive binding. Generally, but not necessarily, reference to binding means preferential binding.

A ligand may refer to a molecule(s) that binds to another molecule(s), e.g., an antigen binding to an antibody, a hormone or neurotransmitter binding to a receptor, or a substrate or allosteric effector binding to an enzyme and include natural and synthetic biomolecules, such as proteins, polypeptides, peptides, nucleic acid molecules, carbohydrates, sugars, lipids, lipoproteins, small molecules, natural and synthetic organic and inorganic materials, synthetic polymers, and the like.

An antigen may refer to a ligand that is bound specifically by an antibody.

A tag or epitope tag may refer to a contiguous sequence of amino acids specifically bound by an antibody when linked to another protein, polypeptide or peptide. Nonlimiting examples of tags include a his tag, a c-myc tag (e.g., the amino acid sequence EQKLISEEDL (SEQ ID NO: 124)), an HA tag (e.g., having the amino acid sequence YPYDVPDYA (SEQ ID NO: 125)) and a V5 tag (e.g., having the amino acid sequence, GKPIPNPLLGLDST (SEQ ID NO: 126)).

A histidine (his) tag may refer to a hexa-histidine sequence that can be linked to a sequence encoding a protein of interest for the purpose of facilitating purification of the protein.

Biological activity or functional activity, when referring to a protein, polypeptide or peptide, may mean that the protein, polypeptide or peptide exhibits a functionality or property that is useful as relating to some biological process, pathway or reaction. Biological or functional activity can refer to, for example, an ability to interact or associate with (e.g., bind to) another polypeptide or molecule, or it can refer to an ability to catalyze or regulate the interaction of other proteins or molecules (e.g., enzymatic reactions).

A library may refer to a mixture of heterogeneous host cells, polypeptides, proteins, nucleic acids, polynucleotides or vectors. Sequence differences between library members are responsible for the diversity present in the library. The library can take the form of a simple mixture of polypeptides or polynucleotides, or can be in the form organisms or cells, for example bacteria, viruses, animal or plant cells and the like, that are transformed with a library of polynucleotides. Where the heterogeneous polypeptides are expressed and exhibited at the surface of the cells or organisms forming the library, the library is a display library. Advantageously, polynucleotides are incorporated into expression vectors, in order to allow expression of the polypeptides encoded by the polynucleotides. Therefore, a library can take the form of a population of host organisms, each organism containing an expression vector containing a single member of the library in polynucleotide form that can be expressed to produce its corresponding polypeptide member. Thus, the population of host organisms has the potential to encode a large repertoire of genetically diverse polypeptide variants.

ATCC refers to American Type Culture Collection located at Manassas, Va. 20108.

A, an and the include plural references unless the context clearly dictates otherwise.

Unless defined otherwise herein, all technical and scientific terms used herein have the same meaning as commonly understood by one of ordinary skill in the art to which this disclosure belongs. Singleton, et al., *Dictionary of Microbiology and Molecular Biology*, second ed., John Wiley and Sons, New York (1994), and Hale & Markham, *The Harper Collins Dictionary of Biology*, Harper Perennial, N.Y. (1991) provide one of skill with a general dictionary of many of the terms used in this disclosure.

Numeric ranges provided herein are inclusive of the numbers defining the range.

Unless otherwise indicated, nucleic acids sequences are written left to right in 5' to 3' orientation; amino acid sequences are written left to right in amino to carboxy orientation, respectively.

Proline-Rich Peptides

The present disclosure provides novel proline-rich peptides. The proline-rich peptides as described herein are capable of displaying a protein of interest associated with a proline-rich peptide on a surface of a host cell. The present disclosure also provides polynucleotides, proteins, vectors and host cells that comprise or encode novel proline-rich peptides, including libraries of such polynucleotides, proteins, vectors and host cells.

Proline-rich peptides may be produced (e.g., identified and/or selected) by a method comprising: generating a library of oligonucleotides that comprise degenerate codons; linking polynucleotides coding for a protein of interest to a generated oligonucleotide; constructing vectors that comprise the polynucleotide coding for the protein of interest linked to the oligonucleotide; introducing the vectors into host cells; expressing the polynucleotide coding for the protein of interest linked to the oligonucleotide; selecting host cells that display the protein of interest at their surface; and recovering the proline-rich peptide from host cells that bind to a detecting agent.

Polynucleotides coding for proline-rich peptides capable of being displayed at a surface of a host cell may be obtained (e.g., identified and/or selected) by: generating a library of oligonucleotides that comprise degenerate codons; linking polynucleotides coding for a protein of interest to a generated oligonucleotide; constructing vectors that comprise the polynucleotide coding for the protein of interest linked to the oligonucleotide; introducing the vectors into host cells; expressing the polynucleotide coding for protein of interest linked to the oligonucleotide; selecting host cells that display the protein of interest at their surface; and recovering the polynucleotide coding for the peptide capable of being displayed at the surface of the host cells.

Non-limiting examples of methods to identify and select peptides, including proline-rich peptides, that are capable of displaying a protein of interest associated with the peptide on the surface of a host cell are described in Example 1.

Exemplary peptides for displaying a protein of interest associated with a peptide on the surface of a host cell include those peptides provided in Table 1.

TABLE 1+

Exemplary Peptide Sequences for Display of a Protein of Interest.

| SEQ ID NO: | Sequence | Length |
|---|---|---|
| - | PPP | 3 |
| 2 | PPPX | 4 |
| 3 | PPPXX | 5 |
| 4 | PPPPPP | 6 |
| 5 | PPPXPPP | 7 |
| 6 | PPPPPPP | 7 |
| 7 | PPPXXPPP | 8 |
| 8 | PPPPPPPPP | 9 |
| 9 | PPPXPPXXPPP | 11 |
| 10 | PPPXXXXXXXXX | 12 |
| 11 | PPPPPPPPPXXXXXX | 15 |
| 12 | PPPPPXXXXXXXXXX | 15 |
| 13 | PPPPPPPPPXXXXXXX | 16 |
| 14 | PPPPPPPPPXXXXXXXX | 18 |
| 15 | PPPXPPXXPPPPPPPPPPP | 20 |
| 16 | PPPXPPXXPPPXXXXXXXX | 20 |
| 17 | PPPPPPPPPPPXXXXXXXX | 20 |
| 18 | PPPPPPPPPPPPXXXXXXXX | 21 |
| 19 | PPPXPPPPPPPPPXPPPPPPPP | 23 |
| 20 | PPPXPPXXPPPPPPPPPPPPPP | 23 |
| 21 | PPPXPPXXPPPPPPPPPPPPPPPPPX | 26 |
| 22 | PPPXXXXXXPPPPPPPPPPPPPPXPPPXXXXXX | 32 |

TABLE 1⁺-continued

Exemplary Peptide Sequences for Display of a Protein of Interest.

| SEQ ID NO: | Sequence | Length |
|---|---|---|
| 23 | XXPPPPPPPPPPPXPPPPPPPXPPXXXXXX | 32 |
| 24 | PPPPPPXPPXPPPPPPPPPPPPPPPPPXXXPX | 32 |
| 25 | PPPPXXXXPPPPXPXPPPPPPPXXXXXXXXX | 33 |
| 26 | PPPXXPPXPXXPPPPPPPPPPPXPXXXXXXX | 33 |
| 27 | PPPXXPPPPPPPPPPPXPPXPPPPPXXXXXX | 33 |
| 28 | PPPXPPXXPPPPPPPPPPPPPPPXXXXXXXX | 34 |
| 29 | XPPPXPPPPPXXXPXPPXPPPXXPXXXXXXX | 34 |
| 30 | PPPXXPXPPXPPPPPPXPPPPPPPXXXXXXX | 34 |
| 31 | PPPPPPPPPPPPPPPPPPPPPXPPXXXXPXXXX | 35 |
| 32 | PPXXXXXXXXXPXXXXXXXXPXPXPXPXXXXXX | 35 |
| 33 | PPPPPXPXPPPPPPPPPPXPXPPPXPXXXXXX | 35 |
| 34 | PXPPXPPPPPPPPXXXXXXXXPPXXXXPXXXXX | 35 |
| 35 | PPPXPXXPXXXXPXXXXXXXXXPXPXXXPXXXXXX | 36 |
| 36 | PPXPXXPXPXXXAPXXXXPPPPPXXXXXXXXXX | 36 |
| 37 | PPPPPPXPPPPPPPPPPPPPPPPPPXXXPXXXXXX | 36 |
| 38 | XPPPPPPXXXPXPPXXXXXXXXPPPXPXPXXXXXX | 37 |
| 39 | PPPPXPXPPPPPPPPPPXPXPXXXXXXXXXXXXX | 37 |
| 40 | PPPPXPPPPPPPPPPPPXXXXPXXXPXXXXXXXX | 37 |
| 41 | PPXPPPPPXPPPXXXXXXXXXXPPPXPXXXXXXX | 37 |
| 42 | PPPPXPPPPPPXPPXPPPXPXPPPPXXXPXXXXX | 37 |
| 43 | PPPPPXPXPPPPPPPPPPPPPPPPPPXXXPXXXXX | 37 |
| 44 | PPPXPPXPPPPPPXXXXXXXPPPXXXXXXXXPXX | 38 |
| 45 | PPPXPPPPPPPXPXXXXPPPPPPPXXXXXXXXPXX | 38 |
| 46 | PPPPPPPPPXPPXPPPPXPXPPPXPXPXXXXXPXX | 38 |
| 47 | PXXXXXXXXPPXPPXXPPXPPXXXXXXXPXXXXPXX | 38 |
| 48 | PPPPXPPPPPPPPPPPPPPPPXXXPXXXPXXXXXPXX | 39 |
| 49 | PXXXXXXPXPXXXXXXPXXXPPPPXPPXPXXXXXPXXPX | 39 |
| 50 | PPXPPXPPPPXPPXXPPXPXPXXXXXXXXPXPXXXXPXX | 41 |
| 51 | PPPXXPPPPPPPPXPPPPPPPPPXPXPXXXXXXXXXXXX | 43 |
| 52 | PPPXPPXXPPPPPPPPPPPPPPPPPXXXXXXXXXXPPPPPXPXX | 43 |
| 53 | PPPXPPPPPPPPPPPPXPPPXXXXXXXPXXXXXXXXXXXPXX | 47 |
| 54 | PPPPPPPPPPPXPPPPPPXPPXXXPXPXXXXXXXXPPXXXPXXXXXX | 50 |

* X may be any amino acid residue.

Exemplary peptides for displaying a protein of interest associated with a peptide on the surface of a host cell also include the proline-rich peptides described in Tables 2, 3 (A and B) and 4 (A, B, and C).

In some embodiments, the proline-rich peptides described herein do not comprise hydroxyproline.

In some embodiments, the proline-rich peptide comprises or consists of any of the amino acid sequences depicted in Tables 1, 2 and 3. In some embodiments, the proline-rich peptide may be an amino acid sequence comprising PPP or any of the amino acid sequences depicted in SEQ ID NOS: 1-116. In some embodiments, the proline-rich peptide may be an amino acid sequence comprising one or more of the following features: (i) at least 3, 4, 5, 6 or more contiguous proline residues; (ii) a number of contiguous proline (P) or (XP) residues (where X is any amino acid) sufficient to produce a polyproline Type II helix with at least 2 turns; (iii) at least about 60%, 65%, 70%, 75%, 80%, 85%, 90%, 95%, 99% or 100% sequence identity to any of the amino acid sequences depicted in SEQ ID NOS: 1 and 55-116; (iv) any of the amino acid sequences depicted in SEQ ID NOS: 2-54; (v) about 3 to about 26 proline residues in a length of about 3 to ≤50 amino acid residues (e.g., about 3 to about 26 amino acid residues); (vi) about 20% to about 100% proline; (vii) a C-terminal amino acid residue of the peptide that is not proline or histidine; (viii) at the C-terminus of the peptide at least 1, 2, 3, 4, 5, 6, 7, 8, 9, 10, 11, 12, 13, 14 or more non-proline amino acid residues; or (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu). Alternatively, the proline-rich peptide may be an amino acid sequence: (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues; (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues; (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues; (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or (v) that is 3 to 11 amino acid residues and wherein no less than 3 and no more than 9 of the amino acid residues of the peptide are proline residues.

In addition to the proline residues as described herein, the proline-rich peptide typically contains additional non-proline amino acid residues. The additional amino acid residues may be naturally-occurring or non-naturally occurring. In some embodiments, the proline-rich peptide contains additional non-proline amino acid residues, with the proviso that the peptide does not contain hydroxyproline.

A protein of interest may be linked either directly or indirectly to a proline-rich peptide including one or more proline-rich peptides.

The proline-rich peptides may be directly linked (e.g., genetically fused) to a protein of interest. Accordingly, the disclosure provides fusion proteins that contain a proline-rich peptide as described herein, genetically linked (e.g., fused) to a protein of interest. The protein of interest may be linked (e.g., fused) at either its N-terminus or its C-terminus to the proline-rich peptide for display on the surface of a host cell.

Alternatively, the proline-rich peptides may be indirectly linked to a protein of interest through a linker. The linker may be a glycine succinate linker. A proline-rich peptide and protein of interest may be linked via a non-covalent or covalent bond. For example, the proline-rich peptide and protein of interest may be linked to a cysteine residue to allow for the formation of a disulfide bond between the proline-rich peptide and protein of interest. The protein of interest may be indirectly linked at either its N-terminus or its C-terminus to the proline-rich peptide for display on the surface of a host cell.

In some embodiments, the linker may include peptide linkers, as well as to chemical bond linkages, such as linkages by disulfide bonds or by chemical bridges.

A linker sequence may contain, without limitation, one or more amino acid sequences selected for non-immunogenicity, detection, quantitation, and/or purification, of the fusion protein. For example, in some embodiments, the linker sequence may contain a peptide sequence that does not affect display of the protein of interest or its function, such as antibody binding to antigen. For example, a linker peptide sequence may contain the amino acid sequence, (GGGGS)$_3$ (SEQ ID NO: 123). In some embodiments, the linker sequence may contain a tag sequence suitable for detection, quantitation and/or purification of the fusion protein, such as, for example, a myc tag. The fusion protein may also contain, in addition to the proline-rich peptide, protein of interest, and optional linker sequence between the proline-rich peptide and the protein of interest, one or more additional tag sequences at the N-terminal and/or C-terminal end of the fusion protein for detection, quantitation, and/or purification of the fusion protein, such as, for example, a his tag.

The protein of interest may be any protein for which display or association with the surface of a host cell is desired. Exemplary proteins of interest may include any known protein (e.g., an antibody molecule), peptide or fragment thereof. Antibody molecules include single chain antibodies (e.g., scFv), single domain antibodies (e.g., $V_H$, $V_L$) or Fab fragments of antibodies.

In some embodiments, a plurality or library of proteins with different amino acid sequences may be linked to the proline-rich peptide for display in a population of host cells. In some embodiments, the protein of interest is binding molecule such as an antibody or fragment thereof, or a library of antibodies or fragments thereof. For example, a library of antibody or antibody fragment fusion proteins may be prepared that recognize a diversity of antigens or epitopes. In some embodiments, the protein of interest is an antibody fragment, for example, a Fab fragment, an scFv fragment, or a Fd fragment, or a library of such antibody fragments.

In some embodiments, the protein of interest is comprised of two or more proteins each with an N-terminus and C-terminus that are covalently or non-covalently linked or associated, wherein the linkage or association is required for functionality of the protein, for example, light and heavy chains of an antibody or antibody fragment, or subunits or domains of a protein or enzyme. In one embodiment, the protein of interest is comprised of two or more proteins each with an N-terminus and C-terminus that are covalently or non-covalently linked or associated, and only one of the proteins is linked to the proline-rich peptide. For example, the heavy chain of an antibody or antibody fragment may be linked to a proline-rich peptide and the light chain is not linked to a proline-rich peptide.

Polynucleotides are also provided that encode any of the proline-rich peptides described herein. In some embodiments, the polynucleotides encode a fusion protein comprising a protein of interest linked to a proline-rich peptide. In some embodiments, a polynucleotide that encodes a proline-rich peptide or a fusion protein is comprised within an expression vector.

The polynucleotide sequence coding for a proline-rich peptide may be operably linked to the 5' end or the 3' end of a DNA sequence coding for a protein of interest. A protein of interest may include any known protein (e.g., an antibody molecule), peptide or fragment thereof. Antibody molecules include single chain antibodies (e.g., scFv), single domain antibodies (e.g., $V_H$, $V_L$) or Fab fragments of antibodies.

Also provided are polypeptides having 60-100%, including 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and 99%, sequence identity to PPP or any one of SEQ ID NOS: 1-116, as well as nucleotides encoding any of these polypeptides, and complements of any of these nucleotides. Percent nucleic acid sequence identity refers to the percentage of nucleotides in a candidate sequence that are identical with the nucleotides in the proline-rich peptide and/or protein of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

Polynucleotides that hybridize under stringent conditions to the polynucleotides coding for the proline-rich peptides of the present disclosure are also provided. The specificity of single stranded polynucleotide to hybridize complementary fragments is determined by the stringency of the reaction conditions. Hybridization stringency increases as the propensity to form DNA duplexes decreases. In nucleic acid hybridization reactions, the stringency can be chosen to either favor specific hybridizations (e.g., high stringency), which can be used to identify, for example, full-length clones from a library. Less-specific hybridizations (e.g., low stringency) can be used to identify related, but not exact, DNA molecules (e.g., homologous, but not identical) or segments.

DNA duplexes are stabilized by: (1) the number of complementary base pairs, (2) the type of base pairs, (3) salt concentration (ionic strength) of the reaction mixture, (4) the temperature of the reaction, and (5) the presence of certain organic solvents, such as formamide which decreases DNA duplex stability. In general, the longer the probe, the higher the temperature required for proper annealing. A common approach is to vary the temperature: higher relative temperatures result in more stringent reaction conditions.

To hybridize under stringent conditions describes hybridization protocols in which nucleotide sequences at least 60% homologous to each other remain hybridized. Generally, stringent conditions are selected to be about 5° C. lower than the thermal melting point (Tm) for the specific sequence at a defined ionic strength and pH.

Stringent hybridization conditions enable a probe, primer, polynucleotide or oligonucleotide to hybridize only to its target sequence. Stringent conditions are sequence-dependent and will differ. Stringent conditions comprise: (1) low ionic strength and high temperature washes (e.g. 15 mM sodium chloride, 1.5 mM sodium citrate, 0.1% sodium dodecyl sulfate at 50° C.); (2) a denaturing agent during hybridization (e.g. 50% (v/v) formamide, 0.1% bovine serum albumin, 0.1% Ficoll, 0.1% polyvinylpyrrolidone, 50 mM sodium phosphate buffer pH 6.5; 750 mM sodium chloride, 75 mM sodium citrate at 42° C.); or (3) 50% formamide. Washes typically also comprise 5×SSC (0.75 M NaCl, 75 mM sodium citrate), 50 mM sodium phosphate (pH 6.8), 0.1% sodium pyrophosphate, 5 times Denhardt's solution, sonicated salmon sperm DNA (50 µg/ml), 0.1% SDS, and 10% dextran sulfate at 42° C., with washes at 42° C. in 0.2 times SSC (sodium chloride/sodium citrate) and 50% formamide at 55° C., followed by a high-stringency wash consisting of 0.1×SSC containing EDTA at 55° C. Preferably, the conditions are such that sequences at least about 65%, 70%, 75%, 85%, 90%, 95%, 98%, or 99% homologous to each other typically remain hybridized to each other.

Changes may be introduced into a polynucleotide coding for a proline-rich peptide that does not alter its function. For example, nucleotide substitutions leading to amino acid substitutions at "non-essential" amino acid residues may be made. A "non-essential" amino acid residue is a residue that can be altered from the wild-type sequences of the proline-rich peptide without altering its biological activity, wherein the biological activity includes, for example, its ability to display a protein of interest on a surface, whereas an "essential" amino acid residue is required for such biological activity. For example, amino acid residues that are conserved among the proline-rich peptides of the disclosure are predicted to be particularly non-amenable to alteration. Amino acids for which conservative substitutions can be made are well known in the art.

The proline-rich peptides of the present disclosure may be operably linked to a protein of interest. The protein of interest may be any protein known in the art. In some embodiments, the protein of interest may be an antibody, for example, a single chain antibody (e.g., scFv), a single domain antibody or Fab fragment. In some embodiments, the single chain antibody comprises a $V_H$ linked by a linker to a $V_L$ (e.g., $V_H$-L-$V_L$ or $V_L$-L-$V_H$). In some embodiments, the protein of interest is a peptide.

In some embodiments, the proline-rich peptide is operably linked to an immunoglobulin variable region polypeptide. An immunoglobulin variable region includes: i) an antibody heavy chain variable domain ($V_H$), or antigen binding fragment thereof, with or without constant region domains ii) an antibody light chain variable domain ($V_L$), or antigen binding fragment thereof, with or without constant region domains iii) a $V_H$ or $V_L$ domain polypeptide without constant region domains linked to another variable domain (a $V_H$ or $V_L$ domain polypeptide) that is with or without constant region domains, (e.g., $V_H$-$V_H$, $V_H$-$V_L$, or $V_L$-$V_L$), and iv) single-chain Fv antibodies (scFv), that is a $V_L$ domain polypeptide without constant regions linked to another $V_H$ domain polypeptide without constant regions ($V_H$-$V_L$ or $V_L$-$V_H$), the variable domains together forming an antigen binding site, including, for example, wherein $V_H$ is linked by a linker to $V_L$ (e.g., $V_H$-L-$V_L$ or $V_L$-L-$V_H$). In an embodiment of option (i), (ii), or (iii), each variable domain forms and antigen binding site independently of any other variable domain. Option (i) or (ii) can be used to form a Fab fragment antibody or an Fv antibody. Thus, an immunoglobulin variable region polypeptide includes antibodies that may or may not contain constant region domains. In addition, immunoglobulin variable region polypeptides include antigen binding antibody fragments that can contain either all or just a portion of the corresponding heavy or light chain constant regions. In addition, an immunoglobulin variable region polypeptide include light chain, heavy chain, heavy and light chains (e.g., scFv), Fd (e.g., $V_H$-$C_{H1}$) or $V_L$-$C_L$. In addition, the term immunoglobulin variable region polypeptide can contain either all or just a portion of the corresponding heavy or light chain constant regions.

Vectors and Host Cells

The present disclosure provides vectors, including vectors comprising one or more polynucleotides coding for a proline-rich peptide. In some embodiments, the polynucleotide coding for a proline-rich peptide may be operably linked to a protein of interest including, for example, a binding peptide such as an antibody or binding fragment thereof. The vectors can be constructed using standard methods (see, e.g., Sambrook et al., Molecular Biology: A Laboratory Manual, Cold Spring Harbor, N.Y. 1989; and Ausubel, et al., Current Protocols in Molecular Biology, Greene Publishing, Co. N.Y, 1995). In an embodiment, the DNA encoding a proline-rich peptide is operably linked to a protein of interest in order that protein of interest can be displayed on the surface of a host cell (e.g., a yeast).

The manipulation of polynucleotides of the present disclosure including polynucleotides coding for a proline-rich peptide and a protein of interest is typically carried out in recombinant vectors. Numerous vectors are publicly available, including bacterial plasmids, bacteriophage, artificial chromosomes, episomal vectors and gene expression vectors, which can all be employed. A vector of use according to the disclosure may be selected to accommodate a protein coding sequence of a desired size. A suitable host cell is transformed with the vector after in vitro cloning manipulations. Host cells may be prokaryotic, such as any of a number of bacterial strains, or may be eukaryotic, such as yeast or other fungal cells, insect or amphibian cells, or mammalian cells including, for example, rodent, simian or human cells. Each vector contains various functional components, which generally include a cloning site, an origin of replication and at least one selectable marker gene. If given vector is an expression vector, it additionally possesses one or more of the following: enhancer element, promoter, transcription termination and signal sequences, each positioned in the vicinity of the cloning site, such that they are operatively linked to the gene encoding a polypeptide repertoire member according to the disclosure.

Vectors, including cloning and expression vectors, may contain nucleic acid sequences that enable the vector to replicate in one or more selected host cells. For example, the sequence may be one that enables the vector to replicate independently of the host chromosomal DNA and may include origins, of replication or autonomously replicating sequences. Such sequences are well known for a variety of bacteria, yeast and viruses. For example, the origin of replication from the plasmid pBR322 is suitable for most Gram-negative bacteria, the 2 micron (2µ) plasmid origin is suitable for yeast, and various viral origins (e.g. SV 40, adenovirus) are useful for cloning vectors in mammalian cells. Generally, the origin of replication is not needed for mammalian expression vectors unless these are used in mammalian cells able to replicate high levels of DNA, such as COS cells.

In some embodiments, a vector is provided that is capable of expressing a multi-chain protein for display on the surface of a host cell, such that a biological activity of the multi-chain protein is exhibited at the surface of the host cell. In one embodiment, a multi-chain protein is expressed from a single display vector. In another embodiment, the vector is a vector set, wherein each chain of a multi-chain protein is encoded on one of a matched set of vectors such that when the vector set is present in a single cell, the chains of the multi-chain protein associate and the biological activity of the multi-chain protein is exhibited at the surface of the host cell.

In some embodiments, a multi-chain display vector contains polynucleotides that encode protein chains of the multi-chain protein. A first polynucleotide encodes a first chain of the multi-chain protein linked to a proline-rich peptide as described herein. Other polynucleotides of the vector (or vector set) encode other chains of the multi-chain protein. All of the polynucleotides of the display vector(s) are operably-situated in the display vector such that a host cell, transformed with the vector (or vector set), displays the multi-chain protein on the surface of the host cell such that the biological activity of the multi-chain protein is exhibited at the surface of the cell. In some embodiments, the multi-chain protein is an antibody or fragment thereof. In one embodiment, the multi-chain protein is a Fab fragment, the heavy chain variable region is linked to the proline-rich peptide, and the light chain variable region is not linked to a proline-rich peptide.

A cloning or expression vector may contain a selection gene also referred to as a selectable marker. This gene encodes a protein necessary for the survival or growth of transformed host cells grown in a selective culture medium. Host cells not transformed with the vector containing the selection gene will therefore not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available in the growth media.

The replication of vectors may be performed in *E. coli* (e.g., strain TB1 or TG1). An *E. coli*-selectable marker, for example, the β-lactamase gene that confers resistance to the antibiotic ampicillin, may be of use. These selectable markers can be obtained from *E. coli* plasmids, such as pBR322 or a pUC plasmid such as pUC18 or pUC19, or pUC119.

Expression vectors may contain a promoter that is recognized by the host organism. The promoter may be operably linked to a coding sequence of interest. Such a promoter may be inducible or constitutive. Polynucleotides are operably linked when the polynucleotides are in a relationship permitting them to function in their intended manner.

Promoters suitable for use with prokaryotic hosts may include, for example, the α-lactamase and lactose promoter systems, alkaline phosphatase, the tryptophan (trp) promoter system and hybrid promoters such as the tac promoter. Promoters for use in bacterial systems will also generally contain a Shine-Delgarno sequence operably linked to the coding sequence.

Viral promoters obtained from the genomes of viruses include promoters from polyoma virus, fowlpox virus, adenovirus (e.g., Adenovirus 2 or 5), herpes simplex virus (thymidine kinase promoter), bovine papilloma virus, avian sarcoma virus, cytomegalovirus, a retrovirus (e.g., MoMLV, or RSV LTR), Hepatitis-B virus, Myeloproliferative sarcoma virus promoter (MPSV), VISNA, and Simian Virus 40 (SV40). Heterologous mammalian promoters include, e.g., the actin promoter, immunoglobulin promoter, heat-shock protein promoters.

The early and late promoters of the SV40 virus are conveniently obtained as a restriction fragment that also contains the SV40 viral origin of replication (see, e.g., Fiers et al., *Nature*, 273:113 (1978); Mulligan and Berg, *Science*, 209:1422-1427 (1980); and Pavlakis et al., *Proc. Natl. Acad. Sci. USA*, 78:7398-7402 (1981)). The immediate early promoter of the human cytomegalovirus (CMV) is conveniently obtained as a Hind III E restriction fragment (see, e.g., Greenaway et al., *Gene*, 18:355-360 (1982)). A broad host range promoter, such as the SV40 early promoter or the Rous sarcoma virus LTR, is suitable for use in the present expression vectors.

Generally, a strong promoter may be employed to provide for high level transcription and expression of the desired product. Among the eukaryotic promoters that have been identified as strong promoters for high-level expression are the SV40 early promoter, adenovirus major late promoter, mouse metallothionein-I promoter, Rous sarcoma virus long terminal repeat, and human cytomegalovirus immediate early promoter (CMV or CMV IE). In an embodiment, the promoter is a SV40 or a CMV early promoter.

The promoters employed may be constitutive or regulatable, e.g., inducible. Exemplary inducible promoters include jun, fos and metallothionein and heat shock promoters. One or both promoters of the transcription units can be an inducible promoter. In an embodiment, the GFP is expressed from a constitutive promoter while an inducible promoter drives transcription of the gene of interest and/or the amplifiable selectable marker.

The transcriptional regulatory region in higher eukaryotes may comprise an enhancer sequence. Many enhancer sequences from mammalian genes are known e.g., from globin, elastase, albumin, α-fetoprotein and insulin genes. A suitable enhancer is an enhancer from a eukaryotic cell virus. Examples include the SV40 enhancer on the late side of the replication origin (bp 100-270), the enhancer of the cytomegalovirus immediate early promoter (Boshart et al. *Cell* 41:521 (1985)), the polyoma enhancer on the late side of the replication origin, and adenovirus enhancers (see also, e.g., Yaniv, *Nature*, 297:17-18 (1982) on enhancing elements for activation of eukaryotic promoters). The enhancer sequences may be introduced into the vector at a position 5' or 3' to the gene of interest, but is preferably located at a site 5' to the promoter.

Sometimes, the polynucleotide encoding the selectable gene and/or the polynucleotide of interest may be preceded by DNA encoding a signal sequence having a specific cleavage site at the N-terminus of the mature protein or polypeptide. In general, the signal sequence may be a component designed into the basic expression vector, or it may be a part of the selectable gene or desired product gene that is inserted into the expression vector. If a heterologous signal sequence is used, it is preferably one that is recognized and processed (e.g., cleaved by a signal peptidase) by the host cell. For mammalian cell expression, the native signal sequence of the protein of interest may be used if the protein is of mammalian origin. Alternatively, the native signal sequence can be substituted by other suitable mammalian signal sequences, such as signal sequences from secreted polypeptides of the same or related species, as well as viral secretory leaders, for example, the herpes simplex gD signal. For yeast expression of a mammalian protein, the native signal sequence of the gene of interest can be replaced by the signal sequence of a native yeast secreted protein. The DNA for such precursor region is operably linked in reading frame to the selectable gene or product gene.

A signal peptide (e.g., a signal sequence) may be fused in frame to the N-terminus or C-terminus of a protein of interest (e.g. an antibody such as a single chain antibody, a single domain antibody or a Fab or a peptide, such as a non-antibody peptide). The signal peptide may be a protein sequence that directs proteins to which it is fused to the periplasmic space of bacteria. In some embodiments, the signal peptide may be derived from a bacteriophage protein. Signal peptides useful in the present disclosure include, for example, the N-terminal signal peptide from the bacteriophage proteins pIII, pVIII, pVII, and pIX. The bacteriophage proteins can be from bacteriophages such as, filamentous bacteriophage, lambda, T4 or MS2. In some embodiments, the signal sequence may be derived from yeast proteins that are transported to the membrane, for insertion into the membrane or cell wall or for secretion. Signal peptides that are particularly useful in the present disclosure include, for example, the N-terminal signal peptide from aga1, aga2, FLO1 or the PIR family of proteins.

The DNA sequences encoding the signal peptides may be obtained from natural sources, for example amplified by PCR from bacteriophage or yeast genomic DNA, or can be made synthetically using synthetic oligonucleotides. Signal sequences useful in the present disclosure are disclosed in WO 03/004636 and U.S. Pat. No. 6,114,147.

Partial signal sequences and variants may also be used as long as the encoded signal peptide sequence directs the polypeptide sequence to which it is attached to the periplasm of bacteria or cell surface of yeast. In some embodiments, hybrid signal peptides that comprise amino acid sequences from at least 2 different signal peptides may be used.

Signal sequences may include, for example, a prokaryotic signal sequence, such as a pectate lyase signal sequence (pelB) (MKYLLPTAAAGLLLLAAQPAMA (SEQ ID NO: 127) (see, e.g., U.S. Pat. Nos. 5,576,195 and 5,846,818) or a eukaryotic signal sequence such as the aga2P (MQLLRCFSIFSVIASVLA) (SEQ ID NO: 128) or invertase (SUC1) (MLLQAFLFLLAGFAALISASM) (SEQ ID NO: 129) signal sequences from *Saccharamyces cerevisiae* (see, e.g., Kaiser and Botstein (1986) *Mol Cell Biol.* 6:2382-2391; Cappellaro et al. (1991) *EMBO J.* 10:4081-4088; U.S. Pat. No. 6,114,147; and U.S. Pat. No. 6,696,251).

The yeast and mammalian expression vectors may contain prokaryotic sequences that facilitate the propagation of the vector in bacteria. Therefore, the vector may have other components such as an origin of replication (e.g., a nucleic acid sequence that enables the vector to replicate in one or more selected host cells), antibiotic resistance genes for selection in bacteria, and/or an amber stop codon which can permit translation to read through the codon. Additional eukaryotic selectable gene(s) may be incorporated. Generally, in cloning vectors the origin of replication is one that enables the vector to replicate independently of the host chromosomal DNA, and includes origins of replication or autonomously replicating sequences. Such sequences are well known, e.g., the ColE1 origin of replication in bacteria. Various viral origins (e.g., SV40, polyoma, adenovirus, VSV or BPV) are useful for cloning vectors in mammalian cells. Generally, a eukaryotic replicon is not needed for expression in mammalian cells unless extrachromosomal (episomal) replication is intended (e.g., the SV40 origin may typically be used only because it contains the early promoter).

To facilitate insertion and expression of different genes of interest (e.g., coding for proteins of interest) from the constructs and expression vectors, the constructs may be designed with at least one cloning site for insertion of any gene of interest (e.g., coding for any protein of interest including an antibody such as a single chain antibody or a Fab). The cloning site may be a multiple cloning site, e.g., containing multiple restriction sites.

The plasmids may be propagated in bacterial host cells to prepare DNA stocks for subcloning steps or for introduction into eukaryotic host cells. Transfection of eukaryotic host cells can be any performed by any method well known in the art. Transfection methods include lipofection, electroporation, calcium phosphate co-precipitation, rubidium chloride or polycation mediated transfection, protoplast fusion and microinjection. Preferably, the transfection is a stable transfection. The transfection method that provides optimal transfection frequency and expression of the construct in the particular host cell line and type, is favored. Suitable methods can be determined by routine procedures. For stable transfectants, the constructs are integrated so as to be stably maintained within the host chromosome.

Vectors (e.g., yeast display vectors) may be introduced to selected host cells by any of a number of suitable methods known to those skilled in the art. For example, vector constructs may be introduced to appropriate cells by any of a number of transformation methods for plasmid vectors. For example, standard calcium-chloride-mediated bacterial transformation is still commonly used to introduce naked DNA to bacteria (see, e.g., Sambrook et al., 1989, Molecular Cloning, A Laboratory Manual, Cold Spring Harbor Laboratory Press, Cold Spring Harbor, N.Y.), but electroporation may also be used (see, e.g., Ausubel et al., 1988, Current Protocols in Molecular Biology, John Wiley & Sons, Inc., NY, N.Y.).

For the introduction of vector constructs to yeast or other fungal cells, chemical transformation methods may be used (e.g., Rose et al., 1990, Methods in Yeast Genetics, Cold Spring Harbor Laboratory Press, Cold Spring Harbor, N.Y.). Transformed cells may be isolated on selective media appropriate to the selectable marker used. Alternatively, or in addition, plates or filters lifted from plates may be scanned for GFP fluorescence to identify transformed clones.

For the introduction of vectors comprising differentially expressed sequences to mammalian cells, the method used may depend upon the form of the vector. Plasmid vectors may be introduced by any of a number of transfection methods, including, for example, lipid-mediated transfection ("lipofection"), DEAE-dextran-mediated transfection, electroporation or calcium phosphate precipitation (see, e.g., Ausubel et al., 1988, Current Protocols in Molecular Biology, John Wiley & Sons, Inc., NY, N.Y.).

Lipofection reagents and methods suitable for transient transfection of a wide variety of transformed and non-transformed or primary cells are widely available, making lipofection an attractive method of introducing constructs to eukaryotic, and particularly mammalian cells in culture. For example, LipofectAMINE™ (Life Technologies) or LipoTaxi™ (Stratagene) kits are available. Other companies offering reagents and methods for lipofection include Bio-Rad Laboratories, CLONTECH, Glen Research, InVitrogen, JBL Scientific, MBI Fermentas, PanVera, Promega, Quantum Biotechnologies, Sigma-Aldrich, and Wako Chemicals USA.

The host cell may be capable of expressing the construct encoding the desired protein, processing the protein and transporting a secreted protein to the cell surface for secretion. Processing includes co- and post-translational modification such as leader peptide cleavage, GPI attachment, glycosylation, ubiquitination, and disulfide bond formation. Immortalized host cell cultures amenable to transfection and in vitro cell culture and of the kind typically employed in genetic engineering are preferred. Examples of useful mammalian host cell lines are monkey kidney CV1 line transformed by SV40 (COS-7, ATCC CRL 1651); human embryonic kidney line (293 or 293 derivatives adapted for growth in suspension culture, Graham et al., *J. Gen Virol.*, 36:59 (1977); baby hamster kidney cells (BHK, ATCC CCL 10); DHFR⁻Chinese hamster ovary cells (ATCC CRL-9096); dp12.CHO cells, a derivative of CHO/DHFR-(EP 307,247 published 15 Mar. 1989); mouse sertoli cells (TM4, Mather, *Biol. Reprod.*, 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383:44-68 (1982)); PEER human acute lymphoblastic cell line (Ravid et al. *Int. J. Cancer* 25:705-710 (1980)); MRC 5 cells; FS4 cells; human hepatoma line (Hep G2), human HT1080 cells, KB cells, JW-2 cells, Detroit 6 cells, NIH-3T3 cells, hybridoma and myeloma cells. Embryonic cells used for generating transgenic animals are also suitable (e.g., zygotes and embryonic stem cells).

Suitable host cells for cloning or expressing polynucleotides (e.g., DNA) in vectors may include, for example, prokaryote, yeast, or higher eukaryote cells. Polynucleotides or vectors include polynucleotides coding for a proline-rich peptide and a protein of interest. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aerugiNOSa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable.

In addition to prokaryotes, eukaryotic microbes such as filamentous fungi or yeast may be suitable cloning or expression hosts for vectors comprising polynucleotides coding for proteins of interest including antibodies. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastors* (EP 183,070); *Candida; Trichoderma* reesia (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

When the protein of interest is glycosylated, such as a glycosylated antibody, suitable host cells for expression may be derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* (silk moth) have been identified. A variety of viral strains for transfection are publicly available, e.g., the L-1 variant of *Autographa californica* NPV and the Bm-5 strain of *Bombyx mori* NPV, and such viruses may be used as the virus herein according to the present disclosure, particularly for transfection of *Spodoptera frugiperda* cells.

Plant cell cultures of cotton, corn, potato, soybean, *petunia*, tomato, tobacco, *lemna*, and other plant cells can also be utilized as host cells.

Examples of useful mammalian host cells are Chinese hamster ovary cells, including CHOK1 cells (ATCC CCL61), DXB-11, DG-44, and Chinese hamster ovary cells/–DHFR (CHO, Urlaub et al., *Proc. Natl. Acad. Sci. USA* 77: 4216 (1980)); monkey kidney CV1 line transformed by SV40 (COS-7, ATCC CRL 1651); human embryonic kidney line (293 or 293 cells subcloned for growth in suspension culture, (Graham et al., *J. Gen Virol.* 36: 59, 1977); baby hamster kidney cells (BHK, ATCC CCL 10); mouse sertoli cells (TM4, Mather, (*Biol. Reprod.* 23: 243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y Acad. Sci.* 383: 44-68 (1982)); MRC 5 cells; FS4 cells; and a human hepatoma line (Hep G2).

Host cells are transformed or transfected with the above-described expression or cloning vectors for production of proteins of interest, for example, antibody production or with polynucleotides coding for proteins of interest, for example, antibodies and cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful and preferred for the expression of antibodies that bind the desired antigen.

Host cells containing desired nucleic acid sequences coding for proteins of interest including, for example, antibodies may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58: 44, (1979); Barnes et al., *Anal. Biochem.* 102: 255 (1980); U.S. Pat. Nos. 4,767,704; 4,657,866; 4,927,762; 4,560,655; or 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adeNOSine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In some embodiments, a host cell is provided that displays a fusion protein at its surface as described herein. The fusion protein contains a protein of interest linked to a proline-rich peptide, and at least a portion of the protein of interest is displayed on the surface of the host cell. In some embodiments, a functional activity of the protein of interest is exhibited as the surface of the cell, e.g., enzymatic activity, antibody recognition of antigen, receptor-ligand interaction, etc. In one embodiment, the host cell displays an antibody or fragment thereof, such as, for example, a Fab, scFv, or Fd, and a sufficient amount of the antibody or fragment is displayed on the surface of the cell such that it is capable of specifically binding to an epitope or antigen that is recognized by the antibody or fragment.

In some embodiments, the host cell is in a medium suitable for expression of the fusion protein and/or growth of the host cell. In one embodiment, a host cell displaying a fusion protein on its surface is in a medium containing secreted fusion protein, wherein a portion of the expressed fusion protein has been secreted into the medium.

Surface Display Libraries

Libraries comprising polynucleotides, proteins, vectors and/or host cells that comprise or encode novel peptides capable of displaying proteins of interest are provided by the present disclosure. Such novel peptides may include novel proline-rich peptides as described herein. The libraries can take the form of polypeptides or polynucleotides, or can be in the form of organisms or cells, for example yeast, bacteria, viruses, animal or plant cells and the like. The libraries may represent diverse repertoires or collections of polynucleotides, proteins, vectors and/or host cells. For example, libraries of polynucleotides may comprise or contain populations of genetically diverse polynucleotides derived from populations of unrelated sequences from total cellular mRNA, tissue mRNA, or related members of a given gene family with some degree of shared homology. For libraries of polynucleotides, proteins, vectors and/or host cells, members may differ from one another by comprising or containing one or more different sequences capable of displaying proteins of interest at a host cell surface. Collectively the polynucleotide, protein, vector and/or host cell libraries may represent a genetically diverse population of sequences capable of displaying protein of interest at a host cell surface. For example, an individual library may represent a genetically diverse population of sequences capable of displaying a selected protein of interest at a host cell surface. Thus, libraries of polynucleotides, proteins, vectors and/or host cells may comprise a diverse collection of members where the members may differ at one or more amino acid positions in one or more of their CDRs and/or framework regions. When the selected protein of interest is an antibody, the polynucleotide, protein, vector and/or host cell library may comprise or contain different sequences capable of displaying antibody sequences (e.g., different variable region sequences). Libraries of host cells may comprise a genetically diverse population of polynucleotides, proteins and vectors. In certain applications, each individual cell can contain two or more members of the library. The nucleic acids may be incorporated into expression vectors, in order to allow expression of the polypeptides encoded by the nucleic acids. In a preferred aspect, therefore, a library can take the form of a population of host cells, each cell containing one or more copies of an expression vector containing a single member of the library in nucleic acid form which can be expressed to produce its corresponding polypeptide member. Thus, the population of host cells has the potential to encode a large repertoire of genetically diverse polypeptide variants. For example, libraries of polynucleotides coding for a proline-rich peptides; proline-rich peptides; polynucleotides coding for proteins of interest operably linked to a proline-rich peptide; proteins of interest operably linked to a proline-rich peptide; vectors comprising proline-rich peptides or polynucleotides coding for proteins of interest operably linked to a proline-rich peptide; vectors comprising a polynucleotide as described herein; and host cells comprising the vectors are provided by the instant disclosure. Such libraries comprising a proline-rich peptide may be used to display a protein of interest on the surface of a host cell.

In some embodiments, the protein of interest is an antibody, for example, a single chain antibody, single domain antibody or Fab. In some embodiments, the protein of interest is a peptide, for example, a non-antibody peptide. In some embodiments, the protein of interest is a multi-chain protein such as Fab.

In some embodiments, the display library may contain a plurality of host cells with vectors encoding proteins of interest, wherein the proteins of interest represent different amino acid sequences. Different host cells in the library express proteins with different amino acid sequences on their surfaces. In some embodiments, one or more amino acids of the protein sequence have been randomized such that different protein sequences are expressed in different host cells. In some embodiments, one or more amino acids have been rationally randomized to mimic natural diversity of the protein sequence. For example, the protein sequences may be rationally randomized using a novel split-pool method as described in Example 4.

For example a vector may comprise a polynucleotide coding for a protein of interest, a polynucleotide coding for a proline-rich peptide, a yeast replication origin, a first polynucleotide for selection in yeast and an inducible yeast promoter.

In some embodiments, the display library contains a plurality of host cells, each displaying a protein of interest on its surface associated with a proline-rich peptide, as described herein, wherein a plurality of proteins with different amino sequences are displayed on the surfaces of different cells in the library. The library may display at least $10^4$, $10^5$, $10^6$, $10^7$, $10^8$, or $10^9$ different protein sequences. In some embodiments, the host cells are microbial cells, for example, fungal cells such as yeast. When the host cells are yeast cells they may be selected from genera *Saccharomyces, Pichia, Hansenula, Schizosaccharomyces, Kluyveromyces, Yarrowia, Debaryomyces*, and *Candida*. For example, the yeast host cell may be *Saccharomyces cerevisiae*. The display library may be in a medium suitable for expression of the protein of interest associated with proline-rich peptides.

Proteins of interest associated with a proline-rich peptide, including libraries of proteins of interest associated with a proline-rich peptide, may be produced by culturing a host cell comprising a polynucleotide coding for a protein of interest and a polynucleotide coding for a proline-rich peptide under conditions wherein the polynucleotides are expressed and the protein of interest and the proline-rich peptide is produced.

In some embodiments, the display library contains a plurality of host cells that express a plurality of proteins with different binding characteristics, such as different binding specificities and/or affinities. Such a library may be used for screening for proteins that bind with a particular level of specificity or affinity to a molecule of interest, such as a ligand, hapten, antigen, protein, polynucleotide, carbohydrate, lipid, etc.

Host cells that express a protein of interest may be selected from a library of host cells by contacting the host cell library with an agent that binds to the protein of interest or the proline-rich peptide; and selecting host cells that bind to the agent, wherein the host cells comprise a polynucleotide coding for a protein of interest and a polynucleotide coding for a proline-rich peptide.

In some embodiments, the display library displays a plurality of antibodies or fragments thereof with different variable region sequences on the surfaces of the host cells. In one embodiment, the display library contains a plurality of antibody fragments, e.g., Fab, scFv, or Fd fragments. For example, the plurality of antibodies or fragments thereof may contain a plurality of different amino acid sequences in at least one CDR. In some embodiments, the antibodies or fragments thereof contain a plurality of different amino acid sequences in any of 1, 2, 3, 4, 5, or 6 CDRs. For example, the amino acid sequences of at least one CDR, i.e., 1, 2, 3, 4, 5, or 6 CDRs, have been rationally randomized to mimic natural human antibody diversity, in exemplary methods, as described in Example 4.

Articles of Manufacture

Articles of manufacture, including, for example kits, are provided for the preparation and/or use of proline-rich peptides, polynucleotides, fusion proteins comprising a proline-rich peptide, vectors, host cells and/or libraries as described herein. The article of manufacture may comprise a container and a label or package insert on or associated with the container. Suitable containers include, for example, bottles, vials or syringes. The containers may be formed from a variety of materials such as glass or plastic. The label or package insert may include directions using a proline-rich peptide for display of a protein of interest on the surface of a host cell.

The kits may include any materials or compositions described herein for making and/or using proline-rich peptides, polynucleotides, fusion proteins comprising a proline-rich peptide, vectors, host cells and/or libraries as described herein. For example, a kit may contain vectors for expression of proline-rich peptides, with or without inserted polynucleotide sequences that encode proteins of interest, host cells, medium for expression of the fusion proteins and/or growth of the host cells, etc. In one embodiment, a kit contains host cells that have been transformed with expression vectors that encode proline-rich peptides operably linked to a protein of interest. In one embodiment, the kit contains a display library that displays antibodies or fragments thereof, e.g., Fab, scFv, or Fd fragments, that have been rationally randomized in at least one CDR sequence and that are operably linked to a proline-rich peptide as described herein.

Kits may optionally include instructions for methods of use of the materials contained therein, for example, any of the methods of making and/or using proline-rich peptides, polynucleotides, fusion proteins comprising a proline-rich peptide, vectors, host cells and/or libraries as described herein. Instructions may be provided in printed form or in the form of an electronic medium such as a floppy disc, CD, or DVD, or in the form of a website address where such instructions may be obtained.

Suitable packaging my also be provided with the articles of manufacture. As used herein, "packaging" refers to a solid matrix or material customarily used in a system and capable of holding within fixed limits any of the materials or compositions contained within the kit. Such materials include, without limitation, glass and plastic (e.g., polyethylene, polypropylene, and polycarbonate) bottles, vials, paper, plastic, and plastic-foil laminated envelopes and the like.

Without further description, it is believed that one of ordinary skill in the art may, using the preceding description and the following illustrative examples, make and utilize the agents of the present disclosure and practice the claimed methods. The following working examples are provided to facilitate the practice of the present disclosure, and are not to be construed as limiting in any way the remainder of the disclosure.

EXAMPLES

Example 1: Isolation of Novel Peptides for Display of Proteins of Interest on Host Cell Surfaces Novel peptides capable of displaying proteins of interest on host cells may be identified, selected and/or isolated by generating and screening a library of peptides with randomized amino acid sequences (e.g., random peptides, including peptides that are 50 amino acids or less such as 10, 15, 20, 25, 30, 35, 40, 45, 50 amino acids in length) that are associated with any protein of interest including a protein of interest that may be used as a marker protein. Such a marker protein may be detected if any of the random peptides are capable of associating with the marker protein and displaying it on a host cell surface. Library clones that display any protein of interest at the host cell surface may then be isolated by any method known in the art, such as magnetic or fluorescence-activated cell sorting (MACS or FACS). In some embodiments, where the protein of interest is a chain of a multi-chain protein (e.g., an antibody or binding fragment thereof such as a Fab), the novel peptides may be used to display a single chain from the multi-chain protein which in turns associates with the other chains of the multi-chain protein.

In an exemplary method, novel peptides for displaying proteins of interest such as an antibody binding fragment, at a host cell surface may be identified and/or selected by using any protein of interest, including a protein of interest that functions as a marker protein. Briefly, a library of peptides was coupled to a heavy chain of a novel anti-PSA Fab fragment as a marker protein, inserted into a yeast vector and then the resulting yeast library was screened for clones that displayed the novel Fab fragment at their surface. The novel anti-PSA antibody was identified from a single chain library and had unexpectedly high affinity binding to the PSA antigen (e.g., Kd of 0.08 nM). The VH and VL from the novel anti-PSA antibody (SEQ ID NO: 130 and 131, respectively) may be linked to a signal sequence to facilitate their export to a cell surface. Such signal sequences may include a eukaryotic signal sequence such as the aga2P signal sequence (MQLLRCFSIFSVIASVLA) (SEQ ID NO: 118).

The signal sequence may be linked to the N-terminus or C-terminus of the antibody VH and/or VL. The heavy chain and light chain variable region of this anti-PSA antibody are shown below, respectively.

```
Heavy-chain variable region:
                                        (SEQ ID NO: 130)
EVQLLESGGGLVQPGGSLRLSCAASGFTVSNYAMSWVRQAPGKGLEWV

GDIYPTSGYTDYADSVKGRFTISRDNSKNTLYLQMNSLRAEDTAVYYC

ARWGYDYKYVASEGSWLFDYWGQGTLVTVSS

Light-chain variable region:
                                        (SEQ ID NO: 131)
DIQMTQSPSSLSASVGDRVTITCRASQVSSTSLNWYQQKPGKAPKLLI

YGASNLASGVPSRFSGSGSGTDFTLTISSLQPEDFATYYCQQYGHPPY

TFGQGTKVEIK
```

To generate a Fab version of the anti-PSA antibody, the VH sequence was coupled to the CH1 region of IgG4 and the VL sequence was coupled to the constant region of kappa 1 to give SEQ ID NO: 132 and SEQ ID NO: 133 as shown below.

```
Heavy-chain variable region-CH1:
                                        (SEQ ID NO: 132)
EVQLLESGGGLVQPGGSLRLSCAASGFTVSNYAMSWVRQAPGKGLEWV

GDIYPTSGYTDYADSVKGRFTISRDNSKNTLYLQMNSLRAEDTAVYYC

ARWGYDYKYVASEGSWLFDYWGQGTLVTVSSASTKGPSVFPLAPSSKS

TSGGTAALGCLVKDYFPEPVTVSWNSGALTSGVHTFPAVLQSSGLYSL

SSVVTVPSSSLGTQTYICNVNHKPSNTKVDKKVEPKSCDKTH

Light-chain variable region-kappa 1:
                                        (SEQ ID NO: 133)
DIQMTQSPSSLSASVGDRVTITCRASQVSSTSLNWYQQKPGKAPKLLI

YGASNLASGVPSRFSGSGSGTDFTLTISSLQPEDFATYYCQQYGHPPY

TFGQGTKVEIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC
```

The anti-PSA Fab may be expressed by introducing the VL sequence coupled to the constant kappa 1 sequence into a pDS-Fab vector at the Bgl II and Not I restriction sites and introducing the VH into the Bam H1 and Hind III sites of the pDS-Fab vector.

The peptide library was designed to be 26 amino acids in length, with the first 23 N-terminal amino acids randomized with repeated VBT codons which code for the following 9 amino acids T (Thr, Threonine), A (Ala, Alanine), P (Pro, Proline), I (Ile, Isoleucine), V (Val, Valine), L (Leu, Leucine), S (Ser, Serine), G (Gly, Glycine), R (Arg, Arginine) and the remaining three amino acids at the C-terminus were derived from a degenerate codon, NNS which codes for all 20 naturally occurring amino acid residues. Additionally, a sequence encoding a hexa-His tag was linked to the C-terminus of the peptide.

The randomized novel peptides were generated from an oligonucleotide comprising degenerate codons. For example, for a 26 amino acid long peptide, the following oligonucleotide was synthesized:

```
                                        (SEQ ID NO: 134)
5'CTCTGGAGGTGGTGGCAGCAAGCTTVBTVBTVBTVBTVBTVBTVBT

VBTVBTVBTVBTVBTVBTVBTVBTVBTVBTVBTVBTVBTVBTVBTVBT

NNSNNSNNSCATCACCATCACCATCACTGAGTTTAA-3'.
```

This oligonucleotide was then converted into double strand DNA fragments which were associated with the novel anti-PSA Fab fragment carrying a V5 epitope tag followed by a (GGGGS)$_3$ (SEQ ID NO: 123) linker. The resulting peptide library was cloned into the Hind III and Pme I sites of the pDS_Fab vector carrying the light and heavy chains for the novel anti-PSA Fab fragment. This vector has a low copy replication origin (CEN6/ARS4) for plasmid replication in yeast; a Zeocin resistant gene (Zeo) for selection in yeast; a gene for the synthesis of Tryptophan in yeast (trp); a pUC Ori for replication in *E. coli*; an ampicillin resistant gene (Amp) for selection in *E. coli*; the randomized novel peptide for displaying fusion proteins at the yeast cell surface and a dual inducible yeast promoter (Gal$\frac{1}{10}$ promoter) for the coordinated expression of the heavy and light chains of a Fab antibody. The leader peptide for both the light chain and heavy chain is that of the agglutinin adhesion subunit. In addition, the vector also contains a portion of the N-terminal of a gene for Leucine (leu) synthesis in yeast cells to support subsequent in vivo homologous recombination (see, FIG. 1). Upon expression of the vector, the Fab heavy chain fragment associated with a novel peptide and the Fab light chain fragment are produced. Both the Fab heavy and light chain fragment are then secreted from the cell where the light chain fragment may associate with the heavy chain fragment to generate a complete Fab comprising both heavy and light chain fragments.

Next, the vectors comprising sequences encoding the randomized peptides associated with the novel anti-PSA Fab fragment were transformed into *E. coli* DH10 B electrocompetent cells. The size of the library was determined to be approximately 2.3 billion independent clones. A large-scale plasmid DNA preparation of the *E. coli* library was made and used to transform the yeast strain, BJ5464, using standard lithium chloride methodology (see, e.g., Gietz R D, Schiestl R H. *Nat Protoc.* 2:38-41(2007)).

Yeast cells were then screened to identify those yeast cells that displayed the heavy chain of the novel anti-PSA Fab fragment on their surface. Briefly, yeast cells from the amplified library were cultured in selective medium lacking tryptophan (7 g/L YNB containing ammonium sulfate, 0.74 g/L amino acids (−Trp), 20 g/L glucose, 8.4 g/L Na$_2$HPO$_4$-7H$_2$O, and 7.8 g/L NaH$_2$PO$_4$—H$_2$O; pH 6.25) at 30° C. overnight. The next day, 5 billion cells were harvested and resuspended at a concentration of 1×10$^7$ cells/ml in induction medium (e.g., selective medium with the 20 g/L glucose substituted with 20 g/L galactose, 20 g/L raffinose, and 1 g/L glucose) and cultured at 20° C. for an additional 16-24 hours. The following day, an aliquot of 5 billion cells was harvested and washed with wash buffer (PBS+5 g BSA/L). The cells were then resuspended in 5 ml of wash buffer containing 50 µl of mouse anti-V5 antibody. Next, the cells were incubated at room temperature for 1 hour followed by 10 minutes on ice. The cells were then washed with 25 ml of ice-cold wash buffer 3 times and resuspended in 2.5 ml of wash buffer containing 150 µl goat anti-mouse IgG conjugated magnetic beads (Miltenyi Biotec, Auburn, Calif.). After incubation on ice for 20 minutes, the cells were washed once with 25 ml of wash buffer and resuspended in 30 ml of fresh wash buffer.

Next, the cell suspension was then loaded onto a magnetic column (Miltenyi Biotech, Auburn Calif.). After washing off un-bound cells, captured cells were released by removing the column from the magnetic field and eluted with wash buffer. A total of $1.8 \times 10^7$ cells were eluted from the column. Next, the cells were expanded in selective medium by incubating and shaking at 30° C. overnight. $2.0 \times 10^8$ cells from the expanded culture were then sorted by FACS (e.g., FACSAria, Becton Dickenson). For FACS, cells were first induced to express Fab-V5-peptide, then washed, labeled with goat anti-V5 antibody and finally incubated in the presence of Alexa 488-conjugated donkey anti-goat secondary antibody. During FACS sorting, cells incubated with Alexa 488-conjugated donkey anti-goat secondary antibody in the absence of goat anti-V5 antibody were used to set the gates for sorting positive cells. Alexa 488 positive cells were then harvested and expanded. After two rounds of FACS, the numbers of cells displaying Fab-V5 were enriched. For a third round of FACS sorting, in addition to the goat anti-V5 antibody, biotin-conjugated antigen (e.g., PSA antigen) was added and binding to the displayed Fab was detected with PE-conjugated streptavidin. Five thousand cells exhibiting the brightest V5 staining were harvested and plated on selective plates. Of a total of 45 clones whose inserts encoding the Fab-peptide were sequenced, 36 distinct peptide sequences (e.g., some clones had identical sequences) were obtained from the clones harvested from the brightest V5 staining. Surprisingly, these peptide sequences expressed by the selected clones are highly proline-rich. In many cases, 50% percent or more of the residues in these peptides are proline, and in some cases, 80-90% or 80-96% (e.g., 88-96%) of the first 25 residues are proline (Table 2).

TABLE 2+

Peptide Sequences expressed by clones exhibiting Fab display.

| Clone No | Sequence | SEQ ID NO: | No. of Pro | Relative Display Level (%) Expt. 1 | Relative Display Level (%) Expt. 2 |
|---|---|---|---|---|---|
| Data Set A# | | | | | |
| DS7 | PPPTPPLPPPPPPPPLLLLLLLLPPPITITITEFKPLI | 56 | 17 | 84.1 | 90.7 |
| DS8 | PPPVLPPPPPPPPPAPPPPPPPP | 57 | 20 | 87.6 | 91.7 |
| DS12 | PPPTPPRTPPPPPPPPPPPPPPPPPLHHHHHHCV | 1 | 22 | 100.0 | 100.0 |
| DS41* | PPPTPPRTPPPPPPPPPPPPPPPPPLHHHHHHCV | 1 | 22 | 93.3 | 92.1 |
| DS46 | KPPPPPLTTPTPPPTTYYCYYSSPPPSPSPSLSLNR | 58 | 15 | 87.4 | 75.2 |
| DS47 | PPPPVTLAPPPPRPRPPPPPPPPLAHHHHHHCV | 59 | 17 | 73.0 | 75.2 |
| DS52* | PPPTPPRTPPPPPPPPPPPPPPPPPLHHHHHHCV | 1 | 22 | 93.0 | |
| DS100* | PPPTPPRTPPPPPPPPPPPPPPPPPLHHHHHHCV | 1 | 22 | 95.0 | |
| DS103* | PPPTPPRTPPPPPPPPPPPPPPPPPLHHHHHHCV | 1 | 22 | 94.7 | |
| DS121 | PPPPPPPPPPPPPPPPPPPPPPHPPSXSPXLCL | 60 | 27 | 71.6 | 75.6 |
| DS123 | PPPRPPPPPPPTPTRTRPPPPPPPPCHHLTITEFKPLI | 61 | 20 | 80.1 | 83.3 |
| DS177 | PPPVLPPPPPPPPPAPPPPPPPPPSPSPSLSLNRCLITTWYM | 62 | 24 | 89.4 | 94.2 |
| Data Set B | | | | | |
| DS12 | PPPTPPRTPPPPPPPPPPPPPPPPPLHHHHHHCV | 1 | 22 | 100 | |
| B1 | PPPPVTLAPPPPRPRPPPPPPPPLAHHHHHHCV | 63 | 17 | 75.6 | |
| B6* | PPPPVTLAPPPPRPRPPPPPPPPLAHHHHHHCV | 63 | 17 | 86.5 | |
| B9 | PPPPLPLPPPPPPPPPPPPHHPRHPGDDDDNQKTLNR | 64 | 19 | 86.5 | |
| B27 | PPPPLPPPPPPPPPPPPLLFSPHYPPPSSSPSLSLNR | 65 | 21 | 37.4 | |
| B28 | PPPALTLTPPPPPPPPPPPPPTPPPHHHHQ | 66 | 20 | 54.4 | |
| B36 | PPPARPPTPTTPPPPPPPPPPPPPRPHHHHHQ | 67 | 20 | 53.3 | |
| B39 | PPTTTTITTRTPPSSYYCYYYYPQPSPSPSLSLNR | 68 | 8 | 61.0 | |
| B40 | PPPTPPPPPPPPPPPPRAPPPTTHVAAGAPGARRCHGITITEFKPLI | 69 | 20 | 67.2 | |
| B47 | PPPPPLPLPPPPPPPPPPPSPRPPPCPSTTTQLN | 70 | 23 | 55.0 | |
| B51 | PPPTPTIPTRTTPNYSYSCYYYYPLPSSSPSLSLNR | 71 | 9 | 45.5 | |

TABLE 2+-continued

Peptide Sequences expressed by clones exhibiting Fab display.

| Clone No | Sequence | SEQ ID NO: | No. of Pro | Relative Display Level (%) Expt. 1 | Expt. 2 |
|---|---|---|---|---|---|
| | Data Set C^ | | | | |
| 1 | PPPPPPPPPPAPPPPPPRPPTVTPTPPRICSYSYYSVPPSSSPSLSLNR | 72 | 25 | | |
| 2 | PPPPLPPPPPPPPPPPPPPPRCSPHHHHPITEFKPLI | 73 | 24 | | |
| 29 | TAPPPPPPPPPPPPLPPPPPPPVPPCHHHHHH | 74 | 21 | | |
| 30 | PPRPPPLPPPRPPLRPPPSPGPCLACLSTYPLPCRFKPLI | 75 | 19 | | |
| 40 | PPTPLAPLPPVRAPRASPPTPPPPPSHHHHHCLNR | 76 | 14 | | |
| 3* | PPPTPPRTPPPPPPPPPPPPPPPLHHHHHCV | 1 | 22 | | |
| 4 | PPPPPPAPPPPPPPPPPPPPPPPPPSSSPSLSLNR | 77 | 26 | | |
| 5** | PPPPPPAPPPPPPPPPPPPPPPPPPSSSPSLSLNR | 77 | 26 | | |
| 7 | PPTPPPPPTPPPPHYSYSFYYSSPPPSSSPSLSLNR | 78 | 16 | | |
| 8 | PPPPLPPPPPPAPPLPPPRPAPPPPPSSSPSLSLNR | 79 | 23 | | |
| 9* | PPPTPPRTPPPPPPPPPPPPPPPPLHHHHHCV | 1 | 22 | | |
| 10* | PPPTPPRTPPPPPPPPPPPPPPPPLHHHHHCV | 1 | 22 | | |
| 11 | PITITATPAPTTSTLTPTTTPPPAPPAPCHHHHPEKPLI | 80 | 11 | | |
| 12 | PPPPPPPPPPLPPTPPPPPPLPYCPPPSPSPSLSNPLI | 81 | 25 | | |
| 14 | PPPRPPPPPPPTPTRPPPPPPPPCHHLTITEFKPLI | 82 | 20 | | |
| 26 | PAATRRVTAPPLPPLAPPPLPPVSGIHHHHPITEKPLI | 83 | 12 | | |
| 28 | PPPPPLPLPPPPPPPPPPPPPPPPPSSSPSLSNR | 84 | 27 | | |
| 31 | PLPPLPPPPPPPPSSSSSSSSPPASSSPSLSLNR | 85 | 15 | | |
| 32*** | PITITATPAPTTSTLTPTTTPPPAPPAPCHHHHPEKPLI | 80 | 11 | | |
| 33 | TPPPRPPPPPTTLPRPPRPPPRLPPHHHHHHCV | 86 | 17 | | |
| 36 | PPPTLPPPPPPPPPPPRPPRPPPPCHHHHHH | 87 | 22 | | |
| 37 | PPPTLPLPPTPPPPPPPLPPPPPPPPCIIITITE | 88 | 21 | | |
| 34 | PPPPPPLPPIPPPPPPPPPPPPPPPPPSSSPS | 89 | 26 | | |

In the A data set, sequences were confirmed by repeated sequencing; residues with doubt over deduced amino acid identity are indicated by X; comparative FACS analysis was performed in two separate experiments: relative display values are the average of the two studies.
*Clones 41, 52, 100 and 103 all expressed the identical sequence that was expressed by clone DS12.
*identical to B1
^The clones in Data Set C were from the original set sorted from the population of yeast cells expressing surface displayed anti-PSA-Fab. The clones were sequenced but not FACS analyzed as individual clone populations.
*Identical sequence to Clone DS12
**Identical sequence to Clone 4
***Identical to Clone 11
†All display levels in Data Sets A-B are relative to clone DS12.

A subset of these clones were then analyzed as populations of cells derived from the individual clones to be able to compare their relative abilities to display the test Fab. The data were compared relative to the Fab display exhibited by clone DS12 within each experiment and the values obtained are shown in the right-most column of Table 2 [Relative Display Level (%)]. For data set A in Table 2, sequences were confirmed and comparative FACS analysis was performed in two separate experiments as shown. For data set B in Table 2, sequences were sequenced once and FACS analysis performed once. For data set C in Table 2, sequences of individual clones isolated from the initial sorted pool of antigen-positive (e.g., PSA-positive) clones were sequenced once and no FACS clonal analysis was performed.

Figure 2:
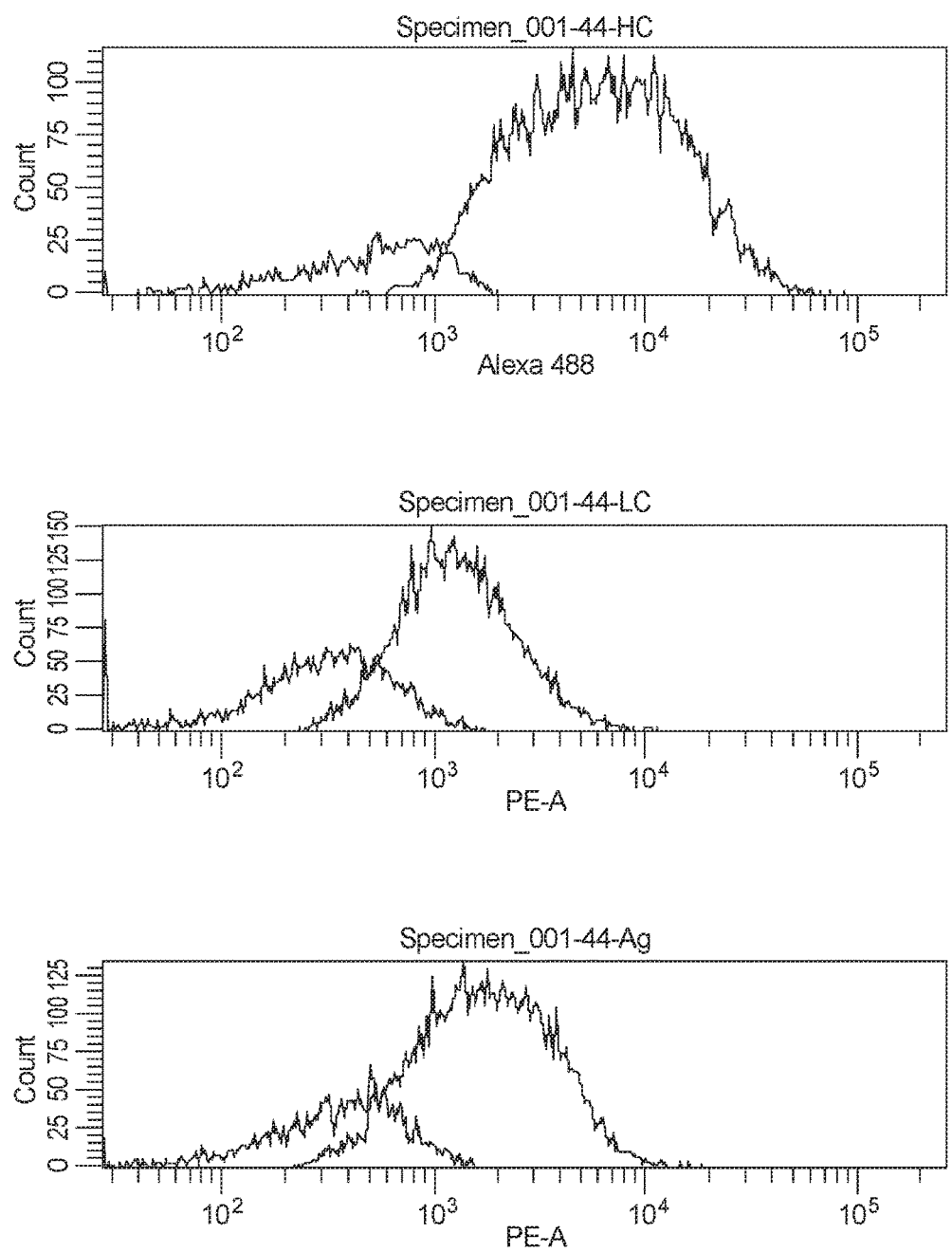
FIG. 2 shows an exemplary cytometric analysis of yeast cells for heavy and light chain expression and antigen binding.
Figure 4A:
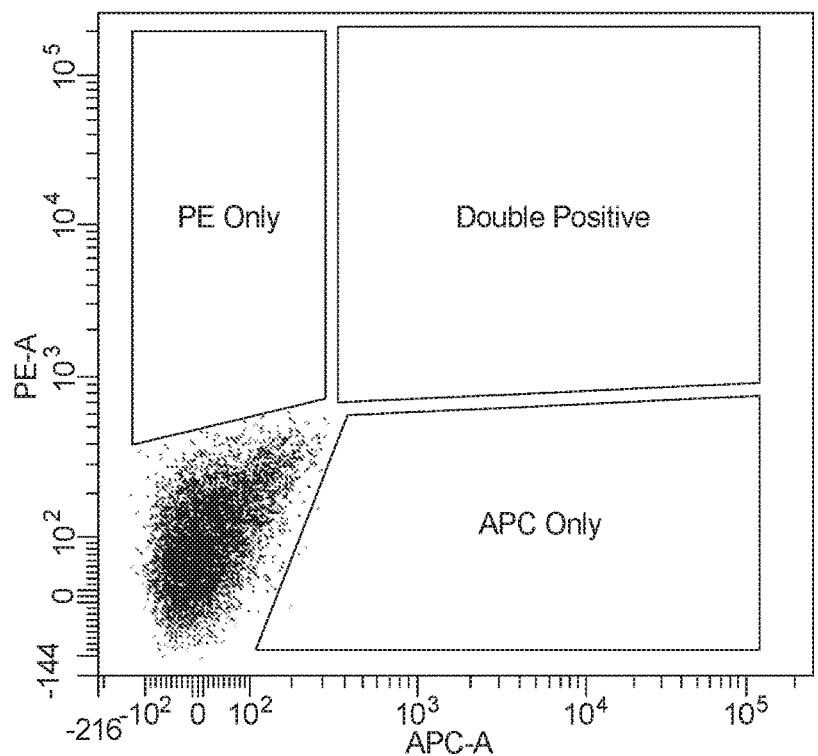
FIGS. 4A-4F depict an exemplary FACS sorting for yeast displayed antibody clones specific for Beta-2 microglobulin.
Figure 4B:
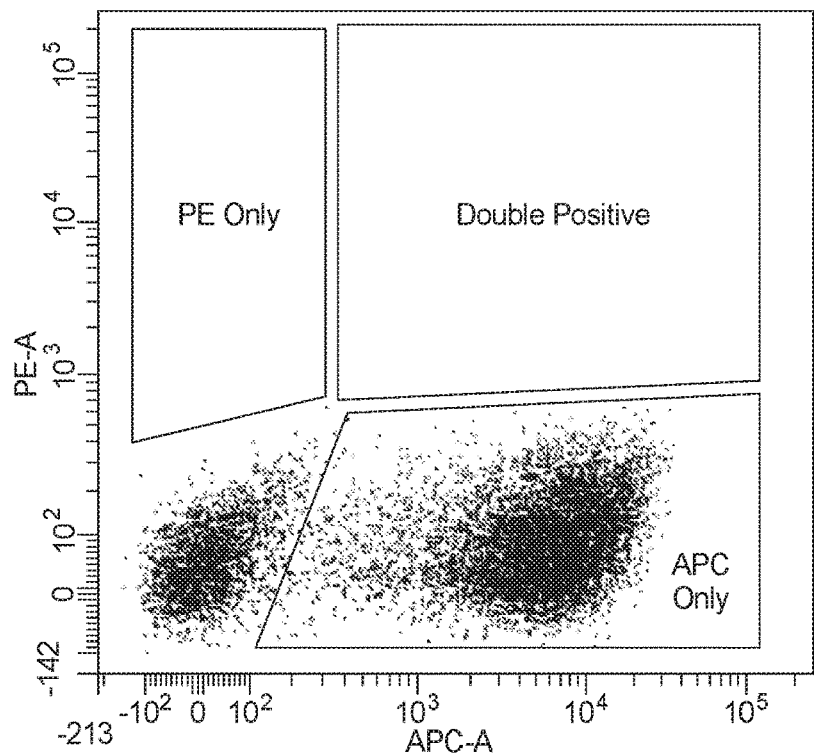
Figure 4C:
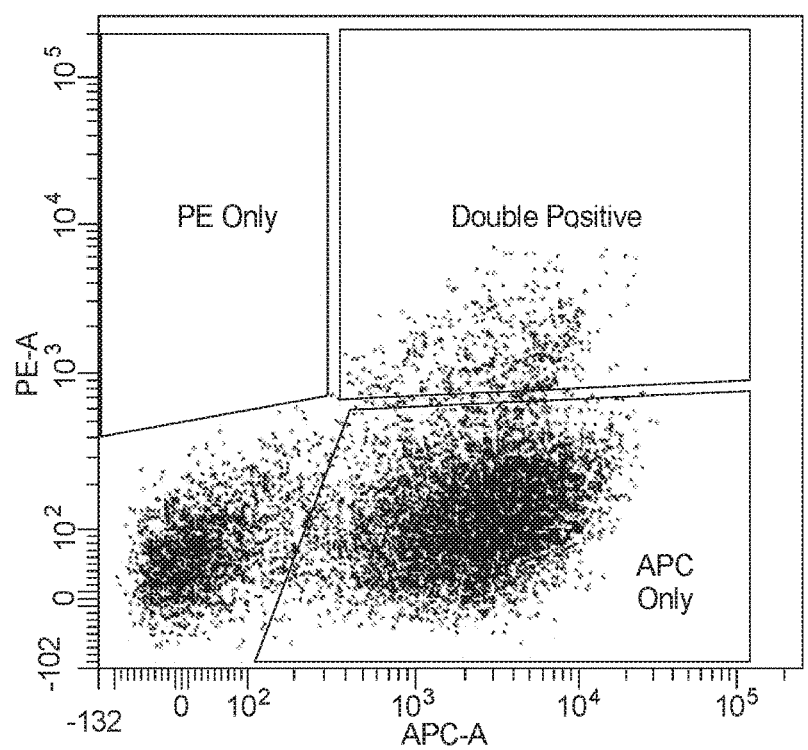
Figure 4D:
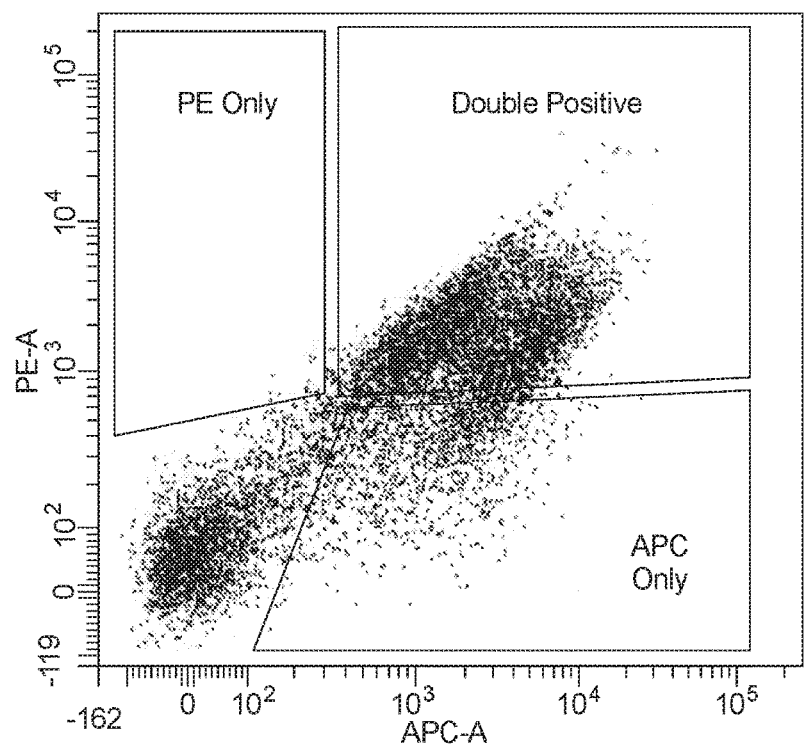
Figure 4E:
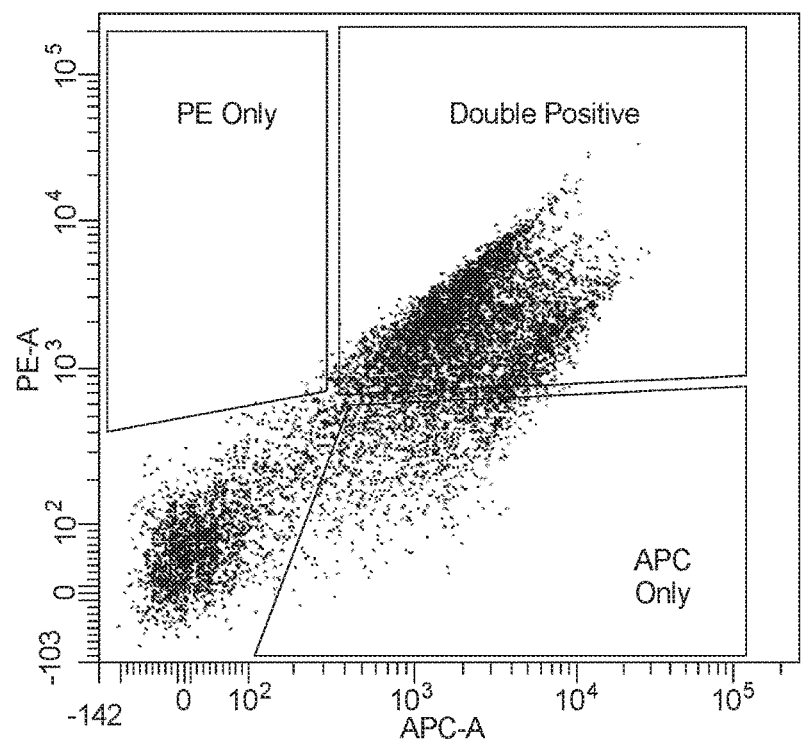
Figure 4F:
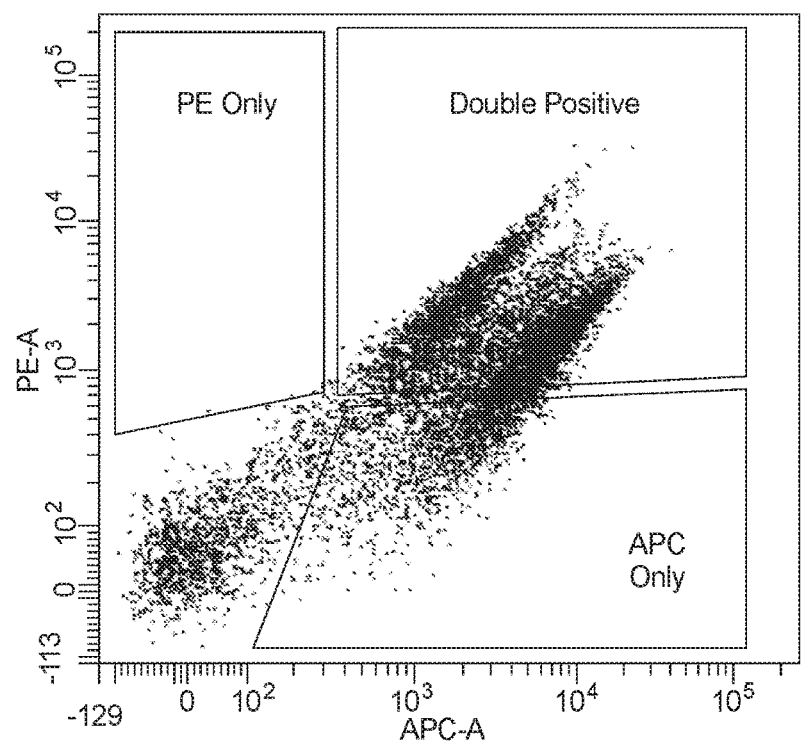

Clone DS12, which expresses the peptide, PPPTPPRTPPPPPPPPPPPPPPPPPLHHHHHHCV (SEQ ID NO: 1), was selected to be analyzed further. The DNA Fab heavy chain insert from clone 1 was modified to replace the V5 tag with a myc tag, then was re-cloned into a the pDS-Fab vector along with the light-chain insert of clone 1 and a fresh set of yeast cells was transformed. The yeast cells were plated onto selective plates lacking tryptophan, incubated at 30° C. for 2 days to allow the transformed cells to form colonies. Individual yeast colonies were picked and cultured in selective medium overnight. The yeast cells were then collected and resuspended in induction medium at a final OD600=0.5 and cultured at 20° C. for 16 hours to induce the expression of the heavy and light chains. Next, the cells were harvested and washed, then incubated with Alexa 488 conjugated anti-myc antibody, or PE conjugated anti-human kappa light chain for the detection of heavy and light chain expression, respectively. Another aliquot of the harvested cell population was incubated with PE-labeled antigen (e.g., PSA antigen) and then analyzed by flow cytometry (e.g., FACSAria, Becton Dickenson). In an exemplary flow cytometric analysis, about 84% and 73% of cells were positive for heavy and light chain expression respectively (FIG. 2, upper and middle panels), and about 70% cells were positive for binding to PSA (FIG. 2, lower panel).

To better understand the key structural features for effective Fab display, a series of directed mutations of the PPPTPPRTPPPPPPPPPPPPPPPPPLHHHHHHCV (SEQ ID NO: 1) peptide were made, including changing the intervening T and R residues systematically to alanine, deleting the terminal His tag and generating progressively shorter contiguous proline sequences, and replacing the C-terminal $(P)_8$ of clone 12-7 with an $(L)_8S$ sequence. These were then tested for their ability to display the novel anti-PSA Fab fragment on the yeast cell surface. Cells were stained for c-myc (heavy chain tag) using a mouse anti-c-myc antibody and Alexa 488 goat anti-mouse secondary antibody. All variants (e.g., peptide derivatives) were compared for display efficiency as percent of positive cells relative to the clone expressing peptide 12 (see, e.g., Table 3A, Relative Display Activity (%)). The display activity of some of the variants (e.g., peptide derivatives) as measured by the number of cells expressing the protein of interest (e.g., Fab) on the yeast cell surface is shown in Table 3B (Display Activity (% positive cells)).

TABLE 3A*

Sequences and relative display activity of peptide derivatives of clone DS12.

| Peptide | SEQ ID NO: | Amino Acid Sequence | Relative Display Activity(%) | | | |
|---|---|---|---|---|---|---|
| | | | 1 | 2 | 3 | Mean ± SEM |
| 12 | 1 | PPPTPPRTPPPPPPPPPPPPPPPPPLHHHHHHCV | 100 | 100 | | |
| 12-1 | 90 | PPPAPPRTPPPPPPPPPPPPPPPPPLHHHHHHCV | 92 | 86 | | |
| 12-2 | 91 | PPPTPPATPPPPPPPPPPPPPPPPPLHHHHHHCV | 87 | 86 | | |
| 12-3 | 92 | PPPTPPRAPPPPPPPPPPPPPPPPPLHHHHHHCV | 90 | 116 | | |
| 12-4 | 93 | PPPTPPRTPPPPPPPPPPPPPPPPPLHHHHHHCVPPPPPKPLI | 87 | 96 | | |
| 12-5 | 55 | PPPTPPRTPPPPPPPPPPPPPPPPPL | 56 | 26 | | |
| 12-6 | 94 | PPPTPPRTPPPPPPPPPPPPPPPP | 42 | 32 | | |
| 12-7 | 95 | PPPTPPRTPPPPPPPPPPPP | 44 | | | |
| V7.4 | 96 | PPPTPPRTPPPLLLLLLLLS | 105 | 93 | | |
| V8 | 97 | PPPPPPPPPPPLHHHHHHCV | 83 | 64 | 77 | 75 ± 6 |
| V16.1 | 98 | PPPPPPPPPHHHHHH | 37 | 37 | 47 | 41 ± 4 |
| V14.1 | 99 | PPPTPPRTPPP | 41 | 28 | 35 | 35 ± 3 |
| V17.2 | 100 | PPPPPP | 34 | 29 | 43 | 35 ± 4 |
| V19.2 | | PPP | 17 | 11 | 32 | 20 ± 7 |
| V17.1 | | | 0 | 0 | 0 | 0 |

TABLE 3A*-continued

Sequences and relative display activity of peptide derivatives of clone DS12.

| Peptide | SEQ ID NO: | Amino Acid Sequence | Relative Display Activity(%) | | | |
|---------|------------|---------------------|---|---|---|---|
| | | | 1 | 2 | 3 | Mean ± SEM |

*Each peptide was tested by inserting after the C-terminus of the heavy chain, replacing peptide 12. Oligonucleotides encoding the motif along with the (GGGS)3 linker region at the 3' end and a 5' region encoding a Pme I site and stop codon (5'-GTTTAAACTCATTAXXXXXXAAGCTTAGAACC-ACCACCACCGG-3' where XXX represents the sequence encoding the motif variant) were synthesized and used to amplify the CH1 domain using a forward primer, CDR3-F1 (5'-ACTGCTGTTTA-TTATTGTGCTAGA-3') using the display vector with DS12 as the template. The PCR products were then cloned into the display vector digested with Apa I and Pme I enzymes to replace the original CH1 domain along with the display motif.

TABLE 3B

Sequences and display activity of peptide derivatives of clone DS12.

| Peptide | SEQ ID NO: | Amino Acid Sequence | Display Activity (% positive cells) | | | |
|---------|------------|---------------------|----|----|----|------|
| | | | 1 | 2 | 3 | Mean |
| 12* | 1 | PPPTPPRTPPPPPPPPPPPPPPPPPLHHHHHHCV | 89 | 81 | 92 | 85 |
| V8 | 97 | PPPPPPPPPPPLHHHHHHCV | 74 | 52 | 72 | 64 |
| V16.1 | 98 | PPPPPPPPPPHHHHHH | 34 | 31 | 45 | 35 |
| V14.1 | 99 | PPPTPPRTPPP | 38 | 24 | 34 | 30 |
| V17.2 | 100 | PPPPPP | 32 | 24 | 41 | 30 |
| V19.2 | | PPP | 17 | 10 | 32 | 18 |
| V17.1 | | | 2 | 2 | 3 | 0 |

*Peptide 12 or clone DS12 refers to the proline-rich peptide having SEQ ID NO: 1 or a clone or cell expressing the peptide.

Additional proline-rich peptides as shown in Table 4 (Table 4A, 4B and 4C) below were generated, including those with a C-terminal region with non-proline amino acid residues and a N-terminal region with a number of proline amino acid residues (see, e.g., V24, V25, V26 and V27 as well as V23, V17.2 and V19.2), and variations of sequences (see, e.g., V16.1, V24, V36, V37, V39 and V40 as well as V23, V17.2, V19.2, and V28 through V35). Yeast cells harboring display constructs encoding different proline-rich peptides or constructs encoding immunoglobulin light and/or heavy chains but not encoding a proline-rich peptide (see, e.g., V17.1 and 38.2 used as negative controls) were grown in selective medium at 30° C. with shaking overnight, then diluted 1:10 in induction medium (e.g., selective medium with the 20 g/L glucose substituted with 20 g/L galactose, 20 g/L raffinose, and 1 g/L glucose, plus 1% casamino acid and 0.001% Triton X-100) and cultured for 2 days at 20° C. Cells were washed, incubated in goat anti-human antibody which recognizes both heavy and light immunoglobulin chains (ImmunoResearch Inc.) diluted to a final concentration of 10 μg/mL and incubated with cells in PBS+1% BSA for 30 minutes at room temperature, followed on ice for 10 minutes. The cells were washed 3 times with ice-cold PBS+1% BSA, and labeled with 1:100 diluted PE conjugated donkey anti-goat antibody (ImmunoResearch Inc, Cat #705-116-147) at 4° C. for 30 minutes. The cells were washed and analyzed using a Guava PCA cytometer.

TABLE 4A

Sequences and relative display activity of proline-rich peptides to display proteins of interest (e.g., Fab).

| Peptide | SEQ ID NO: | Amino Acid Sequence | Relative Display Activity (%) | | | | | |
|---------|------------|---------------------|-----|-----|-----|-----|-----|--------|
| | | | 1 | 2 | 3 | 4 | 5 | Mean |
| DS12 | 1 | PPPTPPRTPPPPPPPPPPPPPPPPPLHHHHHHCV | 100 | 100 | 100 | 100 | 100 | 100.00 |
| 12-1 | 90 | PPPaPPRTPPPPPPPPPPPPPPPPPLHHHHHHCV | | 95 | 108 | | | 102 |
| 12-2 | 91 | PPPTPPaTPPPPPPPPPPPPPPPPPLHHHHHHCV | | 73 | 54 | | | 63 |
| 24 | 101 | PPPPPPPPPLHHHHHH | 86 | 65 | 38 | | | 63 |
| V16.1 | 98 | PPPPPPPPPPHHHHHH | | 71 | 53 | | | 63 |
| V8 | 102 | PPPPPPPPPPPLHHHHHHCV | | 89 | 101 | | | 95 |

TABLE 4A-continued

Sequences and relative display activity of proline-rich peptides to display proteins of interest (e.g., Fab).

| Peptide | SEQ ID NO: | Amino Acid Sequence | Relative Display Activity (%) | | | | | |
|---|---|---|---|---|---|---|---|---|
| | | | 1 | 2 | 3 | 4 | 5 | Mean |
| 25 | 103 | PPPPPPPPPLHHHHHHCV | 96 | 91 | 83 | | | 90 |
| 27 | 104 | PPPPPPLHHHHHHCV | 99 | 90 | 100 | | | 96 |
| 26 | 105 | PPPLHHHHHHCV | 98 | 92 | 76 | | | 89 |
| V7.4 | 96 | PPPTPPRTPPPPLLLLLLLLS | | 97 | 93 | | | 95 |
| V14.1 | 99 | PPPTPPRTPPP | | 66 | 66 | | | 66 |
| 23 | 106 | PPPPPPPPP | 76 | 92 | 37 | | | 68 |
| 29 | 107 | PPPPPPP | 76 | 59 | 31 | | | 56 |
| V17.2 | 100 | PPPPPP | | 67 | 72 | | | 69 |
| V19.2 | | PPP | | 61 | 55 | | | 58 |
| 39-1 | 108 | PPPL | | 58 | 34 | | | 46 |
| 39-2 | 108 | PPPL | | 58 | 28 | | | 43 |
| 40-1 | 109 | PPPCV | | 74 | 49 | | | 61 |
| 28 | 110 | PPPTPPP | 63 | 51 | 60 | | | 58 |
| 30 | 111 | PPPGGPPP | 83 | 77 | 53 | | | 71 |
| 31 | 112 | PPPAPPP | 78 | 74 | 33 | | | 62 |
| 32 | 113 | PPPRPPP | 84 | 63 | 55 | | | 68 |
| 33 | 114 | PPPHPPP | 85 | 61 | 54 | | | 67 |
| 34 | 115 | PPPYPPP | 84 | 68 | 39 | | | 63 |
| 35 | 116 | PPPGPPP | 72 | 49 | 48 | | | 56 |
| 37.1 | 117 | HHHTITNEFKQTRSLI | | 56 | 31 | | | 43 |
| 37-2 | 118 | HHHHHH | | | 35 | | | 35 |
| 36-2 | 119 | HHHHHHCV | | 48 | 39 | | | 43 |
| V17.1 | | | | | | | | |
| 38.2 | | | | 32 | 22 | 9 | | 21 |

TABLE 4B

Sequences and display activity of proline-rich peptides to display proteins of interest (e.g., Fab).

| Peptide | SEQ ID NO: | Amino Acid Sequence | Display Activity (% positive cells) | | | | | |
|---|---|---|---|---|---|---|---|---|
| | | | 1 | 2 | 3 | 4 | 5 | Mean |
| DS12 | 1 | PPPTPPRTPPPPPPPPPPPPPPPPPPLHHHHHHCV | 98 | 90 | 82 | 86 | 83 | 88 |
| 12-1 | 90 | PPPaPPRTPPPPPPPPPPPPPPPPPPLHHHHHHCV | | 85 | 89 | | | 87 |
| 12-2 | 91 | PPPTPPaTPPPPPPPPPPPPPPPPPPLHHHHHHCV | | 68 | 44 | | | 56 |
| 24 | 101 | PPPPPPPPPLHHHHHH | 84 | 58 | 31 | | | 58 |
| V16.1 | 98 | PPPPPPPPPHHHHHH | | 64 | 45 | | | 54 |

TABLE 4B-continued

Sequences and display activity of proline-rich peptides to display proteins of interest (e.g., Fab).

| Peptide | SEQ ID NO: | Amino Acid Sequence | Display Activity (% positive cells) | | | | | |
|---|---|---|---|---|---|---|---|---|
| | | | 1 | 2 | 3 | 4 | 5 | Mean |
| V8 | 102 | PPPPPPPPPPPPLHHHHHHCV | | 80 | 83 | | | 81 |
| 25 | 103 | PPPPPPPPPLHHHHHHCV | 96 | 82 | 68 | | | 82 |
| 27 | 104 | PPPPPPLHHHHHHCV | 97 | 80 | 82 | | | 86 |
| 26 | 105 | PPPLHHHHHHCV | 96 | 82 | 63 | | | 80 |
| V7.4 | 96 | PPPTPPRTPPPPLLLLLLLLS | | 87 | 76 | | | 82 |
| V14.1 | 99 | PPPTPPRTPPP | | 59 | 54 | | | 56 |
| 23 | 106 | PPPPPPPPP | 75 | 82 | 30 | | | 62 |
| 29 | 107 | PPPPPPP | 75 | 53 | 34 | | | 54 |
| V17.2 | 100 | PPPPPP | | 60 | 59 | | | 59 |
| V19.2 | | PPP | | 55 | 45 | | | 50 |
| 39-1 | 108 | PPPL | | 52 | 28 | | | 40 |
| 39-2 | 108 | PPPL | | 52 | 23 | | | 37 |
| 40-1 | 109 | PPPCV | | 66 | 40 | | | 53 |
| 28 | 110 | PPPTPPP | | 62 | 46 | 49 | | 52 |
| 30 | 111 | PPPGGPPP | 81 | 69 | 44 | | | 64 |
| 31 | 112 | PPPAPPP | 77 | 66 | 27 | | | 57 |
| 32 | 113 | PPPRPPP | 83 | 57 | 45 | | | 62 |
| 33 | 114 | PPPHPPP | 83 | 55 | 44 | | | 61 |
| 34 | 115 | PPPYPPP | 82 | 61 | 32 | | | 58 |
| 35 | 116 | PPPGPPP | 71 | 44 | 39 | | | 51 |
| 37.1 | 117 | HHHTITNEFKQTRSLI | | 50 | 25 | | | 38 |
| 37-2 | 118 | HHHHHH | | | 29 | | | 29 |
| 36-2 | 119 | HHHHHHCV | | 43 | 32 | | | 37 |
| V17.1 | | | | 0.8 | 0.1 | | | 0.45 |
| 38.2 | | | | | 26 | 19 | 7 | 17 |

TABLE 4C

Sequences and display activity of proline-rich peptides to display proteins of interest (e.g., Fab) as measured by Positive Mean Intensity (PMI).

| Peptide | SEQ ID NO: | Amino Acid Sequence | PMI (mean fluorsense intensity of positive cells) | | | | | |
|---|---|---|---|---|---|---|---|---|
| | | | 1 | 2 | 3 | 4 | 5 | Mean |
| DS12 | 1 | PPPTPPRTPPPPPPPPPPPPPPPPPLHHHHHHCV | 403 | 254 | 187 | 197 | 192 | 246 |
| 12-1 | 90 | PPPaPPRTPPPPPPPPPPPPPPPPPLHHHHHHCV | | 211 | 175 | | | 193 |
| 12-2 | 91 | PPPTPPaTPPPPPPPPPPPPPPPPPLHHHHHHCV | | 52 | 34 | | | 43 |
| 24 | 101 | PPPPPPPPPLHHHHHH | 82 | 54 | 45 | | | 60 |
| V16.1 | 98 | PPPPPPPPPHHHHHH | | 61 | 44 | | | 53 |

TABLE 4C-continued

Sequences and display activity of proline-rich peptides to display proteins of interest (e.g., Fab) as measured by Positive Mean Intensity (PMI).

| Peptide | SEQ ID NO: | Amino Acid Sequence | PMI (mean fluorsense intensity of positive cells) | | | | | |
|---|---|---|---|---|---|---|---|---|
| | | | 1 | 2 | 3 | 4 | 5 | Mean |
| V8 | 102 | PPPPPPPPPPPPLHHHHHCV | | 138 | 126 | | | 132 |
| 25 | 103 | PPPPPPPPPLHHHHHHCV | 230 | 151 | 101 | | | 161 |
| 27 | 104 | PPPPPPLHHHHHHCV | 238 | 135 | 127 | | | 167 |
| 26 | 105 | PPPLHHHHHHCV | 192 | 147 | 102 | | | 147 |
| V7.4 | 96 | PPPTPPRTPPPPLLLLLLLS | | 141 | 104 | | | 123 |
| V14.1 | 99 | PPPTPPRTPPP | | 36 | 26 | | | 31 |
| 23 | 106 | PPPPPPPPP | 53 | 46 | 27 | | | 42 |
| 29 | 107 | PPPPPPP | 58 | 40 | 36 | | | 45 |
| V17.2 | 100 | PPPPPP | | 48 | 39 | | | 44 |
| V19.2 | | PPP | | 41 | 36 | | | 39 |
| 39-1 | 108 | PPPL | | 41 | 31 | | | 36 |
| 39-2 | 108 | PPPL | | 38 | 28 | | | 33 |
| 40-1 | 109 | PPPCV | | 66 | 43 | | | 54 |
| 28 | 110 | PPPTPPP | 66 | 30 | 33 | | | 43 |
| 30 | 111 | PPPGGPPP | 68 | 44 | 35 | | | 49 |
| 31 | 112 | PPPAPPP | 53 | 45 | 31 | | | 43 |
| 32 | 113 | PPPRPPP | 78 | 43 | 34 | | | 52 |
| 33 | 114 | PPPHPPP | 67 | 41 | 36 | | | 48 |
| 34 | 115 | PPPYPPP | 64 | 49 | 35 | | | 49 |
| 35 | 116 | PPPGPPP | 48 | 35 | 33 | | | 39 |
| 37.1 | 117 | HHHTITNEFKQTRSLI | | 35 | 29 | | | 32 |
| 37-2 | 118 | HHHHHH | | | 27 | | | 27 |
| 36-2 | 119 | HHHHHHCV | | 32 | 35 | | | 33 |
| V17.1 | | | | N/A | N/A | | | N/A |
| 38.2 | | | | 27 | 22 | 23 | | 24 |

Example 2: Construction of Host Displayed Protein Libraries Using Novel Peptides Novel peptides, including proline-rich peptides as identified in Example 1 (e.g., SEQ ID NO: 1; peptide 12 in Table 3A), may be used to display proteins of interest including, for example, antibodies or binding fragments thereof such as a full length antibody (e.g., IgG), Fab, antibody heavy chain or fragment thereof, antibody light chain or fragment thereof, or scFv on the surface of host cells.

A. Exemplary Fab Antibody Library

In an exemplary method, a large yeast display synthetic Fab antibody library was constructed, based on frameworks from a single pair of germline heavy chain variable (VH) and light chain variable (VL) regions with rationally randomized complementarity determining regions (CDRs). The diversity of the antibody library was created by introducing selected residues to selected positions at the CDRs, while retaining the sequences of the human germline framework.

Any VH and VL may be used in the construction of the library. For example, the VH germline VH3-23 (DP47) dominates the human antibody repertoire (Brezinschek et al. (1995) *J Immunol* 155:190-202; Tomlinson et al. (1996) *J. Mol. Biol.*, 256: 813; Kraj et al. (1997) *J Immunol*, 158: 5824-32), indicating that the framework of this germline can support highly diversified CDRs. In addition, VH3-23 pairs very well with almost all light chains. The VL germline A27 (DPK22) occurs most frequently in matured human antibodies (de Wildt et al. (1999) *J Mol Biol* 285:895-901). Therefore, the germline framework from DP47 and DPK 22 were used for the library construction.

Library diversity within the CDRs can then be generated by any method known in the art. In an exemplary method, library diversity was generated by constructing a mini-library for a CDR by tailor-randomizing CDR residues (e.g., residues that are at the periphery of the antigen-binding site and are intimately involved in antigen binding, specifically, residues 30-33 of CDR-H1, residues 49 of FR2, 50 and 52-54, 56, 58 of CDR-H2, residues 28-32 of CDR-L1, residues 50, 53, 55 of CDR-L2, and residues of 91-94 and 96 of CDR-L3).

The novel methods for randomizing one or more amino acid residues in an antibody complementarity determining region (CDR) may comprise (a) selecting one or more amino acid residues in a CDR for randomization; (b) synthesizing oligonucleotides comprising one or more nucleotides that are positioned 3' of a codon for a first CDR residue selected for randomization; (c) splitting the synthesized oligonucleotides into a first number of pools (e.g., columns), wherein the number of pools (e.g., columns) permit a frequency of randomized amino acid residues at the first amino acid position selected for randomization to approximate a predetermined frequency of amino acid residues at the selected position; (d) joining 3 nucleotides, one at a time, to the 5' end of the oligonucleotides in each pool (e.g., column), wherein the 3 nucleotides form a codon that is selected to approximate a predetermined frequency of an amino acid residue occurring at the position selected for randomization; and (e) combining the pools (e.g., columns) comprising oligonucleotides joined to the codon. The methods may further comprise randomizing a second amino acid residue in a CDR selected for randomization by (f) splitting the oligonucleotides of step (e) into a second number of pools (e.g., columns), wherein the number of pools (e.g., columns) permit a frequency of randomized amino acid residues at the second amino acid position selected for randomization to approximate a predetermined frequency of amino acid residues at the selected position; (g) joining 3 nucleotides, one at a time, to the 5' end of the oligonucleotides in each pool (e.g., column), wherein the 3 nucleotides form a codon that is selected to approximate a predetermined frequency of an amino acid residue occurring at the position selected for randomization; and (h) combining the pools (e.g., columns) comprising oligonucleotides joined to the codon. The methods of the present disclosure may further comprise steps for randomizing additional amino acid residues in a CDR selected for randomization, for example, 3, 4, 5, 6, 7, 8, 9, 10, 11, 12, 13, 14, 15, 16, 17, 18, 19, 20 . . . n, where n is the total number of amino acids selected for randomization, by repeating the splitting, joining and combining steps. Optionally, one or more nucleotides may be synthesized that are positioned 3' of a codon for a second CDR residue selected for randomization.

The tailor-randomization of residues at these positions was achieved by synthesizing oligonucleotides using a split and pool method wherein selected codons were incorporated into the oligonucleotides one base at a time for each residue position.

The codons incorporated into a selected CDR position were designed to approximate a predetermined frequency (e.g., percentage or prevelance) of amino acid residues at the amino acid position selected for randomization. For example, the predetermined frequency (e.g., the prevalence or percentage) of each codon at the one or more amino acid positions selected for randomization may be based on the frequency (e.g., the prevalence or percentage) of each amino acid in the 3,600 natural human antibodies included in the Kabat database (see, e.g., Johnson, G. and T. T. Wu (2000) *Nucleic Acids Res* 28(1):214-8.). Alternatively, the frequency (e.g., the prevalence or percentage) of each codon at the one or more amino acid positions selected for randomization may be based on naturally occurring frequencies of the amino acid residues within CDRs of human antibodies including, for example, as described in U.S. Patent Application Publication No. 2008/0003617 (see, e.g., Table 2), Knappik et al., *Mol Biol* 296:57-86 (see, e.g., Table 1), Lee et al., *J. Mol. Biol.* 340:1073-1093 (2004) (see, e.g., Tables 1 and 2) or U.S. Patent Application Publication No. 2005/119455 (see, e.g., FIGS. 1-3). Preferably, the predetermined frequency (e.g., the prevalence or percentage) of each codon at the one or more amino acid positions selected for randomization may be based on naturally occurring frequencies of the amino acid residues within CDRs of human antibodies as set forth in Table 5 below. Additionally, the number of pools (e.g., columns) used for randomization of a CDR residue at the selected position was predetermined to permit the generated oligonucleotide pool comprising randomized amino acids to comprise the minimal number of columns needed to obtain an approximate representation of amino acids residues at a predetermined frequency at the selected position.

TABLE 5

Prevalence of amino acid residues at the CDR positions (Kabat Numbering System) of human antibodies.

| Positions (VL) | Prevalence in natural antibodies (%) | Positions (VH) | Prevalence in natural antibodies (%) |
|---|---|---|---|
| L1-28 | S(33), N(17), V(17), D(12), G(12), I(3) | H1-30 | S(68), T(18), N(4), R(3), D(2), G(2) |
| L1-29 | I(40), S(18), V(16), G(12), N(10) | H1-31 | S(50), N(13), G(10), T(10), D(9), R(2), A(1) |
| L1-30 | S(55), N(11), K(11), G(6), R(5), Y(4), T(2), D(2), A(1) | H1-32 | Y(64), S(9), N(7), G(4), F(3), A(3) |
| L1-31 | S(44), N(32), T(11), R(6), I(2), D(2), K(2), G(1) | H1-33 | A(22), Y(20), W(17), G(14), S(12), D(3), T(3), N(2), V(2) |
| L1-31a | S (63), N (18), T (18) | H2-49 | G (50), S (25), A (25) |
| L1-32 | Y(67), N(8), W(6), F(5), S(4), D(3), R(2) | H2-50 | R(17), Y(10), W(9), V(9), G(9), I(8), E(8), A(6), S(6), N(6), L(4) |
| L2-50 | G(25), A(22), D(19), W(10), K(8), I(6), E(3), | H2-52 | S(26), Y(25), N(17), K(8), I(5), R(3), D(3), T(3) |

TABLE 5-continued

Prevalence of amino acid residues at the CDR positions
(Kabat Numbering System) of human antibodies.

| Positions (VL) | Prevalence in natural antibodies (%) | Positions (VH) | Prevalence in natural antibodies (%) |
|---|---|---|---|
| | S(2) | | |
| L2-53 | S(36), N(29), T(27), K(3), I(2), R(1) | H2-53 | S(24), D(20), Y(11), G(10), H(9), N(8), I(5), T(3), W(2) |
| L2-55 | A(45), Q(24), E(19), F(3), D(3) | H2-54 | G(37), S(26), D(11), N(7), K(6), F(5), T(4) |
| L3-91 | Y(54), S(12), R(11), A(7), G(4), H(3) | H2-56 | S(28), T(16), N(15), D(10), Y(10), E(5), G(5), A(2) |
| L3-92 | Y(23), G(22), N(15), s(12), D(7), L(6), T(4), H(3), I (2), | H2-58 | Y(32), N(25), D(12), R(7), S(4), I(4), T(3), H(2) |
| L3-93 | S(46), N(21), Q(7), T(6), H(4), G(3), D(3), R(2) | H3 (95-102) | G(15), Y(13), S(10), D(7.5), R(6), L (5), V(5), A(5), T(5), P (5), F(4), N(4), W(3), I(3), E(3), H(2), K(1), Q(1), M (1). |
| L3-94 | S(24), T(23), W(18), Y(11), L(7), F(5), A(3), P(3), V(2), I (1) | | |
| L3-96 | L(22), Y(13), W(11), F(9), I(7), R(7), P(3) | | |

For example, in HCDR1, at Kabat position 33, codons GCT and TAT may be joined to oligonucleotides in a selected number of oligonucleotide pools within a set number of oligonucleotide pools (e.g., three out of thirteen of the oligonucleotide pools), codon TGG may be joined to oligonucleotides in a selected number of oligonucleotide pools within a set number of oligonucleotide pools (e.g., two out of thirteen of the oligonucleotide pools), and codons GGT, TCT, GAT, ACT and GTT may be each joined to oligonucleotides in a selected number of oligonucleotide pools within a set number of oligonucleotide pools (e.g., one out of thirteen of the oligonucleotide pools). At Kabat position 32, codon TAT may be joined to oligonucleotides in a selected number of oligonucleotide pools within a set number of oligonucleotide pools (e.g., eight out of thirteen of the oligonucleotide pools), and codons TCT, AAT, GGT, TTT and GCT may be each joined to oligonucleotides in a selected number of oligonucleotide pools within a set number of oligonucleotide pools (e.g., one out of thirteen of the oligonucleotide pools). At Kabat position 31, codon TCT may be joined to oligonucleotides in a selected number of oligonucleotide pools within a set number of oligonucleotide pools (e.g., six out of thirteen of the oligonucleotide pools), codon AAT may be joined to oligonucleotides in a selected number of oligonucleotide pools within a set number of oligonucleotide pools (e.g., two out of thirteen of the oligonucleotide pools), and codons GGT, ACT, GAT, AGA and GCT may be each joined to oligonucleotides in a selected number of oligonucleotide pools within a set number of oligonucleotide pools (e.g., one out of thirteen of the oligonucleotide pools). At Kabat position 30, codon TCT may be joined to oligonucleotides in a selected number of oligonucleotide pools within a set number of oligonucleotide pools (e.g., seven out of thirteen of the oligonucleotide pools), codon ACT may be joined to oligonucleotides in a selected number of oligonucleotide pools within a set number of oligonucleotide pools (e.g., two out of thirteen of the oligonucleotide pools), and codons AAT, AGA, GAT, GGT may be each joined to oligonucleotides in a selected number of oligonucleotide pools within a set number of oligonucleotide pools (e.g., one out of thirteen of the oligonucleotide pools).

For example, in HCDR2, at Kabat position 58, codon TAT may be joined to oligonucleotides in a selected number of oligonucleotide pools within a set number of oligonucleotide pools (e.g., four out of twelve of the oligonucleotide pools), codon AAT may be joined to oligonucleotides in a selected number of oligonucleotide pools within a set number of oligonucleotide pools (e.g., two out of twelve of the oligonucleotide pools), and codons GAT, AGA, TCT, ATT, ACT and CAT may be each joined to oligonucleotides in a selected number of oligonucleotide pools within a set number of oligonucleotide pools (e.g., one out of twelve of the oligonucleotide pools). At Kabat position 57, codon ACT may be joined to oligonucleotides in a selected number of oligonucleotide pools within a set number of oligonucleotide pools (e.g., twelve out of twelve of the oligonucleotide pools). At Kabat position 56, codon TCT may be joined to oligonucleotides in a selected number of oligonucleotide pools within a set number of oligonucleotide pools (e.g., four out of twelve of the oligonucleotide pools), codon ACT may be joined to oligonucleotides in a selected number of oligonucleotide pools within a set number of oligonucleotide pools (e.g., two out of twelve of the oligonucleotide pools), and codons AAT, GAT, TAT, GM, GGT, and GCT may be each joined to oligonucleotides in a selected number of oligonucleotide pools within a set number of oligonucleotide pools (e.g., one out of twelve of the oligonucleotide pools). At Kabat position 55, codon GGT may be joined to oligonucleotides in a selected number of oligonucleotide pools within a set number of oligonucleotide pools (e.g., twelve out of twelve of the oligonucleotide pools). At Kabat position 54, codon GGT may be joined to oligonucleotides in a selected number of oligonucleotide pools within a set number of oligonucleotide pools (e.g., four out of twelve of the oligonucleotide pools), codon TCT may be joined to oligonucleotides in a selected number of oligonucleotide pools in a set number of oligonucleotide pools (e.g., three out of twelve of the oligonucleotide pools), and codons GAT, MT, AM, TTT, ACT may be each joined to oligonucleotides in a selected number of oligonucleotide pools within a set number of oligonucleotide pools (e.g., one out of twelve of the oligonucleotide pools). At Kabat position 53, codon TCT may be joined to oligonucleotides in a selected number of oligonucleotide pools within a set number of oligonucleotide pools (e.g., three out of twelve of the oligonucleotide pools), codon GAT may be joined to oligonucleotides in a selected number of oligonucleotide pools within a set number of oligonucleotide pools (e.g., two out of twelve of the oligonucleotide pools), and codons TAT, GGT, CAT, AAT, ATT, ACT and TGG may be each joined to oligonucleotides in a selected number of oligonucleotide pools within a set number of oligonucleotide pools (e.g., one out of twelve of the oligonucleotide pools). At Kabat position 52a, codon CCA may be joined to oligonucleotides in a selected number of oligonucleotide pools within a set number of oligonucleotide pools (e.g., five out of twelve of the oligonucleotide pools), codon GGT may be joined to oligonucleotides in a selected number of oligonucleotide pools within a set number of oligonucleotide pools (e.g., four out of twelve of the oligonucleotide pools), and codon TCT may be joined to oligonucleotides in a selected number of oligonucleotide pools within a set number of oligonucleotide pools (e.g., three out of twelve of the oligonucleotide pools). At Kabat position 52, codon TCT may be joined to oligonucleotides in a selected number of oligonucleotide pools within a set number of oligonucleotide pools (e.g., three out of twelve of the oligonucleotide pools), codon TAT may be joined to oligonucleotides in a selected number of oligonucleotide pools within a set number of oligonucleotide pools (e.g., three out of twelve of the oligonucleotide pools), and codons AAT, AAA, ATT, AGA, GAT, ACT may be each joined to oligonucleotides in a selected number of oligonucleotide pools within a set number of oligonucleotide pools (e.g., one out of twelve of the oligonucleotide pools). At Kabat position 51, codon ATC may be joined to oligonucleotides in a selected number of oligonucleotide pools within a set number of oligonucleotide pools (e.g., twelve out of twelve of the oligonucleotide pools). At Kabat position 50, codon AGA may be joined to oligonucleotides in a selected number of oligonucleotide pools within a set number of oligonucleotide pools (e.g., two out of twelve of the oligonucleotide pools), and codons TAT, TGG, GTT, GGT, ATT, GAA, GCT, TCT, AAT, TTA may be each joined to oligonucleotides in a selected number of oligonucleotide pools within a set number of oligonucleotide pools (e.g., one out of twelve of the oligonucleotide pools). At Kabat position 49, codon GGT may be joined to oligonucleotides in a selected number of oligonucleotide pools within a set number of oligonucleotide pools (e.g., six out of twelve of the oligonucleotide pools), codon TCT may be joined to oligonucleotides in a selected number of oligonucleotide pools within a set number of oligonucleotide pools (e.g., three out of twelve of the oligonucleotide pools), and codon GCT may be joined to oligonucleotides in a selected number of oligonucleotide pools within a set number of oligonucleotide pools (e.g., three out of twelve of the oligonucleotide pools).

For example, in LCDR1, at Kabat position 32, codon TAT may be joined to oligonucleotides in a selected number of oligonucleotide pools within a set number of oligonucleotide pools (e.g., six out of eleven of the oligonucleotide pools), and codons AAT, TGG, TTT, TCT and GAT may be each joined to oligonucleotides in a selected number of oligonucleotide pools within a set number of oligonucleotide pools (e.g., one out of eleven of the oligonucleotide pools). At Kabat position 31a, codon TCT may be joined to oligonucleotides in a selected number of oligonucleotide pools within a set number of oligonucleotide pools (e.g., seven out of eleven of the oligonucleotide pools), codon AAT may be joined to oligonucleotides in a selected number of oligonucleotide pools within a set number of oligonucleotide pools (e.g., two out of eleven of the oligonucleotide pools) and codon ACT may be joined to oligonucleotides in a selected number of oligonucleotide pools within a set number of oligonucleotide pools (e.g., two out of eleven of the oligonucleotide pools). At Kabat position 31, codon TCT may be joined oligonucleotides in a selected number of oligonucleotide pools within a set number of oligonucleotide pools (e.g., four out of eleven of the oligonucleotide pools), codon AAT may be joined to oligonucleotides in a selected number of oligonucleotide pools within a set number of oligonucleotide pools (e.g., two out of eleven of the oligonucleotide pools), and codons ACT, AGA, ATT, GAT and AAA may be each joined to oligonucleotides in a selected number of oligonucleotide pools within a set number of oligonucleotide pools (e.g., one out of eleven of the oligonucleotide pools). At Kabat position 30, codon TCT may be joined to oligonucleotides in a selected number of oligonucleotide pools within a set number of oligonucleotide pools (e.g., five out of eleven of the oligonucleotide pools), codon AAT may be joined to oligonucleotides in a selected number of oligonucleotide pools within a set number of oligonucleotide pools (e.g., two out of eleven of the oligonucleotide pools), and codons AAA, GGT, AGA and TAT may be each joined to oligonucleotides in a selected number of oligonucleotide pools within a set number of oligonucleotide pools (e.g., one out of eleven of the oligonucleotide pools). At Kabat position 29, codon ATT may be joined to oligonucleotides in a selected number of oligonucleotide pools within a set number of oligonucleotide pools (e.g., five out of eleven of the oligonucleotide pools), codon TCT is joined to oligonucleotides in a selected number of oligonucleotide pools within a set number of oligonucleotide pools (e.g., two out of eleven of the oligonucleotide pools), codon GTT may be joined to oligonucleotides in a selected number of oligonucleotide pools within a set number of oligonucleotide pools (e.g., two out of eleven of the oligonucleotide pools), and codons GGT and AAT may each be joined to oligonucleotides in a selected number of oligonucleotide pools within a set number of oligonucleotide pools (e.g., one out of eleven of the oligonucleotide pools). At Kabat position 28 codon TCT may be joined to oligonucleotides in a selected number of oligonucleotide pools within a set number of oligonucleotide pools (e.g., three out of eleven of the oligonucleotide pools), codon AAT may be joined to oligonucleotides in a selected number of oligonucleotide pools within a set number of oligonucleotide pools (e.g., two out of eleven of the oligonucleotide pools), codon GTT my be joined to oligonucleotides in a selected number of oligonucleotide pools within a set number of oligonucleotide pools (e.g., two out of eleven of the oligonucleotide pools), codon GGT may be joined to oligonucleotides in a selected number of oligonucleotide pools within a set number of oligonucleotide pools (e.g., two out of eleven of the oligonucleotide pools), and codon GAT my be joined oligonucleotides in a selected number of oligonucleotide pools within a set number of oligonucleotide pools (e.g., two out of eleven of the oligonucleotide pools).

For example, in LCDR2, at Kabat position 55, codon GCT may be joined to oligonucleotides in a selected number of oligonucleotide pools within a set number of oligonucleotide pools (e.g., four out of ten of the oligonucleotide pools), codon CM may be joined to oligonucleotides in a selected number of oligonucleotide pools within a set number of oligonucleotide pools (e.g., three out of ten of the oligonucleotide pools), and codon GM may be joined to oligonucleotides in a selected number of oligonucleotide pools within a set number of oligonucleotide pools (e.g., three out of ten of the oligonucleotide pools). At Kabat position 53, codon TCT may be joined to oligonucleotides in a selected number of oligonucleotide pools within a set number of oligonucleotide pools (e.g., four out of ten of the oligonucleotide pools), codon MT may be joined to oligonucleotides in a selected number of oligonucleotide pools within a set number of oligonucleotide pools (e.g., three out of ten of the oligonucleotide pools), and codon ACT may be joined to oligonucleotides in a selected number of oligonucleotide pools within a set number of oligonucleotide pools (e.g., three out of ten of the oligonucleotide pools). At Kabat position 51, codon GCT may be joined to oligonucleotides in a selected number of oligonucleotide pools within a set number of oligonucleotide pools (e.g., ten out of ten of the oligonucleotide pools). At Kabat position 50, codon GGT may be joined to oligonucleotides in a selected number of oligonucleotide pools within a set number of oligonucleotide pools (e.g., two out of ten of the oligonucleotide pools), codon GCT may be joined to oligonucleotides in a selected number of oligonucleotide pools within a set number of oligonucleotide pools (e.g., two out of ten of the oligonucleotide pools), codon GAT may be joined to oligonucleotides in a selected number of oligonucleotide pools within-a set number of oligonucleotide pools (e.g., two out of ten of the oligonucleotide pools), and codons TGG, AAA, TTA and GM may be each joined to oligonucleotides in a selected number of oligonucleotide pools within-a set number of oligonucleotide pools (e.g., one out of ten of the oligonucleotides).

For example, in LCDR3, at Kabat position 96, codon TTA may be joined to oligonucleotides in a selected number of oligonucleotide pools within a set number of oligonucleotide pools (e.g., three out of twelve of the oligonucleotide pools), codon TAT may be joined to oligonucleotides in a selected number of oligonucleotide pools within a set number of oligonucleotide pools (e.g., two out of twelve of the oligonucleotide pools), codon TGG may be joined to oligonucleotides in a selected number of oligonucleotide pools within a set number of oligonucleotide pools (e.g., two out of twelve of the oligonucleotide pools), and codons TTT, ATT, AGA, CCA and TAT may be each joined to oligonucleotides in a selected number of oligonucleotide pools within a set number of oligonucleotide pools (e.g., one out of twelve of the oligonucleotide pools). At Kabat position 94, codon TCT may be joined to oligonucleotides in a selected number of oligonucleotide pools within a set number of oligonucleotide pools (e.g., two out of twelve of the oligonucleotide pools), codon ACT may be joined to oligonucleotides in a selected number of oligonucleotide pools within a set number of oligonucleotide pools (e.g., two out of twelve of the oligonucleotide pools), codon TGG may be joined to oligonucleotides in a selected number of oligonucleotide pools within a set number of oligonucleotide pools (e.g., two out of twelve of the oligonucleotide pools), codon TAT may be joined to oligonucleotides in a selected number of oligonucleotide pools within a set number of oligonucleotide pools (e.g., two out of twelve of the oligonucleotide pools), and codons TTA, TTT, GCT and CCA may be each joined to oligonucleotides in a selected number of oligonucleotide pools within a set number of oligonucleotide pools (e.g., one out of twelve of the oligonucleotide pools). At Kabat position 93, codon TCT may be joined to oligonucleotides in a selected number of oligonucleotide pools within a set number of oligonucleotide pools (e.g., five out of twelve of the oligonucleotide pools), codon MT may be joined to oligonucleotides in a selected number of oligonucleotide pools within a set number of oligonucleotide pools (e.g., two out of twelve of the oligonucleotide pools), and codons CAA, ACT, CAT, GGT and GAT may be each joined to oligonucleotides in a selected number of oligonucleotide pools within a set number of oligonucleotide pools (e.g., one out of twelve of the oligonucleotide pools). At Kabat position 92, codon TAT may be joined to oligonucleotides in a selected number of oligonucleotide pools within a set number of oligonucleotide pools (e.g., three out of twelve of the oligonucleotide pools), codon GGT may be joined to oligonucleotides in a selected number of oligonucleotide pools within a set number of oligonucleotide pools (e.g., two out of twelve of the oligonucleotide pools), and codons MT, TCT, GAT, TTA, ACT, CAT and ATT may be each joined to oligonucleotides in a selected number of oligonucleotide pools within a set number of oligonucleotide pools (e.g., one out of twelve of the oligonucleotide pools). At Kabat position 91 codon TAT may be joined to oligonucleotides in a selected number of oligonucleotide pools within a set number of oligonucleotide pools (e.g., seven out of twelve of the oligonucleotide pools), codon TCT may be joined to oligonucleotides in a selected number of oligonucleotide pools within a set number of oligonucleotide pools (e.g., two out of twelve of the oligonucleotide pools), and codons AGA, GCT and GGT may be each joined oligonucleotides in a selected number of oligonucleotide pools within a set number of oligonucleotide pools (e.g., one out of twelve of the oligonucleotide pools).

For example, in HCDR3, at Kabat position 100b codon GGT may be joined to oligonucleotides in a selected number of oligonucleotide pools within a set number of oligonucleotide pools (e.g., four out of twenty-nine out of twenty-nine of the oligonucleotide pools), codon TAT may be joined to oligonucleotides in a selected number of oligonucleotide pools within a set number of oligonucleotide pools (e.g., four out of twenty-nine of the oligonucleotide pools), codon TCT may be joined to oligonucleotides in a selected number of oligonucleotide pools within a set number of oligonucleotide pools (e.g., four out of twenty-nine of the oligonucleotide pools), codon GAT may be joined to oligonucleotides in a selected number of oligonucleotide pools within a set number of oligonucleotide pools (e.g., two out of twenty-nine of the oligonucleotide pools), and codons AGA, TTA, GTT, GCT, CCA, ACT, AAT, UT, ATT, GAA, CAT, CAA, AAA, ATG and TGG may each be joined to oligonucleotides in a selected number of oligonucleotide pools within a set number of oligonucleotide pools (e.g., one out of twenty-nine of the oligonucleotide pools). At Kabat position 100a, codon GGT may be joined to oligonucleotides in a selected number of oligonucleotide pools within a set number of oligonucleotide pools (e.g., four out of twenty-nine of the oligonucleotide pools), codon TAT may be joined to oligonucleotides in a selected number of oligonucleotide pools within a set number of oligonucleotide pools (e.g., four out of twenty-nine of the oligonucleotide pools), codon TCT may be joined oligonucleotides in a selected number of oligonucleotide pools within a set number of oligonucleotide pools (e.g., four out of twenty-nine of the oligonucleotide pools), codon GAT may be joined to oligonucleotides in a selected number of oligonucleotide pools within a set number of oligonucleotide pools (e.g., two out of twenty-nine of the oligonucleotide pools), and codons AGA, TTA, GTT, GCT, CCA, ACT, AAT, TTT, ATT, GAA, CAT, CAA, AAA, ATG and TGG may each be joined to oligonucleotides in a selected number of oligonucleotide pools within a set number of oligonucleotide pools (e.g., one out of twenty-nine of the oligonucleotide pools). At Kabat position 99, codon GGT may be joined to oligonucleotides in a selected number of oligonucleotide pools within a set number of oligonucleotide pools (e.g., four out of twenty-nine of the oligonucleotide pools), codon TAT may be joined to oligonucleotides in a selected number of oligonucleotide pools within a set number of oligonucleotide pools (e.g., four out of twenty-nine of the oligonucleotide pools), codon TCT may be joined to oligonucleotides in a selected number of oligonucleotide pools within a set number of oligonucleotide pools (e.g., four out of twenty-nine of the oligonucleotide pools), codon GAT may be joined to oligonucleotides in a selected number of oligonucleotide pools within a set number of oligonucleotide pools (e.g., two out of twenty-nine of the oligonucleotide pools), and codons AGA, TTA, GTT, GCT, CCA, ACT, AAT, TTT, ATT, GAA, CAT, CAA, AAA, ATG and TGG may each be joined to oligonucleotides in a selected number of oligonucleotide pools within a set number of oligonucleotide pools (e.g., one out of twenty-nine of the oligonucleotide pools). At Kabat position 98, codon GGT may be joined to oligonucleotides in a selected number of oligonucleotide pools within a set number of oligonucleotide pools (e.g., four out of twenty-nine of the oligonucleotide pools), codon TAT may be joined to oligonucleotides in a selected number of oligonucleotide pools within a set number of oligonucleotide pools (e.g., four out of twenty-nine of the oligonucleotide pools), codon TCT may be joined to oligonucleotides in a selected number of oligonucleotide pools within a set number of oligonucleotide pools (e.g., four out of twenty-nine of the oligonucleotide pools), codon GAT may be joined oligonucleotides in a selected number of oligonucleotide pools within a set number of oligonucleotide pools (e.g., two out of twenty-nine of the oligonucleotide pools), and codons AGA, TTA, GTT, GCT, CCA, ACT, AAT, TTT, ATT, GAA, CAT, CAA, AAA, ATG and TGG may each be joined to oligonucleotides in a selected number of oligonucleotide pools within a set number of oligonucleotide pools (e.g., one out of twenty-nine of the oligonucleotide pools). At Kabat position 97, codon GGT may be joined to oligonucleotides in a selected number of oligonucleotide pools within a set number of oligonucleotide pools (e.g., four out of twenty-nine of the oligonucleotide pools), codon TAT may be joined to oligonucleotides in a selected number of oligonucleotide pools within a set number of oligonucleotide pools (e.g., four out of twenty-nine of the oligonucleotide pools), codon TCT may be joined to oligonucleotides in a selected number of oligonucleotide pools within a set number of oligonucleotide pools (e.g., four out of twenty-nine of the oligonucleotide pools), codon GAT may be joined to oligonucleotides in a selected number of oligonucleotide pools within a set number of oligonucleotide pools (e.g., two out of twenty-nine of the oligonucleotide pools), and codons AGA, TTA, GTT, GCT, CCA, ACT, AAT, TTT, AU, GM, CAT, CM, MA, ATG and TGG may each be joined to oligonucleotides in a selected number of oligonucleotide pools within a set number of oligonucleotide pools (e.g., one out of twenty-nine of the oligonucleotide pools). At Kabat position 96, codon GGT may be joined to oligonucleotides in a selected number of oligonucleotide pools within a set number of oligonucleotide pools (e.g., four out of twenty-nine of the oligonucleotide pools), codon TAT may be joined to oligonucleotides in a selected number of oligonucleotide pools within a set number of oligonucleotide pools (e.g., four out of twenty-nine of the oligonucleotide pools), codon TCT may be joined to oligonucleotides in a selected number of oligonucleotide pools within a set number of oligonucleotide pools (e.g., four out of twenty-nine of the oligonucleotide pools), codon GAT may be joined to oligonucleotides in a selected number of oligonucleotide pools within a set number of oligonucleotide pools (e.g., two out of twenty-nine of the oligonucleotide pools), and codons AGA, TTA, GTT, GCT, CCA, ACT, MT, TTT, ATT, GM, CAT, CM, AAA, ATG and TGG may each be joined to oligonucleotides in a selected number of oligonucleotide pools within a set number of oligonucleotide pools (e.g., one out of twenty-nine of the oligonucleotide pools).

An ABI3900 commercial DNA synthesizer equipped with standard DNA phosphoramidites (dA(Bz), dC(Bz), T, and dG(dmf)) at a concentration of 0.1M in dry acetonitrile and standard oxidation (I2,THF, H2O), capping (Ac2O, pyridine, THF, NMI) and deblock (TCA) were used for the synthesis of the degenerate oligonucleotides pools. The synthesis support used for the manufacturing of these pools was a base specific (3'-base fixed on the support) polystyrene support 40 (PS-40) from SAFC (Hamburg, Germany) loaded at 0.200 µmole per column.

All syntheses were conducted by leaving the trityl-ON at every stage where splitting was necessary. At the end of the synthesis the trityl group was left on for pre-PAGE purification. When the synthesis called for a splitting event, all columns for the corresponding pool were removed from the synthesizer, opened, and the content combined into a 15 mL Falcon tube. A volume of butanol equal to a multiple of the number of columns in which the next synthesis step would be performed was added to the tube. The material was mixed by vortexing and a single transfer performed. This was repeated until all the synthesis columns were filled. Acetonitrile was used to wash the PS-40 to the bottom of the column and another frit placed on top of the support. The columns were then washed with acetonitrile in the ABI3900 prior to the next codon synthesis. This procedure was repeated for the indicated number of split/pool events.

In order to generate a diversified antibody library that mimics the natural human antibody diversity and the biased usage of amino acids found in the CDRs, the following oligonucleotide design was used for the split-pool method. For CDRH1, 13 oligonucleotides were synthesized as follows. A single sequence was synthesized from the 3' end starting from Kabat position 40 up to amino acid position 34. The oligonucleotide product was then split into 13 columns for the incorporation of the next 3 nucleotides, where a total of 8 different codons were incorporated for amino acid position 33, one base at a time. The number of columns and frequency with which a given codon was added is designed to mimic the frequency of the corresponding amino acids at that position. For example, for position 33, after splitting the oligonucleotide pool into 13 columns, codon GCT and TAT were each incorporated into 3 of the oligonucleotide columns, codon TGG was incorporated into two columns and the remaining codons, GGT, TCT, GAT, ACT, or GTT, were each incorporated into one each of the remaining oligonucleotide columns (Table 6). This codon usage was designed so that the resulting oligonucleotides would encode at position 33 approximately 23% cases where the amino acid is A, 23% cases where the amino acid is Y, 15% cases where the resulting codon will encode W and 7.7% cases where G, S, T, N, and V will occur at position 33 to approximate the natural prevalence of 22% A, 20% Y, 17% W, 14% G, 12% S and less than 5% for T, N, or V at this position. After incorporation of the 3 bases for codon 33, the synthesized oligonucleotides were pooled, mixed, and split for the incorporation of the next 3 bases for the next codon, position 32. The 5' and 3' ends of each oligonucleotide for CDRH1 are identical, encoding the flanking framework sequences of framework 1 and 2, at the 5' and 3' end respectively, of the VH3-23 (DP47) germline sequence and serve as the templates for the binding of primers and conversion of the oligonucleotides into double stranded DNA.

Oligonucleotides for CDR2-H (Table 7), CDR1-L (Table 8), CDR2-L (Table 9), and CDR3-L (Table 10) were synthesized using similar split-pool methodology, with the number of columns and codon frequency designed to represent the natural frequency of amino acid usage within the given CDR (see, e.g., Table 5) and each CDR set having the identical corresponding flanking sequences covering portions of the adjacent framework sequences.

After all the oligonucleotides were synthesized, the oligonucleotides were then deprotected in concentrated ammonium hydroxide for 2 hours at 80° C. in a 2 mL centrifuge tube. After filtration of the support, the oligonucleotides were dried, and resuspended in 0.1M TEAA, pH 7. The oligonucleotides were then purified using a reverse phase cartridge and checked for crude quality by ESI-MS. After drying to completion, the oligonucleotides were PAGE purified using an 8% acrylamide mixture. Identifying the desired band to be cut out of the acrylamide gel was performed by UV shadowing. The oligonucleotides were extracted from the acrylamide by electroelution and desalted using a reverse phase cartridge. Upon elution and analysis by ESI-MS, the oligonucleotides were dried on a Speed-Vacuum apparatus.

TABLE 6

Nucleotide sequences of the 13 oligonucleotide pools synthesized for the heavy chain CDR1. Randomized codons at residue positions 30-33 are shown in 13 rows. The highlighted Kabat numbered residues represent the CDR region. The common 5' and 3' sequences are shown only in one row.

| CDR1-H | A | A | S | G | F | T | F | S | S | Y | A | M | S | W | V | R | Q | A |
|---|---|---|---|---|---|---|---|---|---|---|---|---|---|---|---|---|---|---|
| Kabat No | 23 | 24 | 25 | 26 | 27 | 28 | 29 | 30 | 31 | 32 | 33 | 34 | 35 | 36 | 37 | 38 | 39 | 40 |
| | | | | | | | | TCT | TCT | TAT | GCT | | | | | | | |
| | | | | | | | | TCT | TCT | TAT | GCT | | | | | | | |
| | | | | | | | | TCT | TCT | TAT | GCT | | | | | | | |
| | | | | | | | | TCT | TCT | TAT | TAT | | | | | | | |
| | | | | | | | | TCT | TCT | TAT | TAT | | | | | | | |
| | | | | | | | | TCT | TCT | TAT | TAT | | | | | | | |
| | GCT | GCT | TCT | GGT | TTT | ACT | TTT | TCT | AAT | TAT | TGG | ATG | TCT | TGG | GTT | AGA | CAA | GCT |
| | | | | | | | | ACT | AAT | TAT | TGG | | | | | | | |
| | | | | | | | | ACT | GGT | TCT | GGT | | | | | | | |
| | | | | | | | | AAT | ACT | AAT | TCT | | | | | | | |
| | | | | | | | | AGA | GAT | GGT | GAT | | | | | | | |
| | | | | | | | | GAT | AGA | TTT | ACT | | | | | | | |
| | | | | | | | | GGT | GCT | GCT | GTT | | | | | | | |

TABLE 7

Nucleotide sequences of the 12 oligonucleotide pools synthesized for the heavy chain CDR2. Randomized codons at residue positions 49-58 are shown in 12 rows. The highlighted Kabat numbered residues represent the CDR region. The common 5' and 3' sequences are shown only in one row.

| CDR2-H | G | K | G | L | E | W | V | S | A | I | S | P/G/S | S | G | G | S | T | Y | Y |
|---|---|---|---|---|---|---|---|---|---|---|---|---|---|---|---|---|---|---|---|
| Kabat No | 42 | 43 | 44 | 45 | 46 | 47 | 48 | 49 | 50 | 51 | 52 | 53 | 54 | 55 | 56 | 57 | 58 | 59 | |
| | | | | | | | | GGT | AGA | ATC | TCT | CCA | TCT | GGT | GGT | TCT | ACT | TAT | |
| | | | | | | | | GGT | AGA | ATC | TCT | CCA | TCT | GGT | GGT | TCT | ACT | TAT | |
| | | | | | | | | GGT | TAT | ATC | TCT | CCA | TCT | GGT | GGT | TCT | ACT | TAT | |
| | | | | | | | | GGT | TGG | ATC | TAT | CCA | GAT | GGT | GGT | TCT | ACT | TAT | |
| | | | | | | | | GGT | GTT | ATC | TAT | CCA | GAT | TCT | GGT | ACT | ACT | AAT | |
| | GGT | AAA | GGT | TTG | GAA | TGG | GTT | GGT | GGT | ATC | TAT | GGT | TAT | TCT | GGT | ACT | ACT | AAT | TAT |
| | | | | | | | | TCT | ATT | ATC | AAT | GGT | GGT | TCT | GGT | AAT | ACT | GAT | |
| | | | | | | | | TCT | GAA | ATC | AAA | GGT | CAT | GAT | GGT | GAT | ACT | AGA | |

TABLE 7-continued

Nucleotide sequences of the 12 oligonucleotide pools synthesized for the heavy chain CDR2. Randomized codons at residue positions 49-58 are shown in 12 rows. The highlighted Kabat numbered residues represent the CDR region. The common 5' and 3' sequences are shown only in one row.

| | | | | | | | | | |
|---|---|---|---|---|---|---|---|---|---|
| TCT | GCT | ATC | ATT | GGT | AAT | AAT | GGT | TAT | ACT | TCT |
| GCT | TCT | ATC | AGA | TCT | ATT | AAA | GGT | GAA | ACT | ATT |
| GCT | AAT | ATC | GAT | TCT | ACT | TTT | GGT | GGT | ACT | ACT |
| GCT | TTA | ATC | ACT | TCT | TGG | ACT | GGT | GCT | ACT | CAT |

| CDR2-H | A | D | S | V | K | G |
|---|---|---|---|---|---|---|
| Kabat No | 60 | 61 | 62 | 63 | 64 | 65 |
| | GCT | GAT | TCT | GTT | AAA | GGT |

TABLE 8

Nucleotide sequences of the 11 oligonucleotide pools synthesized for the light chain CDR1. The highlighted Kabat numbered residues represent the CDR region. Randomized codons at residue positions 28-32 are shown in 10 rows. The common 5' and 3' sequences are shown only in one row.

| CDR1-L | L | S | C | R | A | S | Q | S | V | S | S | S | Y | L | A | W | Y | Q | Q | K |
|---|---|---|---|---|---|---|---|---|---|---|---|---|---|---|---|---|---|---|---|---|
| Kabat No | 21 | 22 | 23 | 24 | 25 | 26 | 27 | 28 | 29 | 30 | 31 | 31a | 32 | 33 | 34 | 35 | 36 | 37 | 38 | 39 |

TCT ATT TCT TCT TCT TAT

TCT ATT TCT TCT TCT TAT

TCT ATT TCT TCT TCT TAT

AAT ATT TCT TCT TCT TAT

TTG TCT TGT AGA GCT TCT CAA AAT ATT TCT AAT TCT TAT TTG GCT TGG TAT CAA CAA AAA

GTT TCT AAT AAT TCT TAT

GTT TCT AAT ACT TCT AAT

GGT GTT AAA AGA AAT TGG

GGT GTT GGT ATT AAT TTT

GAT GGT AGA GAT ACT TCT

GAT AAT TAT AAA ACT GAT

TABLE 9

Nucleotide sequences of the 10 oligonucleotide pools synthesized for the light chain CDR2 (see, e.g., SEQ ID NO: 217 with sequence comprising CDR 2).

| CDR2-L | Q | A | P | R | L | L | I | Y | G | A | S |
|---|---|---|---|---|---|---|---|---|---|---|---|
| Kabat No | 42 | 43 | 44 | 45 | 46 | 47 | 48 | 49 | 50 | 51 | 52 |
| | | | | | | | | | GGT | | |
| | | | | | | | | | GGT | | |
| | | | | | | | | | GCT | | |
| | | | | | | | | | GCT | | |
| | | | | | | | | | GAT | | |
| | CAA | GCT | CCA | AGA | TTG | TTG | ATC | TAC | GAT | GCT | TCT |
| | | | | | | | | | TGG | | |
| | | | | | | | | | AAA | | |
| | | | | | | | | | TTA | | |

TABLE 9-continued

Nucleotide sequences of the 10 oligonucleotide pools synthesized for the light chain CDR2 (see, e.g., SEQ ID NO: 217 with sequence comprising CDR 2).

|  |  |  |  |  |  |  |  | GAA |  |  |
|---|---|---|---|---|---|---|---|---|---|---|
| CDR2-L | S | R | A | T | G | I | P | D | R | F |
| Kabat No | 53 | 54 | 55 | 56 | 57 | 58 | 59 | 60 | 61 | 62 |
|  | TCT |  | GCT |  |  |  |  |  |  |  |
|  | TCT |  | GCT |  |  |  |  |  |  |  |
|  | TCT |  | GCT |  |  |  |  |  |  |  |
|  | TCT |  | GCT |  |  |  |  |  |  |  |
|  | AAT |  | CAA |  |  |  |  |  |  |  |
|  | AAT | AGA | CAA | ACT | GGT | ATT | CCA | GAT | AGA | ITT |
|  | AAT |  | CAA |  |  |  |  |  |  |  |
|  | ACT |  | GAA |  |  |  |  |  |  |  |
|  | ACT |  | GAA |  |  |  |  |  |  |  |
|  | ACT |  | GAA |  |  |  |  |  |  |  |

The underlined Kabat numbered residues represent the CDR region. Randomized codons at residue position 50, 53 and 55 are shown in 10 rows. The common 5" and 3" sequences and the codons for residues 51, 52 and 54 are shown only in one row (see, e.g., SEQ ID NO: 218 with common sequences).

TABLE 10

Nucleotide sequences of the 12 oligonucleotide pools synthesized for the light chain CDR3 (see, e.g., SEQ ID NO: 219 with sequence comprising CDR 3).

| CDR3-L | A | V | Y | Y | C | Q | Q | Y | G | S |
|---|---|---|---|---|---|---|---|---|---|---|
| Kabat No | 84 | 85 | 86 | 87 | 88 | 89 | 90 | 91 | 92 | 93 |
|  |  |  |  |  |  |  |  | TAT | TAT | TCT |
|  |  |  |  |  |  |  |  | TAT | TAT | TCT |
|  |  |  |  |  |  |  |  | TAT | TAT | TCT |
|  |  |  |  |  |  |  |  | TAT | GGT | TCT |
|  |  |  |  |  |  |  |  | TAT | GGT | TCT |
|  | GCT | GTT | TAC | TAC | TGT | CAA | CAA | TAT | AAT | AAT |
|  |  |  |  |  |  |  |  | TAT | TCT | AAT |
|  |  |  |  |  |  |  |  | TCT | GAT | CAA |
|  |  |  |  |  |  |  |  | TCT | TTA | ACT |
|  |  |  |  |  |  |  |  | AGA | ACT | CAT |
|  |  |  |  |  |  |  |  | GCT | CAT | GGT |
|  |  |  |  |  |  |  |  | GGT | ATT | GAT |

| CDR3-L | S | P | I | T | F | G | Q | G | T | K |
|---|---|---|---|---|---|---|---|---|---|---|
| Kabat No | 94 | 95 | 96 | 97 | 98 | 99 | 100 | 101 | 102 | 103 |
|  | TCT |  | TTA |  |  |  |  |  |  |  |
|  | TCT |  | TTA |  |  |  |  |  |  |  |
|  | ACT |  | TTA |  |  |  |  |  |  |  |
|  | ACT |  | TAT |  |  |  |  |  |  |  |
|  | TGG |  | TAT |  |  |  |  |  |  |  |
|  | TGG | CCA | TGG | ACT | ITT | GGT | CAA | GGT | ACT | AAA |
|  | TAT |  | TGG |  |  |  |  |  |  |  |
|  | TAT |  | TTT |  |  |  |  |  |  |  |
|  | TTA |  | ATT |  |  |  |  |  |  |  |
|  | TTT |  | AGA |  |  |  |  |  |  |  |
|  | GCT |  | CCA |  |  |  |  |  |  |  |
|  | CCA |  | TAT |  |  |  |  |  |  |  |

Randomized codons at residue positions 91-94 (SEQ ID NOS: 220-231), and 96 are shown in 12 rows. The common 5' and 3' sequences and the codon for residue 95 are shown only in one row (see, e.g., SEQ ID NO: 225 with common sequences).

TABLE 11

Nucleotide sequences of the 29 oligonucleotide pools synthesized for the heavy chain CDR3.

| CDR3-H | A | V | Y | Y | C | A | R |  |  |  |  |
|---|---|---|---|---|---|---|---|---|---|---|---|
| Kabat No | 88 | 89 | 90 | 91 | 92 | 93 | 94 | 95 | 96 | 97 | 98 |
|  |  |  |  |  |  |  |  | GGT | GGT | GGT | GGT |
|  |  |  |  |  |  |  |  | GGT | GGT | GGT | GGT |
|  |  |  |  |  |  |  |  | GGT | GGT | GGT | GGT |
|  |  |  |  |  |  |  |  | GGT | GGT | GGT | GGT |

TABLE 11-continued

Nucleotide sequences of the 29 oligonucleotide pools synthesized for the heavy chain CDR3.

| | | | | | | | | | | | |
|---|---|---|---|---|---|---|---|---|---|---|---|
| | | | | | | | TAT | TAT | TAT | TAT |
| | | | | | | | TAT | TAT | TAT | TAT |
| | | | | | | | TAT | TAT | TAT | TAT |
| | | | | | | | TAT | TAT | TAT | TAT |
| | | | | | | | TCT | TCT | TCT | TCT |
| | | | | | | | TCT | TCT | TCT | TCT |
| | | | | | | | TCT | TCT | TCT | TCT |
| | | | | | | | TCT | TCT | TCT | TCT |
| GCT | GTT | TAT | TAT | TGT | GCT | AGA | GAT | GAT | GAT | GAT |
| | | | | | | | GAT | GAT | GAT | GAT |
| | | | | | | | AGA | AGA | AGA | AGA |
| | | | | | | | TTA | TTA | TTA | TTA |
| | | | | | | | GTT | GTT | GTT | GTT |
| | | | | | | | GCT | GCT | GCT | GCT |
| | | | | | | | CCA | CCA | CCA | CCA |
| | | | | | | | ACT | ACT | ACT | ACT |
| | | | | | | | AAT | AAT | AAT | AAT |
| | | | | | | | TTT | TTT | TTT | TTT |
| | | | | | | | ATT | ATT | ATT | ATT |
| | | | | | | | GAA | GAA | GAA | GAA |
| | | | | | | | CAT | CAT | CAT | CAT |
| | | | | | | | CAA | CAA | CAA | CAA |
| | | | | | | | AAA | AAA | AAA | AAA |
| | | | | | | | ATG | ATG | ATG | ATG |
| | | | | | | | TGG | TGG | TGG | TGG |

| CDR3-H | | | | | F | D | Y | W | G | Q | G |
|---|---|---|---|---|---|---|---|---|---|---|---|
| Kabat No | 99 | 100 | 100a | 100b | 100K | 101 | 102 | 103 | 104 | 105 | 106 |
| | GGT | GGT | GGT | GGT | | | | | | | |
| | GGT | GGT | GGT | GGT | | | | | | | |
| | GGT | GGT | GGT | GGT | | | | | | | |
| | GGT | GGT | GGT | GGT | | | | | | | |
| | TAT | TAT | TAT | TAT | | | | | | | |
| | TAT | TAT | TAT | TAT | | | | | | | |
| | TAT | TAT | TAT | TAT | | | | | | | |
| | TAT | TAT | TAT | TAT | | | | | | | |
| | TCT | TCT | TCT | TCT | | | | | | | |
| | TCT | TCT | TCT | TCT | | | | | | | |
| | TCT | TCT | TCT | TCT | | | | | | | |
| | TCT | TCT | TCT | TCT | | | | | | | |
| | GAT | GAT | GAT | GAT | TTT | GAT | TAT | TGG | GGT | CAA | GGT |
| | GAT | GAT | GAT | GAT | | | | | | | |
| | AGA | AGA | AGA | AGA | | | | | | | |
| | TTA | TTA | TTA | TTA | | | | | | | |
| | GTT | GTT | GTT | GTT | | | | | | | |
| | GCT | GCT | GCT | GCT | | | | | | | |
| | CCA | CCA | CCA | CCA | | | | | | | |
| | ACT | ACT | ACT | ACT | | | | | | | |
| | AAT | AAT | AAT | AAT | | | | | | | |
| | TTT | TTT | TTT | TTT | | | | | | | |
| | ATT | ATT | ATT | ATT | | | | | | | |
| | GAA | GAA | GAA | GAA | | | | | | | |
| | CAT | CAT | CAT | CAT | | | | | | | |
| | CAA | CAA | CAA | CAA | | | | | | | |
| | AAA | AAA | AAA | AAA | | | | | | | |
| | ATG | ATG | ATG | ATG | | | | | | | |
| | TGG | TGG | TGG | TGG | | | | | | | |

Randomized codons at residue position 95-100 (SEQ ID NOS: 234-262) are shown in 29 rows. The common 5' and 3' sequences are shown only in one row (see, e.g., SEQ ID NO: 246 with common sequences; see also, e.g., SEQ ID NOS: 232 and 233).

Without wishing to be bound by a theory of the disclosure, it is believed that the CDR-H3 regions of antibody heavy chains play predominant roles in antigen recognition and their lengths vary significantly among different antibodies. In order to generate diversified antigen binding conformations, the amino acid sequences were randomized with 19 amino acids (all 20 amino acids excluding cysteine) at each position, and the length of the CDR-H3 was varied from 5 to 15 randomized residues in length between residue positions 95 and 100. Although the amino acid sequences in CDR-H3 are highly diversified in naturally occurring human antibodies, some biased usages of amino acids are also noted. For example, glycine and tyrosine residues each account for about 15% and 13% of residues found in this region, respectively (see, e.g., Table 4), whereas if truly random, they should be each at a frequency of 5%. To mimic this frequency in the synthetic library, of the 29 oligonucleotide columns (oligonucleotides were synthesized in 29 different columns for CDR-H3), codons for glycine and tyrosine were each incorporated into oligonucleotides in 4 different columns out of the set of 29. Therefore, in the final end-product mixture from these 29 sets of oligonucleotides (oligonucleotides from 29 columns) there is approximately 13% (4 represents 13.8% of 29) glycine or tyrosine residues in CDR-H3. The sequences of all of these oligonucleotides are shown in Table 11. A total of 11 pools of oligonucleotides of different lengths were synthesized. The first pool of oligonucleotides had 5 randomized residues from position 95 to position 99, and at each residue position, 19 possible codons were incorporated. The 2nd pool of oligonucleotides had 6 randomized residues from position 95 to 100, the third pool 7 randomized residues and so on with the last pool of oligonucleotides having 15 residues from position 95 to position 100i.

All oligonucleotides were synthesized, gel purified and used as templates for PCR conversion to double stranded DNA using primers that bind to the common regions at the 5' and 3' of the randomized CDR oligonucleotides. The primers used for all the CDR conversions are listed below in Table 12. Proof reading DNA polymerase, Pfx (Invitrogen) was used for all PCR reactions. In each reaction, greater than 100 ng of the initial templates were used to ensure sufficient diversity of the resultant antibody gene products.

TABLE 12

Primers (sequence from 5' to 3' end) used for antibody library construction.

| Primer Name | Nucleotide sequence (5' to 3') | SEQ ID NO: | Use |
|---|---|---|---|
| LC-FR1-F | GGGCGGCCGCAAACACACATAAT | 135 | For light chain FR1 amplification. |
| LC-FR1-R | TTGAGAAGCTCTACAAGACAAAG | 136 | |
| LC-CDR1-F | AGCTACTTTGTCTTGTAGAGCTTCTCAA | 137 | For light chain CDR1 amplification |
| LC-CDR1-R | GTAGATCAACAATCTTGGAGCTTGACCT GGTTTTTGTTGATACCAAGCCAA | 138 | |
| LC-CDR2-F | CAAGCTCCAAGATTGTTGATCTAC | 139 | For light chain CDR2 amplification |
| LC-CDR2-R | CAGAAAATCTATCTGGAATACCAGT | 140 | |
| LC-FR3-F | ACTGGTATTCCAGATAGATTTTC | 141 | For light chain FR3 amplification |
| LC-FR3-R | TTGTTGACAGTAGTAAACAGCG | 142 | |
| LC-CDR3-F | GAAGATTTCGCTGTTTACTACTGTCAAC AA | 143 | For light chain CDR3 amplification |
| LC-CDR3-R | CTTTTAATTTCAACTTTAGTACCTTGACC AAAAGT | 144 | |
| LC-FR4-F | ACTTTTGGTCAAGGTACTAAAGTTG | 145 | For light chain FR4 and constant region amplification |
| LCC-R | TCAGATCTTCATTAACATTCACCACG | 146 | |
| HC-FR1-F | GCAGGATCCGAAGTTCAATTGTTGGAAT CT | 147 | For heavy chain FR1 amplification |
| HC-FR1-R | AAAAGTAAAACCAGAAGCAGCACAAGA | 148 | |
| HC-CDR1-F | GCTGCTTCTGGTTTTACTTTT | 149 | For heavy chain CDR1 amplification |
| HC-CDR1-R | AACCCATTCCAAACCTTTACCAGGAGCT TGTCTAACCCAAGACAT | 150 | |
| HC-CDR2-F | ATGTCTTGGGTTAGACAAGCTCCTGGTA AAGGTTTGGAATGGGTT | 151 | For heavy chain CDR2 amplification |
| HC-CDR2-R | TCTAGAGATAGTGAATCTACCTTTAACA GAATCAGCATA | 152 | |
| HC-CDR3-F1 | ACTGCTGTTTATTATTGTGCTAGA | 153 | For heavy chain CDR3 amplification |
| HC-CDR3-F2 | TCTAGAGATAACTCTAAAAATACTTTGTA TTTGCAAATGAACTCTTTGAGAGCTGAA GATACTGCTGTTTATTATTGTGCTAGA | 154 | |
| HC-CDR3-R | AGTACCTTGACCCCAATAATCAAA | 155 | |
| HC-FR4-F | TTTGATTATTGGGGTCAAGGTACT | 156 | For heavy chain FR4 and constant region amplification |
| HC-FR4-R | TGGAAGCTTTAGAACCACCACCACCGG | 157 | |

Framework region and constant region templates of the light (A27; Table 13) and heavy (VH 3-23; Table 14) chains were synthesized and each cloned separately into the plasmid vector, pUC57 to ensure no trace amounts of intact germline light and heavy chain could be amplified preferentially during recombinant PCR. This yielded plasmids pUC57-Ldr-FR1-LC, pUC57-FR3-LC, pUC57-FR4-CK-LC (Table 15), pUC57-FR1-HC and pUC57-FR4-CH1-HC (Table 16), which served as DNA templates for PCR amplification.

TABLE 13

Amino acid sequences of the light chain fragments.

| Light chain fragment | Amino acid sequence | SEQ ID NO: |
| --- | --- | --- |
| FR1 | EIVLTQSPGTLSLSPGERATLSC | 163 |
| FR2 | WYQQKPGQAPRLLIY | 164 |
| FR3 | GIPDRFSGSGSGTDFTLTISRLEPEDFAVYYC | 165 |
| FR4 | TFGQGTKVEIK | 166 |
| LC Constant region | RTVAAPSVFIFPPSDEQLKSGTASVVCLLNNFYPREAK VQWKVDNALQSGNSQESVTEQDSKDSTYSLSSTLTLS KADYEKHKVYACEVTHQGLSSPVTKSFNRGEC | 167 |

TABLE 14

Amino acid sequences of the heavy chain fragments.

| Heavy chain fragment | Amino acid sequence | SEQ ID NO: |
| --- | --- | --- |
| FR1 | EVQLLESGGGLVQPGGSLRLSCAASGFTFS | 168 |
| FR2 | WVRQAPGKGLEWVS | 169 |
| FR3 | RFTISRDNSKNTLYLQMNSLRAEDTAVYYCAR | 170 |
| FR4 | WGQGTLVTVSS | 171 |
| CH1 Constant region | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTH | 172 |

TABLE 15

Templates for PCR amplification of the light chain framework and constant regions

| Light chain fragment | Nucleotide sequences of the templates for PCR amplification of the leader sequence, framework and constant regions | SEQ ID NO: | Plasmid |
| --- | --- | --- | --- |
| Leader sequence and FR1-LC | GGGCGGCCGCAAACACACATAATAAAC AAAATGCAATTGTTGAGATGCTTTTCTA TTTTCTCTGTTATCGCTTCTGTTTTGGCT GCTGAAATTGTTTTGACTCAATCTCCAG GTACTTTGTCTTTGTCTCCAGGTGAAAG AGCTACTTTGTCTTGTAGAGCTTCTCAA | 158 | pUC57-Ldr-FR1-LC |
| FR3 | GAGCTACTGGTATTCCAGATAGATTTTC TGGTTCTGGTTCTGGTACCGATTTCACT TTGACTATCTCAAGATTGGAACCAGAAG ATTTCGCTGTTTACTACTGTCAACAA | 159 | pUC57-FR3-LC |
| FR4 and constant region | ACTTTTGGTCAAGGTACTAAAGTTGAAA TTAAAAGAACTGTTGCTGCTCCATCTGT TTTTATTTTTCCACCATCTGATGAACAAT TGAAATCTGGTACTGCTTCTGTTGTTTG TTTGTTGAACAACTTCTACCCAAGAGAA GCTAAGGTTCAATGGAAGGTTGATAAC GCTTTGCAATCTGGTAACTCTCAAGAAT CTGTTACTGAACAAGATTCTAAGGATTC TACTTACTCTTTGTCTTCTACTTTGACTT TGTCTAAGGCTGATTACGAAAAGCATAA | 160 | pUC57-FR4-CK-LC |

TABLE 15-continued

Templates for PCR amplification of the light chain framework and constant regions

| Light chain fragment | Nucleotide sequences of the templates for PCR amplification of the leader sequence, framework and constant regions | SEQ ID NO: | Plasmid |
|---|---|---|---|
| | GGTTTACGCTTGTGAAGTTACTCATCAA GGTTTGTCTTCTCCAGTTACTAAATCTTT TAATCGTGGTGAATGTTAATGAAGATCT GA | | |

TABLE 16

Templates for PCR amplification of the heavy chain framework and constant regions

| Heavy chain fragment | Nucleotide sequences of the templates for PCR amplification of the heavy chain framework and constant regions | SEQ ID NO: | Plasmid |
|---|---|---|---|
| FR1 | GCAGGATCCGAAGTTCAATTGTTGGAATCTGGTGGTGGTTTG GTTCAACCAGGTGGTTCTTTGAGATTGTCTTGTGCTGCTTCT GGTTTTACTTTT | 161 | pUC57-FR1-HC |
| FR4 and constant region | TTTGATTATTGGGGTCAAGGTACTTTGGTTACTGTTTCTTCTG CTTCCACCAAGGGCCCATCGGTCTTCCCCCTGGCACCCTCC TCCAAGAGCACCTCTGGGGGCACAGCGGCCCTGGGCTGCC TGGTCAAGGACTACTTCCCCGAACCGGTGACGGTGTCATGG AACTCAGGCGCCCTGACCAGCGGCGTGCACACCTTCCCGGC TGTCCTACAGTCCTCAGGACTCTACTCCCTCAGCAGCGTGGT GACCGTGCCCTCCAGCAGCTTGGGCACCCAGACCTACATCT GCAACGTGAATCACAAGCCCAGCAACACCAAGGTGGACAAG AAAGTTGAGCCCAAATCTTGTGACAAAACTCACACAGGTTCT TCTGAACAAAAGTTGATCTCTGAAGAAGATTTGGGTGGTGGT GGTTCAGGTGGTGGTGGTTCCGGTGGTGGTGGTTCTAAAGC TTCCA | 162 | pUC57-FR4-CH1-HC |

All PCR products were separated by 2-4% agarose gel electrophoresis, the DNA bands with the correct anticipated sizes were excised and the DNA fragment purified using a Qiagen Gel Extraction Kit. The PCR products for the framework sequences were linked with the double-strand DNA encoding the CDR regions by recombinant PCR.

For construction of the light chain (LC) library, pools of oligonucleotides synthesized by the split-and-pool method to contain tailor-randomized codons at the designed positions as described above were first converted into double-stranded DNA libraries for each CDR; CDR1-L was amplified using LC-CDR1-F and LC-CDR1-R, CDR2-L was amplified using LC-CDR2-F and LC-CDR2-R and so forth. The light chain CDRL1 and CDRL2 were linked by PCR with germline frameworks FR1, FR2, and FR3 as follows. The primers LC-FR1-F and LC-FR1-R were used to amplify the leader sequence and the light chain FR1 using pUC57-Ldr-FR1-LC as a template. The PCR product was then linked with the CDRL1 library using the primers, LC-FR1-F and LC-CDR1-R, to produce PCR products with sequences covering the leader sequence, FR1, CDRL1 and FR2. The amplified CDRL2 was linked with FR3 of the light chain which was amplified using primers LC-FR3-F and LC-FR3-R with pUC57-FR3-LC as a template. The CDRL2-FR3 fragment was then linked to the leader-FR1-CDR1-FR2. (See, FIG. 3A and Tables 15 and 16 for primer and template sequences).

The final PCR products were digested with Not I and Acc 65 I and ligated into the display vector, pDS-Fab, that had been pre-digested with the same enzymes. The ligation products were used to transform E. coli DH10B electrocompetent cells. A library of 4×10$^7$ clones was generated for the first portion of light chain library (pDS-Fab-LC1) which is more than 10 times larger than the theoretical diversity for the combination of the designed CDRL1 and CDRL2 of 1.4×10$^6$.

The ligation products were used to transform E. coli competent cells. Plasmids were prepared from this library carrying the first half of the LC and the DNA used for the cloning of the 2nd half of the LC library whereby the CDRL3 was linked to FR3 and FR4 plus the kappa constant region using primers LC-FR3-F and LCC-R which was amplified using pUC57-FR4-CK-LC as the template DNA. The 5'-FR3-CDR3-FR4-LC constant region-3' DNA fragment produced by PCR amplification was digested with Acc65 I and Bgl II and ligated with Acc65 I and Bgl II digested pDS-Fab-LC1. The ligated DNA was in turn used to transform E. coli. A library of 1.2×10$^{10}$ independent was generated for the full-length light chain (pDS-Fab-LC) which is about 50% of the theoretical diversity for the combinations of CDRL1, CDRL2, and CDRL3. Upon completion of the LC library construction, about 2 mg of plasmid DNA was prepared from cells harvested from LB plates and used for the construction of the heavy chain library.

The heavy chain (HC) library was constructed in a similar way to the LC library. The primers used are listed in Table 12 and the DNA templates and resulting pUC57 vectors are shown in Table 16. The CDRH1 and CDRH2 mini-libraries were linked to FR1, FR2, and FR3 from the human germline VH3-23 (DP47) in a similar manner to the methods described above for the light chain but instead using pUC57-FR1-HC as the template DNA. The DNA fragments comprised of 5'-FR1-CDR1-FR2-CDR2-FR3-3' were PCR amplified and digested with BamH I and Xba I and cloned into a BamH I and Xba I digested pDS-Fab-LC library (see, FIG. 3B). A library of $1.5 \times 10^{10}$ independent clones was produced for the first portion of the heavy chain.

Finally, the 11 pools of CDRH3 DNA libraries were linked with VH3-23 FR3 and FR4 plus the CH1 region using pUC57-FR4-CH1-HC as the DNA template, and the 5'FR3-CDR3-FR4-HC constant region-3' PCR products were digested with Xba I and Hind III and cloned into the Xba I and Hind III digested pDS-Fab-LC-HC1 library to produce the final intact heavy chain library. A total of $1.6 \times 10^{10}$ transformants were obtained for the final library with intact light and heavy chains of antibody Fab molecules.

Constructing the Fab library in this manner provides a means for shuffling CDRs for antibody affinity maturation whereby an existing CDRL3, CDRH3, CDRL1-CDRL2 or CDRH1-CDRH2 can be replaced with a library of CDRL3, CDRH3, CDRL1-CDRL2 or CDRH1-CDRH2, respectively to generate a focused library. Antibodies with improved properties may then be isolated from such focused libraries.

Sequencing analysis of 50 of these clones indicated that the CDRs were well diversified and reflected the designed amino acid compositions for these positions. Large scale plasmid DNA was prepared from 10 L of *E. coli* culture of the final library and used to transform the yeast strain, BJ5464, for antibody Fab display using the LiOAc transformation protocol (Gietz and Woods (2002) *Methods Enzymol.* 350:87-96). A total of $1.0 \times 10^{10}$ independent yeast clones were obtained.

B. Exemplary Full-Length Antibody Library

In an exemplary method, a large yeast display synthetic full-length human antibody (e.g., IgG) library was constructed. A library of light chains generated as described above in section A was cloned into a modified pDS-Fab vector which carries a complete human antibody heavy chain sequence including the human IgG1 constant region coupled to the proline-rich display motif and His tag (SEQ ID NO:173) (Table 17). A total of $9.5 \times 10^{9}$ independent clones were obtained for this light chain library.

The heavy chain (HC) library was constructed as described in Example 2, except that the second half of the variable region and the CH1 constant region of the heavy chain was cloned into Xba I and Apa I sites in the modified pDS-Fab vector and fused to the IgG1 constant region including CH2-CH3 upstream of a V5 tag and the proline-rich peptide 12 (SEQ ID NO:1). A library of $1.6 \times 10^{10}$ independent clones was produced for the final full-length IgG library. A large scale preparation of plasmid DNA was produced from the *E. coli* cells harboring the yeast display vector with the full-length IgG library. The plasmid DNA was then transformed into yeast host BJ5464 using the LiAc-based method described in Example 2 to produce the final yeast library. 50 clones from the primary library plates were randomly picked and amplified and the heavy and light chain regions sequenced. The sequencing data indicated that all 50 clones encoded different heavy and light chain sequences and that 94% of the clones harbored intact light chain sequences and 74% encoded intact full-length heavy chain sequences.

Example 3: Isolation of Proteins of Interest from Libraries of Host Cells

Host cells comprising proteins of interest (e.g., an antibody or binding fragment thereof, including, for example, Fab or IgG) associated with novel peptides displayed on their surface, such as novel proline-rich peptides as described herein, may be screened and isolated by any method known in the art. For example, host cell libraries containing proteins of interest associated with proline-rich peptides may be screened using magnetic beads that comprise a molecule to which the protein of interest binds and/or FACS analysis by exposing the clones to labeled molecules to which the protein of interest may bind.

A. Exemplary Fab Display

In an exemplary method, purified human Beta-2 microglobulin, a cancer biomarker with a molecular weight of 12 kDa, was labeled with biotin and used as an antigen for screening the library described in Example 2. Briefly, the screening process involved a preliminary enrichment for antigen-binding clones using magnetic beads followed by fluorescent activated cell sorting (FACS). For the initial magnetic bead sorting step, $2 \times 10^{10}$ yeast cells were grown and induced to express antibodies as described in Example 2. Next, biotinylated Beta-2 microglobulin at a final concentration of 100 nM was added in 5 ml of binding buffer (PBS plus 5 g/l BSA, but without $Ca^{2+}$ or $Mg^{2+}$). After incubation with the yeast library at room temperature for 1 hour, the cells were incubated on ice for 10 minutes, washed

TABLE 17

Sequence of the heavy chain constant region carrying the display motif.

| Heavy chain constant region and display motif | Amino Acid Sequence | SEQ ID NO: |
| --- | --- | --- |
| CH1-CH3-V5-tag-PRP | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVD KKVEPKSCDKTHTCPPCPAPELLGGPSVFLFPPKPKDTLMISRTPEVT CVVVDVSQEDPEVQFNWYVDGVEVHNAKTKPREEQFNSTYRVVSVL TVLHQDWLNGKEYKCKVSNKGLPSSIEKTISKAKGQPREPQVYTLPP SQEEMTKNQVSLTCLVKGFYPSDIAVEWESNGQPENNYKTTPPVLDS DGSFFLYSRLTVDKSRWQEGNVFSCSVMHEALHNHYTQKSLSLSLG SSKPIPNPLLGLDSTGGGGSGGGGSGGGGSKLPPPTPPRTPPPPPP PPPPPPPPPPPLHHHHHCV | 173 |

3 times with 50 ml binding buffer, followed by incubation with 200 µl of streptavidin-magnetic beads in 5 ml binding buffer for 10 minutes on ice. The cells were then washed once with 50 ml of binding buffer and resuspended in 50 ml of binding buffer, before being passed through a magnetic sorting column (7 ml/loading, 1 ml wash with binding buffer between each loading). After all the cells had passed through the column, the column was washed 3 times with 3 ml binding buffer. Captured cells were then eluted in 10 ml of binding buffer by removing the column from the magnetic field, then pelleted and resuspended in 100 ml of selective medium. Next, the collected cells were grown up and induced for Fab expression as described above and used for a second round of magnetic bead sorting.

The selected cells were then grown up for further selection by FACS. Fab-expressing yeast cells were incubated with 100 nM biotinylated Beta-2 microglobulin and bound Beta-2 microglobulin was detected with phycoerythrin (PE)-conjugated streptavidin, while the displayed Fab was detected with goat anti-human Fab followed by APC conjugated donkey anti-goat antibody. Double positive cells were identified and collected using a FACSAria (Becton Dickenson) at yield mode and at a rate of 20,000 events/second. The harvested cells were expanded and used for the next round of sorting. Generally, the top 0.1-5% of antigen (biotin) and Fab positive cells were collected from each round of selection. A total of four rounds of sorting were carried out. Yeast cells that had not been exposed to detection reagents were used as a negative control (FIG. 4, Panel A). After the first round of FACS at 100 nM antigen, about 5.4% of cells were double positive for both Fab expression (APC labeling) and Beta-2 microglobulin (PE labeling) (FIG. 4, Panel C). After the second round of FAC sorting at 100 nM antigen (FIG. 4, Panel D), more than 50% of cells were double positive for Fab expression and Beta-2 microglobulin binding; thus a single round of FACS resulted in an enrichment from 5.4% to more than 50% in one round of sorting. This was then followed by a third round of sorting at 20 nM (FIG. 4, Panel E) followed by a final (fourth) round at 1 nM antigen concentration, which yielded populations of 56% and 59% antigen-positive binding clones, respectively (FIG. 4, Panel F). Fab expression was also detected in the sub-library selected by MACS®, using goat anti-human Fab antibody and APC conjugated donkey anti-goat antibody. About 78% of the yeast cells display Fab at their surface (FIG. 4, Panel B).

The screening was performed in a similar manner for an additional 2 antigens: Prostate-Specific Antigen (PSA) and Alpha-fetoprotein (AFP). In each case, populations of anti-antigen antibody clones were enriched during successive rounds of FACS.

Figure 5:
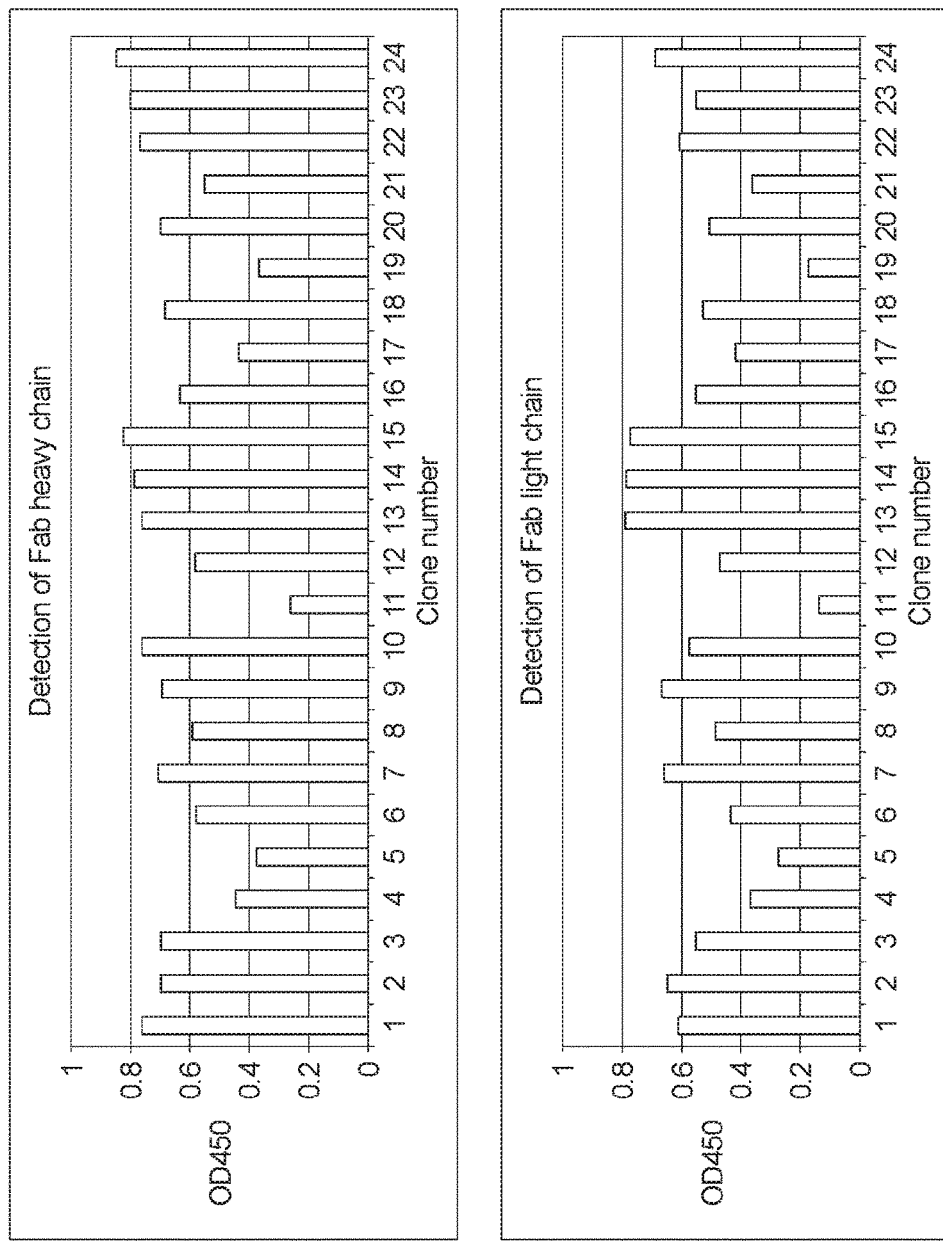
FIG. 5 shows an exemplary ELISA analysis of specific binding of secreted Fab to immobilized Beta-2 microglobulin.

The harvested cells from the final round of FACS were then plated on selective media plates and incubated at 30° C. for 48 hours. Individual colonies were randomly picked from the agar plates and grown in selective medium overnight at 30° C. The medium was replaced with induction medium and cells cultured at 20° C. overnight to induce the expression of Fab antibodies. In this yeast display system, a significant amount of Fab antibody is secreted into the culture medium in addition to those displayed on the yeast cell surface. The secreted Fab in the medium can be used directly for binding assays. 100 ng of antigen (Beta-2 microglobulin, PSA or AFP) or BSA in 100 µl PBS was used to coat the wells of Immulon 2 HB ELISA plates at 4° C. overnight. The next day, unbound antigens were removed, and the wells were blocked with PBS+3% BSA. After washes, the secreted Fab antibodies in 90 µl cultured media were added to the antigen coated wells or BSA coated (control) wells, followed by addition of 10 µl of 10×binding buffer (0.5 M Hepes, 0.5 M NaCl, 5% BSA, pH 7.5) to each well. The plates were incubated at 30° C. for 1 hour, and the bound Fab was detected with either HRP-conjugated mouse anti-myc antibody for the heavy chain portion of the Fab which has a myc epitope tag at its C-terminus (FIG. 5, upper panel), or with HRP conjugated mouse anti-human kappa light chain (FIG. 5, lower panel). Specific binding was determined by subtracting the OD reading to BSA from the OD obtained from binding to antigen. In addition to confirming that sufficient Fab was secreted into the medium to allow it to be used directly for binding assays, the data obtained from these ELISAs indicate an excellent correlation of the amount of heavy and light chains in the culture medium, suggesting that binding is mediated by intact Fab molecules with covalently bound heavy and light chains, rather than free heavy or light chains in the culture medium. Clones with high binding affinity and specificity were selected for further analysis (see, e.g., Example 7).

B. Exemplary IgG Display

To assess the ability of the proline-rich peptide to display intact IgG, one of the isolated clones that exhibited high affinity for Beta2 microglobulin (assayed as described in Example 6) was sequenced and the Fab heavy chain converted into a full-length heavy chain by coupling the CH1 sequence to the CH2-3 region of the Fc region of the IgG4 heavy chain. This construct was then inserted in place of the Fab heavy chain in the display vector. In one case, the heavy chain was linked via the $(GGGGS)_3$ (SEQ ID NO: 123) linker to the proline-rich peptide and a second variant it was linked directly to the proline-rich peptide without the intervening linker. As a control, a construct lacking the proline-rich peptide was also generated. Four independent clones from each construct were cultured in induction medium as described above and then compared by flow cytometry for their ability to display intact IgG. To assess the ability of the proline-rich peptide to support full-length heavy chain display the heavy chain was detected by a goat anti-Fc antibody (Jackson ImmunoResarch Inc, catalog #109-035-008) followed by PE-labelled anti-goat antibody (Jackson ImmunoResearch Inc, catalog #705-116-147). To ensure the light chain had assembled onto the heavy chain to form an intact IgG the light chain was detected using biotin-labeled anti-human kappa (Southern Biotech, catalog #9230-08) followed by PE-streptavidin (Jackson ImmunoResearch Inc, catalog #016-110-084). The proline rich peptide effectively supported display of intact IgG (e.g., IgG4); 79±1 (n=4) percent of the cell population stained positively for the heavy chain and 83±1 (n=4) percent stained positively for the light chain, indicating that the displayed polypeptide was correctly assembled into an intact IgG molecule. In the absence of the proline-rich peptide attached to the heavy chain, levels of IgG associated with the yeast cell populations were reduced.

In an exemplary method, purified human PSA, a cancer biomarker with a molecular weight of 30 kDa, was labeled with biotin and used as an antigen for screening the full-length IgG library described in Example 2. A similar FACS selection was used as described above for the Fab library but with modified induction conditions. The yeast cells were grown in selective medium overnight at 30° C., then diluted 1:10 in induction medium (e.g., selective medium with the 20 g/L glucose substituted with 20 g/L galactose, 20 g/L raffinose, and 1 g/L glucose, plus 1% casamino acid and 0.001% Triton X-100) and cultured for 2 days at 20° C. For FACS library selection, yeast cells were incubated with 100 nM of biotinylated antigen together with goat anti-human antibody (ImmunoResearch Inc, Cat#709-005-149). After washing 3 times, bound antigen and anti-human antibody were detected with APC-conjugated streptavidin and PE-conjugated donkey anti-goat antibody, respectively. The sorting was performed using purity mode at about 25,000 events/second and the double positive cells were harvested.

The concentration of biotinylated antigen used for the first round of FACS was 100 nM. The concentration then lowered to 50 nM, 20 nM and then 1 nM for the subsequent three rounds of FACS.

The screening was performed in a similar manner for an additional 2 antigens: Endophilin and Homer 1. In each case, populations of anti-antigen antibody clones were enriched during successive rounds of FACS.

The harvested cells from the final round of FACS were then plated on selective media plates and incubated at 30° C. for 48 hours. Individual colonies were randomly picked from the agar plates and grown in selective medium overnight at 30° C. The medium was replaced with induction medium and cells cultured at 20° C. overnight to induce the expression of IgG antibodies. In this yeast display system, a significant amount of IgG antibody is secreted into the culture medium in addition to those displayed on the yeast cell surface. The secreted IgG in the medium can be used directly for binding assays. 100 ng of antigen (PSA, Endophilin, or Homer 1) or BSA in 50 µl PBS was used to coat the wells of Immulon 2 HB ELISA plates at 4° C. overnight. The next day, unbound antigens were removed, and the wells were blocked with PBS+3% BSA. After washes, the secreted IgG antibodies in 10 µl cultured media were added to the antigen coated wells or BSA coated (control) wells, followed by addition of 40 µl of binding buffer (PBS, 1% BSA, 0.1% Triton X100, pH 7.5) to each well. The plates were incubated at 30° C. for 1 hour, and the bound IgG was detected with HRP-conjugated goat anti-human antibody which recognizes both heavy and light immunoglobulin chains (Immuno Research). Specific binding was determined by subtracting the OD reading to BSA from the OD obtained from binding to antigen. Clones with high binding affinity and specificity were selected for further analysis (see, e.g., Example 7).

Example 4: Proteins of Interest Displayed on Host Cell Libraries

Libraries comprising proteins of interest (e.g., antibodies or binding fragments thereof) associated with novel peptides, including the proline-rich peptides as described herein, may be assayed for binding to binding partners by any method known in the art (e.g., by screening the library clones against a molecule to which the protein of interest may bind).

A. Exemplary Assay for Displaying Fab on Host Cell Libraries

In an exemplary method, a library was screened for clones specific for an exemplary binding partner of a protein of interest (e.g., Beta-2 microglobulin). The screening was performed with biotinylated Beta-2 microglobulin at 100 nM for two rounds of MACS and two rounds of FACS. All clones that were positive for Beta-2 microglobulin binding from this second round of FACS were collected and plated on plates containing medium lacking tryptophan. Colonies were randomly picked and used directly for PCR amplification of the heavy chain of the Fab, which is used for sequencing the portion covering the CDRH3 and the remainder amplified for a third and fourth round of FACS that were performed with 20 nM and 1 nM biotinylated antigen, respectively. Colonies from this final fourth round were also randomly picked and used directly for PCR amplification of the heavy chain of the Fab, to sequence the portion covering the CDRH3. The primers used for the PCR amplification and sequencing are listed in Table 18. Colonies were picked and resuspended in 3 µl of 20 mM NaOH and heated at 99° C. for 10 minutes. After cooling down, 22 µl of PCR mix containing 0.5 □µM of each forward and reverse primer and 1×Pfx PCR buffer and 0.5 µl of Pfx were added to each tube. The reaction was performed for 30 cycles with the following conditions: 94° C. for 30 seconds, 55° C. for 30 seconds, and 68° C. for 1 minute. The PCR products were then purified with Qiagen PCR purification kit and used for sequencing with the sequencing primer. Of the 31 clones sequenced from the second round of FACS, 30 clones have different sequences for CDRH3. Most of these CDRH3 regions have 7 or 8 amino acids between residue 95 and 100, accounting for 61% of the clones analyzed. Nevertheless, clones with different lengths of the CDRH3 ranging from 6 to 13 amino acids between residues 95 and 100 were also isolated. Of the 15 clones sequenced from the final, fourth round of FACS, 5 unique sequences were obtained. The data are summarized in Table 19.

TABLE 18

Primers used for amplification and sequencing of the heavy chain

| | Primers for PCR amplification of the heavy chain | Primer for sequencing analysis of CDRH3 region |
|---|---|---|
| pDS-Fab-HC-F | CCCGGATCGGACTACTAGCAGCTG (SEQ ID NO: 174) | |
| pDS-Fab-HC-R | TTGTACGAGCTAAAAGTAC (SEQ ID NO: 175) | |
| HC-CDR1-F | | GCTGCTTCTGGTTTTACTTTT (SEQ ID NO: 149) |

TABLE 19

CDRH3 sequencing analysis of isolated clones

| FACS round | CDRH3 length (amino acids) | Number of clones | Percent of total | Number of different sequences | Percent of clones with unique sequence |
|---|---|---|---|---|---|
| 100 nM | 6 | 3 | 9.7% | 3 | 96.7% |
| | 7 | 11 | 35.4% | 10 | |
| | 8 | 8 | 25.8% | 8 | |
| | 9 | 2 | 6.5% | 2 | |
| | 10 | 3 | 9.7% | 3 | |
| | 11 | 2 | 6.5% | 2 | |
| | 12 | 1 | 3.2% | 1 | |
| | 13 | 1 | 3.2% | 1 | |
| 1 nM | 7 | 3 | 20% | 2 | 33% |
| | 8 | 7 | 46.7% | 2 | |
| | 10 | 5 | 33.3% | 1 | |

B. Exemplary Assay for Displaying Full-Length Antibody on Host Cell Libraries

In an exemplary method, the yeast displayed full-length IgG library was screened for clones specific for exemplary binding partners of a protein of interest (e.g., PSA). The screening was performed with biotinylated PSA at a 100 nM concentration for two rounds of magnetic beads based sorting. This was followed by two rounds of FACS at an antigen concentration of 100 nM, followed by three more rounds of FACS where the antigen concentration was reduced to 50, 20 and 1 nM, respectively. All clones that were positive for PSA binding from the 50 and 1 nM round of FACS were collected and plated on plates containing medium lacking tryptophan. Colonies were randomly picked and used directly for PCR amplification of the heavy chain of the antibody genes, which were used for sequencing the portion covering the CDRH3. The PCR amplification was carried as described in Example 4. From the 50 nM round of FACS, of the 32 clones sequenced, 21 clones have different sequences for CDRH3, representing 65.5% unique clones. From the 1 nM round FACS, of the 20 clones sequenced, 12 clones have different sequences for CDRH3, representing 60% unique clones (Table 20).

TABLE 20

CDRH3 sequencing analysis of isolated clones.

| FACS round | CDRH3 length (amino acids) | Number of clones | Percent of total | Number of different sequences | Percent of clones with unique sequence |
|---|---|---|---|---|---|
| 50 nM | 7 | 1 | 3.1% | 1 | 65.5% |
|  | 8 | 3 | 9.4% | 1 |  |
|  | 9 | 3 | 9.4% | 2 |  |
|  | 10 | 2 | 6.3% | 2 |  |
|  | 11 | 9 | 28.1% | 6 |  |
|  | 12 | 1 | 3.1% | 1 |  |
|  | 13 | 2 | 6.3% | 2 |  |
|  | 14 | 3 | 9.4% | 3 |  |
|  | 15 | 8 | 25% | 2 |  |
| 1 nM | 8 | 1 | 5.0% | 1 | 60% |
|  | 10 | 3 | 15.0% | 3 |  |
|  | 11 | 11 | 55.0% | 6 |  |
|  | 12 | 1 | 5% | 1 |  |
|  | 15 | 4 | 20% | 1 |  |

Example 5: Isolation of Humanized Antibodies from Libraries of Host Cells

A library of humanized antibodies may be constructed in a similar manner to the methods described in Example 2, except in this case the CDR3 from the heavy chain of a non-human antibody of interest is linked to FW3 and FW4 of the heavy chain instead of the randomized CDRH3 DNA oligonucleotide pools.

In an exemplary method, the non-human CDR3 is linked to FR3 and FR4 plus the CH1 region of human antibody using pUC57-FR4-CH1-HC as the DNA template, and the 5'FR3-CDRH3-FR4-constant region-3' PCR products are digested with Xba I and Hind III and cloned into the Xba I and Hind III digested pDS-Fab-LC-HC1 library to produce the final intact heavy chain library. This library of antibody molecules has human germline frameworks, CDRL1, CDRL2, CDRL3, CDRH1, and CDRH2 that mimic human CDRs, and a CDRH3 derived from a non-human antibody to be humanized.

The CDRH3 from the non-human antibody provides a key epitope recognition element, while the randomized CDRH1, CDRH2, CDRL1, CDRL2 and CDRL3 provide a large diversity of potential antigen binding sites, which can complement the non-human CDRH3 to form novel antigen binding pockets. Some of these binding pockets will bind the original epitope recognized by the non-human antibody; whereas others will bind epitopes that are different from the original epitope. To isolate those humanized antibodies with the same epitope specificity from the library of humanized antibodies, the non-human antibody is used as a competitor to select for those clones that express humanized antibodies that bind the same epitope recognized by the parental non-human antibody. In this method, the cognate antigen for the non-human antibody is labeled with a first fluorescent tag and the non-human antibody with a second fluorescent tag. The humanized library is first incubated with the labeled antigen and those yeast cell clones expressing humanized antibodies that retain antigen binding properties are sorted by two rounds of MACS and one or two rounds of FACS as described in Example 3. These antigen binding clones are re-incubated with labeled antigen, washed to remove unbound antigen and then incubated with the labeled non-human antibody. Those clones that compete for the same binding site on the labeled antigen are able to prevent binding of the monoclonal non-human antibody to the labeled antigen and will appear as a single labeled population of cells when sorted by MACS or FACS. In contrast, clones that appear to be double labeled represent cells that bind to a different epitope on the antigen; thus bound antigen can also support binding of the monoclonal, non-human antibody. For clones expressing antibodies with greatly reduced affinity relative to the parental monoclonal antibody, the labeled Mab will compete off the bound antigen; such clones will appear as unlabelled with either fluorescent tag.

In addition to the advantages of yielding humanized antibodies with less murine character with greater efficiency compared to traditional CDR grafting methods for antibody humanization, this method also offers the advantage of the potential to isolate clones with higher affinity for the cognate antigen than the parental monoclonal antibody since large numbers of novel antigen binding pockets are created in the humanized antibody library.

Example 6: Methods and Materials for Converting Display Vectors into Expression Vectors Novel methods and materials are provided for converting display vectors into expression vectors. Polynucleotides coding for proteins of interest (e.g., antibodies or binding fragments thereof) in display vectors may be transferred into expression vectors, allowing high level production of the proteins of interest without the proteins being trapped at the cell surface. For example, as described herein, the polynucleotide coding for a protein of interest may be transferred to an expression vector by homologous recombination without further subcloning and sequencing confirmation, and can be expressed in different formats, such as Fab, or full IgG with different isotypes, such as human IgG1, IgG4, rabbit IgG1, or mouse IgGs.

In a novel method, whereby a display vector encoding a protein of interest is converted into an expression vector for the protein of interest by homologous recombination, a vector is used that contains a DNA replacement fragment, which contains two regions that are homologous to regions in the display vector. The first region is immediately upstream of the trapping domain, and the second region encodes a portion of a selective marker, such as a gene required for leucine synthesis (Leu 2): this same portion is also included in the display vector. In between the two regions is a multiple copy replication origin. Co-transformation of the digested display vector with this replacement fragment into yeast and the ensuing homologous recombination between the display vector and the replacement fragment in vivo will result in the vector with the multiple replication origin carrying the antibody lacking the trapping peptide.

To facilitate the downstream analysis of a binder isolated from such a display system, a replacement DNA fragment was designed to convert the display vector into an expression vector directly. The replacement fragment contains the full-length constant region of an IgG heavy chain including CH1-3 (IgG-CH1-3, FIG. 6, forward stripped box), a PGK terminator (PGK TT, FIG. 6, open box), a multiple replication origin (2p Ori, FIG. 6, gray-filled box), the C-terminal portion and a portion of the N-terminus of the gene for leucine synthesis (Leu-2, FIG. 6, open box and backward striped box). Yeast host cells were then transformed with enzyme digested display vector and with the linear replacement fragment and selected on plates lacking leucine. Recombination (represented by the crosses in FIG. 6) between the human IgG CH1 and the N-termini of the gene for leucine synthesis (FIG. 6, right lower panel) in vivo results in a production vector (FIG. 6, right upper panel) with an intact full length IgG heavy chain without the proline-rich peptide (surface anchoring peptide), a high copy number replication origin (2μ☐ Ori), and a full length gene for leucine synthesis. This allows the selection of yeast cells harboring the production vector on synthetic culture medium agar plates lacking leucine that secrete full length IgG into the culture medium upon induction with induction medium. In this way, large numbers of display clones can be converted to full-length IgG expressors in parallel without the need for sub-cloning and additional sequencing confirmation.

For example, a display vector encoding a fusion of Fab-myc-proline-rich peptide was digested with Afl II and Ale I. The replacement fragment containing plasmid was digested with KpnI and Apa I. The digested vector and the replacement fragment were then co-transformed into yeast strain BJ5464 with LiAc method. Cells were then plated onto selective agar plates lacking leucine and incubated at 30° C. for 2 days. Next, colonies were picked and cultured in selective medium lacking leucine and induced for antibody expression in induction medium. Secreted antibodies in the media were used to coat wells of Immulon 2HB plates and bound antibodies were detected with horseradish peroxidase (HRP) conjugated anti-myc antibody or anti-human Fc antibody. The display vector expresses Fab antibody with a myc tag at the C-terminus of the heavy chain. The myc tag along with the yeast cell surface proline-rich peptide (PRP) is replaced by human Fc during the in vivo recombination; therefore, the production vector does not contain a myc tag, but instead directs expression of a full-length human IgG heavy chain. The expression of Fab carrying a myc tag was detected by the anti-myc antibody and the expression of the full-length human IgG was detected by using an anti-human Fc antibody. Yeast cells harboring the display vector secrete Fab antibody with myc-tagged heavy chain into the culture medium, which was detected by the anti-myc antibody. After transformation of the digested vector and replacement fragment, the transformed yeast cells with a functional production vector secrete full human IgG which was detected by an anti-human Fc antibody.

A comparison of antibody expression levels in the culture supernatant from the display vector and the production vector was conducted. In this study, culture supernatants were coated on an ELISA plate. The bound antibodies were detected with HRP conjugated anti-myc for Fab, and anti-human Fc for full-length IgG antibodies. While the anti-myc antibody did not detect significant levels of myc tagged antibody in the culture medium of cells harboring the production vector, the anti-human IgG Fc antibody did detect significant levels of IgG in the culture medium of the production vector harboring cells suggesting that the in vivo recombination successfully converted the display vector into a production vector for expression of antibodies in the desired format. Sequencing analysis confirmed that the production vector carried the correct Fab or full-length IgG construct. This in-vivo conversion was highly effective, with almost 100% of the cells that were able to grow on plates lacking leucine harboring the correct production vectors. Furthermore, the amount of antibody released into the culture medium was significantly greater than from cells harboring the display vector alone. The estimated yield was in the range of 10 mg/L for full-length IgG production in yeast cell culture medium.

Example 7: Assays of Proteins of Interest

Proteins of interest, including proteins that bind to a binding partner such as antibody proteins of interest, may be obtained (e.g., secreted from host cells) and assayed. Assays may include assays for binding affinity determination, by any method known in the art including, for example ELISA or BIACORE.

In an exemplary method, antibodies secreted in the yeast culture medium were purified using Protein A affinity column chromatography. The concentrations of the purified IgG antibodies were determined by Lowry protein assay (Pierce, Rockford Ill.). Briefly, to determine the affinity of the purified antibodies, 100 ng of the corresponding antigens were coated onto wells of 96 well Immulon 4 HB ELISA plates in 100 μl of phosphate buffered saline (PBS). Bovine serum albumin (BSA) was coated on adjacent wells to serve as a negative control. The plates were sealed with plastic sealing films and kept at 4° C. overnight. The next day, unbound antigens and PBS were removed, and the wells were blocked with PBS (for each liter: 8 g NaCl, 0.2 g KCl, 2.68 g $Na_2HPO_4$-$7H_2O$, 0.24 $KH_2PO4$) and 3 g/L of IgG-free BSA (ImmunoResearch, PA) for 2 hrs at room temperature. The plates were then washed 2 times with wash buffer (50 mM Tris-HCl, 150 mM NaCl, 0.05% Triton X-100, pH 7.4). To each well, serial dilutions of the antibodies were added for binding to the antigens. The plates were incubated at room temperature with shaking at 145 rpm for 1 hour. The wells were washed 4 times with wash buffer. 100 μl of HRP-conjugated anti-human Fc antibody (ImmunoResearch, PA) was diluted at 1:10,000 and added to the wells. The plates were incubated at room temperature with shaking at 145 rpm for 1 hour, followed by 4 washes with wash buffer, 100 μl HRP substrate TMB (KPL, MD) was then added to each well and incubated for 10 minutes. The reaction was stopped by adding 100 ☐μl of 100 mM HCl and the absorbance values at 450 nm were determined with a plate reader. The data were analyzed with nonlinear regression and curve fitted to obtain $K_d$ values. Antibodies with affinity in the low nM or sub-nM range were obtained for many antigens tested. For example, when beta-2 microglobulin was used an antigen, several clones were obtained with such affinities (e.g., $K_d$=0.53 nM with an $R^2$=0.98; and $K_d$=5.31 nM with an $R^2$=0.98). Also, for example, when beta-2 microglobulin, PSA and AFP was used an antigen in the screening of the Fab library, several clones were obtained with such affinities and likewise for the antigens used for screening the full-length IgG library (Table 21).

Use of surface plasmon resonance is accepted as a more rigorous assessment of ligand (antigen) receptor (antibody) binding kinetics. Therefore, the affinity of a selected subset of antibody clones was also determined using a Biacore 3000 system. For this, a CM5 sensor chip was coated with anti-human IgG (Fc) antibodies using amine coupling according to the protocol in the Human Antibody Capture Kit provided by the vendor (GE, WI). In brief, a 1:1 (v/v) mixture of EDC (400 mM) and NHS (100 mM) was injected in the cell of a Biacore 3000 for 7 minutes to activate the sensor chip surface. Then, antibody in coupling buffer was injected. Finally, 1 M ethanolamine, pH 8.5 was injected for 7 minutes to block any remaining activity on the surface. This procedure resulted in immobilization of approximately 7200 to 7800 RU of anti-human Fc antibody. (One RU represents approximately 1 pg of protein bound to the surface). The purified test antibodies from the selected clones were each diluted in HBS-EP+ (0.01 M Hepes pH 7.4, 150 mM NaCl, 3 mM EDTA and 0.05% v/v Surfactant 20) and injected over the sensor surface until maximum binding had occurred. Then a concentration series of the cognate antigen ranging from 1.56 nM to 100 nM in concentration was passed over the immobilized antibody. After reaching saturation, the cell was flushed with wash buffer and dissociation rates observed. Several buffer blanks were included for the purpose of double referencing the data. A reference flow cell containing only anti-human Fc, but no human test antibody, was used as a reference flow cell. The data was double referenced by first subtracting the reference flow cell data from the active flow cell data and then subtracting a blank injection. The resulting data was analyzed in the BiaEvaluation software using a Langmuir 1:1 binding model. Full kinetic analysis was performed to determine the association and dissociation rate constants and the affinity of the interactions. The $K_D$ values obtained are summarized in Table 21.

TABLE 21*

Affinities of isolated antibody clones determined by ELISA and Biacore. All isolates from the Fab library were converted to full-length IgG before assessing affinity for their cognate antigen.

| Library | Antigen | Clones | Apparent $K_D$ by ELISA (nM) | Apparent $K_D$ by Biacore (nM) |
|---|---|---|---|---|
| Fab | β2M | A1 | 0.87 | 12.7 |
| | | C1 | 0.47 | 1.07 |
| | | D5 | 0.13 | 0.47 |
| | | C10 | 0.31 | 0.20 |
| | | F10 | 0.09 | 0.48 |
| | AFP | H5 | 0.22 | ND |
| | | G5 | 1.73 | ND |
| | PSA | D8 | 0.51 | ND |
| | | D11 | 1.43 | ND |
| IgG | PSA | A1 | 0.15 | 0.68 |
| | | A7 | 0.16 | ND |
| | | A12 | 0.18 | ND |
| | | B1 | 0.14 | 0.71 |
| | | C5 | 0.8 | 0.14 |
| | | D11 | 1.43 | ND |
| | Endophilin | A11 | 0.74 | ND |
| | | B2 | 3.9 | ND |
| | Homer 1 | B1 | 1.93 | ND |
| | | A10 | 2.0 | ND |

*ND as used throughout this Table means not determined.

Example 8: Novel Peptides for Display of Proteins of Interest

Proteins of interest associated with novel peptides, such as proline-rich peptides, may be displayed at host cell surfaces when the peptides are associated with the proteins of interest (e.g., by linking a proline-rich peptide to either the N-terminal or the C-terminal of a protein of interest). For example, the display of proteins of interest linked at their C-terminus to a proline-rich peptide separated by a (GGGGS)$_3$ (SEQ ID NO: 123) linker is shown in Example 2. Similarly, proline-rich peptides may be tested for their ability to support display of a protein of interest at a host cell surface when operably linked to the N-terminus of the protein of interest.

In an exemplary method for the display of a protein of interest linked at its N-terminus to a proline-rich peptide, the proline-rich peptide of clone DS12, without the His tag and the last two amino acids (PPPTPPRTPPPPPPPPPPPPPPP-PPL; (SEQ ID NO: 55)) was tested for its ability to support the display of a heavy chain of an anti-vWf Fab antibody when placed at the N-terminus of the heavy chain of an anti-vWf Fab antibody. A fusion gene encoding the heavy chain of an anti-vWf Fab antibody coupled to a proline-rich peptide via a (GGGGS)$_3$ (SEQ ID NO: 123) linker was synthesized and cloned into the BamH I and Pme I sites in the display vector carrying the light chain of the anti-vWf Fab antibody. Next, the recombinant plasmid was used to transform yeast host BJ5464. The transformants were then selected on agar plates lacking tryptophan. Colonies were then picked and grown in selective medium and induced for Fab expression in the presence of 2% galactose as described in Example 3. Next, cells were harvested and washed with labeling buffer and labeled with biotinylated mouse anti-human light chain antibody, followed by PE-conjugated streptavidin. About 60% of the cells displayed light chain. Further, a negative control was run with cells harboring a vector carrying the light chain only without the heavy chain. The negative control did not show appreciable staining of light chain. These data suggested that the proline-rich peptide operably linked to the N-terminus of the protein of interest is able to support display of the protein of interest.

Aspects, including embodiments and/or features, of the present subject matter described above may be beneficial alone or in combination, with one or more other aspects. Without limiting the foregoing description, in accordance with one aspect of the subject matter herein, there is provided a library of host cells displaying on their surface proteins of interest associated with a proline-rich peptide.

In accordance with another aspect which may be used or combined with any of the preceding or following aspects, the host cells are yeast.

In accordance with another aspect which may be used or combined with any of the preceding or following aspects, the protein of interest is an antibody or fragment thereof.

In accordance with another aspect which may be used or combined with any of the preceding or following aspects, the antibody or fragment thereof is selected from the group consisting of: full-length antibody, Fab, scFv, Fv, an antibody heavy chain or fragment thereof, an antibody light chain or fragment thereof and a single chain antibody (SCA).

In accordance with another aspect which may be used or combined with any of the preceding or following aspects, the proline-rich peptide is an amino acid sequence comprising any of the amino acid sequences depicted in SEQ ID NOS: 1-116.

In accordance with another aspect which may be used or combined with any of the preceding or following aspects, the proline-rich peptide is (A) an amino acid sequence comprising one or more of the following features: (i) at least 3, 4, 5, 6 or more contiguous proline residues; (ii) a number of contiguous proline (P) or (XP) residues (where X is any amino acid) sufficient to produce a polyproline Type II helix with at least 2 turns; (iii) at least about 60%, 65%, 70%, 75%, 80%, 85%, 90%, 95%, 99% or 100% sequence identity to any of the amino acid sequences depicted in SEQ ID NOS: 1 and 55-116; (iv) any of the amino acid sequences depicted in SEQ ID NOS: 2-54; (v) about 3 to about 26 proline residues in a length of about 3 to 50 amino acid residues (e.g., about 3 to about 26 amino acid residues); (vi) about 20% to about 100% proline; (vii) a C-terminal amino acid residue of the peptide that is not proline or histidine; (viii) at the C-terminus of the peptide at least 1, 2, 3, 4, 5, 6, 7, 8, 9, 10, 11, 12, 13, 14 or more non-proline amino acid residues; or (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu); or the proline-rich peptide is (B) an amino acid sequence: (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues; (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues; (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues; (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or (v) that is 3 to 11 amino acid residues and wherein no less than 3 and no more than 9 of the amino acid residues of the peptide are proline residues.

In accordance with another aspect which may be used or combined with any of the preceding or following aspects, the C-terminal non-proline amino acids residues comprise a S (Ser), L (Leu), C (Cys), V (Val), CV (Cys-Val), HHHHHH (SEQ ID NO: 118), HHHHHHV (SEQ ID NO: 119), LHHHHHH (SEQ ID NO: 122), LLLLLLLL (residues 1-8 of SEQ ID NO: 121), LHHHHHHCV (SEQ ID NO: 120), or LLLLLLLLS (SEQ ID NO: 121).

In accordance with another aspect which may be used or combined with any of the preceding or following aspects, the proline-rich peptide comprises SEQ ID NO: 1.

In accordance with another aspect which may be used or combined with any of the preceding or following aspects, the protein of interest and the proline-rich peptide are directly associated.

In accordance with another aspect which may be used or combined with any of the preceding or following aspects, the protein of interest and the proline-rich peptide are indirectly associated.

In accordance with another aspect which may be used or combined with any of the preceding or following aspects, the protein of interest and the proline-rich peptide are associated through a peptide linker.

In accordance with another aspect which may be used or combined with any of the preceding or following aspects, the peptide linker is (GGGGS)$_3$ (SEQ ID NO: 123).

In accordance with another aspect which may be used or combined with any of the preceding or following aspects, when the protein of interest and the proline-rich peptide are associated, the proline-rich peptide is associated at (e.g., linked to) either the N-terminal or C-terminal of a protein of interest.

In accordance with another aspect which may be used or combined with any of the preceding or following aspects, the proline-rich peptide does not comprise hydroxyproline.

Without limiting the foregoing description, in accordance with another aspect of the subject matter herein, there is provided a library of host cells comprising polynucleotides coding for a protein of interest and a proline-rich peptide.

In accordance with another aspect which may be used or combined with any of the preceding or following aspects, the host cells are yeast.

In accordance with another aspect which may be used or combined with any of the preceding or following aspects, the protein of interest is an antibody or binding fragment thereof.

In accordance with another aspect which may be used or combined with any of the preceding or following aspects, the antibody binding fragment is selected from the group consisting of scFv, Fv, an antibody heavy chain or fragment thereof, an antibody light chain or fragment thereof and a single chain antibody (SCA).

In accordance with another aspect which may be used or combined with any of the preceding or following aspects, the proline-rich peptide is an amino acid sequence comprising PPP or any of the amino acid sequences depicted in SEQ ID NOS: 1-116.

In accordance with another aspect which may be used or combined with any of the preceding or following aspects, the proline-rich peptide is (A) an amino acid sequence comprising one or more of the following features: (i) at least 3, 4, 5, 6 or more contiguous proline residues; (ii) a number of contiguous proline (P) or (XP) residues (where X is any amino acid) sufficient to produce a polyproline Type II helix with at least 2 turns; (iii) at least about 60%, 65%, 70%, 75%, 80%, 85%, 90%, 95%, 99% or 100% sequence identity to any of the amino acid sequences depicted in SEQ ID NOS: 1 and 55-116; (iv) any of the amino acid sequences depicted in SEQ ID NOS: 2-54; (v) about 3 to about 26 proline residues in a length of about 3 to ≤50 amino acid residues (e.g., about 3 to about 26 amino acid residues); (vi) about 20% to about 100% proline; (vii) a C-terminal amino acid residue of the peptide that is not proline or histidine; (viii) at the C-terminus of the peptide at least 1, 2, 3, 4, 5, 6, 7, 8, 9, 10, 11, 12, 13, 14 or more non-proline amino acid residues; or (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu); or the proline-rich peptide is (B) an amino acid sequence: (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues; (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues; (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues; (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or (v) that is 3 to 11 amino acid residues and wherein no less than 3 and no more than 9 of the amino acid residues of the peptide are proline residues.

In accordance with another aspect which may be used or combined with any of the preceding or following aspects, the C-terminal non-proline amino acids residues comprise a S (Ser), L (Leu), C (Cys), V (Val), CV (Cys-Val), HHHHHH (SEQ ID NO: 118), HHHHHHV (SEQ ID NO: 119), LHH-HHHH (SEQ ID NO: 122), LLLLLLLL (residues 1-8 of SEQ ID NO: 121), LHHHHHHCV (SEQ ID NO: 120), or LLLLLLLLS (SEQ ID NO: 121).

In accordance with another aspect which may be used or combined with any of the preceding or following aspects, the proline-rich peptide comprises SEQ ID NO: 1.

In accordance with another aspect which may be used or combined with any of the preceding or following aspects, the protein of interest and the proline-rich peptide are directly associated.

In accordance with another aspect which may be used or combined with any of the preceding or following aspects, the protein of interest and the proline-rich peptide are indirectly associated.

In accordance with another aspect which may be used or combined with any of the preceding or following aspects, the protein of interest and the proline-rich peptide are associated through a peptide linker.

In accordance with another aspect which may be used or combined with any of the preceding or following aspects, the peptide linker is (GGGGS)$_3$ (SEQ ID NO: 123).

In accordance with another aspect which may be used or combined with any of the preceding or following aspects, when the protein of interest and the proline-rich peptide are associated, the proline-rich peptide is associated at (e.g., linked to) either the N-terminal or C-terminal of a protein of interest.

In accordance with another aspect which may be used or combined with any of the preceding or following aspects, the proline-rich peptide does not comprise hydroxyproline.

In accordance with another aspect which may be used or combined with any of the preceding or following aspects, the polynucleotide coding for the protein of interest is operably linked to one or more expression control elements.

In accordance with another aspect which may be used or combined with any of the preceding or following aspects, the expression control element is a promoter.

In accordance with another aspect which may be used or combined with any of the preceding or following aspects, the promoter is a yeast promoter.

Without limiting the foregoing description, in accordance with another aspect of the subject matter herein, there is provided a nucleic acid library comprising a plurality of polynucleotides coding for proteins of interest and a proline-rich peptide.

In accordance with another aspect which may be used or combined with any of the preceding or following aspects, the protein of interest is an antibody or binding fragment thereof.

In accordance with another aspect which may be used or combined with any of the preceding or following aspects, the antibody binding fragment is selected from the group consisting of scFv, Fv, an antibody heavy chain or fragment thereof, an antibody light chain or fragment thereof and a single chain antibody (SCA).

In accordance with another aspect which may be used or combined with any of the preceding or following aspects, the proline-rich peptide is an amino acid sequence comprising PPP or any of the amino acid sequences depicted in SEQ ID NOS: 1-116.

In accordance with another aspect which may be used or combined with any of the preceding or following aspects, the proline-rich peptide is (A) an amino acid sequence comprising one or more of the following features: (i) at least 3, 4, 5, 6 or more contiguous proline residues; (ii) a number of contiguous proline (P) or (XP) residues (where X is any amino acid) sufficient to produce a polyproline Type II helix with at least 2 turns; (iii) at least about 60%, 65%, 70%, 75%, 80%, 85%, 90%, 95%, 99% or 100% sequence identity to any of the amino acid sequences depicted in SEQ ID NOS: 1 and 55-116; (iv) any of the amino acid sequences depicted in SEQ ID NOS: 2-54; (v) about 3 to about 26 proline residues in a length of about 3 to ≤50 amino acid residues (e.g., about 3 to about 26 amino acid residues); (vi) about 20% to about 100% proline; (vii) a C-terminal amino acid residue of the peptide that is not proline or histidine; (viii) at the C-terminus of the peptide at least 1, 2, 3, 4, 5, 6, 7, 8, 9, 10, 11, 12, 13, 14 or more non-proline amino acid residues; or (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu); or the proline-rich peptide is (B) an amino acid sequence: (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues; (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues; (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues; (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or (v) that is 3 to 11 amino acid residues and wherein no less than 3 and no more than 9 of the amino acid residues of the peptide are proline residues.

In accordance with another aspect which may be used or combined with any of the preceding or following aspects, the C-terminal non-proline amino acids residues comprise a S (Ser), L (Leu), C (Cys), V (Val), CV (Cys-Val), HHHHHH (SEQ ID NO: 118), HHHHHHV (SEQ ID NO: 119), LHH-HHHH (SEQ ID NO: 122), LLLLLLLL (residues 1-8 of SEQ ID NO: 121), LHHHHHHCV (SEQ ID NO: 120), or LLLLLLLLS (SEQ ID NO: 121).

In accordance with another aspect which may be used or combined with any of the preceding or following aspects, the proline-rich peptide comprises SEQ ID NO: 1.

In accordance with another aspect which may be used or combined with any of the preceding or following aspects, the protein of interest and the proline-rich peptide are directly associated.

In accordance with another aspect which may be used or combined with any of the preceding or following aspects, the protein of interest and the proline-rich peptide are indirectly associated.

In accordance with another aspect which may be used or combined with any of the preceding or following aspects, the protein of interest and the proline-rich peptide are associated through a peptide linker.

In accordance with another aspect which may be used or combined with any of the preceding or following aspects, the peptide linker is $(GGGGS)_3$ (SEQ ID NO: 123).

In accordance with another aspect which may be used or combined with any of the preceding or following aspects, when the protein of interest and the proline-rich peptide are associated, the proline-rich peptide is associated at (e.g., linked to) either the N-terminal or C-terminal of a protein of interest.

In accordance with another aspect which may be used or combined with any of the preceding or following aspects, the proline-rich peptide does not comprise hydroxyproline.

In accordance with another aspect which may be used or combined with any of the preceding or following aspects, the polynucleotide coding for the protein of interest is operably linked to one or more expression control elements.

In accordance with another aspect which may be used or combined with any of the preceding or following aspects, the expression control element is a promoter.

In accordance with another aspect which may be used or combined with any of the preceding or following aspects, the promoter is a yeast promoter.

Without limiting the foregoing description, in accordance with another aspect of the subject matter herein, there is provided a recombinant protein that comprises a protein of interest associated with a proline-rich peptide.

In accordance with another aspect which may be used or combined with any of the preceding or following aspects, the protein of interest is an antibody or binding fragment thereof.

In accordance with another aspect which may be used or combined with any of the preceding or following aspects, the antibody binding fragment is selected from the group consisting of scFv, Fv, an antibody heavy chain or fragment thereof, an antibody light chain or fragment thereof and a single chain antibody (SCA).

In accordance with another aspect which may be used or combined with any of the preceding or following aspects, the proline-rich peptide is an amino acid sequence comprising PPP or any of the amino acid sequences depicted in SEQ ID NOS: 1-116.

In accordance with another aspect which may be used or combined with any of the preceding or following aspects, the proline-rich peptide is (A) an amino acid sequence comprising one or more of the following features: (i) at least 3, 4, 5, 6 or more contiguous proline residues; (ii) a number of contiguous proline (P) or (XP) residues (where X is any amino acid) sufficient to produce a polyproline Type II helix with at least 2 turns; (iii) at least about 60%, 65%, 70%, 75%, 80%, 85%, 90%, 95%, 99% or 100% sequence identity to any of the amino acid sequences depicted in SEQ ID NOS: 1 and 55-116; (iv) any of the amino acid sequences depicted in SEQ ID NOS: 2-54; (v) about 3 to about 26 proline residues in a length of about 3 to ≤50 amino acid residues (e.g., about 3 to about 26 amino acid residues); (vi) about 20% to about 100% proline; (vii) a C-terminal amino acid residue of the peptide that is not proline or histidine; (viii) at the C-terminus of the peptide at least 1, 2, 3, 4, 5, 6, 7, 8, 9, 10, 11, 12, 13, 14 or more non-proline amino acid residues; or (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu); or the proline-rich peptide is (B) an amino acid sequence: (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues; (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues; (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues; (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or (v) that is 3 to 11 amino acid residues and wherein no less than 3 and no more than 9 of the amino acid residues of the peptide are proline residues.

In accordance with another aspect which may be used or combined with any of the preceding or following aspects, the C-terminal non-proline amino acids residues comprise a S (Ser), L (Leu), C (Cys), V (Val), CV (Cys-Val), HHHHHH (SEQ ID NO: 118), HHHHHHV (SEQ ID NO: 119), LHHHHHH (SEQ ID NO: 122), LLLLLLLL (residues 1-8 of SEQ ID NO: 121), LHHHHHHCV (SEQ ID NO: 120), or LLLLLLLLS (SEQ ID NO: 121).

In accordance with another aspect which may be used or combined with any of the preceding or following aspects, the proline-rich peptide comprises SEQ ID NO: 1.

In accordance with another aspect which may be used or combined with any of the preceding or following aspects, the protein of interest and the proline-rich peptide are directly associated.

In accordance with another aspect which may be used or combined with any of the preceding or following aspects, the protein of interest and the proline-rich peptide are indirectly associated.

In accordance with another aspect which may be used or combined with any of the preceding or following aspects, the protein of interest and the proline-rich peptide are associated through a peptide linker.

In accordance with another aspect which may be used or combined with any of the preceding or following aspects, the peptide linker is $(GGGGS)_3$ (SEQ ID NO: 123).

In accordance with another aspect which may be used or combined with any of the preceding or following aspects, when the protein of interest and the proline-rich peptide are associated, the proline-rich peptide is associated at (e.g., linked to) either the N-terminal or C-terminal of a protein of interest.

In accordance with another aspect which may be used or combined with any of the preceding or following aspects, the proline-rich peptide does not comprise hydroxyproline.

Without limiting the foregoing description, in accordance with another aspect of the subject matter herein, there is provided a recombinant polynucleotide comprising a polynucleotide coding for a protein of interest and a proline-rich peptide.

In accordance with another aspect which may be used or combined with any of the preceding or following aspects, the protein of interest is an antibody or binding fragment thereof.

In accordance with another aspect which may be used or combined with any of the preceding or following aspects, the antibody binding fragment is selected from the group consisting of scFv, Fv, an antibody heavy chain or fragment thereof, an antibody light chain or fragment thereof and a single chain antibody (SCA).

In accordance with another aspect which may be used or combined with any of the preceding or following aspects, the proline-rich peptide is an amino acid sequence comprising PPP or any of the amino acid sequences depicted in SEQ ID NOS: 1-116.

In accordance with another aspect which may be used or combined with any of the preceding or following aspects, the proline-rich peptide is (A) an amino acid sequence comprising one or more of the following features: (i) at least 3, 4, 5, 6 or more contiguous proline residues; (ii) a number of contiguous proline (P) or (XP) residues (where X is any amino acid) sufficient to produce a polyproline Type II helix with at least 2 turns; (iii) at least about 60%, 65%, 70%, 75%, 80%, 85%, 90%, 95%, 99% or 100% sequence identity to any of the amino acid sequences depicted in SEQ ID NOS: 1 and 55-116; (iv) any of the amino acid sequences depicted in SEQ ID NOS: 2-54; (v) about 3 to about 26 proline residues in a length of about 3 to ≤50 amino acid residues (e.g., about 3 to about 26 amino acid residues); (vi) about 20% to about 100% proline; (vii) a C-terminal amino acid residue of the peptide that is not proline or histidine; (viii) at the C-terminus of the peptide at least 1, 2, 3, 4, 5, 6, 7, 8, 9, 10, 11, 12, 13, 14 or more non-proline amino acid residues; or (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu); or the proline-rich peptide is (B) an amino acid sequence: (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues; (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues; (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues; (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or (v) that is 3 to 11 amino acid residues and wherein no less than 3 and no more than 9 of the amino acid residues of the peptide are proline residues.

In accordance with another aspect which may be used or combined with any of the preceding or following aspects, the C-terminal non-proline amino acids residues comprise a S (Ser), L (Leu), C (Cys), V (Val), CV (Cys-Val), HHHHHH (SEQ ID NO: 118), HHHHHHV (SEQ ID NO: 119), LHHHHHH (SEQ ID NO: 122), LLLLLLLL (residues 1-8 of SEQ ID NO: 121), LHHHHHHCV (SEQ ID NO: 120), or LLLLLLLLS (SEQ ID NO: 121).

In accordance with another aspect which may be used or combined with any of the preceding or following aspects, the proline-rich peptide comprises SEQ ID NO: 1.

In accordance with another aspect which may be used or combined with any of the preceding or following aspects, the protein of interest and the proline-rich peptide are directly associated.

In accordance with another aspect which may be used or combined with any of the preceding or following aspects, the protein of interest and the proline-rich peptide are indirectly associated.

In accordance with another aspect which may be used or combined with any of the preceding or following aspects, the protein of interest and the proline-rich peptide are associated through a peptide linker.

In accordance with another aspect which may be used or combined with any of the preceding or following aspects, the peptide linker is $(GGGGS)_3$ (SEQ ID NO: 123).

In accordance with another aspect which may be used or combined with any of the preceding or following aspects, when the protein of interest and the proline-rich peptide are associated, the proline-rich peptide is associated at (e.g., linked to) either the N-terminal or C-terminal of a protein of interest.

In accordance with another aspect which may be used or combined with any of the preceding or following aspects, the proline-rich peptide does not comprise hydroxyproline.

Without limiting the foregoing description, in accordance with another aspect of the subject matter herein, there is provided a vector comprising a polynucleotide that codes for a protein of interest and a polynucleotide that codes for a proline-rich peptide.

In accordance with another aspect which may be used or combined with any of the preceding or following aspects, the protein of interest is an antibody or binding fragment thereof.

In accordance with another aspect which may be used or combined with any of the preceding or following aspects, the antibody binding fragment is selected from the group consisting of scFv, Fv, an antibody heavy chain or fragment thereof, an antibody light chain or fragment thereof and a single chain antibody (SCA).

In accordance with another aspect which may be used or combined with any of the preceding or following aspects, the proline-rich peptide is an amino acid sequence comprising PPP or any of the amino acid sequences depicted in SEQ ID NOS: 1-116.

In accordance with another aspect which may be used or combined with any of the preceding or following aspects, the proline-rich peptide is (A) an amino acid sequence comprising one or more of the following features: (i) at least 3, 4, 5, 6 or more contiguous proline residues; (ii) a number of contiguous proline (P) or (XP) residues (where X is any amino acid) sufficient to produce a polyproline Type II helix with at least 2 turns; (iii) at least about 60%, 65%, 70%, 75%, 80%, 85%, 90%, 95%, 99% or 100% sequence identity to any of the amino acid sequences depicted in SEQ ID NOS: 1 and 55-116; (iv) any of the amino acid sequences depicted in SEQ ID NOS: 2-54; (v) about 3 to about 26 proline residues in a length of about 3 to s 50 amino acid residues (e.g., about 3 to about 26 amino acid residues); (vi) about 20% to about 100% proline; (vii) a C-terminal amino acid residue of the peptide that is not proline or histidine; (viii) at the C-terminus of the peptide at least 1, 2, 3, 4, 5, 6, 7, 8, 9, 10, 11, 12, 13, 14 or more non-proline amino acid residues; or (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu); or the proline-rich peptide is (B) an amino acid sequence: (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues; (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues; (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues; (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or (v) that is 3 to 11 amino acid residues and wherein no less than 3 and no more than 9 of the amino acid residues of the peptide are proline residues.

In accordance with another aspect which may be used or combined with any of the preceding or following aspects, the C-terminal non-proline amino acids residues comprise a S (Ser), L (Leu), C (Cys), V (Val), CV (Cys-Val), HHHHHH (SEQ ID NO: 118), HHHHHHV (SEQ ID NO: 119), LHHHHHH (SEQ ID NO: 122), LLLLLLLL (residues 1-8 of SEQ ID NO: 121), LHHHHHHCV (SEQ ID NO: 120), or LLLLLLLLS (SEQ ID NO: 121).

In accordance with another aspect which may be used or combined with any of the preceding or following aspects, the proline-rich peptide comprises SEQ ID NO: 1.

In accordance with another aspect which may be used or combined with any of the preceding or following aspects, the protein of interest and the proline-rich peptide are directly associated.

In accordance with another aspect which may be used or combined with any of the preceding or following aspects, the protein of interest and the proline-rich peptide are indirectly associated.

In accordance with another aspect which may be used or combined with any of the preceding or following aspects, the protein of interest and the proline-rich peptide are associated through a peptide linker.

In accordance with another aspect which may be used or combined with any of the preceding or following aspects, the peptide linker is (GGGGS)$_3$ (SEQ ID NO: 123).

In accordance with another aspect which may be used or combined with any of the preceding or following aspects, when the protein of interest and the proline-rich peptide are associated, the proline-rich peptide is associated at (e.g., linked to) either the N-terminal or C-terminal of a protein of interest.

In accordance with another aspect which may be used or combined with any of the preceding or following aspects, the proline-rich peptide does not comprise hydroxyproline.

Without limiting the foregoing description, in accordance with another aspect of the subject matter herein, there is provided a host cell comprising a polynucleotide coding for a protein of interest and a polynucleotide coding for a proline-rich peptide.

In accordance with another aspect which may be used or combined with any of the preceding or following aspects, the protein of interest and the proline-rich peptide are coded by the same polynucleotide.

In accordance with another aspect which may be used or combined with any of the preceding or following aspects, the protein of interest and the proline-rich peptide are coded by different polynucleotides.

In accordance with another aspect which may be used or combined with any of the preceding or following aspects, the protein of interest is an antibody or binding fragment thereof.

In accordance with another aspect which may be used or combined with any of the preceding or following aspects, the antibody binding fragment is selected from the group consisting of scFv, Fv, an antibody heavy chain or fragment thereof, an antibody light chain or fragment thereof and a single chain antibody (SCA).

In accordance with another aspect which may be used or combined with any of the preceding or following aspects, the proline-rich peptide is an amino acid sequence comprising PPP or any of the amino acid sequences depicted in SEQ ID NOS: 1-116.

In accordance with another aspect which may be used or combined with any of the preceding or following aspects, the proline-rich peptide is (A) an amino acid sequence comprising one or more of the following features: (i) at least 3, 4, 5, 6 or more contiguous proline residues; (ii) a number of contiguous proline (P) or (XP) residues (where X is any amino acid) sufficient to produce a polyproline Type II helix with at least 2 turns; (iii) at least about 60%, 65%, 70%, 75%, 80%, 85%, 90%, 95%, 99% or 100% sequence identity to any of the amino acid sequences depicted in SEQ ID NOS: 1 and 55-116; (iv) any of the amino acid sequences depicted in SEQ ID NOS: 2-54; (v) about 3 to about 26 proline residues in a length of about 3 to ≤50 amino acid residues (e.g., about 3 to about 26 amino acid residues); (vi) about 20% to about 100% proline; (vii) a C-terminal amino acid residue of the peptide that is not proline or histidine; (viii) at the C-terminus of the peptide at least 1, 2, 3, 4, 5, 6, 7, 8, 9, 10, 11, 12, 13, 14 or more non-proline amino acid residues; or (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu); or the proline-rich peptide is (B) an amino acid sequence: (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues; (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues; (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues; (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or (v) that is 3 to 11 amino acid residues and wherein no less than 3 and no more than 9 of the amino acid residues of the peptide are proline residues.

In accordance with another aspect which may be used or combined with any of the preceding or following aspects, the C-terminal non-proline amino acids residues comprise a S (Ser), L (Leu), C (Cys), V (Val), CV (Cys-Val), HHHHHH (SEQ ID NO: 118), HHHHHHV (SEQ ID NO: 119), LHH-HHHH (SEQ ID NO: 122), LLLLLLLL (residues 1-8 of SEQ ID NO: 121), LHHHHHHCV (SEQ ID NO: 120), or LLLLLLLLS (SEQ ID NO: 121).

In accordance with another aspect which may be used or combined with any of the preceding or following aspects, the proline-rich peptide comprises SEQ ID NO: 1.

In accordance with another aspect which may be used or combined with any of the preceding or following aspects, the protein of interest and the proline-rich peptide are directly associated.

In accordance with another aspect which may be used or combined with any of the preceding or following aspects, the protein of interest and the proline-rich peptide are indirectly associated.

In accordance with another aspect which may be used or combined with any of the preceding or following aspects, the protein of interest and the proline-rich peptide are associated through a peptide linker.

In accordance with another aspect which may be used or combined with any of the preceding or following aspects, the peptide linker is (GGGGS)$_3$ (SEQ ID NO: 123).

In accordance with another aspect which may be used or combined with any of the preceding or following aspects, when the protein of interest and the proline-rich peptide are associated, the proline-rich peptide is associated at (e.g., linked to) either the N-terminal or C-terminal of a protein of interest.

In accordance with another aspect which may be used or combined with any of the preceding or following aspects, the proline-rich peptide does not comprise hydroxyproline.

In accordance with another aspect which may be used or combined with any of the preceding or following aspects, the host cell is a yeast cell.

Without limiting the foregoing description, in accordance with another aspect of the subject matter herein, there is provided a method of producing a protein of interest associated with a proline-rich peptide comprising culturing a host cell comprising a polynucleotide coding for a protein of interest and a polynucleotide coding for a proline-rich peptide under conditions wherein the polynucleotides are expressed and the protein of interest and the proline-rich peptide is produced.

In accordance with another aspect which may be used or combined with any of the preceding or following aspects, the protein of interest and the proline-rich peptide are coded by the same polynucleotide.

In accordance with another aspect which may be used or combined with any of the preceding or following aspects, the protein of interest and the proline-rich peptide are coded by different polynucleotides.

In accordance with another aspect which may be used or combined with any of the preceding or following aspects, the protein of interest is an antibody or binding fragment thereof.

In accordance with another aspect which may be used or combined with any of the preceding or following aspects, the antibody binding fragment is selected from the group consisting of scFv, Fv, an antibody heavy chain or fragment thereof, an antibody light chain or fragment thereof and a single chain antibody (SCA).

In accordance with another aspect which may be used or combined with any of the preceding or following aspects, the proline-rich peptide is an amino acid sequence comprising PPP or any of the amino acid sequences depicted in SEQ ID NOS: 1-116.

In accordance with another aspect which may be used or combined with any of the preceding or following aspects, the proline-rich peptide is (A) an amino acid sequence comprising one or more of the following features: (i) at least 3, 4, 5, 6 or more contiguous proline residues; (ii) a number of contiguous proline (P) or (XP) residues (where X is any amino acid) sufficient to produce a polyproline Type II helix with at least 2 turns; (iii) at least about 60%, 65%, 70%, 75%, 80%, 85%, 90%, 95%, 99% or 100% sequence identity to any of the amino acid sequences depicted in SEQ ID NOS: 1 and 55-116; (iv) any of the amino acid sequences depicted in SEQ ID NOS: 2-54; (v) about 3 to about 26 proline residues in a length of about 3 to ≤50 amino acid residues (e.g., about 3 to about 26 amino acid residues); (vi) about 20% to about 100% proline; (vii) a C-terminal amino acid residue of the peptide that is not proline or histidine; (viii) at the C-terminus of the peptide at least 1, 2, 3, 4, 5, 6, 7, 8, 9, 10, 11, 12, 13, 14 or more non-proline amino acid residues; or (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu); or the proline-rich peptide is (B) an amino acid sequence: (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues; (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues; (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues; (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or (v) that is 3 to 11 amino acid residues and wherein no less than 3 and no more than 9 of the amino acid residues of the peptide are proline residues.

In accordance with another aspect which may be used or combined with any of the preceding or following aspects, the C-terminal non-proline amino acids residues comprise a S (Ser), L (Leu), C (Cys), V (Val), CV (Cys-Val), HHHHHH (SEQ ID NO: 118), HHHHHHV (SEQ ID NO: 119), LHHHHHH (SEQ ID NO: 122), LLLLLLLL (residues 1-8 of SEQ ID NO: 121), LHHHHHHCV (SEQ ID NO: 120), or LLLLLLLLS (SEQ ID NO: 121).

In accordance with another aspect which may be used or combined with any of the preceding or following aspects, the proline-rich peptide comprises SEQ ID NO: 1.

In accordance with another aspect which may be used or combined with any of the preceding or following aspects, the protein of interest and the proline-rich peptide are directly associated.

In accordance with another aspect which may be used or combined with any of the preceding or following aspects, the protein of interest and the proline-rich peptide are indirectly associated.

In accordance with another aspect which may be used or combined with any of the preceding or following aspects, the protein of interest and the proline-rich peptide are associated through a peptide linker.

In accordance with another aspect which may be used or combined with any of the preceding or following aspects, the peptide linker is (GGGGS)$_3$ (SEQ ID NO: 123).

In accordance with another aspect which may be used or combined with any of the preceding or following aspects, when the protein of interest and the proline-rich peptide are associated, the proline-rich peptide is associated at (e.g., linked to) either the N-terminal or C-terminal of a protein of interest.

In accordance with another aspect which may be used or combined with any of the preceding or following aspects, the proline-rich peptide does not comprise hydroxyproline.

In accordance with another aspect which may be used or combined with any of the preceding or following aspects, the host cell is a yeast cell.

In accordance with another aspect which may be used or combined with any of the preceding or following aspects, the method may further comprise recovering the protein of interest from the host cell culture.

Without limiting the foregoing description, in accordance with another aspect of the subject matter herein, there is provided a method of displaying a protein of interest associated with a proline-rich peptide on a surface of a host cell, the method comprising: culturing a host cell comprising a polynucleotide coding for a protein of interest and a polynucleotide coding for a proline-rich peptide under conditions wherein the polynucleotide sequences are expressed and the protein of interest and the proline-rich peptide are displayed.

In accordance with another aspect which may be used or combined with any of the preceding or following aspects, the protein of interest and the proline-rich peptide are coded by the same polynucleotide.

In accordance with another aspect which may be used or combined with any of the preceding or following aspects, the protein of interest and the proline-rich peptide are coded by different polynucleotides.

In n accordance with another aspect which may be used or combined with any of the preceding or following aspects, the protein of interest is an antibody or binding fragment thereof.

In accordance with another aspect which may be used or combined with any of the preceding or following aspects, the antibody binding fragment is selected from the group consisting of scFv, Fv, an antibody heavy chain or fragment thereof, an antibody light chain or fragment thereof and a single chain antibody (SCA).

In accordance with another aspect which may be used or combined with any of the preceding or following aspects, the proline-rich peptide is an amino acid sequence comprising PPP or any of the amino acid sequences depicted in SEQ ID NOS: 1-116.

In accordance with another aspect which may be used or combined with any of the preceding or following aspects, the proline-rich peptide is (A) an amino acid sequence comprising one or more of the following features: (i) at least 3, 4, 5, 6 or more contiguous proline residues; (ii) a number of contiguous proline (P) or (XP) residues (where X is any amino acid) sufficient to produce a polyproline Type II helix with at least 2 turns; (iii) at least about 60%, 65%, 70%, 75%, 80%, 85%, 90%, 95%, 99% or 100% sequence identity to any of the amino acid sequences depicted in SEQ ID NOS: 1 and 55-116; (iv) any of the amino acid sequences depicted in SEQ ID NOS: 2-54; (v) about 3 to about 26 proline residues in a length of about 3 to ≤50 amino acid residues (e.g., about 3 to about 26 amino acid residues); (vi) about 20% to about 100% proline; (vii) a C-terminal amino acid residue of the peptide that is not proline or histidine; (viii) at the C-terminus of the peptide at least 1, 2, 3, 4, 5, 6, 7, 8, 9, 10, 11, 12, 13, 14 or more non-proline amino acid residues; or (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu); or the proline-rich peptide is (B) an amino acid sequence: (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-praline amino acid residues; or (b) wherein the N-terminal 11 amino acid residues of the peptide comprise 8 to 11 proline residues; (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues; (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues; (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or (v) that is 3 to 11 amino acid residues and wherein no less than 3 and no more than 9 of the amino acid residues of the peptide are proline residues.

In accordance with another aspect which may be used or combined with any of the preceding or following aspects, the C-terminal non-proline amino acids residues comprise a S (Ser), L (Leu), C (Cys), V (Val), CV (Cys-Val), HHHHHH (SEQ ID NO: 118), HHHHHHV (SEQ ID NO: 119), LHHHHHH (SEQ ID NO: 122), LLLLLLLL (residues 1-8 of SEQ ID NO: 121), LHHHHHHCV (SEQ ID NO: 120), or LLLLLLLLS (SEQ ID NO: 121).

In accordance with another aspect which may be used or combined with any of the preceding or following aspects, the proline-rich peptide comprises SEQ ID NO: 1.

In accordance with another aspect which may be used or combined with any of the preceding or following aspects, the protein of interest and the proline-rich peptide are directly associated.

In accordance with another aspect which may be used or combined with any of the preceding or following aspects, the protein of interest and the proline-rich peptide are indirectly associated.

In accordance with another aspect which may be used or combined with any of the preceding or following aspects, the protein of interest and the proline-rich peptide are associated through a peptide linker.

In accordance with another aspect which may be used or combined with any of the preceding or following aspects, the peptide linker is (GGGGS)$_3$ (SEQ ID NO: 123).

In accordance with another aspect which may be used or combined with any of the preceding or following aspects, when the protein of interest and the proline-rich peptide are associated, the proline-rich peptide is associated at (e.g., linked to) either the N-terminal or C-terminal of a protein of interest.

In accordance with another aspect which may be used or combined with any of the preceding or following aspects, the proline-rich peptide does not comprise hydroxyproline.

In accordance with another aspect which may be used or combined with any of the preceding or following aspects, the host cell is a yeast cell.

Without limiting the foregoing description, in accordance with another aspect of the subject matter herein, there is provided a method for selecting a host cell that displays a protein of interest from a library of host cells, the method comprising: (a) contacting the host cell library with an agent that binds to the protein of interest associated with the proline-rich peptide; and (b) selecting host cells that bind to the agent, wherein the host cells comprise a polynucleotide coding for a protein of interest and a polynucleotide coding for a proline-rich peptide.

In accordance with another aspect which may be used or combined with any of the preceding or following aspects, the protein of interest and the proline-rich peptide are coded by the same polynucleotide.

In accordance with another aspect which may be used or combined with any of the preceding or following aspects, the protein of interest and the proline-rich peptide are coded by different polynucleotides.

In accordance with another aspect which may be used or combined with any of the preceding or following aspects, the agent is a binding partner for the protein of interest.

In accordance with another aspect which may be used or combined with any of the preceding or following aspects, the binding partner is an antigen and the protein of interest is an antibody.

In accordance with another aspect which may be used or combined with any of the preceding or following aspects, the protein of interest is an antibody or fragment thereof.

In accordance with another aspect which may be used or combined with any of the preceding or following aspects, the antibody binding fragment is selected from the group consisting of scFv, Fv, an antibody heavy chain or fragment thereof, an antibody light chain or fragment thereof and a single chain antibody (SCA).

In accordance with another aspect which may be used or combined with any of the preceding or following aspects, the proline-rich peptide is an amino acid sequence comprising PPP or any of the amino acid sequences depicted in SEQ ID NOS: 1-116.

In accordance with another aspect which may be used or combined with any of the preceding or following aspects, the proline-rich peptide is (A) an amino acid sequence comprising one or more of the following features: (i) at least 3, 4, 5, 6 or more contiguous proline residues; (ii) a number of contiguous proline (P) or (XP) residues (where X is any amino acid) sufficient to produce a polyproline Type II helix with at least 2 turns; (iii) at least about 60%, 65%, 70%, 75%, 80%, 85%, 90%, 95%, 99% or 100% sequence identity to any of the amino acid sequences depicted in SEQ ID NOS: 1 and 55-116; (iv) any of the amino acid sequences depicted in SEQ ID NOS: 2-54; (v) about 3 to about 26 proline residues in a length of about 3 to ≤50 amino acid residues (e.g., about 3 to about 26 amino acid residues); (vi) about 20% to about 100% proline; (vii) a C-terminal amino acid residue of the peptide that is not proline or histidine; (viii) at the C-terminus of the peptide at least 1, 2, 3, 4, 5, 6, 7, 8, 9, 10, 11, 12, 13, 14 or more non-proline amino acid residues; or (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu); or the proline-rich peptide is (B) an amino acid sequence: (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues; (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues; (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues; (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or (v) that is 3 to 11 amino acid residues and wherein no less than 3 and no more than 9 of the amino acid residues of the peptide are proline residues.

In accordance with another aspect which may be used or combined with any of the preceding or following aspects, the C-terminal non-proline amino acids residues comprise a S (Ser), L (Leu), C (Cys), V (Val), CV (Cys-Val), HHHHHH (SEQ ID NO: 118), HHHHHHV (SEQ ID NO: 119), LHH-HHHH (SEQ ID NO: 122), LLLLLLLL (residues 1-8 of SEQ ID NO: 121), LHHHHHHCV (SEQ ID NO: 120), or LLLLLLLLS (SEQ ID NO: 121).

In accordance with another aspect which may be used or combined with any of the preceding or following aspects, the proline-rich peptide comprises SEQ ID NO: 1.

In accordance with another aspect which may be used or combined with any of the preceding or following aspects, the protein of interest and the proline-rich peptide are directly associated.

In accordance with another aspect which may be used or combined with any of the preceding or following aspects, the protein of interest and the proline-rich peptide are indirectly associated.

In accordance with another aspect which may be used or combined with any of the preceding or following aspects, the protein of interest and the proline-rich peptide are associated through a peptide linker.

In accordance with another aspect which may be used or combined with any of the preceding or following aspects, the peptide linker is (GGGGS)$_3$ (SEQ ID NO: 123).

In accordance with another aspect which may be used or combined with any of the preceding or following aspects, when the protein of interest and the proline-rich peptide are associated, the proline-rich peptide is associated at (e.g., linked to) either the N-terminal or C-terminal of a protein of interest.

In accordance with another aspect which may be used or combined with any of the preceding or following aspects, the proline-rich peptide does not comprise hydroxyproline.

In accordance with another aspect which may be used or combined with any of the preceding or following aspects, the polynucleotide coding for the protein of interest is operably linked to one or more expression control elements.

In accordance with another aspect which may be used or combined with any of the preceding or following aspects, the expression control element is a promoter.

In accordance with another aspect which may be used or combined with any of the preceding or following aspects, the promoter is a yeast promoter.

Without limiting the foregoing description, in accordance with another aspect of the subject matter herein, there is provided a method for isolating a polynucleotide coding for a protein of interest from a host cell library that displays the protein of interest associated with a proline-rich peptide at its surface, the method comprising: a.) contacting the host cell library with an agent that binds to the protein of interest associated with the proline-rich peptide; b.) selecting host cells that bind to the agent; and c.) recovering a polynucleotide coding for the protein of interest from the host cells that bind to the agent.

In accordance with another aspect which may be used or combined with any of the preceding or following aspects, the agent is a binding partner for the protein of interest.

In accordance with another aspect which may be used or combined with any of the preceding or following aspects, the binding partner is an antigen and the protein of interest is an antibody.

In accordance with another aspect which may be used or combined with any of the preceding or following aspects, the method may further comprise identifying the sequence of the polynucleotide coding for a protein of interest.

In accordance with another aspect which may be used or combined with any of the preceding or following aspects, the host cell is a yeast cell.

In accordance with another aspect which may be used or combined with any of the preceding or following aspects, the protein of interest is an antibody or binding fragment thereof.

In accordance with another aspect which may be used or combined with any of the preceding or following aspects, the antibody binding fragment is selected from the group consisting of scFv, Fv, an antibody heavy chain or fragment thereof, an antibody light chain or fragment thereof and a single chain antibody (SCA).

In accordance with another aspect which may be used or combined with any of the preceding or following aspects, the proline-rich peptide is an amino acid sequence comprising PPP or any of the amino acid sequences depicted in SEQ ID NOS: 1-116.

In accordance with another aspect which may be used or combined with any of the preceding or following aspects, the proline-rich peptide is (A) an amino acid sequence comprising one or more of the following features: (i) at least 3, 4, 5, 6 or more contiguous proline residues; (ii) a number of contiguous proline (P) or (XP) residues (where X is any amino acid) sufficient to produce a polyproline Type II helix with at least 2 turns; (iii) at least about 60%, 65%, 70%, 75%, 80%, 85%, 90%, 95%, 99% or 100% sequence identity to any of the amino acid sequences depicted in SEQ ID NOS: 1 and 55-116; (iv) any of the amino acid sequences depicted in SEQ ID NOS: 2-54; (v) about 3 to about 26 proline residues in a length of about 3 to ≤50 amino acid residues (e.g., about 3 to about 26 amino acid residues); (vi) about 20% to about 100% proline; (vii) a C-terminal amino acid residue of the peptide that is not proline or histidine; (viii) at the C-terminus of the peptide at least 1, 2, 3, 4, 5, 6, 7, 8, 9, 10, 11, 12, 13, 14 or more non-proline amino acid residues; or (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu); or the proline-rich peptide is (B) an amino acid sequence: (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues; (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues; (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues; (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or (v) that is 3 to 11 amino acid residues and wherein no less than 3 and no more than 9 of the amino acid residues of the peptide are proline residues.

In accordance with another aspect which may be used or combined with any of the preceding or following aspects, the C-terminal non-proline amino acids residues comprise a S (Ser), L (Leu), C (Cys), V (Val), CV (Cys-Val), HHHHHH (SEQ ID NO: 118), HHHHHHV (SEQ ID NO: 119), LHH-HHHH (SEQ ID NO: 122), LLLLLLLL (residues 1-8 of SEQ ID NO: 121), LHHHHHHCV (SEQ ID NO: 120), or LLLLLLLLS (SEQ ID NO: 121).

In accordance with another aspect which may be used or combined with any of the preceding or following aspects, the proline-rich peptide comprises SEQ ID NO: 1.

In accordance with another aspect which may be used or combined with any of the preceding or following aspects, the protein of interest and the proline-rich peptide are directly associated.

In accordance with another aspect which may be used or combined with any of the preceding or following aspects, the protein of interest and the proline-rich peptide are indirectly associated.

In accordance with another aspect which may be used or combined with any of the preceding or following aspects, the protein of interest and the proline-rich peptide are associated through a peptide linker.

In accordance with another aspect which may be used or combined with any of the preceding or following aspects, the peptide linker is (GGGGS)$_3$ (SEQ ID NO: 123).

In accordance with another aspect which may be used or combined with any of the preceding or following aspects, when the protein of interest and the proline-rich peptide are associated, the proline-rich peptide is associated at (e.g., linked to) either the N-terminal or C-terminal of a protein of interest.

In accordance with another aspect which may be used or combined with any of the preceding or following aspects, the proline-rich peptide does not comprise hydroxyproline.

Without limiting the foregoing description, in accordance with another aspect of the subject matter herein, there is provided a method for isolating a peptide capable of displaying a marker protein at a surface of a host cell, the method comprising: a.) contacting the host cell library with an agent that binds to a marker protein; b.) selecting host cells that bind to the agent; and c.) recovering a peptide displayed at a surface of a host cell, wherein the peptide displayed on the surface of the host cell is a peptide of 50 amino acids or less and is associated with the marker protein.

In accordance with another aspect which may be used or combined with any of the preceding or following aspects, the agent is a binding partner for the marker protein.

In accordance with another aspect which may be used or combined with any of the preceding or following aspects, the binding partner is an antigen and the marker protein is an antibody.

In accordance with another aspect which may be used or combined with any of the preceding or following aspects, the host cell is a yeast cell.

In accordance with another aspect which may be used or combined with any of the preceding or following aspects, the marker protein is an antibody or binding fragment thereof.

In accordance with another aspect which may be used or combined with any of the preceding or following aspects, the antibody binding fragment is selected from the group consisting of full length antibody, Fab, scFv, Fv, an antibody heavy chain or fragment thereof, an antibody light chain or fragment thereof and a single chain antibody (SCA).

In accordance with another aspect which may be used or combined with any of the preceding or following aspects, the marker protein and the peptide capable of displaying the marker protein at a surface of a host cell are directly associated.

In accordance with another aspect which may be used or combined with any of the preceding or following aspects, the marker protein and the peptide capable of displaying the marker protein at a surface of a host cell are indirectly associated.

In accordance with another aspect which may be used or combined with any of the preceding or following aspects, the marker protein and the peptide capable of displaying the marker protein at a surface of a host cell are associated through a peptide linker.

In accordance with another aspect which may be used or combined with any of the preceding or following aspects, the peptide linker is (GGGGS)$_3$ (SEQ ID NO: 123).

In accordance with another aspect which may be used or combined with any of the preceding or following aspects, when the protein of interest and the proline-rich peptide are associated, the proline-rich peptide is associated at (e.g., linked to) either the N-terminal or C-terminal of a protein of interest.

In accordance with another aspect which may be used or combined with any of the preceding or following aspects, the peptide capable of displaying the marker protein at a surface of a host cell does not comprise hydroxyproline.

Without limiting the foregoing description, in accordance with another aspect of the subject matter herein, there is provided a method for isolating a polynucleotide coding for a peptide capable of displaying a marker protein at a surface of a host cell, the method comprising: a.) generating a library of oligonucleotides that comprise degenerate codons; b.) linking polynucleotides coding for a marker protein to oligonucleotides generated in step (a); c.) constructing vectors that comprise the polynucleotide coding for the marker protein linked to the oligonucleotides generated in step (a); d.) introducing the vectors into host cells; e.) expressing the polynucleotide coding for the marker protein linked to the oligonucleotides generated in step (a); f.) selecting host cells that display the marker protein at their surface; and g.) recovering the polynucleotide coding for the peptide capable of displaying the marker protein at the surface of the host cells.

In accordance with another aspect which may be used or combined with any of the preceding or following aspects, the oligonucleotides comprise a repeat of degenerate VBT codons that code for threonine, alanine, proline, isoleucine, valine, leucine, serine, glycine or arginine.

In accordance with another aspect which may be used or combined with any of the preceding or following aspects, oligonucleotides further comprise one or more degenerate NNS codons.

In accordance with another aspect which may be used or combined with any of the preceding or following aspects, the oligonucleotides comprise twenty-three VBT codons and three NNS codons.

In accordance with another aspect which may be used or combined with any of the preceding or following aspects, codons 1-23 are VBT codons and codons 24-26 are NNS codons.

In accordance with another aspect which may be used or combined with any of the preceding or following aspects, the polynucleotide comprises a nucleotide sequence encoding a tag.

In accordance with another aspect which may be used or combined with any of the preceding or following aspects, the tag is a histidine tag or a myc tag.

In accordance with another aspect which may be used or combined with any of the preceding or following aspects, the library of oligonucleotides comprise degenerated codons of NNN, NNS, or NNK.

In accordance with another aspect which may be used or combined with any of the preceding or following aspects, the host cell is a yeast cell.

In accordance with another aspect which may be used or combined with any of the preceding or following aspects, the marker protein is an antibody.

Without limiting the foregoing description, in accordance with another aspect of the subject matter herein, there is provided a method for isolating a peptide capable of displaying a marker protein at a surface of a host cell, the method comprising: a.) generating a library of oligonucleotides that comprise degenerate codons; b.) linking polynucleotides coding for a marker protein to oligonucleotides generated in step (a); c.) constructing vectors that comprise the polynucleotide coding for the marker protein linked to the oligonucleotides generated in step (a); d.) introducing the vectors into host cells; e.) expressing the polynucleotide coding for the marker protein linked to the oligonucleotides generated in step (a); f.) selecting host cells that display the marker protein at their surface; and g.) recovering the peptide capable of displaying the marker protein at the surface of the host cell.

In accordance with another aspect which may be used or combined with any of the preceding or following aspects, the oligonucleotides comprise a repeat of degenerate VBT codons that code for threonine, alanine, proline, isoleucine, valine, leucine, serine, glycine or arginine.

In accordance with another aspect which may be used or combined with any of the preceding or following aspects, oligonucleotides further comprise one or more degenerate NNS codons.

In accordance with another aspect which may be used or combined with any of the preceding or following aspects, the oligonucleotides comprise twenty-three VBT codons and three NNS codons.

In accordance with another aspect which may be used or combined with any of the preceding or following aspects, codons 1-23 are VBT codons and codons 24-26 are NNS codons.

In accordance with another aspect which may be used or combined with any of the preceding or following aspects, the polynucleotide comprises a nucleotide sequence encoding a tag.

In accordance with another aspect which may be used or combined with any of the preceding or following aspects, the tag is a histidine tag or a myc tag.

In accordance with another aspect which may be used or combined with any of the preceding or following aspects, the library of oligonucleotides comprise degenerated codons of NNN, NNS, or NNK.

In accordance with another aspect which may be used or combined with any of the preceding or following aspects, the host cell is a yeast cell.

In accordance with another aspect which may be used or combined with any of the preceding or following aspects, the marker protein is an antibody.

Without limiting the foregoing description, in accordance with another aspect of the subject matter herein, there is provided a library of peptides coded by a randomized polynucleotide comprising a repeat of degenerate VBT codons, wherein the VBT codons code for threonine, alanine, proline, isoleucine, valine, leucine, serine, glycine or arginine.

In accordance with another aspect which may be used or combined with any of the preceding or following aspects, the polynucleotide comprises twenty-three VBT codons.

In accordance with another aspect which may be used or combined with any of the preceding or following aspects, the polynucleotide further comprises one or more NNS codons, wherein the NNS codons code for any amino acid.

In accordance with another aspect which may be used or combined with any of the preceding or following aspects, the polynucleotide comprises twenty-three VBT codons and three NNS codons.

In accordance with another aspect which may be used or combined with any of the preceding or following aspects, the polynucleotide comprises a nucleotide sequence coding for a tag.

In accordance with another aspect which may be used or combined with any of the preceding or following aspects, the tag is a histidine tag or a myc tag.

Without limiting the foregoing description, in accordance with another aspect of the subject matter herein, there is provided a vector for display of a proline-rich peptide associated with a protein of interest, the vector comprising: a polynucleotide coding for a protein of interest, a polynucleotide coding for a proline-rich peptide, a yeast replication origin, a first polynucleotide for selection in yeast and an inducible yeast promoter.

In accordance with another aspect which may be used or combined with any of the preceding or following aspects, the vector further comprises a bacteria origin of replication and a polynucleotide for selection in bacteria.

In accordance with another aspect which may be used or combined with any of the preceding or following aspects, the vector further comprises a portion of a second polynucleotide for selection in yeast.

In accordance with another aspect which may be used or combined with any of the preceding or following aspects, the protein of interest is an antibody or binding fragment thereof.

In accordance with another aspect which may be used or combined with any of the preceding or following aspects, the antibody binding fragment is selected from the group consisting of scFv, Fv, an antibody heavy chain or fragment thereof, an antibody light chain or fragment thereof and a single chain antibody (SCA).

In accordance with another aspect which may be used or combined with any of the preceding or following aspects, the yeast replication origin is a low copy replication origin.

In accordance with another aspect which may be used or combined with any of the preceding or following aspects, the yeast low copy replication origin is CEN6/ARS4.

In accordance with another aspect which may be used or combined with any of the preceding or following aspects, the polynucleotide for selection in yeast is Zeocin.

In accordance with another aspect which may be used or combined with any of the preceding or following aspects, the bacteria origin of replication is from E. coli.

In accordance with another aspect which may be used or combined with any of the preceding or following aspects, the bacteria replication origin is a high copy replication origin.

In accordance with another aspect which may be used or combined with any of the preceding or following aspects, the bacteria high copy replication origin is pUC Ori.

In accordance with another aspect which may be used or combined with any of the preceding or following aspects, the polynucleotide for selection in bacteria is ampicillin.

In accordance with another aspect which may be used or combined with any of the preceding or following aspects, the inducible yeast promoter is Gal 1/10.

In accordance with another aspect which may be used or combined with any of the preceding or following aspects, the portion of the second polynucleotide for selection in yeast is the N-terminus of Leu-2.

In accordance with another aspect which may be used or combined with any of the preceding or following aspects, the proline-rich peptide is an amino acid sequence comprising PPP or any of the amino acid sequences depicted in SEQ ID NOS: 1-116.

In accordance with another aspect which may be used or combined with any of the preceding or following aspects, the proline-rich peptide is (A) an amino acid sequence comprising one or more of the following features: (i) at least 3, 4, 5, 6 or more contiguous proline residues; (ii) a number of contiguous proline (P) or (XP) residues (where X is any amino acid) sufficient to produce a polyproline Type II helix with at least 2 turns; (iii) at least about 60%, 65%, 70%, 75%, 80%, 85%, 90%, 95%, 99% or 100% sequence identity to any of the amino acid sequences depicted in SEQ ID NOS: 1 and 55-116; (iv) any of the amino acid sequences depicted in SEQ ID NOS: 2-54; (v) about 3 to about 26 proline residues in a length of about 3 to ≤50 amino acid residues (e.g., about 3 to about 26 amino acid residues); (vi) about 20% to about 100% proline; (vii) a C-terminal amino acid residue of the peptide that is not proline or histidine; (viii) at the C-terminus of the peptide at least 1, 2, 3, 4, 5, 6, 7, 8, 9, 10, 11, 12, 13, 14 or more non-proline amino acid residues; or (ix) at the C-terminus of the peptide an amino acid sequence with at least about 60%, 65%, 70%, 75%, 80%, 85%, 90%, 95%, 99% or 100% sequence identity to any of the amino acid sequences selected from the group consisting of: LHHHHHHCV (SEQ ID NO: 120), LLLLLLLLS (SEQ ID NO: 121), LHHHHHH (SEQ ID NO: 122), HHHHHH (SEQ ID NO: 118), CV (Cys-Val) or L (Leu); or the proline-rich peptide is (B) an amino acid sequence: (i) that is less than or equal to 50 amino acid residues, and optionally (a) wherein the N-terminal 25 amino acid residues of the peptide comprise 20 to 25 prolines residues and/or wherein the C-terminal 1 to 24 amino acid residues of the peptide comprise non-proline amino acid residues; or (b) wherein the N-terminal 11 amino acid residues of the peptide comprise 8 to 11 proline residues; (ii) that is 34 amino acid residues, and optionally wherein the N-terminal 25 amino acid residues of the peptide comprise 20 to 25 proline residues and/or wherein the C-terminal 9 amino acid residues of the peptide comprise non-proline amino acid residues; (iii) that is 20 amino acid residues, and optionally wherein the N-terminal 11 amino acids of the peptide comprise 8 to 11 proline residues and/or wherein the C-terminal 9 amino acids of the peptide comprise non-proline amino acid residues; (iv) that is 12 to 21 amino acid residues, and optionally wherein the N-terminal 3 to 12 amino acid residues of the peptide are proline residues and/or wherein the C-terminal 9 amino acid residues of the peptide are non-proline residues; or (v) that is 3 to 11 amino acid residues and wherein no less than 3 and no more than 9 of the amino acid residues of the peptide are proline residues.

In accordance with another aspect which may be used or combined with any of the preceding or following aspects, the C-terminal non-proline amino acids residues comprise a S (Ser), L (Leu), C (Cys), V (Val), CV (Cys-Val), HHHHHH (SEQ ID NO: 118), HHHHHHV (SEQ ID NO: 119), LHHHHH (SEQ ID NO: 122), LLLLLLLL (residues 1-8 of SEQ ID NO: 121), LHHHHHHCV (SEQ ID NO: 120), or LLLLLLLLS (SEQ ID NO: 121).

In accordance with another aspect which may be used or combined with any of the preceding or following aspects, the protein of interest or the proline-rich peptide further comprise a tag.

In accordance with another aspect which may be used or combined with any of the preceding or following aspects, the tag is a histidine tag or a myc tag.

Without limiting the foregoing description, in accordance with another aspect of the subject matter herein, there is provided a proline-rich peptide produced by a method comprising: a.) generating a library of oligonucleotides that comprise degenerate codons; b.) linking polynucleotides coding for a marker protein to an oligonucleotide generated in step (a); c.) constructing vectors that comprise the polynucleotide coding for the marker protein linked to the oligonucleotide; d.) introducing the vectors into host cells; e.) expressing the polynucleotide coding for the marker protein linked to the oligonucleotides generated in step (a); f.) selecting host cells that display the marker protein at their surface; and g.) recovering the proline-rich peptide from host cells that bind to a detecting agent.

In accordance with another aspect which may be used or combined with any of the preceding or following aspects, the oligonucleotides comprise a repeat of degenerate VBT codons that code for threonine, alanine, proline, isoleucine, valine, leucine, serine, glycine or arginine.

In accordance with another aspect which may be used or combined with any of the preceding or following aspects, oligonucleotides further comprise one or more degenerate NNS codons.

In accordance with another aspect which may be used or combined with any of the preceding or following aspects, the oligonucleotides comprise twenty-three VBT codons and three NNS codons.

In accordance with another aspect which may be used or combined with any of the preceding or following aspects, codons 1-23 are VBT codons and codons 24-26 are NNS codons.

In accordance with another aspect which may be used or combined with any of the preceding or following aspects, the polynucleotide comprises a nucleotide sequence encoding a tag.

In accordance with another aspect which may be used or combined with any of the preceding or following aspects, the tag is a histidine tag.

Without limiting the foregoing description, in accordance with another aspect of the subject matter herein, there is provided a method for randomizing one or more amino acid residues in an antibody complementarity determining region (CDR), the method comprising: a.) selecting one or more amino acid residues in a CDR for randomization; b.) synthesizing oligonucleotides comprising one or more nucleotides that are positioned 3' of a codon for a first CDR residue selected for randomization; c.) splitting the synthesized oligonucleotides into a first number of pools, wherein the number of pools permit a frequency of randomized amino acid residues at the first amino acid position selected for randomization to approximate a predetermined frequency of amino acid residues at the selected position; d.) joining 3 nucleotides, one at a time, to the 5' end of the oligonucleotides in each pool, wherein the 3 nucleotides form a codon that is selected to approximate a predetermined frequency of an amino acid residue occurring at the position selected for randomization; and e.) combining the pools comprising oligonucleotides joined to the codon.

In accordance with another aspect which may be used or combined with any of the preceding or following aspects, the method further comprises randomizing a second amino acid residue in a CDR selected for randomization, the method comprising: f.) splitting the oligonucleotides of step (e) into a second number of pools, wherein the number of pools permit a frequency of randomized amino acid residues at the second amino acid position selected for randomization to approximate a predetermined frequency of amino acid residues at the selected position; g.) joining 3 nucleotides, one at a time, to the 5' end of the oligonucleotides in each pool, wherein the 3 nucleotides form a codon that is selected to approximate a predetermined frequency of an amino acid residue occurring at the position selected for randomization; and h.) combining the pools comprising oligonucleotides joined to the codon.

In accordance with another aspect which may be used or combined with any of the preceding or following aspects, the method further comprises randomizing additional amino acid residues in a CDR selected for randomization by repeating steps (f)-(h) until the additional amino acid residues are randomized.

In accordance with another aspect which may be used or combined with any of the preceding or following aspects, the first number of pools and the second number of pools are the same.

In accordance with another aspect which may be used or combined with any of the preceding or following aspects, the first number of pools and the second number of pools are different.

In accordance with another aspect which may be used or combined with any of the preceding or following aspects, the method further comprises generating an oligonucleotide coding for a CDR with one or more randomized amino acids.

In accordance with another aspect which may be used or combined with any of the preceding or following aspects, amino acid residues in HCDR1 are randomized.

In accordance with another aspect which may be used or combined with any of the preceding or following aspects, the synthesized oligonucleotides are split into 13 pools.

In accordance with another aspect which may be used or combined with any of the preceding or following aspects, for Kabat position 33 in HCDR1 codons GCT and TAT are joined to three of the oligonucleotide pools, codon TGG is joined to two of the oligonucleotide pools, and codons GGT, TCT, GAT, ACT and GTT are each joined to one of the oligonucleotide pools.

In accordance with another aspect which may be used or combined with any of the preceding or following aspects, for Kabat position 32 in HCDR1 codon TAT is joined to eight of the oligonucleotide pools and codons TCT, AAT, GGT, TTT and GCT are each joined to one of the oligonucleotide pools.

In accordance with another aspect which may be used or combined with any of the preceding or following aspects, for Kabat position 31 in HCDR1 codon TCT is joined to six of the oligonucleotide pools, codon AAT is joined to two of the oligonucleotide pools, and codons GGT, ACT, GAT, AGA and GCT are each joined to one of the oligonucleotide pools.

In accordance with another aspect which may be used or combined with any of the preceding or following aspects, for position 30 in HCDR1 codon TCT is joined to seven of the oligonucleotide pools, codon ACT is joined to two of the oligonucleotide pools, and codons AAT, AGA, GAT, GGT are each joined to one of the oligonucleotide pools.

In accordance with another aspect which may be used or combined with any of the preceding or following aspects, amino acid residues in HCDR2 are randomized.

In accordance with another aspect which may be used or combined with any of the preceding or following aspects, the synthesized oligonucleotides are split into 12 pools.

In accordance with another aspect which may be used or combined with any of the preceding or following aspects, for Kabat position 58 codon TAT is joined to four of the oligonucleotide pools, codon AAT is joined to two of the oligonucleotide pools, and codons GAT, AGA, TCT, ATT, ACT and CAT are each joined to one of the oligonucleotide pools.

In accordance with another aspect which may be used or combined with any of the preceding or following aspects, for Kabat position 57 codon ACT is joined to twelve of the oligonucleotide pools.

In accordance with another aspect which may be used or combined with any of the preceding or following aspects, for Kabat position 56 codon TCT is joined to four of the oligonucleotide pools, codon ACT is joined to two of the oligonucleotide pools, and codons AAT, GAT, TAT, GM, GGT, and GCT are each joined to one of the oligonucleotide pools.

In accordance with another aspect which may be used or combined with any of the preceding or following aspects, for Kabat position 55 codon GGT is joined to twelve of the oligonucleotide pools.

In accordance with another aspect which may be used or combined with any of the preceding or following aspects, for Kabat position 54 codon GGT is joined to four of the oligonucleotide pools, codon TCT is joined to three of the oligonucleotide pools, and codons GAT, AAT, MA, TTT, ACT are each joined to one of the oligonucleotide pools.

In accordance with another aspect which may be used or combined with any of the preceding or following aspects, for Kabat position 53 codon TCT is joined to three of the oligonucleotide pools, codon GAT is joined to two of the oligonucleotide pools, and codons TAT, GGT, CAT, AAT, ATT, ACT and TGG are each joined to one of the oligonucleotide pools.

In accordance with another aspect which may be used or combined with any of the preceding or following aspects, for Kabat position 52a codon CCA is joined to five of the oligonucleotide pools, codon GGT is joined to four of the oligonucleotide pools and codon TCT is joined to three of the oligonucleotide pools.

In accordance with another aspect which may be used or combined with any of the preceding or following aspects, for Kabat position 52 codon TCT is joined to three of the oligonucleotide pools, codon TAT is joined to three of the oligonucleotide pools, and codons AAT, AAA, ATT, AGA, GAT, ACT are each joined to one of the oligonucleotide pools.

In accordance with another aspect which may be used or combined with any of the preceding or following aspects, for Kabat position 51 codon ATC is joined to twelve of the oligonucleotide pools.

In accordance with another aspect which may be used or combined with any of the preceding or following aspects, for Kabat position 50 codon AGA is joined to two of the oligonucleotide pools, and codons TAT, TGG, GTT, GGT, ATT, GAA, GCT, TCT, AAT, TTA are each joined to one of the oligonucleotide pools.

In accordance with another aspect which may be used or combined with any of the preceding or following aspects, for Kabat position 49 codon GGT is joined to six of the oligonucleotide pools, codon TCT is joined to three of the oligonucleotide pools, and codon GCT is joined to three of the oligonucleotide pools.

In accordance with another aspect which may be used or combined with any of the preceding or following aspects, amino acid residues in LCDR1 are randomized.

In accordance with another aspect which may be used or combined with any of the preceding or following aspects, the synthesized oligonucleotides are split into 11 pools.

In accordance with another aspect which may be used or combined with any of the preceding or following aspects, for Kabat position 32 codon TAT is joined to six of the oligonucleotide pools, and codons AAT, TGG, TTT, TCT and GAT are each joined to one of the oligonucleotide pools.

In accordance with another aspect which may be used or combined with any of the preceding or following aspects, for Kabat position 31a codon TCT is joined to seven of the oligonucleotide pools, codon AAT is joined to two of the oligonucleotide pools and codon ACT is joined to two of the oligonucleotide pools.

In accordance with another aspect which may be used or combined with any of the preceding or following aspects, for Kabat position 21 codon TCT is joined to four of the oligonucleotide pools, codon AAT is joined to two of the oligonucleotide pools, and codons ACT, AGA, ATT, GAT and AAA are each joined to one of the oligonucleotide pools.

In accordance with another aspect which may be used or combined with any of the preceding or following aspects, for Kabat position 30 codon TCT is joined to five of the oligonucleotide pools, codon AAT is joined to two of the oligonucleotide pools, and codons AAA, GGT, AGA and TAT are each joined to one of the oligonucleotide pools.

In accordance with another aspect which may be used or combined with any of the preceding or following aspects, for Kabat position 29 codon ATT is joined to five of the oligonucleotide pools, codon TCT is joined to two of the oligonucleotide pools, codon GTT is joined to two of the oligonucleotide pools, and codons GGT and AAT are each joined to one of the oligonucleotide pools.

In accordance with another aspect which may be used or combined with any of the preceding or following aspects, for Kabat position 28 codon TCT is joined to three of the oligonucleotide pools, codon AAT is joined to two of the oligonucleotide pools, codon GTT is joined to two of the oligonucleotide pools, codon GGT is joined to two of the oligonucleotide pools, and codon GAT is joined to two of the oligonucleotide pools.

In accordance with another aspect which may be used or combined with any of the preceding or following aspects, amino acid residues in LCDR2 are randomized.

In accordance with another aspect which may be used or combined with any of the preceding or following aspects, the synthesized oligonucleotides are split into 10 pools.

In accordance with another aspect which may be used or combined with any of the preceding or following aspects, for Kabat position 55 codon GCT is joined to four of the oligonucleotide pools, codon CAA is joined to three of the oligonucleotide pools, and codon GAA is joined to three of the oligonucleotide pools.

In accordance with another aspect which may be used or combined with any of the preceding or following aspects, for Kabat position 53 codon TCT is joined to four of the oligonucleotide pools, codon AAT is joined to three of the oligonucleotide pools and codon ACT is joined to three of the oligonucleotide pools.

In accordance with another aspect which may be used or combined with any of the preceding or following aspects, for Kabat position 51 codon GCT is joined to ten of the oligonucleotides.

In accordance with another aspect which may be used or combined with any of the preceding or following aspects, for Kabat position 50 codon GGT is joined to two of the oligonucleotide pools, codon GCT is joined to two of the oligonucleotide pools, codon GAT is joined to two of the oligonucleotide pools, and codons TGG, AAA, TTA and GAA are each joined to one of the oligonucleotide pools.

In accordance with another aspect which may be used or combined with any of the preceding or following aspects, amino acid residues in LCDR3 are randomized.

In accordance with another aspect which may be used or combined with any of the preceding or following aspects, the synthesized oligonucleotides are split into 12 pools.

In accordance with another aspect which may be used or combined with any of the preceding or following aspects, for Kabat position 96 codon TTA is joined to three of the oligonucleotide pools, codon TAT is joined to two of the oligonucleotide pools, codon TGG is joined to two of the oligonucleotide pools, and codons TTT, ATT, AGA, CCA and TAT are each joined to one of the oligonucleotide pools.

In accordance with another aspect which may be used or combined with any of the preceding or following aspects, for Kabat position 94 codon TCT is joined to two of the oligonucleotide pools, codon ACT is joined to two of the oligonucleotide pools, codon TGG is joined to two of the oligonucleotide pools, codon TAT is joined to two of the oligonucleotide pools, and codons TTA, TTT, GCT and CCA are each joined to one of the oligonucleotide pools.

In accordance with another aspect which may be used or combined with any of the preceding or following aspects, for Kabat position 93 codon TCT is joined to five of the oligonucleotide pools, codon AAT is joined to two of the oligonucleotide pools, and codons CAA, ACT, CAT, GGT and GAT are each joined to one of the oligonucleotide pools.

In accordance with another aspect which may be used or combined with any of the preceding or following aspects, for Kabat position 92 codon TAT is joined to three of the oligonucleotide pools, codon GGT is joined to two of the oligonucleotide pools, and codons AAT, TCT, GAT, TTA, ACT, CAT and ATT are each joined to one of the oligonucleotide pools.

In accordance with another aspect which may be used or combined with any of the preceding or following aspects, for Kabat position 91 codon TAT is joined to seven of the oligonucleotide pools, codon TCT is joined to two of the oligonucleotide pools, and codons AGA, GCT and GGT are each joined to one of the oligonucleotide pools.

In accordance with another aspect which may be used or combined with any of the preceding or following aspects, amino acid residues in HCDR3 are randomized.

In accordance with another aspect which may be used or combined with any of the preceding or following aspects, the synthesized oligonucleotides are split into 29 pools.

In accordance with another aspect which may be used or combined with any of the preceding or following aspects, for Kabat position 100b codon GGT is joined to four of the oligonucleotide pools, codon TAT is joined to four of the oligonucleotides, codon TCT is joined to four of the oligonucleotide pools, codon GAT is joined to two of the oligonucleotide pools, and codons AGA, TTA, GTT, GCT, CCA, ACT, AAT, TTT, ATT, GAA, CAT, CAA, AAA, ATG and TGG are each joined to one of the oligonucleotide pools.

In accordance with another aspect which may be used or combined with any of the preceding or following aspects, for Kabat position 100a codon GGT is joined to four of the oligonucleotide pools, codon TAT is joined to four of the oligonucleotide pools, codon TCT is joined to four of the oligonucleotide pools, codon GAT is joined to two of the oligonucleotide pools, and codons AGA, TTA, GTT, GCT, CCA, ACT, AAT, TTT, ATT, GAA, CAT, CAA, AAA, ATG and TGG are each joined to one of the oligonucleotide pools.

In accordance with another aspect which may be used or combined with any of the preceding or following aspects, for Kabat position 100 codon GGT is joined to four of the oligonucleotide pools, codon TAT is joined to four of the oligonucleotide pools, codon TCT is joined to four of the oligonucleotide pools, codon GAT is joined to two of the oligonucleotide pools, and codons AGA, TTA, GTT, GCT, CCA, ACT, AAT, TTT, ATT, GAA, CAT, CAA, AAA, ATG and TGG are each joined to one of the oligonucleotide pools.

In accordance with another aspect which may be used or combined with any of the preceding or following aspects, for Kabat position 99 codon GGT is joined to four of the oligonucleotide pools, codon TAT is joined to four of the oligonucleotide pools, codon TCT is joined to four of the oligonucleotide pools, codon GAT is joined to two of the oligonucleotides, and codons AGA, TTA, GTT, GCT, CCA, ACT, MT, UT, ATT, GAA, CAT, CM, AAA, ATG and TGG are each joined to one of the oligonucleotide pools.

In accordance with another aspect which may be used or combined with any of the preceding or following aspects, for Kabat position 98 codon GGT is joined to four of the oligonucleotide pools, codon TAT is joined to four of the oligonucleotide pools, codon TCT is joined to four of the oligonucleotide pools, codon GAT is joined to two of the oligonucleotide pools, and codons AGA, TTA, GTT, GCT, CCA, ACT, AAT, TTT, ATT, GM, CAT, CM, AAA, ATG and TGG are each joined to one of the oligonucleotide pools.

In accordance with another aspect which may be used or combined with any of the preceding or following aspects, for Kabat position 97 codon GGT is joined to four of the oligonucleotide pools, codon TAT is joined to four of the oligonucleotide pools, codon TCT is joined to four of the oligonucleotide pools, codon GAT is joined to two of the oligonucleotide pools, and codons AGA, TTA, GTT, GCT, CCA, ACT, MT, TTT, ATT, GM, CAT, CM, AAA, ATG and TGG are each joined to one of the oligonucleotide pools.

In accordance with another aspect which may be used or combined with any of the preceding or following aspects, for Kabat position 96 codon GGT is joined to four of the oligonucleotide pools, codon TAT is joined to four of the oligonucleotide pools, codon TCT is joined to four of the oligonucleotide pools, codon GAT is joined to two of the oligonucleotide pools, and codons AGA, TTA, GTT, GCT, CCA, ACT, MT, TTT, AU, GM, CAT, CM, AAA, ATG and TGG are each joined to one of the oligonucleotide pools.

In accordance with another aspect which may be used or combined with any of the preceding or following aspects, for Kabat position 95 codon GGT is joined to four of the oligonucleotide pools, codon TAT is joined to four of the oligonucleotide pools, codon TCT is joined to four of the oligonucleotide pools, codon GAT is joined to two of the oligonucleotide pools, and codons AGA, TTA, GTT, GCT, CCA, ACT, MT, TTT, AU, GM, CAT, CM, AAA, ATG and TGG are each joined to one of the oligonucleotide pools.

In accordance with another aspect which may be used or combined with any of the preceding or following aspects, the synthesized oligonucleotides comprise framework nucleotides.

In accordance with another aspect which may be used or combined with any of the preceding or following aspects, all of the amino acid resides in a CDR are randomized.

In accordance with another aspect which may be used or combined with any of the preceding or following aspects, the CDRs are from an antibody heavy chain.

In accordance with another aspect which may be used or combined with any of the preceding or following aspects, the CDRs are from an antibody light chain.

In accordance with another aspect which may be used or combined with any of the preceding or following aspects, the prevalence of an amino acid residue naturally occurring at the position selected for randomization is shown in Table 5.

Without limiting the foregoing description, in accordance with another aspect of the subject matter herein, there is provided a method for generating a library of antibody variable region sequences that comprises randomized amino acid residues at one or more positions in a CDR that approximate the prevalence of the amino acid residue, naturally occurring at the one or more positions, the method comprising: a.) converting the oligonucleotides generated in claim 207 to a double stranded DNA fragment; b.) linking the double-stranded DNA fragment to antibody framework regions; and c.) introducing the linked fragments into a vector thereby generating a library of antibody variable regions.

In accordance with another aspect which may be used or combined with any of the preceding or following aspects, the oligonucleotides are converted to double-stranded DNA fragments by PCR amplification where the forward and reverse primers anneal to the 5' and 3' end of the generated oligonucleotide.

Without limiting the foregoing description, in accordance with another aspect of the subject matter herein, there is provided a method for the in-vivo conversion of a display vector to a secretion vector, the method comprising: a.) mixing: (i) a display vector that comprises a first polynucleotide region and a second polynucleotide region, wherein the display vector further comprises a polynucleotide coding for an antibody fragment associated with one or more proline-rich peptides and a polynucleotide that codes for a selectable marker fragment positioned between the first and the second polynucleotide regions, and wherein the display vector is digested to remove a polynucleotide fragment from the vector that comprises a coding region for the proline-rich peptide; and (ii) a replacement fragment that comprises a first polynucleotide region and a second polynucleotide region that are homologous to the first polynucleotide region and the second polynucleotide region in the digested display vector, wherein the replacement fragment further comprises a polynucleotide coding for an antibody fragment and a selectable marker fragment positioned between the first and the second polynucleotide regions; b.) permitting the digested display vector and the replacement fragment to undergo homologous recombination to create a secretion vector, wherein the antibody fragment from the display vector and the antibody fragment from the replacement fragment are recombined to generate a full-length antibody and wherein the selectable marker fragment from the display vector and the selectable marker fragment from the replacement fragment are recombined to generate a complete selectable marker; c.) expressing the secretion vector; and d.) selecting yeast cells that are capable of growth on a selectable medium, wherein cells that are capable of growth on the selectable medium have undergone homologous recombination between the display vector and the replacement fragment resulting in the production of an secretion vector that comprises a full-length antibody and that expresses a selectable marker.

In accordance with another aspect which may be used or combined with any of the preceding or following aspects, the replacement vector comprises the full length constant region of an IgG heavy chain.

In accordance with another aspect which may be used or combined with any of the preceding or following aspects, the selectable marker is isopropylmalate isomerase.

In accordance with another aspect which may be used or combined with any of the preceding or following aspects, the display vector comprises low copy replication origin positioned between the first and the second polynucleotide regions.

In accordance with another aspect which may be used or combined with any of the preceding or following aspects, the replication origin is ARSH4.

In accordance with another aspect which may be used or combined with any of the preceding or following aspects, the replacement fragment comprises a high copy replication origin positioned between the first and the second polynucleotide regions.

In accordance with another aspect which may be used or combined with any of the preceding or following aspects, the replication origin is 2p.

Without limiting the foregoing description, in accordance with another aspect of the subject matter herein, there is provided a method for the in-vivo conversion of a display vector to a secretion vector, the method comprising: a.) mixing: (i) a display vector that comprises a first polynucleotide region and a second polynucleotide region, wherein the display vector further comprises a polynucleotide coding for an antibody fragment associated with one or more cell wall proteins and a polynucleotide that codes for a selectable marker fragment positioned between the first and the second polynucleotide regions, and wherein the display vector is digested to remove a polynucleotide fragment from the vector that comprises a coding region for the cell wall protein; and (ii) a replacement fragment that comprises a first polynucleotide region and a second polynucleotide region that are homologous to the first polynucleotide region and the second polynucleotide region in the digested display vector, wherein the replacement fragment further comprises a polynucleotide coding for an antibody fragment and a selectable marker fragment positioned between the first and the second polynucleotide regions; b.) permitting the digested display vector and the replacement fragment to undergo homologous recombination to create a secretion vector, wherein the antibody fragment from the display vector and the antibody fragment from the replacement fragment are recombined to generate a full-length antibody and wherein the selectable marker fragment from the display vector and the selectable marker fragment from the replacement fragment are recombined to generate a complete selectable marker; c.) expressing the secretion vector; and d.) selecting yeast cells that are capable of growth on a selectable medium, wherein cells that are capable of growth on the selectable medium have undergone homologous recombination between the display vector and the replacement fragment resulting in the production of an secretion vector that comprises a full-length antibody and that expresses a selectable marker.

In accordance with another aspect which may be used or combined with any of the preceding or following aspects, the replacement vector comprises the full length constant region of an IgG heavy chain.

In accordance with another aspect which may be used or combined with any of the preceding or following aspects, the selectable marker is isopropylmalate isomerase.

In accordance with another aspect which may be used or combined with any of the preceding or following aspects, the display vector comprises low copy replication origin positioned between the first and the second polynucleotide regions.

In accordance with another aspect which may be used or combined with any of the preceding or following aspects, the replication origin is ARSH4.

In accordance with another aspect which may be used or combined with any of the preceding or following aspects, the replacement fragment comprises a high copy replication origin positioned between the first and the second polynucleotide regions.

In accordance with another aspect which may be used or combined with any of the preceding or following aspects, the replication origin is 2p.

In accordance with another aspect which may be used or combined with any of the preceding or following aspects, the cell wall protein is an endogenous yeast cell wall protein.

In accordance with another aspect which may be used or combined with any of the preceding or following aspects, the endogenous yeast cell wall protein is Aga1, FLO or Aga2p.

Without limiting the foregoing description, in accordance with another aspect of the subject matter herein, there is provided an antibody or fragment thereof specific for prostate specific antigen (PSA) comprising a heavy chain variable region comprising SEQ ID NO: 130.

Without limiting the foregoing description, in accordance with another aspect of the subject matter herein, there is provided an antibody or fragment thereof specific for prostate specific antigen (PSA) comprising a light chain variable region comprising SEQ ID NO: 131.

Without limiting the foregoing description, in accordance with another aspect of the subject matter herein, there is provided an antibody or fragment thereof specific for prostate specific antigen (PSA) comprising a heavy chain variable region comprising SEQ ID NO: 130 and a light chain variable region comprising SEQ ID NO: 131.

Without limiting the foregoing description, in accordance with another aspect of the subject matter herein, there is provided an antibody or fragment thereof specific for prostate specific antigen (PSA) comprising a heavy chain variable region that is 70%, 75%, 80%, 85%, 90%, 95% or 99% identical to SEQ ID NO: 130.

Without limiting the foregoing description, in accordance with another aspect of the subject matter herein, there is provided an antibody or fragment thereof specific for prostate specific antigen (PSA) comprising a light chain variable region that is 70%, 75%, 80%, 85%, 90%, 95% or 99% identical to SEQ ID NO: 131.

In accordance with another aspect which may be used or combined with any of the preceding or following aspects, the antibody fragment is a Fab.

In accordance with another aspect which may be used or combined with any of the preceding or following aspects, the heavy chain variable region is coupled to a CH1 region of IgG1.

In accordance with another aspect which may be used or combined with any of the preceding or following aspects, the light chain variable region sequence is coupled to a constant region of kappa 1.

Without limiting the foregoing description, in accordance with another aspect of the subject matter herein, there is provided a method for obtaining a humanized antibody, the method comprising: a) generating a library of humanized antibody molecules comprising (i.) CDRH3 from a non-human antibody of interest; and (ii.) CDRH1, CDRH2, CDRL1, CDRL2 and CDRL3 from a synthetic human antibody library, wherein one or more amino acid residues in CDRH1, CDRH2, CDRL1, CDRL2 and/or CDRL3 are randomized; b) exposing the antibody library to a labeled antigen comprising an epitope recognized by the non-human antibody of interest; c) washing unbound labeled antigen from the antibody library; d) exposing the antibody library to the non-human antibody labeled with a different label than the antigen; and e) selecting members from the antibody library that bind to the labeled antigen and that inhibit binding of the non-human antibody to the labeled antigen, wherein the library of antibody molecules are displayed at a surface of a host cell associated with a proline-rich peptide.

In accordance with another aspect which may be used or combined with any of the preceding or following aspects, the host cell is a yeast cell.

In accordance with another aspect which may be used or combined with any of the preceding or following aspects, one or more amino acid residues in CDRH1, CDRH2, CDRL1, CDRL2 and/or CDRL3 are randomized by a.) selecting one or more amino acid residues in a CDR for randomization; b.) synthesizing oligonucleotides comprising one or more nucleotides that are positioned 3' of a codon for a first CDR residue selected for randomization; c.) splitting the synthesized oligonucleotides into a first number of pools, wherein the number of pools permit a frequency of randomized amino acid residues at the first amino acid position selected for randomization to approximate a predetermined frequency of amino acid residues at the selected position; d.) joining 3 nucleotides, one at a time, to the 5' end of the oligonucleotides in each pool, wherein the 3 nucleotides form a codon that is selected to approximate a predetermined frequency of an amino acid residue occurring at the position selected for randomization; and e.) combining the pools comprising oligonucleotides joined to the codon.

In accordance with another aspect which may be used or combined with any of the preceding or following aspects, the method may further comprise randomizing a second amino acid residue in a CDR selected for randomization, the method comprising: f.) splitting the oligonucleotides of step (e) into a second number of pools, wherein the number of pools permit a frequency of randomized amino acid residues at the second amino acid position selected for randomization to approximate a predetermined frequency of amino acid residues at the selected position; g. joining 3 nucleotides, one at a time, to the 5' end of the oligonucleotides in each pool, wherein the 3 nucleotides form a codon that is selected to approximate a predetermined frequency of an amino acid residue occurring at the position selected for randomization; and h. combining the pools comprising oligonucleotides joined to the codon.

In accordance with another aspect which may be used or combined with any of the preceding or following aspects, the method may further comprise randomizing additional amino acid residues in a CDR selected for randomization by repeating steps (f)-(h) until the additional amino acid residues are randomized.

In accordance with another aspect which may be used or combined with any of the preceding or following aspects, each of the residues in CDRH1, CDRH2, CDRL1, CDRL2 and/or CDRL3 are randomized.

In accordance with another aspect which may be used or combined with any of the preceding or following aspects, the first number of pools and the second number of pools are the same.

In accordance with another aspect which may be used or combined with any of the preceding or following aspects, the first number of pools and the second number of pools are different.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

The invention claimed is:

1. A library of host cells displaying on their surface proteins of interest associated with a proline-rich peptide, wherein the proline-rich peptide comprises SEQ ID NO: 1.

2. The library of host cells of claim 1, wherein the host cells are yeast.

3. The library of host cells of claim 1, wherein the protein of interest is an antibody or fragment thereof.

4. A method of displaying a protein of interest associated with a proline-rich peptide on a surface of a host cell, the method comprising: culturing a host cell comprising a polynucleotide coding for a protein of interest and a polynucleotide coding for a proline-rich peptide under conditions wherein the polynucleotide sequences are expressed and the protein of interest and the proline-rich peptide are displayed, wherein the proline-rich peptide comprises SEQ ID NO: 1.

5. The method of claim 4, wherein the protein of interest is an antibody or binding fragment thereof.

6. The method of claim 4, wherein the host cell is a yeast cell.

7. The library of host cells of claim 3, wherein the antibody binding fragment is selected from the group consisting of scFv, Fv, an antibody heavy chain or fragment thereof, an antibody light chain or fragment thereof and a single chain antibody (SCA).

8. The library of host cells of claim 1, wherein the protein of interest and the proline-rich peptide are directly associated.

9. The library of host cells of claim 1, wherein the protein of interest and the proline-rich peptide are indirectly associated.

10. The library of host cells of claim 1, wherein the protein of interest and the proline-rich peptide are associated through a peptide linker.

11. The library of host cells of claim 1, wherein the peptide linker is (GGGGS)3 (SEQ ID NO: 123).

12. The method of claim 5, wherein the antibody binding fragment is selected from the group consisting of scFv, Fv, an antibody heavy chain or fragment thereof, an antibody light chain or fragment thereof and a single chain antibody (SCA).

13. The method of claim 4, wherein the protein of interest and the proline-rich peptide are coded by the same polynucleotide.

14. The method of claim 4, wherein the protein of interest and the proline-rich peptide are coded by different polynucleotides.

* * * * *

SEQUENCE LISTING

<160> NUMBER OF SEQ ID NOS: 262

<210> SEQ ID NO 1
<211> LENGTH: 34
<212> TYPE: PRT
<213> ORGANISM: Artificial

```
<220> FEATURE:
<223> OTHER INFORMATION: Synthesized: Clones DS12, 3, 9, 10, DS41, DS52,
      DS100 and DS103

<400> SEQUENCE: 1

Pro Pro Pro Thr Pro Pro Arg Thr Pro Pro Pro Pro Pro Pro Pro
1               5                   10                  15

Pro Pro Pro Pro Pro Pro Pro Pro Leu His His His His His His
                20                  25                  30

Cys Val

<210> SEQ ID NO 2
<211> LENGTH: 4
<212> TYPE: PRT
<213> ORGANISM: Artificial
<220> FEATURE:
<223> OTHER INFORMATION: Synthesized: Proline-rich peptide 1
<220> FEATURE:
<221> NAME/KEY: misc_feature
<222> LOCATION: (4)..(4)
<223> OTHER INFORMATION: Xaa can be any amino acid

<400> SEQUENCE: 2

Pro Pro Pro Xaa
1

<210> SEQ ID NO 3
<211> LENGTH: 5
<212> TYPE: PRT
<213> ORGANISM: Artificial
<220> FEATURE:
<223> OTHER INFORMATION: Synthesized: Proline-rich peptide 2
<220> FEATURE:
<221> NAME/KEY: misc_feature
<222> LOCATION: (4)..(5)
<223> OTHER INFORMATION: Xaa can be any amino acid

<400> SEQUENCE: 3

Pro Pro Pro Xaa Xaa
1               5

<210> SEQ ID NO 4
<211> LENGTH: 6
<212> TYPE: PRT
<213> ORGANISM: Artificial
<220> FEATURE:
<223> OTHER INFORMATION: Synthesized: Proline-rich peptide 3

<400> SEQUENCE: 4

Pro Pro Pro Pro Pro Pro
1               5

<210> SEQ ID NO 5
<211> LENGTH: 7
<212> TYPE: PRT
<213> ORGANISM: Artificial
<220> FEATURE:
<223> OTHER INFORMATION: Synthesized: Proline-rich peptide 4
<220> FEATURE:
<221> NAME/KEY: misc_feature
<222> LOCATION: (4)..(4)
<223> OTHER INFORMATION: Xaa can be any amino acid

<400> SEQUENCE: 5

Pro Pro Pro Xaa Pro Pro Pro
1               5
```

-continued

```
<210> SEQ ID NO 6
<211> LENGTH: 7
<212> TYPE: PRT
<213> ORGANISM: Artificial
<220> FEATURE:
<223> OTHER INFORMATION: Synthesized: Proline-rich peptide 5

<400> SEQUENCE: 6

Pro Pro Pro Pro Pro Pro Pro
1               5

<210> SEQ ID NO 7
<211> LENGTH: 8
<212> TYPE: PRT
<213> ORGANISM: Artificial
<220> FEATURE:
<223> OTHER INFORMATION: Synthesized: Proline-rich peptide 6
<220> FEATURE:
<221> NAME/KEY: misc_feature
<222> LOCATION: (4)..(5)
<223> OTHER INFORMATION: Xaa can be any amino acid

<400> SEQUENCE: 7

Pro Pro Pro Xaa Xaa Pro Pro Pro
1               5

<210> SEQ ID NO 8
<211> LENGTH: 9
<212> TYPE: PRT
<213> ORGANISM: Artificial
<220> FEATURE:
<223> OTHER INFORMATION: Synthesized: Proline-rich peptide 7

<400> SEQUENCE: 8

Pro Pro Pro Pro Pro Pro Pro Pro Pro
1               5

<210> SEQ ID NO 9
<211> LENGTH: 11
<212> TYPE: PRT
<213> ORGANISM: Artificial
<220> FEATURE:
<223> OTHER INFORMATION: Synthesized: Proline-rich peptide 8
<220> FEATURE:
<221> NAME/KEY: misc_feature
<222> LOCATION: (4)..(4)
<223> OTHER INFORMATION: Xaa can be any amino acid
<220> FEATURE:
<221> NAME/KEY: misc_feature
<222> LOCATION: (7)..(8)
<223> OTHER INFORMATION: Xaa can be any amino acid

<400> SEQUENCE: 9

Pro Pro Pro Xaa Pro Pro Xaa Xaa Pro Pro Pro
1               5                   10

<210> SEQ ID NO 10
<211> LENGTH: 12
<212> TYPE: PRT
<213> ORGANISM: Artificial
<220> FEATURE:
<223> OTHER INFORMATION: Synthesized: Proline-rich peptide 9
<220> FEATURE:
<221> NAME/KEY: misc_feature
<222> LOCATION: (4)..(12)
<223> OTHER INFORMATION: Xaa can be any amino acid

<400> SEQUENCE: 10

Pro Pro Pro Xaa Xaa Xaa Xaa Xaa Xaa Xaa Xaa Xaa
1               5                   10
```

```
<210> SEQ ID NO 11
<211> LENGTH: 15
<212> TYPE: PRT
<213> ORGANISM: Artificial
<220> FEATURE:
<223> OTHER INFORMATION: Synthesized: Proline-rich peptide 10
<220> FEATURE:
<221> NAME/KEY: misc_feature
<222> LOCATION: (10)..(15)
<223> OTHER INFORMATION: Xaa can be any amino acid

<400> SEQUENCE: 11

Pro Pro Pro Pro Pro Pro Pro Pro Pro Xaa Xaa Xaa Xaa Xaa Xaa
1               5                   10                  15

<210> SEQ ID NO 12
<211> LENGTH: 15
<212> TYPE: PRT
<213> ORGANISM: Artificial
<220> FEATURE:
<223> OTHER INFORMATION: Synthesized: Proline-rich peptide 11
<220> FEATURE:
<221> NAME/KEY: misc_feature
<222> LOCATION: (7)..(15)
<223> OTHER INFORMATION: Xaa can be any amino acid

<400> SEQUENCE: 12

Pro Pro Pro Pro Pro Pro Xaa Xaa Xaa Xaa Xaa Xaa Xaa Xaa Xaa
1               5                   10                  15

<210> SEQ ID NO 13
<211> LENGTH: 16
<212> TYPE: PRT
<213> ORGANISM: Artificial
<220> FEATURE:
<223> OTHER INFORMATION: Synthesized: Proline-rich peptide 12
<220> FEATURE:
<221> NAME/KEY: misc_feature
<222> LOCATION: (10)..(16)
<223> OTHER INFORMATION: Xaa can be any amino acid

<400> SEQUENCE: 13

Pro Pro Pro Pro Pro Pro Pro Pro Pro Xaa Xaa Xaa Xaa Xaa Xaa Xaa
1               5                   10                  15

<210> SEQ ID NO 14
<211> LENGTH: 18
<212> TYPE: PRT
<213> ORGANISM: Artificial
<220> FEATURE:
<223> OTHER INFORMATION: Synthesized: Proline-rich peptide 13
<220> FEATURE:
<221> NAME/KEY: misc_feature
<222> LOCATION: (10)..(18)
<223> OTHER INFORMATION: Xaa can be any amino acid

<400> SEQUENCE: 14

Pro Pro Pro Pro Pro Pro Pro Pro Pro Xaa Xaa Xaa Xaa Xaa Xaa Xaa
1               5                   10                  15

Xaa Xaa

<210> SEQ ID NO 15
<211> LENGTH: 20
<212> TYPE: PRT
<213> ORGANISM: Artificial
<220> FEATURE:
<223> OTHER INFORMATION: Synthesized: Proline-rich peptide 14
<220> FEATURE:
```

<221> NAME/KEY: misc_feature
<222> LOCATION: (4)..(4)
<223> OTHER INFORMATION: Xaa can be any amino acid
<220> FEATURE:
<221> NAME/KEY: misc_feature
<222> LOCATION: (7)..(8)
<223> OTHER INFORMATION: Xaa can be any amino acid

<400> SEQUENCE: 15

Pro Pro Pro Xaa Pro Pro Xaa Xaa Pro Pro Pro Pro Pro Pro Pro
1               5                   10                  15

Pro Pro Pro Pro
            20

<210> SEQ ID NO 16
<211> LENGTH: 20
<212> TYPE: PRT
<213> ORGANISM: Artificial
<220> FEATURE:
<223> OTHER INFORMATION: Synthesized: Proline-rich peptide 15
<220> FEATURE:
<221> NAME/KEY: misc_feature
<222> LOCATION: (4)..(4)
<223> OTHER INFORMATION: Xaa can be any amino acid
<220> FEATURE:
<221> NAME/KEY: misc_feature
<222> LOCATION: (7)..(8)
<223> OTHER INFORMATION: Xaa can be any amino acid
<220> FEATURE:
<221> NAME/KEY: misc_feature
<222> LOCATION: (12)..(20)
<223> OTHER INFORMATION: Xaa can be any amino acid

<400> SEQUENCE: 16

Pro Pro Pro Xaa Pro Pro Xaa Xaa Pro Pro Xaa Xaa Xaa Xaa Xaa
1               5                   10                  15

Xaa Xaa Xaa Xaa
            20

<210> SEQ ID NO 17
<211> LENGTH: 20
<212> TYPE: PRT
<213> ORGANISM: Artificial
<220> FEATURE:
<223> OTHER INFORMATION: Synthesized: Proline-rich peptide 16
<220> FEATURE:
<221> NAME/KEY: misc_feature
<222> LOCATION: (12)..(20)
<223> OTHER INFORMATION: Xaa can be any amino acid

<400> SEQUENCE: 17

Pro Pro Pro Pro Pro Pro Pro Pro Pro Pro Pro Xaa Xaa Xaa Xaa
1               5                   10                  15

Xaa Xaa Xaa Xaa
            20

<210> SEQ ID NO 18
<211> LENGTH: 21
<212> TYPE: PRT
<213> ORGANISM: Artificial
<220> FEATURE:
<223> OTHER INFORMATION: Synthesized: Proline-rich peptide 17
<220> FEATURE:
<221> NAME/KEY: misc_feature
<222> LOCATION: (13)..(21)
<223> OTHER INFORMATION: Xaa can be any amino acid

<400> SEQUENCE: 18

Pro Pro Pro Pro Pro Pro Pro Pro Pro Pro Pro Pro Xaa Xaa Xaa Xaa

```
1               5                   10                  15
Xaa Xaa Xaa Xaa Xaa
            20
```

<210> SEQ ID NO 19
<211> LENGTH: 23
<212> TYPE: PRT
<213> ORGANISM: Artificial
<220> FEATURE:
<223> OTHER INFORMATION: Synthesized: Proline-rich peptide 18
<220> FEATURE:
<221> NAME/KEY: misc_feature
<222> LOCATION: (4)..(5)
<223> OTHER INFORMATION: Xaa can be any amino acid
<220> FEATURE:
<221> NAME/KEY: misc_feature
<222> LOCATION: (15)..(15)
<223> OTHER INFORMATION: Xaa can be any amino acid

<400> SEQUENCE: 19

```
Pro Pro Pro Xaa Xaa Pro Pro Pro Pro Pro Pro Pro Pro Pro Xaa Pro
1               5                   10                  15

Pro Pro Pro Pro Pro Pro Pro
            20
```

<210> SEQ ID NO 20
<211> LENGTH: 23
<212> TYPE: PRT
<213> ORGANISM: Artificial
<220> FEATURE:
<223> OTHER INFORMATION: Synthesized: Proline-rich peptide 19
<220> FEATURE:
<221> NAME/KEY: misc_feature
<222> LOCATION: (4)..(4)
<223> OTHER INFORMATION: Xaa can be any amino acid
<220> FEATURE:
<221> NAME/KEY: misc_feature
<222> LOCATION: (7)..(8)
<223> OTHER INFORMATION: Xaa can be any amino acid

<400> SEQUENCE: 20

```
Pro Pro Pro Xaa Pro Pro Xaa Xaa Pro Pro Pro Pro Pro Pro Pro Pro
1               5                   10                  15

Pro Pro Pro Pro Pro Pro Pro
            20
```

<210> SEQ ID NO 21
<211> LENGTH: 26
<212> TYPE: PRT
<213> ORGANISM: Artificial
<220> FEATURE:
<223> OTHER INFORMATION: Synthesized: Proline-rich peptide 20
<220> FEATURE:
<221> NAME/KEY: misc_feature
<222> LOCATION: (4)..(4)
<223> OTHER INFORMATION: Xaa can be any amino acid
<220> FEATURE:
<221> NAME/KEY: misc_feature
<222> LOCATION: (7)..(8)
<223> OTHER INFORMATION: Xaa can be any amino acid
<220> FEATURE:
<221> NAME/KEY: misc_feature
<222> LOCATION: (26)..(26)
<223> OTHER INFORMATION: Xaa can be any amino acid

<400> SEQUENCE: 21

```
Pro Pro Pro Xaa Pro Pro Xaa Xaa Pro Pro Pro Pro Pro Pro Pro Pro
1               5                   10                  15

Pro Pro Pro Pro Pro Pro Pro Pro Pro Xaa
```

```
            20                  25

<210> SEQ ID NO 22
<211> LENGTH: 32
<212> TYPE: PRT
<213> ORGANISM: Artificial
<220> FEATURE:
<223> OTHER INFORMATION: Synthesized: Proline-rich peptide 21
<220> FEATURE:
<221> NAME/KEY: misc_feature
<222> LOCATION: (4)..(8)
<223> OTHER INFORMATION: Xaa can be any amino acid
<220> FEATURE:
<221> NAME/KEY: misc_feature
<222> LOCATION: (23)..(23)
<223> OTHER INFORMATION: Xaa can be any amino acid
<220> FEATURE:
<221> NAME/KEY: misc_feature
<222> LOCATION: (27)..(32)
<223> OTHER INFORMATION: Xaa can be any amino acid

<400> SEQUENCE: 22

Pro Pro Pro Xaa Xaa Xaa Xaa Xaa Pro Pro Pro Pro Pro Pro Pro Pro
1               5                   10                  15

Pro Pro Pro Pro Pro Pro Xaa Pro Pro Pro Xaa Xaa Xaa Xaa Xaa Xaa
            20                  25                  30

<210> SEQ ID NO 23
<211> LENGTH: 32
<212> TYPE: PRT
<213> ORGANISM: Artificial
<220> FEATURE:
<223> OTHER INFORMATION: Synthesized: Proline-rich peptide 22
<220> FEATURE:
<221> NAME/KEY: misc_feature
<222> LOCATION: (1)..(2)
<223> OTHER INFORMATION: Xaa can be any amino acid
<220> FEATURE:
<221> NAME/KEY: misc_feature
<222> LOCATION: (15)..(15)
<223> OTHER INFORMATION: Xaa can be any amino acid
<220> FEATURE:
<221> NAME/KEY: misc_feature
<222> LOCATION: (23)..(23)
<223> OTHER INFORMATION: Xaa can be any amino acid
<220> FEATURE:
<221> NAME/KEY: misc_feature
<222> LOCATION: (26)..(32)
<223> OTHER INFORMATION: Xaa can be any amino acid

<400> SEQUENCE: 23

Xaa Xaa Pro Pro Pro Pro Pro Pro Pro Pro Pro Pro Pro Pro Xaa Pro
1               5                   10                  15

Pro Pro Pro Pro Pro Pro Xaa Pro Pro Xaa Xaa Xaa Xaa Xaa Xaa Xaa
            20                  25                  30

<210> SEQ ID NO 24
<211> LENGTH: 32
<212> TYPE: PRT
<213> ORGANISM: Artificial
<220> FEATURE:
<223> OTHER INFORMATION: Synthesized: Proline-rich peptide 23
<220> FEATURE:
<221> NAME/KEY: misc_feature
<222> LOCATION: (7)..(7)
<223> OTHER INFORMATION: Xaa can be any amino acid
<220> FEATURE:
<221> NAME/KEY: misc_feature
<222> LOCATION: (10)..(10)
<223> OTHER INFORMATION: Xaa can be any amino acid
<220> FEATURE:
<221> NAME/KEY: misc_feature
```

```
<222> LOCATION: (28)..(30)
<223> OTHER INFORMATION: Xaa can be any amino acid
<220> FEATURE:
<221> NAME/KEY: misc_feature
<222> LOCATION: (32)..(32)
<223> OTHER INFORMATION: Xaa can be any amino acid

<400> SEQUENCE: 24

Pro Pro Pro Pro Pro Pro Xaa Pro Pro Xaa Pro Pro Pro Pro Pro
1               5                   10                  15

Pro Pro Pro Pro Pro Pro Pro Pro Pro Xaa Xaa Xaa Pro Xaa
            20                  25                  30

<210> SEQ ID NO 25
<211> LENGTH: 33
<212> TYPE: PRT
<213> ORGANISM: Artificial
<220> FEATURE:
<223> OTHER INFORMATION: Synthesized: Proline-rich peptide 24
<220> FEATURE:
<221> NAME/KEY: misc_feature
<222> LOCATION: (5)..(8)
<223> OTHER INFORMATION: Xaa can be any amino acid
<220> FEATURE:
<221> NAME/KEY: misc_feature
<222> LOCATION: (13)..(13)
<223> OTHER INFORMATION: Xaa can be any amino acid
<220> FEATURE:
<221> NAME/KEY: misc_feature
<222> LOCATION: (15)..(15)
<223> OTHER INFORMATION: Xaa can be any amino acid
<220> FEATURE:
<221> NAME/KEY: misc_feature
<222> LOCATION: (24)..(33)
<223> OTHER INFORMATION: Xaa can be any amino acid

<400> SEQUENCE: 25

Pro Pro Pro Pro Xaa Xaa Xaa Xaa Pro Pro Pro Pro Xaa Pro Xaa Pro
1               5                   10                  15

Pro Pro Pro Pro Pro Pro Pro Xaa Xaa Xaa Xaa Xaa Xaa Xaa Xaa
            20                  25                  30

Xaa

<210> SEQ ID NO 26
<211> LENGTH: 33
<212> TYPE: PRT
<213> ORGANISM: Artificial
<220> FEATURE:
<223> OTHER INFORMATION: Synthesized: Proline-rich peptide 25
<220> FEATURE:
<221> NAME/KEY: misc_feature
<222> LOCATION: (4)..(5)
<223> OTHER INFORMATION: Xaa can be any amino acid
<220> FEATURE:
<221> NAME/KEY: misc_feature
<222> LOCATION: (8)..(8)
<223> OTHER INFORMATION: Xaa can be any amino acid
<220> FEATURE:
<221> NAME/KEY: misc_feature
<222> LOCATION: (10)..(11)
<223> OTHER INFORMATION: Xaa can be any amino acid
<220> FEATURE:
<221> NAME/KEY: misc_feature
<222> LOCATION: (25)..(25)
<223> OTHER INFORMATION: Xaa can be any amino acid
<220> FEATURE:
<221> NAME/KEY: misc_feature
<222> LOCATION: (27)..(33)
<223> OTHER INFORMATION: Xaa can be any amino acid

<400> SEQUENCE: 26
```

Pro Pro Pro Xaa Xaa Pro Pro Xaa Pro Xaa Xaa Pro Pro Pro Pro
1               5                   10                  15

Pro Pro Pro Pro Pro Pro Pro Pro Xaa Pro Xaa Xaa Xaa Xaa Xaa
                20                  25                  30

Xaa

<210> SEQ ID NO 27
<211> LENGTH: 33
<212> TYPE: PRT
<213> ORGANISM: Artificial
<220> FEATURE:
<223> OTHER INFORMATION: Synthesized: Proline-rich peptide 26
<220> FEATURE:
<221> NAME/KEY: misc_feature
<222> LOCATION: (4)..(5)
<223> OTHER INFORMATION: Xaa can be any amino acid
<220> FEATURE:
<221> NAME/KEY: misc_feature
<222> LOCATION: (18)..(18)
<223> OTHER INFORMATION: Xaa can be any amino acid
<220> FEATURE:
<221> NAME/KEY: misc_feature
<222> LOCATION: (21)..(21)
<223> OTHER INFORMATION: Xaa can be any amino acid
<220> FEATURE:
<221> NAME/KEY: misc_feature
<222> LOCATION: (27)..(33)
<223> OTHER INFORMATION: Xaa can be any amino acid

<400> SEQUENCE: 27

Pro Pro Pro Xaa Xaa Pro Pro Pro Pro Pro Pro Pro Pro Pro Pro
1               5                   10                  15

Pro Pro Xaa Pro Pro Xaa Pro Pro Pro Pro Xaa Xaa Xaa Xaa Xaa Xaa
                20                  25                  30

Xaa

<210> SEQ ID NO 28
<211> LENGTH: 34
<212> TYPE: PRT
<213> ORGANISM: Artificial
<220> FEATURE:
<223> OTHER INFORMATION: Synthesized: Proline-rich peptide 27
<220> FEATURE:
<221> NAME/KEY: misc_feature
<222> LOCATION: (4)..(4)
<223> OTHER INFORMATION: Xaa can be any amino acid
<220> FEATURE:
<221> NAME/KEY: misc_feature
<222> LOCATION: (7)..(8)
<223> OTHER INFORMATION: Xaa can be any amino acid
<220> FEATURE:
<221> NAME/KEY: misc_feature
<222> LOCATION: (26)..(34)
<223> OTHER INFORMATION: Xaa can be any amino acid

<400> SEQUENCE: 28

Pro Pro Pro Xaa Pro Pro Xaa Xaa Pro Pro Pro Pro Pro Pro Pro
1               5                   10                  15

Pro Pro Pro Pro Pro Pro Pro Pro Pro Xaa Xaa Xaa Xaa Xaa Xaa Xaa
                20                  25                  30

Xaa Xaa

<210> SEQ ID NO 29
<211> LENGTH: 34
<212> TYPE: PRT
<213> ORGANISM: Artificial
<220> FEATURE:
<223> OTHER INFORMATION: Synthesized: Proline-rich peptide 28

```
<220> FEATURE:
<221> NAME/KEY: misc_feature
<222> LOCATION: (1)..(1)
<223> OTHER INFORMATION: Xaa can be any amino acid
<220> FEATURE:
<221> NAME/KEY: misc_feature
<222> LOCATION: (5)..(5)
<223> OTHER INFORMATION: Xaa can be any amino acid
<220> FEATURE:
<221> NAME/KEY: misc_feature
<222> LOCATION: (12)..(14)
<223> OTHER INFORMATION: Xaa can be any amino acid
<220> FEATURE:
<221> NAME/KEY: misc_feature
<222> LOCATION: (16)..(16)
<223> OTHER INFORMATION: Xaa can be any amino acid
<220> FEATURE:
<221> NAME/KEY: misc_feature
<222> LOCATION: (19)..(19)
<223> OTHER INFORMATION: Xaa can be any amino acid
<220> FEATURE:
<221> NAME/KEY: misc_feature
<222> LOCATION: (23)..(24)
<223> OTHER INFORMATION: Xaa can be any amino acid
<220> FEATURE:
<221> NAME/KEY: misc_feature
<222> LOCATION: (27)..(34)
<223> OTHER INFORMATION: Xaa can be any amino acid

<400> SEQUENCE: 29

Xaa Pro Pro Pro Xaa Pro Pro Pro Pro Pro Xaa Xaa Xaa Pro Xaa
1               5                   10                  15

Pro Pro Xaa Pro Pro Pro Xaa Xaa Pro Pro Xaa Xaa Xaa Xaa Xaa
            20                  25                  30

Xaa Xaa

<210> SEQ ID NO 30
<211> LENGTH: 34
<212> TYPE: PRT
<213> ORGANISM: Artificial
<220> FEATURE:
<223> OTHER INFORMATION: Synthesized: Proline-rich peptide 29
<220> FEATURE:
<221> NAME/KEY: misc_feature
<222> LOCATION: (4)..(5)
<223> OTHER INFORMATION: Xaa can be any amino acid
<220> FEATURE:
<221> NAME/KEY: misc_feature
<222> LOCATION: (7)..(7)
<223> OTHER INFORMATION: Xaa can be any amino acid
<220> FEATURE:
<221> NAME/KEY: misc_feature
<222> LOCATION: (10)..(10)
<223> OTHER INFORMATION: Xaa can be any amino acid
<220> FEATURE:
<221> NAME/KEY: misc_feature
<222> LOCATION: (18)..(18)
<223> OTHER INFORMATION: Xaa can be any amino acid
<220> FEATURE:
<221> NAME/KEY: misc_feature
<222> LOCATION: (27)..(34)
<223> OTHER INFORMATION: Xaa can be any amino acid

<400> SEQUENCE: 30

Pro Pro Pro Xaa Xaa Pro Xaa Pro Pro Xaa Pro Pro Pro Pro Pro
1               5                   10                  15

Pro Xaa Pro Pro Pro Pro Pro Pro Pro Pro Xaa Xaa Xaa Xaa Xaa
            20                  25                  30

Xaa Xaa

<210> SEQ ID NO 31
```

```
<211> LENGTH: 35
<212> TYPE: PRT
<213> ORGANISM: Artificial
<220> FEATURE:
<223> OTHER INFORMATION: Synthesized: Proline-rich peptide 30
<220> FEATURE:
<221> NAME/KEY: misc_feature
<222> LOCATION: (25)..(25)
<223> OTHER INFORMATION: Xaa can be any amino acid
<220> FEATURE:
<221> NAME/KEY: misc_feature
<222> LOCATION: (28)..(30)
<223> OTHER INFORMATION: Xaa can be any amino acid
<220> FEATURE:
<221> NAME/KEY: misc_feature
<222> LOCATION: (32)..(35)
<223> OTHER INFORMATION: Xaa can be any amino acid

<400> SEQUENCE: 31

Pro Pro Pro Pro Pro Pro Pro Pro Pro Pro Pro Pro Pro Pro Pro
1               5                   10                  15

Pro Pro Pro Pro Pro Pro Pro Pro Xaa Pro Pro Xaa Xaa Xaa Pro Xaa
            20                  25                  30

Xaa Xaa Xaa
        35

<210> SEQ ID NO 32
<211> LENGTH: 35
<212> TYPE: PRT
<213> ORGANISM: Artificial
<220> FEATURE:
<223> OTHER INFORMATION: Synthesized: Proline-rich peptide 31
<220> FEATURE:
<221> NAME/KEY: misc_feature
<222> LOCATION: (3)..(11)
<223> OTHER INFORMATION: Xaa can be any amino acid
<220> FEATURE:
<221> NAME/KEY: misc_feature
<222> LOCATION: (14)..(22)
<223> OTHER INFORMATION: Xaa can be any amino acid
<220> FEATURE:
<221> NAME/KEY: misc_feature
<222> LOCATION: (24)..(24)
<223> OTHER INFORMATION: Xaa can be any amino acid
<220> FEATURE:
<221> NAME/KEY: misc_feature
<222> LOCATION: (26)..(26)
<223> OTHER INFORMATION: Xaa can be any amino acid
<220> FEATURE:
<221> NAME/KEY: misc_feature
<222> LOCATION: (28)..(28)
<223> OTHER INFORMATION: Xaa can be any amino acid
<220> FEATURE:
<221> NAME/KEY: misc_feature
<222> LOCATION: (30)..(35)
<223> OTHER INFORMATION: Xaa can be any amino acid

<400> SEQUENCE: 32

Pro Pro Xaa Xaa Xaa Xaa Xaa Xaa Xaa Xaa Xaa Pro Pro Xaa Xaa Xaa
1               5                   10                  15

Xaa Xaa Xaa Xaa Xaa Xaa Pro Xaa Pro Xaa Pro Xaa Pro Xaa Xaa Xaa
            20                  25                  30

Xaa Xaa Xaa
        35

<210> SEQ ID NO 33
<211> LENGTH: 35
<212> TYPE: PRT
<213> ORGANISM: Artificial
<220> FEATURE:
<223> OTHER INFORMATION: Synthesized: Proline-rich peptide 32
```

```
<220> FEATURE:
<221> NAME/KEY: misc_feature
<222> LOCATION: (6)..(6)
<223> OTHER INFORMATION: Xaa can be any amino acid
<220> FEATURE:
<221> NAME/KEY: misc_feature
<222> LOCATION: (8)..(8)
<223> OTHER INFORMATION: Xaa can be any amino acid
<220> FEATURE:
<221> NAME/KEY: misc_feature
<222> LOCATION: (21)..(21)
<223> OTHER INFORMATION: Xaa can be any amino acid
<220> FEATURE:
<221> NAME/KEY: misc_feature
<222> LOCATION: (23)..(23)
<223> OTHER INFORMATION: Xaa can be any amino acid
<220> FEATURE:
<221> NAME/KEY: misc_feature
<222> LOCATION: (27)..(27)
<223> OTHER INFORMATION: Xaa can be any amino acid
<220> FEATURE:
<221> NAME/KEY: misc_feature
<222> LOCATION: (29)..(35)
<223> OTHER INFORMATION: Xaa can be any amino acid

<400> SEQUENCE: 33

Pro Pro Pro Pro Pro Xaa Pro Xaa Pro Pro Pro Pro Pro Pro Pro
1               5                   10                  15

Pro Pro Pro Pro Xaa Pro Xaa Pro Pro Pro Xaa Pro Xaa Xaa Xaa Xaa
                20                  25                  30

Xaa Xaa Xaa
        35

<210> SEQ ID NO 34
<211> LENGTH: 35
<212> TYPE: PRT
<213> ORGANISM: Artificial
<220> FEATURE:
<223> OTHER INFORMATION: Synthesized: Proline-rich peptide 33
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: misc_feature
<222> LOCATION: (5)..(5)
<223> OTHER INFORMATION: Xaa can be any amino acid
<220> FEATURE:
<221> NAME/KEY: misc_feature
<222> LOCATION: (15)..(22)
<223> OTHER INFORMATION: Xaa can be any amino acid
<220> FEATURE:
<221> NAME/KEY: misc_feature
<222> LOCATION: (25)..(28)
<223> OTHER INFORMATION: Xaa can be any amino acid
<220> FEATURE:
<221> NAME/KEY: misc_feature
<222> LOCATION: (30)..(35)
<223> OTHER INFORMATION: Xaa can be any amino acid

<400> SEQUENCE: 34

Pro Xaa Pro Pro Xaa Pro Pro Pro Pro Pro Pro Pro Pro Xaa Xaa
1               5                   10                  15

Xaa Xaa Xaa Xaa Xaa Xaa Pro Pro Xaa Xaa Xaa Xaa Pro Xaa Xaa Xaa
                20                  25                  30

Xaa Xaa Xaa
        35

<210> SEQ ID NO 35
<211> LENGTH: 36
<212> TYPE: PRT
```

```
<213> ORGANISM: Artificial
<220> FEATURE:
<223> OTHER INFORMATION: Synthesized: Proline-rich peptide 34
<220> FEATURE:
<221> NAME/KEY: misc_feature
<222> LOCATION: (4)..(4)
<223> OTHER INFORMATION: Xaa can be any amino acid
<220> FEATURE:
<221> NAME/KEY: misc_feature
<222> LOCATION: (6)..(7)
<223> OTHER INFORMATION: Xaa can be any amino acid
<220> FEATURE:
<221> NAME/KEY: misc_feature
<222> LOCATION: (9)..(12)
<223> OTHER INFORMATION: Xaa can be any amino acid
<220> FEATURE:
<221> NAME/KEY: misc_feature
<222> LOCATION: (14)..(23)
<223> OTHER INFORMATION: Xaa can be any amino acid
<220> FEATURE:
<221> NAME/KEY: misc_feature
<222> LOCATION: (25)..(25)
<223> OTHER INFORMATION: Xaa can be any amino acid
<220> FEATURE:
<221> NAME/KEY: misc_feature
<222> LOCATION: (27)..(29)
<223> OTHER INFORMATION: Xaa can be any amino acid
<220> FEATURE:
<221> NAME/KEY: misc_feature
<222> LOCATION: (31)..(36)
<223> OTHER INFORMATION: Xaa can be any amino acid

<400> SEQUENCE: 35

Pro Pro Pro Xaa Pro Xaa Xaa Pro Xaa Xaa Xaa Xaa Pro Xaa Xaa Xaa
1               5                   10                  15

Xaa Xaa Xaa Xaa Xaa Xaa Xaa Pro Xaa Pro Xaa Xaa Pro Xaa Xaa
            20                  25                  30

Xaa Xaa Xaa Xaa
        35

<210> SEQ ID NO 36
<211> LENGTH: 36
<212> TYPE: PRT
<213> ORGANISM: Artificial
<220> FEATURE:
<223> OTHER INFORMATION: Synthesized: Proline-rich peptide 35
<220> FEATURE:
<221> NAME/KEY: misc_feature
<222> LOCATION: (3)..(3)
<223> OTHER INFORMATION: Xaa can be any amino acid
<220> FEATURE:
<221> NAME/KEY: misc_feature
<222> LOCATION: (5)..(6)
<223> OTHER INFORMATION: Xaa can be any amino acid
<220> FEATURE:
<221> NAME/KEY: misc_feature
<222> LOCATION: (8)..(8)
<223> OTHER INFORMATION: Xaa can be any amino acid
<220> FEATURE:
<221> NAME/KEY: misc_feature
<222> LOCATION: (11)..(13)
<223> OTHER INFORMATION: Xaa can be any amino acid
<220> FEATURE:
<221> NAME/KEY: misc_feature
<222> LOCATION: (15)..(17)
<223> OTHER INFORMATION: Xaa can be any amino acid
<220> FEATURE:
<221> NAME/KEY: misc_feature
<222> LOCATION: (20)..(20)
<223> OTHER INFORMATION: Xaa can be any amino acid
<220> FEATURE:
<221> NAME/KEY: misc_feature
<222> LOCATION: (26)..(36)
<223> OTHER INFORMATION: Xaa can be any amino acid
```

<400> SEQUENCE: 36

Pro Pro Xaa Pro Xaa Xaa Pro Xaa Pro Pro Xaa Xaa Xaa Pro Xaa Xaa
1               5                   10                  15

Xaa Pro Pro Xaa Pro Pro Pro Pro Xaa Xaa Xaa Xaa Xaa Xaa
            20                  25                  30

Xaa Xaa Xaa Xaa
        35

<210> SEQ ID NO 37
<211> LENGTH: 36
<212> TYPE: PRT
<213> ORGANISM: Artificial
<220> FEATURE:
<223> OTHER INFORMATION: Synthesized: Proline-rich peptide 36
<220> FEATURE:
<221> NAME/KEY: misc_feature
<222> LOCATION: (7)..(7)
<223> OTHER INFORMATION: Xaa can be any amino acid
<220> FEATURE:
<221> NAME/KEY: misc_feature
<222> LOCATION: (27)..(29)
<223> OTHER INFORMATION: Xaa can be any amino acid
<220> FEATURE:
<221> NAME/KEY: misc_feature
<222> LOCATION: (31)..(36)
<223> OTHER INFORMATION: Xaa can be any amino acid

<400> SEQUENCE: 37

Pro Pro Pro Pro Pro Xaa Pro Pro Pro Pro Pro Pro Pro Pro Pro Pro
1               5                   10                  15

Pro Pro Pro Pro Pro Pro Pro Pro Pro Xaa Xaa Xaa Pro Xaa Xaa
            20                  25                  30

Xaa Xaa Xaa Xaa
        35

<210> SEQ ID NO 38
<211> LENGTH: 37
<212> TYPE: PRT
<213> ORGANISM: Artificial
<220> FEATURE:
<223> OTHER INFORMATION: Synthesized: Proline-rich peptide 37
<220> FEATURE:
<221> NAME/KEY: misc_feature
<222> LOCATION: (1)..(1)
<223> OTHER INFORMATION: Xaa can be any amino acid
<220> FEATURE:
<221> NAME/KEY: misc_feature
<222> LOCATION: (8)..(10)
<223> OTHER INFORMATION: Xaa can be any amino acid
<220> FEATURE:
<221> NAME/KEY: misc_feature
<222> LOCATION: (12)..(12)
<223> OTHER INFORMATION: Xaa can be any amino acid
<220> FEATURE:
<221> NAME/KEY: misc_feature
<222> LOCATION: (16)..(24)
<223> OTHER INFORMATION: Xaa can be any amino acid
<220> FEATURE:
<221> NAME/KEY: misc_feature
<222> LOCATION: (28)..(28)
<223> OTHER INFORMATION: Xaa can be any amino acid
<220> FEATURE:
<221> NAME/KEY: misc_feature
<222> LOCATION: (30)..(30)
<223> OTHER INFORMATION: Xaa can be any amino acid
<220> FEATURE:
<221> NAME/KEY: misc_feature
<222> LOCATION: (32)..(37)
<223> OTHER INFORMATION: Xaa can be any amino acid

<400> SEQUENCE: 38

```
Xaa Pro Pro Pro Pro Pro Xaa Xaa Xaa Pro Xaa Pro Pro Pro Xaa
1               5                   10                  15

Xaa Xaa Xaa Xaa Xaa Xaa Xaa Pro Pro Xaa Pro Xaa Pro Xaa
            20                  25                  30

Xaa Xaa Xaa Xaa Xaa
        35
```

<210> SEQ ID NO 39
<211> LENGTH: 37
<212> TYPE: PRT
<213> ORGANISM: Artificial
<220> FEATURE:
<223> OTHER INFORMATION: Synthesized: Proline-rich peptide 38
<220> FEATURE:
<221> NAME/KEY: misc_feature
<222> LOCATION: (5)..(5)
<223> OTHER INFORMATION: Xaa can be any amino acid
<220> FEATURE:
<221> NAME/KEY: misc_feature
<222> LOCATION: (7)..(7)
<223> OTHER INFORMATION: Xaa can be any amino acid
<220> FEATURE:
<221> NAME/KEY: misc_feature
<222> LOCATION: (20)..(21)
<223> OTHER INFORMATION: Xaa can be any amino acid
<220> FEATURE:
<221> NAME/KEY: misc_feature
<222> LOCATION: (23)..(24)
<223> OTHER INFORMATION: Xaa can be any amino acid
<220> FEATURE:
<221> NAME/KEY: misc_feature
<222> LOCATION: (26)..(37)
<223> OTHER INFORMATION: Xaa can be any amino acid

<400> SEQUENCE: 39

```
Pro Pro Pro Pro Xaa Pro Xaa Pro Pro Pro Pro Pro Pro Pro Pro
1               5                   10                  15

Pro Pro Pro Xaa Xaa Pro Xaa Xaa Pro Xaa Xaa Xaa Xaa Xaa Xaa
            20                  25                  30

Xaa Xaa Xaa Xaa Xaa
        35
```

<210> SEQ ID NO 40
<211> LENGTH: 37
<212> TYPE: PRT
<213> ORGANISM: Artificial
<220> FEATURE:
<223> OTHER INFORMATION: Synthesized: Proline-rich peptide 39
<220> FEATURE:
<221> NAME/KEY: misc_feature
<222> LOCATION: (5)..(5)
<223> OTHER INFORMATION: Xaa can be any amino acid
<220> FEATURE:
<221> NAME/KEY: misc_feature
<222> LOCATION: (18)..(21)
<223> OTHER INFORMATION: Xaa can be any amino acid
<220> FEATURE:
<221> NAME/KEY: misc_feature
<222> LOCATION: (23)..(24)
<223> OTHER INFORMATION: Xaa can be any amino acid
<220> FEATURE:
<221> NAME/KEY: misc_feature
<222> LOCATION: (28)..(30)
<223> OTHER INFORMATION: Xaa can be any amino acid
<220> FEATURE:
<221> NAME/KEY: misc_feature
<222> LOCATION: (32)..(37)
<223> OTHER INFORMATION: Xaa can be any amino acid

<400> SEQUENCE: 40

```
Pro Pro Pro Pro Xaa Pro Pro Pro Pro Pro Pro Pro Pro Pro Pro
1               5                   10                  15

Pro Xaa Xaa Xaa Xaa Pro Xaa Xaa Pro Pro Pro Xaa Xaa Xaa Pro Xaa
            20                  25                  30

Xaa Xaa Xaa Xaa Xaa
        35

<210> SEQ ID NO 41
<211> LENGTH: 37
<212> TYPE: PRT
<213> ORGANISM: Artificial
<220> FEATURE:
<223> OTHER INFORMATION: Synthesized: Proline-rich peptide 40
<220> FEATURE:
<221> NAME/KEY: misc_feature
<222> LOCATION: (3)..(3)
<223> OTHER INFORMATION: Xaa can be any amino acid
<220> FEATURE:
<221> NAME/KEY: misc_feature
<222> LOCATION: (10)..(10)
<223> OTHER INFORMATION: Xaa can be any amino acid
<220> FEATURE:
<221> NAME/KEY: misc_feature
<222> LOCATION: (15)..(24)
<223> OTHER INFORMATION: Xaa can be any amino acid
<220> FEATURE:
<221> NAME/KEY: misc_feature
<222> LOCATION: (28)..(30)
<223> OTHER INFORMATION: Xaa can be any amino acid
<220> FEATURE:
<221> NAME/KEY: misc_feature
<222> LOCATION: (32)..(37)
<223> OTHER INFORMATION: Xaa can be any amino acid

<400> SEQUENCE: 41

Pro Pro Xaa Pro Pro Pro Pro Pro Pro Xaa Pro Pro Pro Pro Xaa Xaa
1               5                   10                  15

Xaa Xaa Xaa Xaa Xaa Xaa Xaa Xaa Pro Pro Pro Xaa Xaa Xaa Pro Xaa
            20                  25                  30

Xaa Xaa Xaa Xaa Xaa
        35

<210> SEQ ID NO 42
<211> LENGTH: 37
<212> TYPE: PRT
<213> ORGANISM: Artificial
<220> FEATURE:
<223> OTHER INFORMATION: Synthesized: Proline-rich peptide 41
<220> FEATURE:
<221> NAME/KEY: misc_feature
<222> LOCATION: (5)..(5)
<223> OTHER INFORMATION: Xaa can be any amino acid
<220> FEATURE:
<221> NAME/KEY: misc_feature
<222> LOCATION: (13)..(13)
<223> OTHER INFORMATION: Xaa can be any amino acid
<220> FEATURE:
<221> NAME/KEY: misc_feature
<222> LOCATION: (16)..(16)
<223> OTHER INFORMATION: Xaa can be any amino acid
<220> FEATURE:
<221> NAME/KEY: misc_feature
<222> LOCATION: (20)..(20)
<223> OTHER INFORMATION: Xaa can be any amino acid
<220> FEATURE:
<221> NAME/KEY: misc_feature
<222> LOCATION: (22)..(22)
<223> OTHER INFORMATION: Xaa can be any amino acid
<220> FEATURE:
<221> NAME/KEY: misc_feature
<222> LOCATION: (28)..(30)
<223> OTHER INFORMATION: Xaa can be any amino acid
```

```
<220> FEATURE:
<221> NAME/KEY: misc_feature
<222> LOCATION: (32)..(37)
<223> OTHER INFORMATION: Xaa can be any amino acid

<400> SEQUENCE: 42

Pro Pro Pro Pro Xaa Pro Pro Pro Pro Pro Pro Xaa Pro Pro Xaa
1               5                   10                  15

Pro Pro Pro Xaa Pro Xaa Pro Pro Pro Pro Xaa Xaa Xaa Pro Xaa
            20                  25                  30

Xaa Xaa Xaa Xaa Xaa
        35

<210> SEQ ID NO 43
<211> LENGTH: 37
<212> TYPE: PRT
<213> ORGANISM: Artificial
<220> FEATURE:
<223> OTHER INFORMATION: Synthesized: Proline-rich peptide 42
<220> FEATURE:
<221> NAME/KEY: misc_feature
<222> LOCATION: (6)..(6)
<223> OTHER INFORMATION: Xaa can be any amino acid
<220> FEATURE:
<221> NAME/KEY: misc_feature
<222> LOCATION: (8)..(8)
<223> OTHER INFORMATION: Xaa can be any amino acid
<220> FEATURE:
<221> NAME/KEY: misc_feature
<222> LOCATION: (29)..(31)
<223> OTHER INFORMATION: Xaa can be any amino acid
<220> FEATURE:
<221> NAME/KEY: misc_feature
<222> LOCATION: (33)..(37)
<223> OTHER INFORMATION: Xaa can be any amino acid

<400> SEQUENCE: 43

Pro Pro Pro Pro Pro Xaa Pro Xaa Pro Pro Pro Pro Pro Pro Pro
1               5                   10                  15

Pro Pro Pro Pro Pro Pro Pro Pro Pro Pro Pro Pro Xaa Xaa Xaa Pro
            20                  25                  30

Xaa Xaa Xaa Xaa Xaa
        35

<210> SEQ ID NO 44
<211> LENGTH: 38
<212> TYPE: PRT
<213> ORGANISM: Artificial
<220> FEATURE:
<223> OTHER INFORMATION: Synthesized: Proline-rich peptide 43
<220> FEATURE:
<221> NAME/KEY: misc_feature
<222> LOCATION: (4)..(4)
<223> OTHER INFORMATION: Xaa can be any amino acid
<220> FEATURE:
<221> NAME/KEY: misc_feature
<222> LOCATION: (7)..(7)
<223> OTHER INFORMATION: Xaa can be any amino acid
<220> FEATURE:
<221> NAME/KEY: misc_feature
<222> LOCATION: (16)..(23)
<223> OTHER INFORMATION: Xaa can be any amino acid
<220> FEATURE:
<221> NAME/KEY: misc_feature
<222> LOCATION: (27)..(35)
<223> OTHER INFORMATION: Xaa can be any amino acid
<220> FEATURE:
<221> NAME/KEY: misc_feature
<222> LOCATION: (37)..(38)
<223> OTHER INFORMATION: Xaa can be any amino acid
```

<400> SEQUENCE: 44

Pro Pro Pro Xaa Pro Pro Xaa Pro Pro Pro Pro Pro Pro Pro Xaa
1               5                   10                  15

Xaa Xaa Xaa Xaa Xaa Xaa Xaa Pro Pro Pro Xaa Xaa Xaa Xaa Xaa
            20                  25                  30

Xaa Xaa Xaa Pro Xaa Xaa
        35

<210> SEQ ID NO 45
<211> LENGTH: 38
<212> TYPE: PRT
<213> ORGANISM: Artificial
<220> FEATURE:
<223> OTHER INFORMATION: Synthesized: Proline-rich peptide 44
<220> FEATURE:
<221> NAME/KEY: misc_feature
<222> LOCATION: (4)..(4)
<223> OTHER INFORMATION: Xaa can be any amino acid
<220> FEATURE:
<221> NAME/KEY: misc_feature
<222> LOCATION: (12)..(12)
<223> OTHER INFORMATION: Xaa can be any amino acid
<220> FEATURE:
<221> NAME/KEY: misc_feature
<222> LOCATION: (14)..(17)
<223> OTHER INFORMATION: Xaa can be any amino acid
<220> FEATURE:
<221> NAME/KEY: misc_feature
<222> LOCATION: (26)..(35)
<223> OTHER INFORMATION: Xaa can be any amino acid
<220> FEATURE:
<221> NAME/KEY: misc_feature
<222> LOCATION: (37)..(38)
<223> OTHER INFORMATION: Xaa can be any amino acid

<400> SEQUENCE: 45

Pro Pro Pro Xaa Pro Pro Pro Pro Pro Pro Xaa Pro Xaa Xaa Xaa
1               5                   10                  15

Xaa Pro Pro Pro Pro Pro Pro Pro Pro Xaa Xaa Xaa Xaa Xaa Xaa
            20                  25                  30

Xaa Xaa Xaa Pro Xaa Xaa
        35

<210> SEQ ID NO 46
<211> LENGTH: 38
<212> TYPE: PRT
<213> ORGANISM: Artificial
<220> FEATURE:
<223> OTHER INFORMATION: Synthesized: Proline-rich peptide 45
<220> FEATURE:
<221> NAME/KEY: misc_feature
<222> LOCATION: (11)..(11)
<223> OTHER INFORMATION: Xaa can be any amino acid
<220> FEATURE:
<221> NAME/KEY: misc_feature
<222> LOCATION: (14)..(14)
<223> OTHER INFORMATION: Xaa can be any amino acid
<220> FEATURE:
<221> NAME/KEY: misc_feature
<222> LOCATION: (21)..(21)
<223> OTHER INFORMATION: Xaa can be any amino acid
<220> FEATURE:
<221> NAME/KEY: misc_feature
<222> LOCATION: (23)..(24)
<223> OTHER INFORMATION: Xaa can be any amino acid
<220> FEATURE:
<221> NAME/KEY: misc_feature
<222> LOCATION: (28)..(28)
<223> OTHER INFORMATION: Xaa can be any amino acid
<220> FEATURE:
<221> NAME/KEY: misc_feature

```
<222> LOCATION: (30)..(30)
<223> OTHER INFORMATION: Xaa can be any amino acid
<220> FEATURE:
<221> NAME/KEY: misc_feature
<222> LOCATION: (32)..(35)
<223> OTHER INFORMATION: Xaa can be any amino acid
<220> FEATURE:
<221> NAME/KEY: misc_feature
<222> LOCATION: (37)..(38)
<223> OTHER INFORMATION: Xaa can be any amino acid

<400> SEQUENCE: 46

Pro Pro Pro Pro Pro Pro Pro Pro Pro Xaa Pro Xaa Pro Pro
1               5                   10                  15

Pro Pro Pro Pro Xaa Pro Xaa Xaa Pro Pro Pro Xaa Pro Xaa Pro Xaa
            20                  25                  30

Xaa Xaa Xaa Pro Xaa Xaa
        35

<210> SEQ ID NO 47
<211> LENGTH: 38
<212> TYPE: PRT
<213> ORGANISM: Artificial
<220> FEATURE:
<223> OTHER INFORMATION: Synthesized: Proline-rich peptide 46
<220> FEATURE:
<221> NAME/KEY: misc_feature
<222> LOCATION: (2)..(9)
<223> OTHER INFORMATION: Xaa can be any amino acid
<220> FEATURE:
<221> NAME/KEY: misc_feature
<222> LOCATION: (12)..(12)
<223> OTHER INFORMATION: Xaa can be any amino acid
<220> FEATURE:
<221> NAME/KEY: misc_feature
<222> LOCATION: (15)..(16)
<223> OTHER INFORMATION: Xaa can be any amino acid
<220> FEATURE:
<221> NAME/KEY: misc_feature
<222> LOCATION: (20)..(20)
<223> OTHER INFORMATION: Xaa can be any amino acid
<220> FEATURE:
<221> NAME/KEY: misc_feature
<222> LOCATION: (23)..(30)
<223> OTHER INFORMATION: Xaa can be any amino acid
<220> FEATURE:
<221> NAME/KEY: misc_feature
<222> LOCATION: (32)..(35)
<223> OTHER INFORMATION: Xaa can be any amino acid
<220> FEATURE:
<221> NAME/KEY: misc_feature
<222> LOCATION: (37)..(38)
<223> OTHER INFORMATION: Xaa can be any amino acid

<400> SEQUENCE: 47

Pro Xaa Xaa Xaa Xaa Xaa Xaa Xaa Xaa Pro Pro Xaa Pro Pro Xaa Xaa
1               5                   10                  15

Pro Pro Pro Xaa Pro Pro Xaa Xaa Xaa Xaa Xaa Xaa Xaa Xaa Pro Xaa
            20                  25                  30

Xaa Xaa Xaa Pro Xaa Xaa
        35

<210> SEQ ID NO 48
<211> LENGTH: 39
<212> TYPE: PRT
<213> ORGANISM: Artificial
<220> FEATURE:
<223> OTHER INFORMATION: Synthesized: Proline-rich peptide 47
<220> FEATURE:
<221> NAME/KEY: misc_feature
<222> LOCATION: (5)..(5)
```

```
<223> OTHER INFORMATION: Xaa can be any amino acid
<220> FEATURE:
<221> NAME/KEY: misc_feature
<222> LOCATION: (23)..(25)
<223> OTHER INFORMATION: Xaa can be any amino acid
<220> FEATURE:
<221> NAME/KEY: misc_feature
<222> LOCATION: (27)..(30)
<223> OTHER INFORMATION: Xaa can be any amino acid
<220> FEATURE:
<221> NAME/KEY: misc_feature
<222> LOCATION: (32)..(36)
<223> OTHER INFORMATION: Xaa can be any amino acid
<220> FEATURE:
<221> NAME/KEY: misc_feature
<222> LOCATION: (38)..(39)
<223> OTHER INFORMATION: Xaa can be any amino acid

<400> SEQUENCE: 48

Pro Pro Pro Pro Xaa Pro Pro Pro Pro Pro Pro Pro Pro Pro Pro
1               5                   10                  15

Pro Pro Pro Pro Pro Pro Xaa Xaa Xaa Pro Xaa Xaa Xaa Pro Xaa
                20                  25                  30

Xaa Xaa Xaa Xaa Pro Xaa Xaa
                35

<210> SEQ ID NO 49
<211> LENGTH: 39
<212> TYPE: PRT
<213> ORGANISM: Artificial
<220> FEATURE:
<223> OTHER INFORMATION: Synthesized: Proline-rich peptide 48
<220> FEATURE:
<221> NAME/KEY: misc_feature
<222> LOCATION: (2)..(7)
<223> OTHER INFORMATION: Xaa can be any amino acid
<220> FEATURE:
<221> NAME/KEY: misc_feature
<222> LOCATION: (9)..(9)
<223> OTHER INFORMATION: Xaa can be any amino acid
<220> FEATURE:
<221> NAME/KEY: misc_feature
<222> LOCATION: (11)..(16)
<223> OTHER INFORMATION: Xaa can be any amino acid
<220> FEATURE:
<221> NAME/KEY: misc_feature
<222> LOCATION: (18)..(20)
<223> OTHER INFORMATION: Xaa can be any amino acid
<220> FEATURE:
<221> NAME/KEY: misc_feature
<222> LOCATION: (24)..(24)
<223> OTHER INFORMATION: Xaa can be any amino acid
<220> FEATURE:
<221> NAME/KEY: misc_feature
<222> LOCATION: (27)..(27)
<223> OTHER INFORMATION: Xaa can be any amino acid
<220> FEATURE:
<221> NAME/KEY: misc_feature
<222> LOCATION: (29)..(33)
<223> OTHER INFORMATION: Xaa can be any amino acid
<220> FEATURE:
<221> NAME/KEY: misc_feature
<222> LOCATION: (35)..(36)
<223> OTHER INFORMATION: Xaa can be any amino acid
<220> FEATURE:
<221> NAME/KEY: misc_feature
<222> LOCATION: (38)..(39)
<223> OTHER INFORMATION: Xaa can be any amino acid

<400> SEQUENCE: 49

Pro Xaa Xaa Xaa Xaa Xaa Xaa Pro Xaa Pro Xaa Xaa Xaa Xaa Xaa Xaa
1               5                   10                  15

Pro Xaa Xaa Xaa Pro Pro Pro Xaa Pro Xaa Pro Xaa Xaa Xaa Xaa
```

```
                 20                  25                  30

Xaa Pro Xaa Xaa Pro Xaa Xaa
             35

<210> SEQ ID NO 50
<211> LENGTH: 41
<212> TYPE: PRT
<213> ORGANISM: Artificial
<220> FEATURE:
<223> OTHER INFORMATION: Synthesized: Proline-rich peptide 49
<220> FEATURE:
<221> NAME/KEY: misc_feature
<222> LOCATION: (3)..(3)
<223> OTHER INFORMATION: Xaa can be any amino acid
<220> FEATURE:
<221> NAME/KEY: misc_feature
<222> LOCATION: (7)..(7)
<223> OTHER INFORMATION: Xaa can be any amino acid
<220> FEATURE:
<221> NAME/KEY: misc_feature
<222> LOCATION: (12)..(12)
<223> OTHER INFORMATION: Xaa can be any amino acid
<220> FEATURE:
<221> NAME/KEY: misc_feature
<222> LOCATION: (15)..(16)
<223> OTHER INFORMATION: Xaa can be any amino acid
<220> FEATURE:
<221> NAME/KEY: misc_feature
<222> LOCATION: (20)..(20)
<223> OTHER INFORMATION: Xaa can be any amino acid
<220> FEATURE:
<221> NAME/KEY: misc_feature
<222> LOCATION: (22)..(22)
<223> OTHER INFORMATION: Xaa can be any amino acid
<220> FEATURE:
<221> NAME/KEY: misc_feature
<222> LOCATION: (24)..(31)
<223> OTHER INFORMATION: Xaa can be any amino acid
<220> FEATURE:
<221> NAME/KEY: misc_feature
<222> LOCATION: (33)..(33)
<223> OTHER INFORMATION: Xaa can be any amino acid
<220> FEATURE:
<221> NAME/KEY: misc_feature
<222> LOCATION: (35)..(38)
<223> OTHER INFORMATION: Xaa can be any amino acid
<220> FEATURE:
<221> NAME/KEY: misc_feature
<222> LOCATION: (40)..(41)
<223> OTHER INFORMATION: Xaa can be any amino acid

<400> SEQUENCE: 50

Pro Pro Xaa Pro Pro Pro Xaa Pro Pro Pro Xaa Pro Pro Xaa Xaa
1               5                  10                  15

Pro Pro Pro Xaa Pro Xaa Pro Xaa Xaa Xaa Xaa Xaa Xaa Xaa Pro
             20                  25                  30

Xaa Pro Xaa Xaa Xaa Xaa Pro Xaa Xaa
             35                  40

<210> SEQ ID NO 51
<211> LENGTH: 43
<212> TYPE: PRT
<213> ORGANISM: Artificial
<220> FEATURE:
<223> OTHER INFORMATION: Synthesized: Proline-rich peptide 50
<220> FEATURE:
<221> NAME/KEY: misc_feature
<222> LOCATION: (4)..(5)
<223> OTHER INFORMATION: Xaa can be any amino acid
<220> FEATURE:
<221> NAME/KEY: misc_feature
<222> LOCATION: (15)..(15)
<223> OTHER INFORMATION: Xaa can be any amino acid
```

```
<220> FEATURE:
<221> NAME/KEY: misc_feature
<222> LOCATION: (26)..(26)
<223> OTHER INFORMATION: Xaa can be any amino acid
<220> FEATURE:
<221> NAME/KEY: misc_feature
<222> LOCATION: (28)..(28)
<223> OTHER INFORMATION: Xaa can be any amino acid
<220> FEATURE:
<221> NAME/KEY: misc_feature
<222> LOCATION: (30)..(43)
<223> OTHER INFORMATION: Xaa can be any amino acid

<400> SEQUENCE: 51

Pro Pro Pro Xaa Xaa Pro Pro Pro Pro Pro Pro Pro Pro Xaa Pro
1               5                   10                  15

Pro Pro Pro Pro Pro Pro Pro Pro Pro Xaa Pro Xaa Pro Xaa Xaa Xaa
            20                  25                  30

Xaa Xaa Xaa Xaa Xaa Xaa Xaa Xaa Xaa Xaa Xaa
        35                  40

<210> SEQ ID NO 52
<211> LENGTH: 43
<212> TYPE: PRT
<213> ORGANISM: Artificial
<220> FEATURE:
<223> OTHER INFORMATION: Synthesized: Proline-rich peptide 51
<220> FEATURE:
<221> NAME/KEY: misc_feature
<222> LOCATION: (4)..(4)
<223> OTHER INFORMATION: Xaa can be any amino acid
<220> FEATURE:
<221> NAME/KEY: misc_feature
<222> LOCATION: (7)..(8)
<223> OTHER INFORMATION: Xaa can be any amino acid
<220> FEATURE:
<221> NAME/KEY: misc_feature
<222> LOCATION: (26)..(34)
<223> OTHER INFORMATION: Xaa can be any amino acid
<220> FEATURE:
<221> NAME/KEY: misc_feature
<222> LOCATION: (40)..(40)
<223> OTHER INFORMATION: Xaa can be any amino acid
<220> FEATURE:
<221> NAME/KEY: misc_feature
<222> LOCATION: (42)..(43)
<223> OTHER INFORMATION: Xaa can be any amino acid

<400> SEQUENCE: 52

Pro Pro Pro Xaa Pro Pro Xaa Xaa Pro Pro Pro Pro Pro Pro Pro
1               5                   10                  15

Pro Pro Pro Pro Pro Pro Pro Pro Pro Xaa Xaa Xaa Xaa Xaa Xaa Xaa
            20                  25                  30

Xaa Xaa Pro Pro Pro Pro Pro Xaa Pro Xaa Xaa
        35                  40

<210> SEQ ID NO 53
<211> LENGTH: 47
<212> TYPE: PRT
<213> ORGANISM: Artificial
<220> FEATURE:
<223> OTHER INFORMATION: Synthesized: Proline-rich peptide 52
<220> FEATURE:
<221> NAME/KEY: misc_feature
<222> LOCATION: (4)..(4)
<223> OTHER INFORMATION: Xaa can be any amino acid
<220> FEATURE:
<221> NAME/KEY: misc_feature
<222> LOCATION: (17)..(18)
<223> OTHER INFORMATION: Xaa can be any amino acid
<220> FEATURE:
```

```
<221> NAME/KEY: misc_feature
<222> LOCATION: (22)..(29)
<223> OTHER INFORMATION: Xaa can be any amino acid
<220> FEATURE:
<221> NAME/KEY: misc_feature
<222> LOCATION: (31)..(44)
<223> OTHER INFORMATION: Xaa can be any amino acid
<220> FEATURE:
<221> NAME/KEY: misc_feature
<222> LOCATION: (46)..(47)
<223> OTHER INFORMATION: Xaa can be any amino acid

<400> SEQUENCE: 53

Pro Pro Pro Xaa Pro Pro Pro Pro Pro Pro Pro Pro Pro Pro Pro
1               5                   10                  15

Xaa Xaa Pro Pro Pro Xaa Xaa Xaa Xaa Xaa Xaa Xaa Xaa Pro Xaa Xaa
            20                  25                  30

Xaa Xaa Xaa Xaa Xaa Xaa Xaa Xaa Xaa Xaa Xaa Pro Xaa Xaa
        35                  40                  45

<210> SEQ ID NO 54
<211> LENGTH: 50
<212> TYPE: PRT
<213> ORGANISM: Artificial
<220> FEATURE:
<223> OTHER INFORMATION: Synthesized: Proline-rich peptide 53
<220> FEATURE:
<221> NAME/KEY: misc_feature
<222> LOCATION: (12)..(12)
<223> OTHER INFORMATION: Xaa can be any amino acid
<220> FEATURE:
<221> NAME/KEY: misc_feature
<222> LOCATION: (19)..(19)
<223> OTHER INFORMATION: Xaa can be any amino acid
<220> FEATURE:
<221> NAME/KEY: misc_feature
<222> LOCATION: (22)..(24)
<223> OTHER INFORMATION: Xaa can be any amino acid
<220> FEATURE:
<221> NAME/KEY: misc_feature
<222> LOCATION: (26)..(26)
<223> OTHER INFORMATION: Xaa can be any amino acid
<220> FEATURE:
<221> NAME/KEY: misc_feature
<222> LOCATION: (29)..(38)
<223> OTHER INFORMATION: Xaa can be any amino acid
<220> FEATURE:
<221> NAME/KEY: misc_feature
<222> LOCATION: (41)..(43)
<223> OTHER INFORMATION: Xaa can be any amino acid
<220> FEATURE:
<221> NAME/KEY: misc_feature
<222> LOCATION: (45)..(50)
<223> OTHER INFORMATION: Xaa can be any amino acid

<400> SEQUENCE: 54

Pro Pro Pro Pro Pro Pro Pro Pro Pro Pro Pro Xaa Pro Pro Pro
1               5                   10                  15

Pro Pro Xaa Pro Pro Xaa Xaa Xaa Pro Xaa Pro Pro Xaa Xaa Xaa Xaa
            20                  25                  30

Xaa Xaa Xaa Xaa Xaa Pro Pro Xaa Xaa Xaa Pro Xaa Xaa Xaa Xaa
        35                  40                  45

Xaa Xaa
    50

<210> SEQ ID NO 55
<211> LENGTH: 26
<212> TYPE: PRT
<213> ORGANISM: Artificial
<220> FEATURE:
```

<223> OTHER INFORMATION: Synthesized: Clone 12.5

<400> SEQUENCE: 55

Pro Pro Pro Thr Pro Pro Arg Thr Pro Pro Pro Pro Pro Pro Pro Pro
1               5                   10                  15

Pro Pro Pro Pro Pro Pro Pro Pro Leu
            20                  25

<210> SEQ ID NO 56
<211> LENGTH: 38
<212> TYPE: PRT
<213> ORGANISM: Artificial
<220> FEATURE:
<223> OTHER INFORMATION: Synthesized: Clone DS 7

<400> SEQUENCE: 56

Pro Pro Pro Thr Pro Pro Leu Pro Pro Pro Pro Pro Pro Pro Pro Leu
1               5                   10                  15

Leu Leu Leu Leu Leu Leu Leu Pro Pro Ile Thr Ile Thr Ile Thr
            20                  25                  30

Glu Phe Lys Pro Leu Ile
        35

<210> SEQ ID NO 57
<211> LENGTH: 23
<212> TYPE: PRT
<213> ORGANISM: Artificial
<220> FEATURE:
<223> OTHER INFORMATION: Synthesized: Clone DS 8

<400> SEQUENCE: 57

Pro Pro Pro Val Leu Pro Pro Pro Pro Pro Pro Pro Ala Pro
1               5                   10                  15

Pro Pro Pro Pro Pro Pro Pro
            20

<210> SEQ ID NO 58
<211> LENGTH: 37
<212> TYPE: PRT
<213> ORGANISM: Artificial
<220> FEATURE:
<223> OTHER INFORMATION: Synthesized: Clone DS 46

<400> SEQUENCE: 58

Lys Pro Pro Pro Pro Pro Leu Thr Thr Pro Thr Pro Pro Thr
1               5                   10                  15

Thr Tyr Tyr Cys Tyr Tyr Ser Ser Pro Pro Ser Pro Ser Pro Ser
            20                  25                  30

Leu Ser Leu Asn Arg
        35

<210> SEQ ID NO 59
<211> LENGTH: 33
<212> TYPE: PRT
<213> ORGANISM: Artificial
<220> FEATURE:
<223> OTHER INFORMATION: Synthesized: Clone DS 47

<400> SEQUENCE: 59

Pro Pro Pro Pro Val Thr Leu Ala Pro Pro Pro Arg Pro Arg Pro
1               5                   10                  15

Pro Pro Pro Pro Pro Pro Pro Leu Ala His His His His His Cys
            20                  25                  30

Val

```
<210> SEQ ID NO 60
<211> LENGTH: 35
<212> TYPE: PRT
<213> ORGANISM: Artificial
<220> FEATURE:
<223> OTHER INFORMATION: Synthesized: Clone DS121
<220> FEATURE:
<221> NAME/KEY: misc_feature
<222> LOCATION: (29)..(29)
<223> OTHER INFORMATION: Xaa can be any amino acid
<220> FEATURE:
<221> NAME/KEY: misc_feature
<222> LOCATION: (32)..(32)
<223> OTHER INFORMATION: Xaa can be any amino acid

<400> SEQUENCE: 60
```

Pro Pro Pro Pro Pro Pro Pro Pro Pro Pro Pro Pro Pro Pro Pro Pro
1               5                   10                  15

Pro Pro Pro Pro Pro Pro Pro His Pro Pro Ser Xaa Ser Pro Xaa
            20                  25                  30

Leu Cys Leu
        35

```
<210> SEQ ID NO 61
<211> LENGTH: 38
<212> TYPE: PRT
<213> ORGANISM: Artificial
<220> FEATURE:
<223> OTHER INFORMATION: Synthesized: Clone DS123

<400> SEQUENCE: 61
```

Pro Pro Pro Arg Pro Pro Pro Pro Pro Pro Thr Pro Thr Arg Thr
1               5                   10                  15

Arg Pro Pro Pro Pro Pro Pro Pro Cys His His Leu Thr Ile Thr
            20                  25                  30

Glu Phe Lys Pro Leu Ile
        35

```
<210> SEQ ID NO 62
<211> LENGTH: 43
<212> TYPE: PRT
<213> ORGANISM: Artificial
<220> FEATURE:
<223> OTHER INFORMATION: Synthesized: Clone DS177

<400> SEQUENCE: 62
```

Pro Pro Pro Val Leu Pro Pro Pro Pro Pro Pro Pro Pro Ala Pro
1               5                   10                  15

Pro Pro Pro Pro Pro Pro Pro Ser Pro Ser Pro Ser Leu Ser
            20                  25                  30

Leu Asn Arg Cys Leu Ile Thr Thr Trp Tyr Met
        35                  40

```
<210> SEQ ID NO 63
<211> LENGTH: 33
<212> TYPE: PRT
<213> ORGANISM: Artificial
<220> FEATURE:
<223> OTHER INFORMATION: Synthesized: Clone B1 and B6

<400> SEQUENCE: 63
```

Pro Pro Pro Pro Val Thr Leu Ala Pro Pro Pro Pro Arg Pro Arg Pro

<210> SEQ ID NO 64
<211> LENGTH: 37
<212> TYPE: PRT
<213> ORGANISM: Artificial
<220> FEATURE:
<223> OTHER INFORMATION: Synthesized: Clone B9

<400> SEQUENCE: 64

Pro Pro Pro Pro Leu Pro Leu Pro Pro Pro Pro Pro Pro Pro Pro
1               5                   10                  15

Pro Pro Pro His His Pro Arg His Pro Gly Asp Asp Asp Asp Asn Gln
            20                  25                  30

Lys Thr Leu Asn Arg
        35

<210> SEQ ID NO 65
<211> LENGTH: 37
<212> TYPE: PRT
<213> ORGANISM: Artificial
<220> FEATURE:
<223> OTHER INFORMATION: Synthesized: Clone B27

<400> SEQUENCE: 65

Pro Pro Pro Pro Leu Pro Pro Pro Pro Pro Pro Pro Pro Pro Pro
1               5                   10                  15

Pro Leu Leu Phe Ser Pro His Tyr Pro Pro Pro Ser Ser Pro Ser
            20                  25                  30

Leu Ser Leu Asn Arg
        35

<210> SEQ ID NO 66
<211> LENGTH: 32
<212> TYPE: PRT
<213> ORGANISM: Artificial
<220> FEATURE:
<223> OTHER INFORMATION: Synthesized: Clone B28

<400> SEQUENCE: 66

Pro Pro Pro Ala Leu Thr Leu Thr Pro Pro Pro Pro Pro Pro Pro
1               5                   10                  15

Pro Pro Pro Pro Pro Pro Thr Pro Pro His His His His Gln
            20                  25                  30

<210> SEQ ID NO 67
<211> LENGTH: 33
<212> TYPE: PRT
<213> ORGANISM: Artificial
<220> FEATURE:
<223> OTHER INFORMATION: Synthesized: Clone B36

<400> SEQUENCE: 67

Pro Pro Pro Ala Arg Pro Pro Thr Pro Thr Thr Pro Pro Pro Pro
1               5                   10                  15

Pro Pro Pro Pro Pro Pro Pro Arg Pro His His His His His
            20                  25                  30

Gln

<210> SEQ ID NO 68
<211> LENGTH: 35
<212> TYPE: PRT
<213> ORGANISM: Artificial
<220> FEATURE:
<223> OTHER INFORMATION: Synthesized: Clone B39

<400> SEQUENCE: 68

Pro Pro Thr Thr Thr Thr Ile Thr Thr Arg Thr Pro Ser Ser Tyr
1               5                   10                  15

Tyr Cys Tyr Tyr Tyr Tyr Pro Gln Pro Ser Pro Ser Pro Ser Leu Ser
            20                  25                  30

Leu Asn Arg
        35

<210> SEQ ID NO 69
<211> LENGTH: 47
<212> TYPE: PRT
<213> ORGANISM: Artificial
<220> FEATURE:
<223> OTHER INFORMATION: Synthesized: Clone B40

<400> SEQUENCE: 69

Pro Pro Pro Thr Pro Pro Pro Pro Pro Pro Pro Pro Pro Pro Pro
1               5                   10                  15

Arg Ala Pro Pro Pro Thr Thr His Val Ala Ala Gly Ala Pro Gly Ala
            20                  25                  30

Arg Arg Cys His Gly Ile Thr Ile Thr Glu Phe Lys Pro Leu Ile
        35                  40                  45

<210> SEQ ID NO 70
<211> LENGTH: 35
<212> TYPE: PRT
<213> ORGANISM: Artificial
<220> FEATURE:
<223> OTHER INFORMATION: Synthesized: Clone B47

<400> SEQUENCE: 70

Pro Pro Pro Pro Pro Leu Pro Leu Pro Pro Pro Pro Pro Pro Pro
1               5                   10                  15

Pro Pro Pro Pro Ser Pro Arg Pro Pro Pro Cys Pro Ser Thr Thr Thr
            20                  25                  30

Gln Leu Asn
        35

<210> SEQ ID NO 71
<211> LENGTH: 36
<212> TYPE: PRT
<213> ORGANISM: Artificial
<220> FEATURE:
<223> OTHER INFORMATION: Synthesized: Clone B51

<400> SEQUENCE: 71

Pro Pro Pro Thr Pro Thr Ile Pro Thr Arg Thr Thr Pro Asn Tyr Ser
1               5                   10                  15

Tyr Ser Cys Tyr Tyr Tyr Tyr Pro Leu Pro Ser Ser Ser Pro Ser Leu
            20                  25                  30

Ser Leu Asn Arg
        35

<210> SEQ ID NO 72
<211> LENGTH: 50

<212> TYPE: PRT
<213> ORGANISM: Artificial
<220> FEATURE:
<223> OTHER INFORMATION: Synthesized: Clone 1

<400> SEQUENCE: 72

Pro Pro Pro Pro Pro Pro Pro Pro Pro Ala Pro Pro Pro Pro Pro
1               5                   10                  15

Pro Pro Arg Pro Pro Thr Val Thr Pro Thr Pro Pro Arg Ile Cys Ser
            20                  25                  30

Tyr Ser Tyr Tyr Ser Val Pro Pro Ser Ser Ser Pro Ser Leu Ser Leu
                35                  40                  45

Asn Arg
    50

<210> SEQ ID NO 73
<211> LENGTH: 39
<212> TYPE: PRT
<213> ORGANISM: Artificial
<220> FEATURE:
<223> OTHER INFORMATION: Synthesized: Clone 2

<400> SEQUENCE: 73

Pro Pro Pro Pro Leu Pro Pro Pro Pro Pro Pro Pro Pro Pro Pro
1               5                   10                  15

Pro Pro Pro Pro Pro Pro Arg Cys Ser Pro His His His His Pro Ile
            20                  25                  30

Thr Glu Phe Lys Pro Leu Ile
            35

<210> SEQ ID NO 74
<211> LENGTH: 32
<212> TYPE: PRT
<213> ORGANISM: Artificial
<220> FEATURE:
<223> OTHER INFORMATION: Synthesized: Clone 29

<400> SEQUENCE: 74

Thr Ala Pro Pro Pro Pro Pro Pro Pro Pro Pro Pro Pro Leu Pro
1               5                   10                  15

Pro Pro Pro Pro Pro Val Pro Pro Cys His His His His His His
            20                  25                  30

<210> SEQ ID NO 75
<211> LENGTH: 41
<212> TYPE: PRT
<213> ORGANISM: Artificial
<220> FEATURE:
<223> OTHER INFORMATION: Synthesized: Clone 30

<400> SEQUENCE: 75

Pro Pro Arg Pro Pro Pro Leu Pro Pro Pro Arg Pro Pro Leu Arg
1               5                   10                  15

Pro Pro Pro Ser Pro Gly Pro Cys Leu Ala Cys Leu Ser Thr Tyr Pro
            20                  25                  30

Leu Pro Cys Arg Phe Lys Pro Leu Ile
            35                  40

<210> SEQ ID NO 76
<211> LENGTH: 36
<212> TYPE: PRT
<213> ORGANISM: Artificial
<220> FEATURE:

<223> OTHER INFORMATION: Synthesized: Clone 40

<400> SEQUENCE: 76

Pro Pro Thr Pro Leu Ala Pro Leu Pro Val Arg Ala Pro Arg Ala
1               5                   10                  15

Ser Pro Pro Thr Pro Pro Pro Pro Ser His His His His His
            20                  25                  30

Cys Leu Asn Arg
        35

<210> SEQ ID NO 77
<211> LENGTH: 36
<212> TYPE: PRT
<213> ORGANISM: Artificial
<220> FEATURE:
<223> OTHER INFORMATION: Synthesized: Clone 4

<400> SEQUENCE: 77

Pro Pro Pro Pro Pro Ala Pro Pro Pro Pro Pro Pro Pro Pro Pro
1               5                   10                  15

Pro Pro Pro Pro Pro Pro Pro Pro Pro Ser Ser Ser Pro Ser Leu
            20                  25                  30

Ser Leu Asn Arg
        35

<210> SEQ ID NO 78
<211> LENGTH: 37
<212> TYPE: PRT
<213> ORGANISM: Artificial
<220> FEATURE:
<223> OTHER INFORMATION: Synthesized: Clone 7

<400> SEQUENCE: 78

Pro Pro Thr Pro Pro Pro Pro Pro Thr Pro Pro Pro Pro His Tyr
1               5                   10                  15

Ser Tyr Ser Phe Tyr Tyr Ser Ser Pro Pro Pro Ser Ser Pro Ser
            20                  25                  30

Leu Ser Leu Asn Arg
        35

<210> SEQ ID NO 79
<211> LENGTH: 37
<212> TYPE: PRT
<213> ORGANISM: Artificial
<220> FEATURE:
<223> OTHER INFORMATION: Synthesized: Clone 8

<400> SEQUENCE: 79

Pro Pro Pro Pro Leu Pro Pro Pro Pro Pro Pro Ala Pro Pro Leu
1               5                   10                  15

Pro Pro Pro Arg Pro Ala Pro Pro Pro Pro Ser Ser Ser Pro Ser
            20                  25                  30

Leu Ser Leu Asn Arg
        35

<210> SEQ ID NO 80
<211> LENGTH: 39
<212> TYPE: PRT
<213> ORGANISM: Artificial
<220> FEATURE:
<223> OTHER INFORMATION: Synthesized: Clones 11 and 32

<400> SEQUENCE: 80

```
Pro Ile Thr Ile Thr Ala Thr Pro Ala Pro Thr Thr Ser Thr Leu Thr
1               5                   10                  15

Pro Thr Thr Thr Pro Pro Pro Ala Pro Ala Pro Cys His His His
                20                  25                  30

His Pro Glu Lys Pro Leu Ile
        35
```

<210> SEQ ID NO 81
<211> LENGTH: 38
<212> TYPE: PRT
<213> ORGANISM: Artificial
<220> FEATURE:
<223> OTHER INFORMATION: Synthesized: Clone 12

<400> SEQUENCE: 81

```
Pro Pro Pro Pro Pro Pro Pro Pro Leu Pro Pro Thr Pro Pro
1               5                   10                  15

Pro Pro Pro Pro Leu Pro Tyr Cys Pro Pro Ser Pro Ser Pro Ser
                20                  25                  30

Leu Ser Asn Pro Leu Ile
        35
```

<210> SEQ ID NO 82
<211> LENGTH: 38
<212> TYPE: PRT
<213> ORGANISM: Artificial
<220> FEATURE:
<223> OTHER INFORMATION: Synthesized: Clone 14

<400> SEQUENCE: 82

```
Pro Pro Pro Arg Pro Pro Pro Pro Pro Pro Thr Pro Thr Arg Thr
1               5                   10                  15

Arg Pro Pro Pro Pro Pro Pro Pro Cys His His Leu Thr Ile Thr
                20                  25                  30

Glu Phe Lys Pro Leu Ile
        35
```

<210> SEQ ID NO 83
<211> LENGTH: 38
<212> TYPE: PRT
<213> ORGANISM: Artificial
<220> FEATURE:
<223> OTHER INFORMATION: Synthesized: Clone 26

<400> SEQUENCE: 83

```
Pro Ala Ala Thr Arg Arg Val Thr Ala Pro Pro Leu Pro Pro Leu Ala
1               5                   10                  15

Pro Pro Pro Leu Pro Pro Val Ser Gly Ile His His His Pro Ile
                20                  25                  30

Thr Glu Lys Pro Leu Ile
        35
```

<210> SEQ ID NO 84
<211> LENGTH: 37
<212> TYPE: PRT
<213> ORGANISM: Artificial
<220> FEATURE:
<223> OTHER INFORMATION: Synthesized: Clone 28

<400> SEQUENCE: 84

```
Pro Pro Pro Pro Pro Leu Pro Leu Pro Pro Pro Pro Pro Pro Pro Pro
1               5                   10                  15
```

Pro Pro Pro Pro Pro Pro Pro Pro Pro Pro Ser Ser Ser Pro
            20                  25                  30

Ser Leu Ser Asn Arg
        35

<210> SEQ ID NO 85
<211> LENGTH: 35
<212> TYPE: PRT
<213> ORGANISM: Artificial
<220> FEATURE:
<223> OTHER INFORMATION: Synthesized: Clone 31

<400> SEQUENCE: 85

Pro Leu Pro Pro Leu Pro Pro Pro Pro Pro Pro Pro Pro Ser Ser
1               5                   10                  15

Ser Ser Ser Ser Ser Ser Pro Pro Ala Ser Ser Ser Pro Ser Leu Ser
            20                  25                  30

Leu Asn Arg
        35

<210> SEQ ID NO 86
<211> LENGTH: 34
<212> TYPE: PRT
<213> ORGANISM: Artificial
<220> FEATURE:
<223> OTHER INFORMATION: Synthesized: Clone 33

<400> SEQUENCE: 86

Thr Pro Pro Pro Arg Pro Pro Pro Pro Pro Thr Thr Leu Pro Arg
1               5                   10                  15

Pro Pro Arg Pro Pro Pro Arg Leu Pro Pro His His His His His His
            20                  25                  30

Cys Val

<210> SEQ ID NO 87
<211> LENGTH: 33
<212> TYPE: PRT
<213> ORGANISM: Artificial
<220> FEATURE:
<223> OTHER INFORMATION: Synthesized: Clone 36

<400> SEQUENCE: 87

Pro Pro Pro Thr Leu Pro Pro Pro Pro Pro Pro Pro Pro Pro Pro
1               5                   10                  15

Pro Arg Pro Pro Arg Pro Pro Pro Pro Cys His His His His His
            20                  25                  30

His

<210> SEQ ID NO 88
<211> LENGTH: 34
<212> TYPE: PRT
<213> ORGANISM: Artificial
<220> FEATURE:
<223> OTHER INFORMATION: Synthesized: Clone 37

<400> SEQUENCE: 88

Pro Pro Pro Thr Leu Pro Leu Pro Thr Pro Pro Pro Pro Pro Pro
1               5                   10                  15

Pro Leu Pro Pro Pro Pro Pro Pro Pro Cys Ile Ile Ile Thr Ile
            20                  25                  30

Thr Glu

```
<210> SEQ ID NO 89
<211> LENGTH: 32
<212> TYPE: PRT
<213> ORGANISM: Artificial
<220> FEATURE:
<223> OTHER INFORMATION: Synthesized: Clone 34

<400> SEQUENCE: 89

Pro Pro Pro Pro Pro Pro Leu Pro Pro Ile Pro Pro Pro Pro Pro Pro
1               5                   10                  15

Pro Pro Pro Pro Pro Pro Pro Pro Pro Pro Ser Ser Ser Pro Ser
            20                  25                  30

<210> SEQ ID NO 90
<211> LENGTH: 34
<212> TYPE: PRT
<213> ORGANISM: Artificial
<220> FEATURE:
<223> OTHER INFORMATION: Synthesized: Peptide 12-1

<400> SEQUENCE: 90

Pro Pro Pro Ala Pro Pro Arg Thr Pro Pro Pro Pro Pro Pro Pro Pro
1               5                   10                  15

Pro Pro Pro Pro Pro Pro Pro Pro Pro Leu His His His His His His
            20                  25                  30

Cys Val

<210> SEQ ID NO 91
<211> LENGTH: 34
<212> TYPE: PRT
<213> ORGANISM: Artificial
<220> FEATURE:
<223> OTHER INFORMATION: Synthesized: Peptide 12-2

<400> SEQUENCE: 91

Pro Pro Pro Thr Pro Pro Ala Thr Pro Pro Pro Pro Pro Pro Pro Pro
1               5                   10                  15

Pro Pro Pro Pro Pro Pro Pro Pro Pro Leu His His His His His His
            20                  25                  30

Cys Val

<210> SEQ ID NO 92
<211> LENGTH: 34
<212> TYPE: PRT
<213> ORGANISM: Artificial
<220> FEATURE:
<223> OTHER INFORMATION: Synthesized: Peptide 12-3

<400> SEQUENCE: 92

Pro Pro Pro Thr Pro Pro Arg Ala Pro Pro Pro Pro Pro Pro Pro Pro
1               5                   10                  15

Pro Pro Pro Pro Pro Pro Pro Pro Pro Leu His His His His His His
            20                  25                  30

Cys Val

<210> SEQ ID NO 93
<211> LENGTH: 43
<212> TYPE: PRT
<213> ORGANISM: Artificial
<220> FEATURE:
<223> OTHER INFORMATION: Synthesized: Peptide 12-4
```

<400> SEQUENCE: 93

Pro Pro Pro Thr Pro Pro Arg Thr Pro Pro Pro Pro Pro Pro Pro
1               5                   10                  15
Pro Pro Pro Pro Pro Pro Pro Pro Leu His His His His His His
                20                  25                  30
Cys Val Pro Pro Pro Pro Lys Pro Leu Ile
            35                  40

<210> SEQ ID NO 94
<211> LENGTH: 23
<212> TYPE: PRT
<213> ORGANISM: Artificial
<220> FEATURE:
<223> OTHER INFORMATION: Synthesized: Peptide 12-6

<400> SEQUENCE: 94

Pro Pro Pro Thr Pro Pro Arg Thr Pro Pro Pro Pro Pro Pro Pro
1               5                   10                  15
Pro Pro Pro Pro Pro Pro Pro
                20

<210> SEQ ID NO 95
<211> LENGTH: 20
<212> TYPE: PRT
<213> ORGANISM: Artificial
<220> FEATURE:
<223> OTHER INFORMATION: Synthesized: Peptide 12-7

<400> SEQUENCE: 95

Pro Pro Pro Thr Pro Pro Arg Thr Pro Pro Pro Pro Pro Pro Pro
1               5                   10                  15
Pro Pro Pro Pro
                20

<210> SEQ ID NO 96
<211> LENGTH: 20
<212> TYPE: PRT
<213> ORGANISM: Artificial
<220> FEATURE:
<223> OTHER INFORMATION: Synthesized: Peptide V7.4

<400> SEQUENCE: 96

Pro Pro Pro Thr Pro Pro Arg Thr Pro Pro Leu Leu Leu Leu Leu
1               5                   10                  15
Leu Leu Leu Ser
                20

<210> SEQ ID NO 97
<211> LENGTH: 20
<212> TYPE: PRT
<213> ORGANISM: Artificial
<220> FEATURE:
<223> OTHER INFORMATION: Synthesized: Peptide V8

<400> SEQUENCE: 97

Pro Pro Pro Pro Pro Pro Pro Pro Pro Pro Leu His His His His
1               5                   10                  15
His His Cys Val
                20

<210> SEQ ID NO 98
<211> LENGTH: 15
<212> TYPE: PRT

```
<213> ORGANISM: Artificial
<220> FEATURE:
<223> OTHER INFORMATION: Synthesized: Peptide V16.1

<400> SEQUENCE: 98

Pro Pro Pro Pro Pro Pro Pro Pro Pro His His His His His His
1               5                   10                  15

<210> SEQ ID NO 99
<211> LENGTH: 11
<212> TYPE: PRT
<213> ORGANISM: Artificial
<220> FEATURE:
<223> OTHER INFORMATION: Synthesized: Peptide V14.1

<400> SEQUENCE: 99

Pro Pro Pro Thr Pro Pro Arg Thr Pro Pro Pro
1               5                   10

<210> SEQ ID NO 100
<211> LENGTH: 6
<212> TYPE: PRT
<213> ORGANISM: Artificial
<220> FEATURE:
<223> OTHER INFORMATION: Synthesized: Peptide V17.2

<400> SEQUENCE: 100

Pro Pro Pro Pro Pro Pro
1               5

<210> SEQ ID NO 101
<211> LENGTH: 16
<212> TYPE: PRT
<213> ORGANISM: Artificial
<220> FEATURE:
<223> OTHER INFORMATION: Synthesized: Peptide 24

<400> SEQUENCE: 101

Pro Pro Pro Pro Pro Pro Pro Pro Leu His His His His His His
1               5                   10                  15

<210> SEQ ID NO 102
<211> LENGTH: 21
<212> TYPE: PRT
<213> ORGANISM: Artificial
<220> FEATURE:
<223> OTHER INFORMATION: Synthesized: Peptide 8-1

<400> SEQUENCE: 102

Pro Pro Pro Pro Pro Pro Pro Pro Pro Pro Leu His His
1               5                   10                  15

His His His Cys Val
            20

<210> SEQ ID NO 103
<211> LENGTH: 18
<212> TYPE: PRT
<213> ORGANISM: Artificial
<220> FEATURE:
<223> OTHER INFORMATION: Synthesized: Peptide 25

<400> SEQUENCE: 103

Pro Pro Pro Pro Pro Pro Pro Pro Leu His His His His His His
1               5                   10                  15

Cys Val
```

<210> SEQ ID NO 104
<211> LENGTH: 15
<212> TYPE: PRT
<213> ORGANISM: Artificial
<220> FEATURE:
<223> OTHER INFORMATION: Synthesized: Peptide 27

<400> SEQUENCE: 104

Pro Pro Pro Pro Pro Pro Leu His His His His His His Cys Val
1               5                   10                  15

<210> SEQ ID NO 105
<211> LENGTH: 12
<212> TYPE: PRT
<213> ORGANISM: Artificial
<220> FEATURE:
<223> OTHER INFORMATION: Synthesized: Peptide 26

<400> SEQUENCE: 105

Pro Pro Pro Leu His His His His His His Cys Val
1               5                   10

<210> SEQ ID NO 106
<211> LENGTH: 9
<212> TYPE: PRT
<213> ORGANISM: Artificial
<220> FEATURE:
<223> OTHER INFORMATION: Synthesized: Peptide 23

<400> SEQUENCE: 106

Pro Pro Pro Pro Pro Pro Pro Pro Pro
1               5

<210> SEQ ID NO 107
<211> LENGTH: 7
<212> TYPE: PRT
<213> ORGANISM: Artificial
<220> FEATURE:
<223> OTHER INFORMATION: Synthesized: Peptide 29

<400> SEQUENCE: 107

Pro Pro Pro Pro Pro Pro Pro
1               5

<210> SEQ ID NO 108
<211> LENGTH: 4
<212> TYPE: PRT
<213> ORGANISM: Artificial
<220> FEATURE:
<223> OTHER INFORMATION: Synthesized: Peptide 39-1

<400> SEQUENCE: 108

Pro Pro Pro Leu
1

<210> SEQ ID NO 109
<211> LENGTH: 5
<212> TYPE: PRT
<213> ORGANISM: Artificial
<220> FEATURE:
<223> OTHER INFORMATION: Synthesized: Peptide 40-1

<400> SEQUENCE: 109

Pro Pro Pro Cys Val
1               5

```
<210> SEQ ID NO 110
<211> LENGTH: 7
<212> TYPE: PRT
<213> ORGANISM: Artificial
<220> FEATURE:
<223> OTHER INFORMATION: Synthesized: Peptide 28

<400> SEQUENCE: 110

Pro Pro Pro Thr Pro Pro Pro
1               5

<210> SEQ ID NO 111
<211> LENGTH: 8
<212> TYPE: PRT
<213> ORGANISM: Artificial
<220> FEATURE:
<223> OTHER INFORMATION: Synthesized: Peptide 30

<400> SEQUENCE: 111

Pro Pro Pro Gly Gly Pro Pro Pro
1               5

<210> SEQ ID NO 112
<211> LENGTH: 7
<212> TYPE: PRT
<213> ORGANISM: Artificial
<220> FEATURE:
<223> OTHER INFORMATION: Synthesized: Peptide 31

<400> SEQUENCE: 112

Pro Pro Pro Ala Pro Pro Pro
1               5

<210> SEQ ID NO 113
<211> LENGTH: 7
<212> TYPE: PRT
<213> ORGANISM: Artificial
<220> FEATURE:
<223> OTHER INFORMATION: Synthesized: Peptide 32

<400> SEQUENCE: 113

Pro Pro Pro Arg Pro Pro Pro
1               5

<210> SEQ ID NO 114
<211> LENGTH: 7
<212> TYPE: PRT
<213> ORGANISM: Artificial
<220> FEATURE:
<223> OTHER INFORMATION: Synthesized: Peptide 33

<400> SEQUENCE: 114

Pro Pro Pro His Pro Pro Pro
1               5

<210> SEQ ID NO 115
<211> LENGTH: 7
<212> TYPE: PRT
<213> ORGANISM: Artificial
<220> FEATURE:
<223> OTHER INFORMATION: Synthesized: Peptide 34

<400> SEQUENCE: 115

Pro Pro Pro Tyr Pro Pro Pro
1               5

<210> SEQ ID NO 116
```

```
<211> LENGTH: 7
<212> TYPE: PRT
<213> ORGANISM: Artificial
<220> FEATURE:
<223> OTHER INFORMATION: Synthesized: Peptide 35

<400> SEQUENCE: 116

Pro Pro Pro Gly Pro Pro Pro
1               5

<210> SEQ ID NO 117
<211> LENGTH: 16
<212> TYPE: PRT
<213> ORGANISM: Artificial
<220> FEATURE:
<223> OTHER INFORMATION: Synthesized: Peptide 37.1

<400> SEQUENCE: 117

His His His Thr Ile Thr Asn Glu Phe Lys Gln Thr Arg Ser Leu Ile
1               5                   10                  15

<210> SEQ ID NO 118
<211> LENGTH: 6
<212> TYPE: PRT
<213> ORGANISM: Artificial
<220> FEATURE:
<223> OTHER INFORMATION: Synthesized: Peptide 37-2; His tag

<400> SEQUENCE: 118

His His His His His His
1               5

<210> SEQ ID NO 119
<211> LENGTH: 8
<212> TYPE: PRT
<213> ORGANISM: Artificial
<220> FEATURE:
<223> OTHER INFORMATION: Synthesized: Peptide 36-2

<400> SEQUENCE: 119

His His His His His His Cys Val
1               5

<210> SEQ ID NO 120
<211> LENGTH: 9
<212> TYPE: PRT
<213> ORGANISM: Artificial
<220> FEATURE:
<223> OTHER INFORMATION: Synthesized: C-terminal peptide 1

<400> SEQUENCE: 120

Leu His His His His His His Cys Val
1               5

<210> SEQ ID NO 121
<211> LENGTH: 9
<212> TYPE: PRT
<213> ORGANISM: Artificial
<220> FEATURE:
<223> OTHER INFORMATION: Synthesized: C-terminal peptide 2

<400> SEQUENCE: 121

Leu Leu Leu Leu Leu Leu Leu Leu Ser
1               5

<210> SEQ ID NO 122
<211> LENGTH: 7
```

```
<212> TYPE: PRT
<213> ORGANISM: Artificial
<220> FEATURE:
<223> OTHER INFORMATION: Synthesized: C-terminal peptide 3

<400> SEQUENCE: 122

Leu His His His His His His
1               5

<210> SEQ ID NO 123
<211> LENGTH: 15
<212> TYPE: PRT
<213> ORGANISM: Artificial
<220> FEATURE:
<223> OTHER INFORMATION: Synthesized: Peptide linker

<400> SEQUENCE: 123

Gly Gly Gly Gly Ser Gly Gly Gly Gly Ser Gly Gly Gly Gly Ser
1               5                   10                  15

<210> SEQ ID NO 124
<211> LENGTH: 10
<212> TYPE: PRT
<213> ORGANISM: Artificial
<220> FEATURE:
<223> OTHER INFORMATION: Synthesized: C-myc tag

<400> SEQUENCE: 124

Glu Gln Lys Leu Ile Ser Glu Glu Asp Leu
1               5                   10

<210> SEQ ID NO 125
<211> LENGTH: 9
<212> TYPE: PRT
<213> ORGANISM: Artificial
<220> FEATURE:
<223> OTHER INFORMATION: Synthesized: HA tag

<400> SEQUENCE: 125

Tyr Pro Tyr Asp Val Pro Asp Tyr Ala
1               5

<210> SEQ ID NO 126
<211> LENGTH: 14
<212> TYPE: PRT
<213> ORGANISM: Artificial
<220> FEATURE:
<223> OTHER INFORMATION: Synthesized: V5 tag

<400> SEQUENCE: 126

Gly Lys Pro Ile Pro Asn Pro Leu Leu Gly Leu Asp Ser Thr
1               5                   10

<210> SEQ ID NO 127
<211> LENGTH: 22
<212> TYPE: PRT
<213> ORGANISM: Artificial
<220> FEATURE:
<223> OTHER INFORMATION: Synthesized: Pectate lyase signal sequence

<400> SEQUENCE: 127

Met Lys Tyr Leu Leu Pro Thr Ala Ala Ala Gly Leu Leu Leu Leu Ala
1               5                   10                  15

Ala Gln Pro Ala Met Ala
            20
```

```
<210> SEQ ID NO 128
<211> LENGTH: 18
<212> TYPE: PRT
<213> ORGANISM: Artificial
<220> FEATURE:
<223> OTHER INFORMATION: Synthesized: aga2P signal sequence

<400> SEQUENCE: 128

Met Gln Leu Leu Arg Cys Phe Ser Ile Phe Ser Val Ile Ala Ser Val
1               5                   10                  15

Leu Ala

<210> SEQ ID NO 129
<211> LENGTH: 21
<212> TYPE: PRT
<213> ORGANISM: Artificial
<220> FEATURE:
<223> OTHER INFORMATION: Synthesized: invertase (SUC1) signal sequence

<400> SEQUENCE: 129

Met Leu Leu Gln Ala Phe Leu Phe Leu Leu Ala Gly Phe Ala Ala Leu
1               5                   10                  15

Ile Ser Ala Ser Met
                20

<210> SEQ ID NO 130
<211> LENGTH: 127
<212> TYPE: PRT
<213> ORGANISM: Artificial
<220> FEATURE:
<223> OTHER INFORMATION: Synthesized: Anti-PSA heavy chain variable
      region

<400> SEQUENCE: 130

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Asn Tyr
                20                  25                  30

Ala Met Ser Trp Val Arg Gln Ala Pro Gly Lys Gly Leu Glu Trp Val
            35                  40                  45

Gly Asp Ile Tyr Pro Thr Ser Gly Tyr Thr Asp Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Tyr Asp Tyr Lys Tyr Val Ala Ser Glu Gly Ser Trp
            100                 105                 110

Leu Phe Asp Tyr Trp Gly Gln Gly Thr Leu Val Thr Val Ser Ser
        115                 120                 125

<210> SEQ ID NO 131
<211> LENGTH: 107
<212> TYPE: PRT
<213> ORGANISM: Artificial
<220> FEATURE:
<223> OTHER INFORMATION: Synthesized: Anti-PSA light chain variable
      region

<400> SEQUENCE: 131

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Val Ser Thr Ser
            20                  25                  30

Leu Asn Trp Tyr Gln Gln Lys Pro Gly Lys Ala Pro Lys Leu Leu Ile
        35                  40                  45

Tyr Gly Ala Ser Asn Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly His Pro Pro Tyr
                85                  90                  95

Thr Phe Gly Gln Gly Thr Lys Val Glu Ile Lys
            100                 105
```

<210> SEQ ID NO 132
<211> LENGTH: 234
<212> TYPE: PRT
<213> ORGANISM: Artificial
<220> FEATURE:
<223> OTHER INFORMATION: Synthesized: Heavy-chain variable region- CH1

<400> SEQUENCE: 132

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Asn Tyr
            20                  25                  30

Ala Met Ser Trp Val Arg Gln Ala Pro Gly Lys Gly Leu Glu Trp Val
        35                  40                  45

Gly Asp Ile Tyr Pro Thr Ser Gly Tyr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Tyr Asp Tyr Lys Tyr Val Ala Ser Glu Gly Ser Trp
            100                 105                 110

Leu Phe Asp Tyr Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His
225                 230
```

<210> SEQ ID NO 133
<211> LENGTH: 214
<212> TYPE: PRT
<213> ORGANISM: Artificial
<220> FEATURE:

<223> OTHER INFORMATION: Synthesized: Light-chain variable region-
      kappa 1

<400> SEQUENCE: 133

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ser Ser Thr Ser
            20                  25                  30

Leu Asn Trp Tyr Gln Gln Lys Pro Gly Lys Ala Pro Lys Leu Leu Ile
        35                  40                  45

Tyr Gly Ala Ser Asn Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly His Pro Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 134
<211> LENGTH: 130
<212> TYPE: DNA
<213> ORGANISM: Artificial
<220> FEATURE:
<223> OTHER INFORMATION: Synthesized: 26 amino acid long randomized
      peptide
<220> FEATURE:
<221> NAME/KEY: misc_feature
<222> LOCATION: (95)..(96)
<223> OTHER INFORMATION: n is a, c, g, or t
<220> FEATURE:
<221> NAME/KEY: misc_feature
<222> LOCATION: (98)..(99)
<223> OTHER INFORMATION: n is a, c, g, or t
<220> FEATURE:
<221> NAME/KEY: misc_feature
<222> LOCATION: (101)..(102)
<223> OTHER INFORMATION: n is a, c, g, or t

<400> SEQUENCE: 134
ctctggaggt ggtggcagca agcttvbtvb tvbtvbtvbt vbtvbtvbtv btvbtvbtvb    60
tvbtvbtvbt vbtvbtvbtv btvbtvbtvb tvbtnnsnns nnscatcacc atcaccatca   120
ctgagtttaa                                                         130

<210> SEQ ID NO 135
<211> LENGTH: 23

```
<212> TYPE: DNA
<213> ORGANISM: Artificial
<220> FEATURE:
<223> OTHER INFORMATION: Synthesized: Primer: LC-FR1-F

<400> SEQUENCE: 135
gggcggccgc aaacacacat aat                                              23

<210> SEQ ID NO 136
<211> LENGTH: 23
<212> TYPE: DNA
<213> ORGANISM: Artificial
<220> FEATURE:
<223> OTHER INFORMATION: Synthesized: Primer: LC-FR1-R

<400> SEQUENCE: 136
ttgagaagct ctacaagaca aag                                              23

<210> SEQ ID NO 137
<211> LENGTH: 28
<212> TYPE: DNA
<213> ORGANISM: Artificial
<220> FEATURE:
<223> OTHER INFORMATION: Synthesized: Primer: LC-CDR1-F

<400> SEQUENCE: 137
agctactttg tcttgtagag cttctcaa                                         28

<210> SEQ ID NO 138
<211> LENGTH: 51
<212> TYPE: DNA
<213> ORGANISM: Artificial
<220> FEATURE:
<223> OTHER INFORMATION: Synthesized: Primer: LC-CDR1-R

<400> SEQUENCE: 138
gtagatcaac aatcttggag cttgacctgg tttttgttga taccaagcca a               51

<210> SEQ ID NO 139
<211> LENGTH: 24
<212> TYPE: DNA
<213> ORGANISM: Artificial
<220> FEATURE:
<223> OTHER INFORMATION: Synthesized: Primer: LC-CDR2-F

<400> SEQUENCE: 139
caagctccaa gattgttgat ctac                                             24

<210> SEQ ID NO 140
<211> LENGTH: 25
<212> TYPE: DNA
<213> ORGANISM: Artificial
<220> FEATURE:
<223> OTHER INFORMATION: Synthesized: Primer: LC-CDR2-R

<400> SEQUENCE: 140
cagaaaatct atctggaata ccagt                                            25

<210> SEQ ID NO 141
<211> LENGTH: 23
<212> TYPE: DNA
<213> ORGANISM: Artificial
<220> FEATURE:
<223> OTHER INFORMATION: Synthesized: Primer: LC-FR3-F

<400> SEQUENCE: 141
```

```
actggtattc cagatagatt ttc                                           23

<210> SEQ ID NO 142
<211> LENGTH: 22
<212> TYPE: DNA
<213> ORGANISM: Artificial
<220> FEATURE:
<223> OTHER INFORMATION: Synthesized: Primer: LC-FR3-R

<400> SEQUENCE: 142
ttgttgacag tagtaaacag cg                                            22

<210> SEQ ID NO 143
<211> LENGTH: 30
<212> TYPE: DNA
<213> ORGANISM: Artificial
<220> FEATURE:
<223> OTHER INFORMATION: Synthesized: Primer: LC-CDR3-F

<400> SEQUENCE: 143
gaagatttcg ctgtttacta ctgtcaacaa                                    30

<210> SEQ ID NO 144
<211> LENGTH: 35
<212> TYPE: DNA
<213> ORGANISM: Artificial
<220> FEATURE:
<223> OTHER INFORMATION: Synthesized: Primer: LC-CDR3-R

<400> SEQUENCE: 144
cttttaattt caactttagt accttgacca aaagt                              35

<210> SEQ ID NO 145
<211> LENGTH: 25
<212> TYPE: DNA
<213> ORGANISM: Artificial
<220> FEATURE:
<223> OTHER INFORMATION: Synthesized: Primer: LC-FR4-F

<400> SEQUENCE: 145
acttttggtc aaggtactaa agttg                                         25

<210> SEQ ID NO 146
<211> LENGTH: 26
<212> TYPE: DNA
<213> ORGANISM: Artificial
<220> FEATURE:
<223> OTHER INFORMATION: Synthesized: Primer: LCC-R

<400> SEQUENCE: 146
tcagatcttc attaacattc accacg                                        26

<210> SEQ ID NO 147
<211> LENGTH: 30
<212> TYPE: DNA
<213> ORGANISM: Artificial
<220> FEATURE:
<223> OTHER INFORMATION: Synthesized: Primer: HC-FR1-F

<400> SEQUENCE: 147
gcaggatccg aagttcaatt gttggaatct                                    30

<210> SEQ ID NO 148
<211> LENGTH: 27
<212> TYPE: DNA
<213> ORGANISM: Artificial
```

<220> FEATURE:
<223> OTHER INFORMATION: Synthesized: Primer: HC-FR1-R

<400> SEQUENCE: 148
aaaagtaaaa ccagaagcag cacaaga                                        27

<210> SEQ ID NO 149
<211> LENGTH: 21
<212> TYPE: DNA
<213> ORGANISM: Artificial
<220> FEATURE:
<223> OTHER INFORMATION: Synthesized: Primer: HC-CDR1-F

<400> SEQUENCE: 149
gctgcttctg gttttactttt t                                             21

<210> SEQ ID NO 150
<211> LENGTH: 45
<212> TYPE: DNA
<213> ORGANISM: Artificial
<220> FEATURE:
<223> OTHER INFORMATION: Synthesized: Primer: HC-CDR1-R

<400> SEQUENCE: 150
aacccattcc aaacctttac caggagcttg tctaacccaa gacat                    45

<210> SEQ ID NO 151
<211> LENGTH: 45
<212> TYPE: DNA
<213> ORGANISM: Artificial
<220> FEATURE:
<223> OTHER INFORMATION: Synthesized: Primer: HC-CDR2-F

<400> SEQUENCE: 151
atgtcttggg ttagacaagc tcctggtaaa ggtttggaat gggtt                    45

<210> SEQ ID NO 152
<211> LENGTH: 39
<212> TYPE: DNA
<213> ORGANISM: Artificial
<220> FEATURE:
<223> OTHER INFORMATION: Synthesized: Primer: HC-CDR2-R

<400> SEQUENCE: 152
tctagagata gtgaatctac ctttaacaga atcagcata                           39

<210> SEQ ID NO 153
<211> LENGTH: 24
<212> TYPE: DNA
<213> ORGANISM: Artificial
<220> FEATURE:
<223> OTHER INFORMATION: Synthesized: Primer: HC-CDR3-F1

<400> SEQUENCE: 153
actgctgttt attattgtgc taga                                           24

<210> SEQ ID NO 154
<211> LENGTH: 84
<212> TYPE: DNA
<213> ORGANISM: Artificial
<220> FEATURE:
<223> OTHER INFORMATION: Synthesized: Primer: HC-CDR3-F2

<400> SEQUENCE: 154
tctagagata actctaaaaa tactttgtat ttgcaaatga actctttgag agctgaagat    60

```
actgctgttt attattgtgc taga                                              84

<210> SEQ ID NO 155
<211> LENGTH: 24
<212> TYPE: DNA
<213> ORGANISM: Artificial
<220> FEATURE:
<223> OTHER INFORMATION: Synthesized: Primer: HC-CDR3-R

<400> SEQUENCE: 155
agtaccttga ccccaataat caaa                                              24

<210> SEQ ID NO 156
<211> LENGTH: 24
<212> TYPE: DNA
<213> ORGANISM: Artificial
<220> FEATURE:
<223> OTHER INFORMATION: Synthesized: Primer: HC-FR4-F

<400> SEQUENCE: 156
tttgattatt ggggtcaagg tact                                              24

<210> SEQ ID NO 157
<211> LENGTH: 27
<212> TYPE: DNA
<213> ORGANISM: Artificial
<220> FEATURE:
<223> OTHER INFORMATION: Synthesized: Primer: HC-FR4-R

<400> SEQUENCE: 157
tggaagcttt agaaccacca ccaccgg                                           27

<210> SEQ ID NO 158
<211> LENGTH: 168
<212> TYPE: DNA
<213> ORGANISM: Artificial
<220> FEATURE:
<223> OTHER INFORMATION: Synthesized: Leader sequence and FR1-LC

<400> SEQUENCE: 158
gggcggccgc aaacacacat aataaacaaa atgcaattgt tgagatgctt ttctattttc       60
tctgttatcg cttctgtttt ggctgctgaa attgttttga ctcaatctcc aggtactttg      120
tctttgtctc caggtgaaag agctactttg tcttgtagag cttctcaa                   168

<210> SEQ ID NO 159
<211> LENGTH: 110
<212> TYPE: DNA
<213> ORGANISM: Artificial
<220> FEATURE:
<223> OTHER INFORMATION: Synthesized: LC-FR3

<400> SEQUENCE: 159
gagctactgg tattccagat agattttctg gttctggttc tggtaccgat ttcactttga       60
ctatctcaag attggaacca gaagatttcg ctgtttacta ctgtcaacaa                 110

<210> SEQ ID NO 160
<211> LENGTH: 368
<212> TYPE: DNA
<213> ORGANISM: Artificial
<220> FEATURE:
<223> OTHER INFORMATION: Synthesized: FR4 and LC constant region

<400> SEQUENCE: 160 actttggtc aaggtactaa agttgaaatt aaaagaactg ttgctgctcc atctgttttt        60
```

```
atttttccac catctgatga acaattgaaa tctggtactg cttctgttgt ttgtttgttg    120
aacaacttct acccaagaga agctaaggtt caatggaagg ttgataacgc tttgcaatct    180
ggtaactctc aagaatctgt tactgaacaa gattctaagg attctactta ctctttgtct    240
tctactttga ctttgtctaa ggctgattac gaaaagcata aggtttacgc ttgtgaagtt    300
actcatcaag gtttgtcttc tccagttact aaatctttta atcgtggtga atgttaatga    360
agatctga                                                             368
```

<210> SEQ ID NO 161
<211> LENGTH: 96
<212> TYPE: DNA
<213> ORGANISM: Artificial
<220> FEATURE:
<223> OTHER INFORMATION: Synthesized: HC FR1

<400> SEQUENCE: 161

```
gcaggatccg aagttcaatt gttggaatct ggtggtggtt tggttcaacc aggtggttct    60
ttgagattgt cttgtgctgc ttctggtttt acttttt                              96
```

<210> SEQ ID NO 162
<211> LENGTH: 460
<212> TYPE: DNA
<213> ORGANISM: Artificial
<220> FEATURE:
<223> OTHER INFORMATION: Synthesized: FR4 and HC constant region

<400> SEQUENCE: 162

```
tttgattatt ggggtcaagg tactttggtt actgtttctt ctgcttccac caagggccca    60
tcggtcttcc cctggcacc ctcctccaag agcacctctg ggggcacagc ggccctgggc     120
tgcctggtca aggactactt ccccgaaccg gtgacggtgt catggaactc aggcgccctg    180
accagcggcg tgcacacctt cccggctgtc ctacagtcct caggactcta ctccctcagc    240
agcgtggtga ccgtgccctc cagcagcttg ggcacccaga cctacatctg caacgtgaat    300
cacaagccca gcaacaccaa ggtggacaag aaagttgagc ccaaatcttg tgacaaaact    360
cacacaggtt cttctgaaca aaagttgatc tctgaagaag atttggggtgg tggtggttca   420 ggtggtggtg gttccggtgg tggtggttct aaagcttcca                          460
```

<210> SEQ ID NO 163
<211> LENGTH: 23
<212> TYPE: PRT
<213> ORGANISM: Artificial
<220> FEATURE:
<223> OTHER INFORMATION: Synthesized: Light chain FR1

<400> SEQUENCE: 163

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 164
<211> LENGTH: 15
<212> TYPE: PRT
<213> ORGANISM: Artificial
<220> FEATURE:
<223> OTHER INFORMATION: Synthesized: Light chain FR2

<400> SEQUENCE: 164

Trp Tyr Gln Gln Lys Pro Gly Gln Ala Pro Arg Leu Leu Ile Tyr
1               5                   10                  15

<210> SEQ ID NO 165
<211> LENGTH: 32
<212> TYPE: PRT
<213> ORGANISM: Artificial
<220> FEATURE:
<223> OTHER INFORMATION: Synthesized: Light chain FR3

<400> SEQUENCE: 165

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 166
<211> LENGTH: 11
<212> TYPE: PRT
<213> ORGANISM: Artificial
<220> FEATURE:
<223> OTHER INFORMATION: Synthesized: Light chain FR4

<400> SEQUENCE: 166

Thr Phe Gly Gln Gly Thr Lys Val Glu Ile Lys
1               5                   10

<210> SEQ ID NO 167
<211> LENGTH: 107
<212> TYPE: PRT
<213> ORGANISM: Artificial
<220> FEATURE:
<223> OTHER INFORMATION: Synthesized: LC Constant region

<400> SEQUENCE: 167

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 168
<211> LENGTH: 30
<212> TYPE: PRT
<213> ORGANISM: Artificial
<220> FEATURE:
<223> OTHER INFORMATION: Synthesized: Heavy chain FR1

<400> SEQUENCE: 168

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

```
<210> SEQ ID NO 169
<211> LENGTH: 14
<212> TYPE: PRT
<213> ORGANISM: Artificial
<220> FEATURE:
<223> OTHER INFORMATION: Synthesized: Heavy chain FR2

<400> SEQUENCE: 169

Trp Val Arg Gln Ala Pro Gly Lys Gly Leu Glu Trp Val Ser
1               5                   10

<210> SEQ ID NO 170
<211> LENGTH: 32
<212> TYPE: PRT
<213> ORGANISM: Artificial
<220> FEATURE:
<223> OTHER INFORMATION: Synthesized: Heavy chain FR3

<400> SEQUENCE: 170

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 171
<211> LENGTH: 11
<212> TYPE: PRT
<213> ORGANISM: Artificial
<220> FEATURE:
<223> OTHER INFORMATION: Synthesized: Heavy chain FR4

<400> SEQUENCE: 171

Trp Gly Gln Gly Thr Leu Val Thr Val Ser Ser
1               5                   10

<210> SEQ ID NO 172
<211> LENGTH: 107
<212> TYPE: PRT
<213> ORGANISM: Artificial
<220> FEATURE:
<223> OTHER INFORMATION: Synthesized: CH1 Constant region

<400> SEQUENCE: 172

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His
            100                 105

<210> SEQ ID NO 173
<211> LENGTH: 395
<212> TYPE: PRT
<213> ORGANISM: Artificial
<220> FEATURE:
```

<223> OTHER INFORMATION: Synthesized: CH1-CH3-V5 tag-PRP

<400> SEQUENCE: 173

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser Gln Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Gly Leu Pro Ser Ser Ile Glu Lys Thr Ile Ser Lys Ala Lys Gly
    210                 215                 220

Gln Pro Arg Glu Pro Gln Val Tyr Thr Leu Pro Pro Ser Gln Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Glu Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Leu Gly Ser Ser Lys Pro Ile Pro Asn
                325                 330                 335

Pro Leu Leu Gly Leu Asp Ser Thr Gly Gly Gly Ser Gly Gly Gly
            340                 345                 350

Gly Ser Gly Gly Gly Gly Ser Lys Leu Pro Pro Thr Pro Pro Arg
    355                 360                 365

Thr Pro Pro Pro Pro Pro Pro Pro Pro Pro Pro Pro Pro
        370                 375                 380

Pro Pro Leu His His His His His Cys Val
385                 390                 395
```

<210> SEQ ID NO 174
<211> LENGTH: 24
<212> TYPE: DNA
<213> ORGANISM: Artificial
<220> FEATURE:
<223> OTHER INFORMATION: Synthesized: Primer: pDS-Fab-HC-F

<400> SEQUENCE: 174
cccggatcgg actactagca gctg                                        24

<210> SEQ ID NO 175
<211> LENGTH: 19
<212> TYPE: DNA
<213> ORGANISM: Artificial
<220> FEATURE:
<223> OTHER INFORMATION: Synthesized: Primer: pDS-Fab-HC-R

<400> SEQUENCE: 175
ttgtacgagc taaaagtac                                              19

<210> SEQ ID NO 176
<211> LENGTH: 4
<212> TYPE: PRT
<213> ORGANISM: Artificial Sequence
<220> FEATURE:
<223> OTHER INFORMATION: Synthesized: Linker sequence; (GGGS)3 is
      GGGSGGGSGGGS linker region

<400> SEQUENCE: 176

Gly Gly Gly Ser
1

<210> SEQ ID NO 177
<211> LENGTH: 43
<212> TYPE: DNA
<213> ORGANISM: Artificial Sequence
<220> FEATURE:
<223> OTHER INFORMATION: Synthesized: Oligonucleotide comprising a Pme I
      site and stop codon
<220> FEATURE:
<221> NAME/KEY: misc_feature
<222> LOCATION: (15)..(17) and (18)..(20)
<223> OTHER INFORMATION: nnn (XXX) represents the sequence encoding the
      motif variant

<400> SEQUENCE: 177
gtttaaactc attannnnnn aagcttagaa ccaccaccac cgg                   43

<210> SEQ ID NO 178
<211> LENGTH: 18
<212> TYPE: PRT
<213> ORGANISM: Artificial Sequence
<220> FEATURE:
<223> OTHER INFORMATION: Synthesized: Sequence comprising CDR1

<400> SEQUENCE: 178

Ala Ala Ser Gly Phe Thr Phe Ser Ser Tyr Ala Met Ser Trp Val Arg
1               5                   10                  15

Gln Ala

<210> SEQ ID NO 179
<211> LENGTH: 12
<212> TYPE: DNA
<213> ORGANISM: Artificial Sequence
<220> FEATURE:
<223> OTHER INFORMATION: Synthesized: Codons at residue positions 30-33

-continued

<400> SEQUENCE: 179
tcttcttatg ct                                                              12

<210> SEQ ID NO 180
<211> LENGTH: 12
<212> TYPE: DNA
<213> ORGANISM: Artificial Sequence
<220> FEATURE:
<223> OTHER INFORMATION: Synthesized: Codons at residue positions 30-33

<400> SEQUENCE: 180
tcttcttatg ct                                                              12

<210> SEQ ID NO 181
<211> LENGTH: 12
<212> TYPE: DNA
<213> ORGANISM: Artificial Sequence
<220> FEATURE:
<223> OTHER INFORMATION: Synthesized: Codons at residue positions 30-33

<400> SEQUENCE: 181
tcttcttatg ct                                                              12

<210> SEQ ID NO 182
<211> LENGTH: 12
<212> TYPE: DNA
<213> ORGANISM: Artificial Sequence
<220> FEATURE:
<223> OTHER INFORMATION: Synthesized: Codons at residue positions 30-33

<400> SEQUENCE: 182
tcttcttatt at                                                              12

<210> SEQ ID NO 183
<211> LENGTH: 12
<212> TYPE: DNA
<213> ORGANISM: Artificial Sequence
<220> FEATURE:
<223> OTHER INFORMATION: Synthesized: Codons at residue positions 30-33

<400> SEQUENCE: 183
tcttcttatt at                                                              12

<210> SEQ ID NO 184
<211> LENGTH: 12
<212> TYPE: DNA
<213> ORGANISM: Artificial Sequence
<220> FEATURE:
<223> OTHER INFORMATION: Synthesized: Codons at residue positions 30-33

<400> SEQUENCE: 184
tcttcttatt at                                                              12

<210> SEQ ID NO 185
<211> LENGTH: 54
<212> TYPE: DNA
<213> ORGANISM: Artificial Sequence
<220> FEATURE:
<223> OTHER INFORMATION: Synthesized: Codons at residue positions 23-40

<400> SEQUENCE: 185
gctgcttctg gttttacttt ttctaattat tggatgtctt gggttagaca agct               54

<210> SEQ ID NO 186
<211> LENGTH: 12

```
<212> TYPE: DNA
<213> ORGANISM: Artificial Sequence
<220> FEATURE:
<223> OTHER INFORMATION: Synthesized: Codons at residue positions 30-33

<400> SEQUENCE: 186
actaattatt gg                                                          12

<210> SEQ ID NO 187
<211> LENGTH: 12
<212> TYPE: DNA
<213> ORGANISM: Artificial Sequence
<220> FEATURE:
<223> OTHER INFORMATION: Synthesized: Codons at residue positions 30-33

<400> SEQUENCE: 187
actggttctg gt                                                          12

<210> SEQ ID NO 188
<211> LENGTH: 12
<212> TYPE: DNA
<213> ORGANISM: Artificial Sequence
<220> FEATURE:
<223> OTHER INFORMATION: Synthesized: Codons at residue positions 30-33

<400> SEQUENCE: 188
aatactaatt ct                                                          12

<210> SEQ ID NO 189
<211> LENGTH: 12
<212> TYPE: DNA
<213> ORGANISM: Artificial Sequence
<220> FEATURE:
<223> OTHER INFORMATION: Synthesized: Codons at residue positions 30-33

<400> SEQUENCE: 189
agagatggtg at                                                          12

<210> SEQ ID NO 190
<211> LENGTH: 12
<212> TYPE: DNA
<213> ORGANISM: Artificial Sequence
<220> FEATURE:
<223> OTHER INFORMATION: Synthesized: Codons at residue positions 30-33

<400> SEQUENCE: 190
gatagattta ct                                                          12

<210> SEQ ID NO 191
<211> LENGTH: 12
<212> TYPE: DNA
<213> ORGANISM: Artificial Sequence
<220> FEATURE:
<223> OTHER INFORMATION: Synthesized: Codons at residue positions 30-33

<400> SEQUENCE: 191
ggtgctgctg tt                                                          12

<210> SEQ ID NO 192
<211> LENGTH: 25
<212> TYPE: PRT
<213> ORGANISM: Artificial Sequence
<220> FEATURE:
<223> OTHER INFORMATION: Synthesized: Sequence comprising CDR2
<220> FEATURE:
<221> NAME/KEY: misc_feature
<222> LOCATION: (12)..(12)
```

<223> OTHER INFORMATION: Xaa can be P (Pro), G (Gly) or S (Ser) at
      residue position 52a

<400> SEQUENCE: 192

Gly Lys Gly Leu Glu Trp Val Ser Ala Ile Ser Xaa Ser Gly Gly Ser
1               5                   10                  15

Thr Tyr Tyr Ala Asp Ser Val Lys Gly
            20                  25

<210> SEQ ID NO 193
<211> LENGTH: 33
<212> TYPE: DNA
<213> ORGANISM: Artificial Sequence
<220> FEATURE:
<223> OTHER INFORMATION: Synthesized: Codons at residue positions 49-58

<400> SEQUENCE: 193
ggtagaatct ctccatctgg tggttctact tat                              33

<210> SEQ ID NO 194
<211> LENGTH: 33
<212> TYPE: DNA
<213> ORGANISM: Artificial Sequence
<220> FEATURE:
<223> OTHER INFORMATION: Synthesized: Codons at residue positions 49-58

<400> SEQUENCE: 194
ggtagaatct ctccatctgg tggttctact tat                              33

<210> SEQ ID NO 195
<211> LENGTH: 33
<212> TYPE: DNA
<213> ORGANISM: Artificial Sequence
<220> FEATURE:
<223> OTHER INFORMATION: Synthesized: Codons at residue positions 49-58

<400> SEQUENCE: 195
ggttatatct ctccatctgg tggttctact tat                              33

<210> SEQ ID NO 196
<211> LENGTH: 33
<212> TYPE: DNA
<213> ORGANISM: Artificial Sequence
<220> FEATURE:
<223> OTHER INFORMATION: Synthesized: Codons at residue positions 49-58

<400> SEQUENCE: 196
ggttggatct atccagatgg tggttctact tat                              33

<210> SEQ ID NO 197
<211> LENGTH: 33
<212> TYPE: DNA
<213> ORGANISM: Artificial Sequence
<220> FEATURE:
<223> OTHER INFORMATION: Synthesized: Codons at residue positions 49-58

<400> SEQUENCE: 197
ggtgttatct atccagattc tggtactact aat                              33

<210> SEQ ID NO 198
<211> LENGTH: 75
<212> TYPE: DNA
<213> ORGANISM: Artificial Sequence
<220> FEATURE:
<223> OTHER INFORMATION: Synthesized: Codons at residue positions 42-65

```
<400> SEQUENCE: 198
ggtaaaggtt tggaatgggt tggtggtatc tatggttatt ctggtactac taattatgct    60
gattctgtta aaggt                                                     75

<210> SEQ ID NO 199
<211> LENGTH: 33
<212> TYPE: DNA
<213> ORGANISM: Artificial Sequence
<220> FEATURE:
<223> OTHER INFORMATION: Synthesized: Codons at residue positions 49-58

<400> SEQUENCE: 199
tctattatca atggtggttc tggtaatact gat                                  33

<210> SEQ ID NO 200
<211> LENGTH: 33
<212> TYPE: DNA
<213> ORGANISM: Artificial Sequence
<220> FEATURE:
<223> OTHER INFORMATION: Synthesized: Codons at residue positions 49-58

<400> SEQUENCE: 200
tctgaaatca aaggtcatga tggtgatact aga                                  33

<210> SEQ ID NO 201
<211> LENGTH: 33
<212> TYPE: DNA
<213> ORGANISM: Artificial Sequence
<220> FEATURE:
<223> OTHER INFORMATION: Synthesized: Codons at residue positions 49-58

<400> SEQUENCE: 201
tctgctatca ttggtaataa tggttatact tct                                  33

<210> SEQ ID NO 202
<211> LENGTH: 33
<212> TYPE: DNA
<213> ORGANISM: Artificial Sequence
<220> FEATURE:
<223> OTHER INFORMATION: Synthesized: Codons at residue positions 49-58

<400> SEQUENCE: 202
gcttctatca gatctattaa aggtgaaact att                                  33

<210> SEQ ID NO 203
<211> LENGTH: 33
<212> TYPE: DNA
<213> ORGANISM: Artificial Sequence
<220> FEATURE:
<223> OTHER INFORMATION: Synthesized: Codons at residue positions 49-58

<400> SEQUENCE: 203
gctaatatcg attctacttt tggtggtact act                                  33

<210> SEQ ID NO 204
<211> LENGTH: 33
<212> TYPE: DNA
<213> ORGANISM: Artificial Sequence
<220> FEATURE:
<223> OTHER INFORMATION: Synthesized: Codons at residue positions 49-58

<400> SEQUENCE: 204
gctttaatca cttcttggac tggtgctact cat                                  33
```

<210> SEQ ID NO 205
<211> LENGTH: 20
<212> TYPE: PRT
<213> ORGANISM: Artificial Sequence
<220> FEATURE:
<223> OTHER INFORMATION: Synthesized: Sequence comprising CDR1

<400> SEQUENCE: 205

Leu Ser Cys Arg Ala Ser Gln Ser Val Ser Ser Ser Tyr Leu Ala Trp
1               5                   10                  15

Tyr Gln Gln Lys
            20

<210> SEQ ID NO 206
<211> LENGTH: 18
<212> TYPE: DNA
<213> ORGANISM: Artificial Sequence
<220> FEATURE:
<223> OTHER INFORMATION: Synthesized: Codons at residue positions 28-32

<400> SEQUENCE: 206
tctatttctt cttcttat                                             18

<210> SEQ ID NO 207
<211> LENGTH: 18
<212> TYPE: DNA
<213> ORGANISM: Artificial Sequence
<220> FEATURE:
<223> OTHER INFORMATION: Synthesized: Codons at residue positions 28-32

<400> SEQUENCE: 207
tctatttctt cttcttat                                             18

<210> SEQ ID NO 208
<211> LENGTH: 18
<212> TYPE: DNA
<213> ORGANISM: Artificial Sequence
<220> FEATURE:
<223> OTHER INFORMATION: Synthesized: Codons at residue positions 28-32

<400> SEQUENCE: 208
tctatttctt cttcttat                                             18

<210> SEQ ID NO 209
<211> LENGTH: 18
<212> TYPE: DNA
<213> ORGANISM: Artificial Sequence
<220> FEATURE:
<223> OTHER INFORMATION: Synthesized: Codons at residue positions 28-32

<400> SEQUENCE: 209
aatatttctt cttcttat                                             18

<210> SEQ ID NO 210
<211> LENGTH: 60
<212> TYPE: DNA
<213> ORGANISM: Artificial Sequence
<220> FEATURE:
<223> OTHER INFORMATION: Synthesized: Codons at residue positions 21-39

<400> SEQUENCE: 210
ttgtcttgta gagcttctca aaatatttct aattcttatt tggcttggta tcaacaaaaa    60

<210> SEQ ID NO 211
<211> LENGTH: 18
<212> TYPE: DNA

```
<213> ORGANISM: Artificial Sequence
<220> FEATURE:
<223> OTHER INFORMATION: Synthesized: Codons at residue positions 28-32

<400> SEQUENCE: 211
gtttctaata attcttat                                                    18

<210> SEQ ID NO 212
<211> LENGTH: 18
<212> TYPE: DNA
<213> ORGANISM: Artificial Sequence
<220> FEATURE:
<223> OTHER INFORMATION: Synthesized: Codons at residue positions 28-32

<400> SEQUENCE: 212
gtttctaata cttctaat                                                    18

<210> SEQ ID NO 213
<211> LENGTH: 18
<212> TYPE: DNA
<213> ORGANISM: Artificial Sequence
<220> FEATURE:
<223> OTHER INFORMATION: Synthesized: Codons at residue positions 28-32

<400> SEQUENCE: 213
ggtgttaaaa gaaattgg                                                    18

<210> SEQ ID NO 214
<211> LENGTH: 18
<212> TYPE: DNA
<213> ORGANISM: Artificial Sequence
<220> FEATURE:
<223> OTHER INFORMATION: Synthesized: Codons at residue positions 28-32

<400> SEQUENCE: 214
ggtgttggta ttaatttt                                                    18

<210> SEQ ID NO 215
<211> LENGTH: 18
<212> TYPE: DNA
<213> ORGANISM: Artificial Sequence
<220> FEATURE:
<223> OTHER INFORMATION: Synthesized: Codons at residue positions 28-32

<400> SEQUENCE: 215
gatggtagag atacttct                                                    18

<210> SEQ ID NO 216
<211> LENGTH: 18
<212> TYPE: DNA
<213> ORGANISM: Artificial Sequence
<220> FEATURE:
<223> OTHER INFORMATION: Synthesized: Codons at residue positions 28-32

<400> SEQUENCE: 216
gataattata aaactgat                                                    18

<210> SEQ ID NO 217
<211> LENGTH: 21
<212> TYPE: PRT
<213> ORGANISM: Artificial Sequence
<220> FEATURE:
<223> OTHER INFORMATION: Synthesized: Sequence comprising CDR2

<400> SEQUENCE: 217

Gln Ala Pro Arg Leu Leu Ile Tyr Gly Ala Ser Ser Arg Ala Thr Gly
```

Ile Pro Asp Arg Phe
            20

<210> SEQ ID NO 218
<211> LENGTH: 63
<212> TYPE: DNA
<213> ORGANISM: Artificial Sequence
<220> FEATURE:
<223> OTHER INFORMATION: Synthesized: Codons at residue positions 42-62

<400> SEQUENCE: 218
caagctccaa gattgttgat ctacgatgct tctaatagac aaactggtat tccagataga    60
ttt                                                                  63

<210> SEQ ID NO 219
<211> LENGTH: 20
<212> TYPE: PRT
<213> ORGANISM: Artificial Sequence
<220> FEATURE:
<223> OTHER INFORMATION: Synthesized: Sequence comprising CDR3

<400> SEQUENCE: 219

Ala Val Tyr Tyr Cys Gln Gln Tyr Gly Ser Ser Pro Ile Thr Phe Gly
1               5                   10                  15

Gln Gly Thr Lys
            20

<210> SEQ ID NO 220
<211> LENGTH: 12
<212> TYPE: DNA
<213> ORGANISM: Artificial Sequence
<220> FEATURE:
<223> OTHER INFORMATION: Synthesized: Codons at residue positions 91-94

<400> SEQUENCE: 220
tattattctt ct                                                        12

<210> SEQ ID NO 221
<211> LENGTH: 12
<212> TYPE: DNA
<213> ORGANISM: Artificial Sequence
<220> FEATURE:
<223> OTHER INFORMATION: Synthesized: Codons at residue positions 91-94

<400> SEQUENCE: 221
tattattctt ct                                                        12

<210> SEQ ID NO 222
<211> LENGTH: 12
<212> TYPE: DNA
<213> ORGANISM: Artificial Sequence
<220> FEATURE:
<223> OTHER INFORMATION: Synthesized: Codons at residue positions 91-94

<400> SEQUENCE: 222
tattattcta ct                                                        12

<210> SEQ ID NO 223
<211> LENGTH: 12
<212> TYPE: DNA
<213> ORGANISM: Artificial Sequence
<220> FEATURE:
<223> OTHER INFORMATION: Synthesized: Codons at residue positions 91-94

```
<400> SEQUENCE: 223
tatggttcta ct                                                          12

<210> SEQ ID NO 224
<211> LENGTH: 12
<212> TYPE: DNA
<213> ORGANISM: Artificial Sequence
<220> FEATURE:
<223> OTHER INFORMATION: Synthesized: Codons at residue positions 91-94

<400> SEQUENCE: 224
tatggttctt gg                                                          12

<210> SEQ ID NO 225
<211> LENGTH: 60
<212> TYPE: DNA
<213> ORGANISM: Artificial Sequence
<220> FEATURE:
<223> OTHER INFORMATION: Synthesized: Codons at residue positions 84-103

<400> SEQUENCE: 225
gctgtttact actgtcaaca atataataat tggccatgga cttttggtca aggtactaaa      60

<210> SEQ ID NO 226
<211> LENGTH: 12
<212> TYPE: DNA
<213> ORGANISM: Artificial Sequence
<220> FEATURE:
<223> OTHER INFORMATION: Synthesized: Codons at residue positions 91-94

<400> SEQUENCE: 226
tattctaatt at                                                          12

<210> SEQ ID NO 227
<211> LENGTH: 12
<212> TYPE: DNA
<213> ORGANISM: Artificial Sequence
<220> FEATURE:
<223> OTHER INFORMATION: Synthesized: Codons at residue positions 91-94

<400> SEQUENCE: 227
tctgatcaat at                                                          12

<210> SEQ ID NO 228
<211> LENGTH: 12
<212> TYPE: DNA
<213> ORGANISM: Artificial Sequence
<220> FEATURE:
<223> OTHER INFORMATION: Synthesized: Codons at residue positions 91-94

<400> SEQUENCE: 228
tctttaactt ta                                                          12

<210> SEQ ID NO 229
<211> LENGTH: 12
<212> TYPE: DNA
<213> ORGANISM: Artificial Sequence
<220> FEATURE:
<223> OTHER INFORMATION: Synthesized: Codons at residue positions 91-94

<400> SEQUENCE: 229
agaactcatt tt                                                          12

<210> SEQ ID NO 230
<211> LENGTH: 12
```

```
<212> TYPE: DNA
<213> ORGANISM: Artificial Sequence
<220> FEATURE:
<223> OTHER INFORMATION: Synthesized: Codons at residue positions 91-94

<400> SEQUENCE: 230
gctcatggtg ct                                                          12

<210> SEQ ID NO 231
<211> LENGTH: 12
<212> TYPE: DNA
<213> ORGANISM: Artificial Sequence
<220> FEATURE:
<223> OTHER INFORMATION: Synthesized: Codons at residue positions 91-94

<400> SEQUENCE: 231
ggtattgatc ca                                                          12

<210> SEQ ID NO 232
<211> LENGTH: 7
<212> TYPE: PRT
<213> ORGANISM: Artificial Sequence
<220> FEATURE:
<223> OTHER INFORMATION: Synthesized: Sequence

<400> SEQUENCE: 232

Ala Val Tyr Tyr Cys Ala Arg
1               5

<210> SEQ ID NO 233
<211> LENGTH: 7
<212> TYPE: PRT
<213> ORGANISM: Artificial Sequence
<220> FEATURE:
<223> OTHER INFORMATION: Synthesized: Sequence

<400> SEQUENCE: 233

Phe Asp Tyr Trp Gly Gln Gly
1               5

<210> SEQ ID NO 234
<211> LENGTH: 24
<212> TYPE: DNA
<213> ORGANISM: Artificial Sequence
<220> FEATURE:
<223> OTHER INFORMATION: Synthesized: Codons at residue positions
      95-100b

<400> SEQUENCE: 234
ggtggtggtg gtggtggtgg tggt                                             24

<210> SEQ ID NO 235
<211> LENGTH: 24
<212> TYPE: DNA
<213> ORGANISM: Artificial Sequence
<220> FEATURE:
<223> OTHER INFORMATION: Synthesized: Codons at residue positions
      95-100b

<400> SEQUENCE: 235
ggtggtggtg gtggtggtgg tggt                                             24

<210> SEQ ID NO 236
<211> LENGTH: 24
<212> TYPE: DNA
<213> ORGANISM: Artificial Sequence
<220> FEATURE:
```

```
<223> OTHER INFORMATION: Synthesized: Codons at residue positions
      95-100b

<400> SEQUENCE: 236
ggtggtggtg gtggtggtgg tggt                                              24

<210> SEQ ID NO 237
<211> LENGTH: 24
<212> TYPE: DNA
<213> ORGANISM: Artificial Sequence
<220> FEATURE:
<223> OTHER INFORMATION: Synthesized: Codons at residue positions
      95-100b

<400> SEQUENCE: 237
ggtggtggtg gtggtggtgg tggt                                              24

<210> SEQ ID NO 238
<211> LENGTH: 24
<212> TYPE: DNA
<213> ORGANISM: Artificial Sequence
<220> FEATURE:
<223> OTHER INFORMATION: Synthesized: Codons at residue positions
      95-100b

<400> SEQUENCE: 238
tattattatt attattatta ttat                                              24

<210> SEQ ID NO 239
<211> LENGTH: 24
<212> TYPE: DNA
<213> ORGANISM: Artificial Sequence
<220> FEATURE:
<223> OTHER INFORMATION: Synthesized: Codons at residue positions
      95-100b

<400> SEQUENCE: 239
tattattatt attattatta ttat                                              24

<210> SEQ ID NO 240
<211> LENGTH: 24
<212> TYPE: DNA
<213> ORGANISM: Artificial Sequence
<220> FEATURE:
<223> OTHER INFORMATION: Synthesized: Codons at residue positions
      95-100b

<400> SEQUENCE: 240
tattattatt attattatta ttat                                              24

<210> SEQ ID NO 241
<211> LENGTH: 24
<212> TYPE: DNA
<213> ORGANISM: Artificial Sequence
<220> FEATURE:
<223> OTHER INFORMATION: Synthesized: Codons at residue positions
      95-100b

<400> SEQUENCE: 241
tattattatt attattatta ttat                                              24

<210> SEQ ID NO 242
<211> LENGTH: 24
<212> TYPE: DNA
<213> ORGANISM: Artificial Sequence
<220> FEATURE:
<223> OTHER INFORMATION: ENTER DESCRIPTION
```

```
<400> SEQUENCE: 242
tcttcttctt cttcttcttc ttct                                          24

<210> SEQ ID NO 243
<211> LENGTH: 24
<212> TYPE: DNA
<213> ORGANISM: Artificial Sequence
<220> FEATURE:
<223> OTHER INFORMATION: Synthesized: Codons at residue positions
      95-100b

<400> SEQUENCE: 243
tcttcttctt cttcttcttc ttct                                          24

<210> SEQ ID NO 244
<211> LENGTH: 24
<212> TYPE: DNA
<213> ORGANISM: Artificial Sequence
<220> FEATURE:
<223> OTHER INFORMATION: Synthesized: Codons at residue positions
      95-100b

<400> SEQUENCE: 244
tcttcttctt cttcttcttc ttct                                          24

<210> SEQ ID NO 245
<211> LENGTH: 24
<212> TYPE: DNA
<213> ORGANISM: Artificial Sequence
<220> FEATURE:
<223> OTHER INFORMATION: Synthesized: Codons at residue positions
      95-100b

<400> SEQUENCE: 245
tcttcttctt cttcttcttc ttct                                          24

<210> SEQ ID NO 246
<211> LENGTH: 66
<212> TYPE: DNA
<213> ORGANISM: Artificial Sequence
<220> FEATURE:
<223> OTHER INFORMATION: Synthesized: Codons at residue positions 88-106

<400> SEQUENCE: 246
gctgtttatt attgtgctag agatgatgat gatgatgatg atgattttga ttattggggt   60
caaggt                                                              66

<210> SEQ ID NO 247
<211> LENGTH: 24
<212> TYPE: DNA
<213> ORGANISM: Artificial Sequence
<220> FEATURE:
<223> OTHER INFORMATION: Synthesized: Codons at residue positions
      95-100b

<400> SEQUENCE: 247
gatgatgatg atgatgatga tgat                                          24

<210> SEQ ID NO 248
<211> LENGTH: 24
<212> TYPE: DNA
<213> ORGANISM: Artificial Sequence
<220> FEATURE:
<223> OTHER INFORMATION: Synthesized: Codons at residue positions
      95-100b
```

<400> SEQUENCE: 248
agaagaagaa gaagaagaag aaga                                              24

<210> SEQ ID NO 249
<211> LENGTH: 24
<212> TYPE: DNA
<213> ORGANISM: Artificial Sequence
<220> FEATURE:
<223> OTHER INFORMATION: Synthesized: Codons at residue positions
      95-100b

<400> SEQUENCE: 249
ttattattat tattattatt atta                                              24

<210> SEQ ID NO 250
<211> LENGTH: 24
<212> TYPE: DNA
<213> ORGANISM: Artificial Sequence
<220> FEATURE:
<223> OTHER INFORMATION: Synthesized: Codons at residue positions
      95-100b

<400> SEQUENCE: 250
gttgttgttg ttgttgttgt tgtt                                              24

<210> SEQ ID NO 251
<211> LENGTH: 24
<212> TYPE: DNA
<213> ORGANISM: Artificial Sequence
<220> FEATURE:
<223> OTHER INFORMATION: Synthesized: Codons at residue positions
      95-100b

<400> SEQUENCE: 251
gctgctgctg ctgctgctgc tgct                                              24

<210> SEQ ID NO 252
<211> LENGTH: 24
<212> TYPE: DNA
<213> ORGANISM: Artificial Sequence
<220> FEATURE:
<223> OTHER INFORMATION: Synthesized: Codons at residue positions
      95-100b

<400> SEQUENCE: 252
ccaccaccac caccaccacc acca                                              24

<210> SEQ ID NO 253
<211> LENGTH: 24
<212> TYPE: DNA
<213> ORGANISM: Artificial Sequence
<220> FEATURE:
<223> OTHER INFORMATION: Synthesized: Codons at residue positions
      95-100b

<400> SEQUENCE: 253
actactacta ctactactac tact                                              24

<210> SEQ ID NO 254
<211> LENGTH: 24
<212> TYPE: DNA
<213> ORGANISM: Artificial Sequence
<220> FEATURE:
<223> OTHER INFORMATION: Synthesized: Codons at residue positions
      95-100b

```
<400> SEQUENCE: 254
aataataata ataataataa taat                                          24

<210> SEQ ID NO 255
<211> LENGTH: 24
<212> TYPE: DNA
<213> ORGANISM: Artificial Sequence
<220> FEATURE:
<223> OTHER INFORMATION: Synthesized: Codons at residue positions
      95-100b

<400> SEQUENCE: 255
tttttttttt tttttttttt tttt                                          24

<210> SEQ ID NO 256
<211> LENGTH: 24
<212> TYPE: DNA
<213> ORGANISM: Artificial Sequence
<220> FEATURE:
<223> OTHER INFORMATION: Synthesized: Codons at residue positions
      95-100b

<400> SEQUENCE: 256
attattatta ttattattat tatt                                          24

<210> SEQ ID NO 257
<211> LENGTH: 24
<212> TYPE: DNA
<213> ORGANISM: Artificial Sequence
<220> FEATURE:
<223> OTHER INFORMATION: Synthesized: Codons at residue positions
      95-100b

<400> SEQUENCE: 257
gaagaagaag aagaagaaga agaa                                          24

<210> SEQ ID NO 258
<211> LENGTH: 24
<212> TYPE: DNA
<213> ORGANISM: Artificial Sequence
<220> FEATURE:
<223> OTHER INFORMATION: Synthesized: Codons at residue positions
      95-100b

<400> SEQUENCE: 258
catcatcatc atcatcatca tcat                                          24

<210> SEQ ID NO 259
<211> LENGTH: 24
<212> TYPE: DNA
<213> ORGANISM: Artificial Sequence
<220> FEATURE:
<223> OTHER INFORMATION: Synthesized: Codons at residue positions
      95-100b

<400> SEQUENCE: 259
catcatcatc atcatcatca tcat                                          24

<210> SEQ ID NO 260
<211> LENGTH: 24
<212> TYPE: DNA
<213> ORGANISM: Artificial Sequence
<220> FEATURE:
<223> OTHER INFORMATION: Synthesized: Codons at residue positions
      95-100b

<400> SEQUENCE: 260
```

```
aaaaaaaaaa aaaaaaaaaa aaaa                                              24

<210> SEQ ID NO 261
<211> LENGTH: 24
<212> TYPE: DNA
<213> ORGANISM: Artificial Sequence
<220> FEATURE:
<223> OTHER INFORMATION: Synthesized: Codons at residue positions
      95-100b

<400> SEQUENCE: 261
atgatgatga tgatgatgat gatg                                              24

<210> SEQ ID NO 262
<211> LENGTH: 24
<212> TYPE: DNA
<213> ORGANISM: Artificial Sequence
<220> FEATURE:
<223> OTHER INFORMATION: Synthesized: Codons at residue positions
      95-100b

<400> SEQUENCE: 262
tggtggtggt ggtggtggtg gtgg                                              24
```